US006878706B1

(12) United States Patent
Gilmore et al.

(10) Patent No.: US 6,878,706 B1
(45) Date of Patent: Apr. 12, 2005

(54) CYANAMIDES USEFUL AS REVERSIBLE INHIBITORS OF CYSTEINE PROTEASES

(75) Inventors: Thomas A. Gilmore, Salem, MA (US); Eugene Richard Hickey, Danbury, CT (US); Weimin Liu, Sandy Hook, CT (US); Peter Allen Nemoto, Southbury, CT (US); Denice M. Spero, West Redding, CT (US)

(73) Assignee: Boehringer Ingelheim Pharmaceuticals Inc., Ridgefield, CT (US)

( * ) Notice: Subject to any disclaimer, the term of this patent is extended or adjusted under 35 U.S.C. 154(b) by 146 days.

(21) Appl. No.: 10/400,385

(22) Filed: Mar. 27, 2003

Related U.S. Application Data

(60) Provisional application No. 60/370,368, filed on Apr. 5, 2002.

(51) Int. Cl.[7] .................. A61K 31/535; A61K 31/4965; A61K 31/44; A01N 43/70; A01N 43/12

(52) U.S. Cl. ................................ 514/237.5; 514/239.2; 514/255.01; 514/255.06; 514/306; 514/309; 514/330; 514/331; 514/419; 514/448; 514/463; 514/469; 514/609; 544/146; 544/153; 544/163; 544/355; 544/391; 544/392; 544/406; 546/141; 546/146; 546/226; 548/492; 549/57; 549/471; 549/441; 564/103; 564/105; 564/106

(58) Field of Search ........................... 514/237.5, 239.2, 514/255.01, 255.06, 306, 309, 330, 331, 419, 448, 463, 469, 609; 544/146, 153, 163, 395, 391, 392, 406; 546/141, 146, 226; 548/492; 549/57, 471, 441; 564/103, 105, 106

(56) References Cited

U.S. PATENT DOCUMENTS

2003/0229226 A1 12/2003 Okamoto et al.

FOREIGN PATENT DOCUMENTS

WO WO 00/49007 A1 8/2000
WO WO 01/77073 A1 10/2001

*Primary Examiner*—Richard L. Raymond
*Assistant Examiner*—Zachary C. Tucker
(74) *Attorney, Agent, or Firm*—M. P. Morris; M. E. Devlin; P. I. Datlow

(57) ABSTRACT

Compounds according to the following formula (I):

(I)

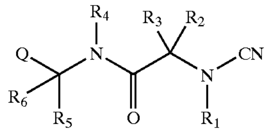

wherein the variables Q and $R_1$ to $R_6$ are as described herein, which reversibly inhibit the cysteine proteases, such as cathepsins K, S, F, L and B; pharmaceutical compositions containing such compounds, and method of treating diseases and pathological conditions exacerbated by these cysteine proteases such as, but not limited to rheumatoid arthritis, multiple sclerosis and other autoimmune diseases, osteoporosis, asthma, Alzheimer's disease, atherosclerosis and endometriosis.

25 Claims, No Drawings

CYANAMIDES USEFUL AS REVERSIBLE INHIBITORS OF CYSTEINE PROTEASES

This application claims the benefit of U.S. Provisional Application No. 60/370,368, filed on Apr. 5, 2002, which application is herein incorporated by reference in its entirety.

FIELD OF THE INVENTION

This invention relates to cyanamide compounds useful as reversible inhibitors of the cysteine proteases cathepsins S, K, F, L and B. Certain embodiments described are preferable for inhibition of cathepsin K. The compounds are therefore useful in the treatment of cysteine protease mediated diseases including osteoporosis, autoimmune diseases and other related diseases. The invention also relates to processes for preparing such compounds and pharmaceutical compositions comprising them.

BACKGROUND OF THE INVENTION

Cathepsin K and cathepsin S are members of the papain family, within the papain superfamily of cysteine proteases. The papain family is the largest group of cysteine proteases and includes proteases such as cathepsins B, H, K, L, O and S. (A. J. Barrett et al., 1996, Perspectives in Drug Discovery and Design, 6, 1). The cysteine proteases have important roles in human biology and diseases including osteoporosis, chronic inflammation and immune disorders, atherosclerosis, and emphysema (H. A. Chapman et al., 1997, Ann. Rev. Physiol., 59, 63). Cysteine proteases are also involved in the pathogenesis of some infectious diseases, including malaria (A. Semenov et al., Antimicrobial Agents and Chemotherapy, 1998, 42, 2254) and Chagas' disease, (J. C. Engel et al., J. Exp. Med., 1998, 188, 725). Bacterial cysteine proteases contribute to the pathogenesis of gingivitis (J. Potempa et al., Perspectives in Drug Discovery and Design, 1994, 2, 445).

Cathepsin K has been found to be highly expressed in osteoclasts, cells involved in bone resorption (F. H. Drake et al., J. Biol. Chem., 1996, 271, 12511). Collagen and osteonectin, two protein components of bone matrix have been found to be substrates of activated cathepsin K (M. J. Bossard et al., J. Biol. Chem., 1996, 271, 12517). Inhibitors of cathepsin K have been shown to have anti-resorptive activity in vitro and in vivo (S. K. Thompson et al., Proc. Natl. Acad. Sci. USA, 1997, 94, 14249). The essential role of cathepsin K in bone resorption has also been confirmed in cells and organisms lacking this protease. At the cellular level, cathepsin K deficient osteoclasts, when tested for functional activity on dentine, produced fewer resorption pits as compared to wild-type osteoclasts (P. Saftig et al., Proc Natl Acad Sci USA 1998, 95,13453). Cathepsin K knockout mice develop osteopetrosis, a disease characterized by an increase in bone mass, due to a deficit in matrix degradation but not demineralization of hydroxyapatite. These knockout mice displayed osteopetrosis of the long bones and vertebrae as well as abnormal joint morphology (M. Gowen et al., J. Bone Miner Res. 1999, 14, 1654). The phenotype of the cathepsin K knockout mice resembles the human genetic disorder pycnodysostosis which is due to a mutation in the cathepsin K gene (W-S Hu et al., Journal of Clinical Investigation, 1999, 103, 731; B. D. Gelb et al, Science, 1996, 273, 1236). Patients with this disease have short, dense bones. These and other findings suggest that cathepsin K may play an important role in diseases involving bone resorption, excessive bone loss or cartilage or bone matrix degradation including osteoporosis (D. S Yamashita et al, Current Pharmaceutical Design, 2000, 6, 1), Gaucher disease (M. T. Moran et al, Blood, 2000, 96, 1969), Paget's disease, gingivitis, and periodontitis (G. A. Rodan et al, Science, 2000, 289, 1508), and rheumatoid arthritis (K. M. Hummel et al, J. Rheumatol., 1998, 25, 1887) (also see for example H. A. Chapman et al, Annu. Rev. Physiol., 1997, 59, 63; M. Gowen, Exp. Opin. Invest. Drugs, 1997, 6, 1199; W. W. Smith et al., Exp. Opin. Ther. Patents, 1999, 9, 683).

The inhibition of cathepsin K has been described by B. D. Gelb et al (U.S. Pat. No. 5,830,850) as a method to ameliorate symptoms caused by bone resorption disorders, including osteoporosis, arthritides and periodontal disease, and damage caused by macrophage-mediated inflammatory processes. Studies in breast cancer research have shown that invading breast cancer cells have expressed low levels of Cathepsin K suggesting that these tumor cells may be able to directly resorb bone by the release of Cathepsin K. Inhibition of Cathepsin K may play a role in the metastatic potential and course of the disease (A. J. Littlewood-Evans et al, Cancer Research, 1997, 57, 5386). Increases in bone resorption and demineralization of bone are skeletal complications associated with many cancers and with bone metastases of breast and prostate tumors (G. A. Rodan et al, Science, 2000, 289, 1508). Cathepsin K has also been observed in giant cell aortitis suggesting that disorders associated with excessive elastin degradation such as lymphangiomyomatosis, vascular inflammation, and cardiovascular disease such as atherosclerosis may be attenuated with Cathepsin K inhibitors (H. A. Chapman et al, Annu. Rev. Physiol., 1997, 59, 63; D. S Yamashita et al, Current Pharmaceutical Design, 2000, 6, 1; G. K. Sukhova et al, J. Clin. Invest., 1998, 102, 576).

Cathepsin S plays a key role in regulating antigen presentation and immunity (H. A. Chapman, 1998, Current Opinion in Immunology, 10, 93; R. J. Riese et al., 1998, J. Clin. Invest., 101, 2351; R. J. Riese et al., 1996, Immunity, 4, 357). Cathepsin S deficient mice have impaired invariant chain degradation resulting in decreased antigen presentation and germinal center formation, and diminished susceptibility to collagen-induced arthritis indicating the therapeutic potential for a cathepsin S inhibitor (G. Shi et al., 1999, Immunity, 10, 197; T. Y. Nakagawa et al, 1999, Immunity, 10, 207).

Control of antigen-specific immune responses has long been desirable as a useful therapy for autoimmune diseases. Such diseases include Crohn's disease, rheumatoid arthritis, and Multiple Sclerosis, as well as other T-cell-mediated immune responses (C. Janeway and P. Travers, 1996, Immunobiology, The Immune System in Health and Disease, Chapter 12). Furthermore, cathepsin S, which has broad pH specificity, has been implicated in a variety of other diseases involving extracellular proteolysis, such as Alzheimer's disease (U. Muller-Ladner et al., 1996, Perspectives in Drug Discovery and Design, 6, 87), atherosclerosis (G. K. Sukhova et al., 1998, J. Clin. Invest., 102, 576) and endometriosis (WO 9963115, 1999). A cathepsin S inhibitor has been found to block the rise in IgE titers and eosinophil infiltration in the lung in a mouse model of pulmonary hypersensitivity, suggesting that cathepsin S may be involved in asthma (R. J. Riese et al., J. Clin. Investigation, 1998, 101, 2351).

Another cysteine protease, cathepsin F has been found in macrophages and is also involved in antigen processing. It has been postulated that cathepsin F in stimulated lung macrophages and possibly other antigen presenting cells could play a role in airway inflammation (G.-P. Shi et al., J. Exp. Med., 2000, 191, 1177).

Cysteine proteases are characterized by having a cysteine residue at the active site which serves as a nucleophile. The active site also contains a histidine residue. The imidazole ring on the histidine serves as a base to generate a thiolate anion on the active site cysteine, increasing its nucleophilicity. When a substrate is recognized by the protease, the amide bond to be cleaved is directed to the active site, where the thiolate attacks the carbonyl carbon forming an acyl-enzyme intermediate and cleaving the amide bond, liberating an amine. Subsequently, water cleaves the acyl-enzyme species regenerating the enzyme and liberating the other cleavage product of the substrate, a carboxylic acid.

Inhibitors of cysteine proteases contain a functionality that can react reversibly or irreversibly with the active site cysteine. Examples of reactive functionalities that have been described (D. Rasnick, 1996, Perspectives in Drug Discovery and Design, 6, 47) on cysteine protease inhibitors include peptidyl diazomethanes, epoxides, monofluoroalkanes and acyloxymethanes, which irreversibly alkylate the cysteine thiol. Other irreversible inhibitors include Michael acceptors such as peptidyl vinyl esters and other carboxylic acid derivatives (S. Liu et al., J. Med Chem., 1992, 35, 1067) and vinyl sulfones (J. T. Palmer et al., 1995, J. Med Chem., 38, 3193).

Reactive functionalities that form reversible complexes with the active site cysteine include peptidyl aldehydes (R. P. Hanzlik et al., 1991, Biochim. Biophys. Acta., 1073, 33), which are non-selective, inhibiting both cysteine and serine proteases as well as other nucleophiles. Peptidyl nitriles (R. P. Hanzlik et al., 1990, Biochim. Biophys. Acta., 1035, 62) are less reactive than aldehydes and therefore more selective for the more nucleophilic cysteine proteases. Various reactive ketones have also been reported to be reversible inhibitors of cysteine proteases (D. Rasnick, 1996, ibid). In addition to reacting with the nucleophilic cysteine of the active site, reactive ketones may react with water, forming a hemiketal which may act as a transition state inhibitor.

Inhibitors of cathepsin K have been reported in the literature. D. S. Yamashita et al., (J. Am. Chem. Soc., 1997, 119, 11351) described 1,3-diamino-2-propanone inhibitors. S. K. Thompson et al. (Proc. Natl. Acad. Sci. USA, 1997, 94, 14249) described bis-aza analogs of these propanones as well as an aza-thiazole derivative. Introduction of a conformational constraint to the 1,3-diamino-2-propanones has led to 3-amido-pyrrolidin-4-one derivatives, 4-amido-piperidin-3-one derivatives, and eventually to azapanone-based inhibitors of Cathepsin K, as reported by R. W. Marquis et al. (J. Med. Chem. 1998, 41, 3563; J. Med. Chem. 2001, 44, 725; J. Med. Chem. 2001, 44, 1380). R. W. Marquis et al. (Bioorg. and Med. Chem. Letters, 1999, 7, 581) described peptidic alkoxymethylketones and thiomethylketones as cathepsin K inhibitors. Peptidyl vinyl sulfone cathepsin K inhibitors were described by L. Xia et al. (Biological Chem., 1999, 380, 679). Peptide aldehyde inhibitors of cathepsin K were reported by B. J. Votta et al. (J. Bone & Mineral Res., 1997, 12, 1396). J.-P. Falgueyret et al. (J. Med. Chem. 2001, 44, 94) described non-peptidic cyanamides as potent Cathepsin K inhibitors. T. Gamble et al. ($49^{th}$ Annual American Society for Mass Spectrometry Conference, May 27–31, 2001, Chicago, Ill., WO 01/77073) described in vitro metabolism studies on cyanamide-containing Cathepsin K inhibitors. D. F. Veber has discussed numerous inhibitors of Cathepsin K including the following: 1,5-diacylcarbohydrazides (Biochemistry, 1999, 38, 15893; J. Med. Chem. 1998, 41, 3923), conformationally constrained 1,3-diamino ketones (J. Med. Chem. 1998, 41, 3563), and 1,3-bis(acylamino)-2-butanones, (J. Combinatorial Chem. 1999, 1, 207; J. Am. Chem. Soc. 1998, 120, 9114; J. Am. Chem. Soc. 1997, 119, 11351).

Examples of cathepsin S inhibitors have been reported. J. L. Klaus et al. (WO 9640737) described reversible inhibitors of cysteine proteases including cathepsin S, containing an ethylene diamine. In U.S. Pat. No. 5,776,718, Palmer et al. disclosed in it's broadest generic aspect, a protease inhibitor comprising a targeting group linked through a two carbon atom chain to an electron withdrawing group (EWG). Other examples of cathepsin S inhibitors have been reported by E. T. Altmann et al, (WO 9924460, 1999) which describes dipeptide nitriles asserted to have activity as inhibitors of Cathepsins B, K, L and S. Certain acetamido acetonitrile derivatives have been disclosed by Tucker et al. (WO 00/49007) as inhibitors of cathepsin S and L.

Certain other cathepsin inhibitors have recently been disclosed, for example by Marquis et al. (WO 00/38687 and WO 00/39115), Altmann et al. (WO 00/48993), Buysse et al. (WO 00/55124), Singh et al. (WO 00/59881) and Cowen (WO 01/87828). Cathepsin inhibitors containing a cyclic cyanamide functionality were described by P. Prasit et al. (WO 01/77073). However, this WO publication does not disclose or suggest any compounds possessing the acyclic cyanamide moiety, as in the novel compounds according to the present invention.

Even though the novel compounds of the present invention contain functionalized N-substituted glycine groups, which also exist in classical peptoids, they should not be classified as classical peptoids because classical peptoids lack the acyclic cyanamide moiety which is present in the novel compounds of the present invention. Several reports of biologically active compounds containing the cyanamide moiety have appeared. For example, M. A. Patane et al. (U.S. Pat. No. 5,977,115) generically disclose cyanamide-containing compounds as alpha 1A adrenergic receptor antagonists. Opiate receptor ligands including some containing a cyanamide functionality were generically described by D. C. Spellmeyer et al. (U.S. Pat. No. 5,536, 853). F. Clemence et al. (U.S. Pat. No. 5,190,974) describe analgesic, psychotropic and enkephalinase-inhibiting compounds, some containing the cyanamide moiety.

A reversible inhibitor presents a more attractive therapy than irreversible inhibitors. Covalent modification of an enzyme by an irreversible inhibitor could potentially generate an antibody response by acting as a hapten. Furthermore, any toxic effects resulting from inactivation of the target enzyme would be mitigated by reversible inhibitors, and could be easily remedied by modified or lower dosing.

In light of the above, there is a clear need for compounds which reversibly and selectively inhibit cysteine proteases such as cathepsin K and cathepsin S for indications in which these proteases exacerbate disease.

SUMMARY OF THE INVENTION

It is therefore an object of this invention to provide novel compounds according to the following formula (I):

(I)

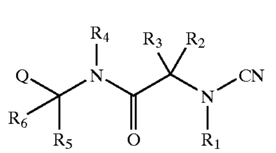

wherein the variables Q and $R_1$ to $R_6$ are as described herein which reversibly inhibit the cysteine proteases, such as cathepsins K, S, F, L and B. It is a further object of the invention to provide methods for treating diseases and pathological conditions exacerbated by these cysteine proteases such as, but not limited to rheumatoid arthritis, multiple sclerosis, and other autoimmune diseases, osteoporosis, asthma, Alzheimer's disease, atherosclerosis and endometriosis. It is yet a further object of the invention to provide novel processes for preparation of the above-mentioned novel compounds.

DETAILED DESCRIPTION OF THE INVENTION

A proposed mechanism of action of the cysteine protease inhibitors of this invention is that the inhibitors contain a functionality that can react (reversibly or irreversibly) with the active site cysteine. The reactive functionality is attached to a peptide or peptide mimic that can be recognized and accommodated by the protease surrounding the active site. The nature of both the reactive functionality and the remaining portion of the inhibitor determine the degree of selectivity and potency toward a particular protease.

Given the similarity of the active sites in cysteine proteases, it may be anticipated that a given class of inhibitors might have activity against more that one cysteine protease. It may also be expected that due to structural differences between individual cysteine proteases, different compounds of the invention may have different inhibitory potencies against different cysteine proteases. Thus some of the compounds of the invention may also be expected to be most effective in treating diseases mediated by cysteine proteases that they inhibit most potently. The activity of particular compounds disclosed herein against cysteine proteases cathepsin K, S, F, L and B may be determined by the screens described in the section entitled "Assessment of Biological Properties."

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, C1–10 alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk-Ar-, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the divalent radical and vice versa. Unless otherwise specified, conventional definitions of terms control and conventional stable atom valences are presumed and achieved in all formulas and groups.

The term "alkyl" refers to a saturated aliphatic hydrocarbon radical or a mono- or polyunsaturated aliphatic hydrocarbon radical. The mono- or polyunsaturated aliphatic hydrocarbon radical contains at least one double or triple bond, respectively. "Alkyl" refers to both branched and unbranched alkyl groups, each optionally partially or fully halogenated. Examples of "alkyl" include alkyl groups which are straight chain alkyl groups containing from one to eight carbon atoms and branched alkyl groups containing from three to eight carbon atoms. Other examples include alkyl groups which are straight chain alkyl groups containing from one to six carbon atoms and branched alkyl groups containing from three to six carbon atoms. This term is exemplified by groups such as methyl, ethyl, n-propyl, 1-methylethyl (isopropyl), n-butyl, n-pentyl, 1,1-dimethylethyl (tert-butyl), and the like. It may be abbreviated "Alk". It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom, respectively. "Alkanoyl" refers to an alkyl group linked to a carbonyl group (C═O).

The term "alkenyl" means a branched or straight-chain aliphatic hydrocarbon monovalent radical containing at least one carbon-carbon double bond. This term is exemplified by groups such as ethenyl, propenyl, n-butenyl, isobutenyl, 3-methylbut-2-enyl, n-pentenyl, heptenyl, octenyl, cyclohexylbutenyl, decenyl, and the like.

The terms "alkylcarbonyl" or "alkanoyl" mean a monovalent radical of the formula AlkC(O)—, where Alk is alkyl.

The terms "arylcarbonyl" or "aroyl" mean a monovalent radical of the formula ArC(O)—, where Ar is aryl.

The terms "alkoxycarbonyl" means a monovalent radical of the formula AlkO—C(O)—, where Alk is alkyl. Exemplary alkoxycarbonyl groups include methoxycarbonyl, ethoxycarbonyl, tert-butyloxycarbonyl, and the like.

The terms "aryloxycarbonyl" means a monovalent radical of the formula ArO—C(O)—, where Ar is aryl.

The terms "alkylcarbonyloxy" or "alkanoyloxy" mean a monovalent radical of the formula AlkC(O)O—, where Alk is alkyl.

The terms "arylcarbonyloxy" or "aroyloxy" mean a monovalent radical of the formula ArC(O)O—, where Ar is aryl.

The terms "alkylcarbonylamino" or "alkanoylamino" mean a monovalent radical of the formula AlkC(O)NH—, where Alk is alkyl. Exemplary alkylcarbonylamino groups include acetamido ($CH_3C(O)NH$—).

The terms "arylcarbonylamino" or "aroylamino" mean a monovalent radical of the formula ArC(O)NH—, wherein Ar is aryl. Exemplary arylcarbonylamino groups include benzoylamino (phenylC(O)NH—).

The terms "alkoxycarbonylamino" and "aryloxycarbonylamino" refer, respectively, to monovalent radicals of the formula AlkOC(O)NH— and ArOC(O)NH—, wherein Alk is alkyl and Ar is aryl.

The terms "alkylcarbamoyloxy" and "arylcarbamoyloxy" refer, respectively, to monovalent radicals of the formula AlkNHC(O)O— and ArNHC(O)O— wherein Alk is alkyl and Ar is aryl.

The terms "alkylsulfonylamino" and "arylsulfonylamino" refer, respectively, to monovalant radicals of the formula $AlkS(O)_2NH$— and $ArS(O)_2NH$—, wherein Alk is alkyl and Ar is aryl.

The terms "alkylaminosulfonyl" and "arylaminosulfonyl" refer, respectively, to monovalent radicals of the formula $AlkNHS(O)_2$— and $ArNHS(O)_2$— wherein Alk is alkyl and Ar is aryl.

The term "carbamoyl" means a monovalent radical of the formula $NH_2C(O)$—.

The term "cycloalkyl" refers to the mono- or polycyclic analogs of an alkyl group, as defined above, including fully saturated and mono- or polyunsaturated groups. Unless otherwise specified, the cycloalkyl ring may be attached at any carbon atom which results in a stable structure and, if substituted, may be substituted at any suitable carbon atom which results in a stable structure. Examples of cycloalkyl groups are saturated cycloalkyl groups containing from three to eight carbon atoms, for example, three to six carbon atoms. Exemplary cycloalkyl groups include cyclopropyl, cyclobutyl, cyclopentyl, cyclohexyl, cycloheptyl, cyclooctyl, cyclononyl, cyclodecyl, norbornane, adamantyl, tetrahydronaphthyl (tetralin), indanyl, 1-decalinyl, bicyclo[2.2.2]octanyl, 1-methylcyclopropyl, 2-methylcyclopentyl, 2-methylcyclooctyl, and the like.

The term "cycloalkyloxy" refers to a monovalent radical of the formula cycloalkyl-O—, i.e., a cycloalkyl group linked to a second group via an oxygen atom.

The term "halo" refers to a halogen radical selected from fluoro, chloro, bromo or iodo. Representative halo groups of the invention are fluoro, chloro and bromo.

The term "aryl" refers to 6–10 membered mono- or polycyclic aromatic carbocycles, for example, phenyl and naphthyl. Unless otherwise specified, the aryl ring may be attached at any carbon atom which results in a stable structure and, if substituted, may be substituted at any suitable carbon atom which results in a stable structure. The term "aryl" includes aryl groups that are optionally partially or fully halogenated.

The term "heterocycle" or "heterocyclyl" refers to a stable 4–8 membered (but preferably, 5 or 6 membered) monocyclic or 8–11 membered bicyclic heterocycle radical which may be either saturated or unsaturated, and is non-aromatic, and may be optionally partially or fully halogenated. Each heterocycle contains carbon atoms and from 1 to 4 heteroatoms independently chosen from nitrogen, oxygen and sulfur, wherein any sulfur heteroatom may optionally be oxidized and any nitrogen heteroatom may optionally be oxidized or quaternized. Unless otherwise specified, the heterocyclyl ring may be attached at any suitable heteroatom or carbon atom which results in a stable structure and, if substituted, may be substituted at any suitable heteroatom or carbon atom which results in a stable structure. Examples of "heterocycle" include radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, tetrahydroquinoline, tetrahydroisoquinoline, azetidinyl, oxetanyl, dihydrobenzofuranyl, dihydrobenzothienyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

The term "heteroaryl" refers to a stable 5–8 membered (but preferably, 5 or 6 membered) monocyclic or 8–11 membered bicyclic aromatic heterocycle radical, each optionally partially or fully halogenated. Each heteroaryl contains carbon atoms and from 1 to 4 heteroatoms independently chosen from nitrogen, oxygen and sulfur, wherein any sulfur heteroatom may optionally be oxidized and any nitrogen heteroatom may optionally be oxidized or quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzothiazolyl, benzoxazolyl, benzisoxazolyl, benzisothiazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl, Each aryl or heteroaryl unless otherwise specified includes its partially or fully hydrogenated derivative. For example, quinolinyl may include decahydroquinolinyl and tetrahydroquinolinyl, naphthyl may include its hydrogenated derivatives such as tetrahydronaphthyl. Other partially or fully hydrogenated derivatives of the aryl and heteroaryl compounds described herein will be apparent to one of ordinary skill in the art.

The terms "heterocyclyl", "heteroaryl" or "aryl", when associated with another moiety, unless otherwise specified shall have the same meaning as given above.

In all alkyl groups or carbon chains where one or more carbon atoms or methylene groups are optionally replaced by heteroatoms: O, S or N, it shall be understood that if N is not indicated as substituted then it is NH. It shall also be understood that the heteroatoms may replace either terminal carbon atoms or internal carbon atoms, or both, within a branched or unbranched carbon chain. Such alkyl groups can also be substituted as described herein by various groups such as oxo to result in definitions such as but not limited to: alkyl, alkylene, alkoxyalkyl, alkoxycarbonylalkyl, alkylthioalkyl, alkylthiosulfonealkyl, alkylthiosulfonylalkyl, aminoalkyl, alkylamino, mono or di-alkylaminoalkyl, mono or di-alkylamidoC1–5 alkyl. For example, a C1–5alkyl group in which one carbon atom is replace by a nitrogen and which is also substituted by an oxo (═O) can result in radicals of the formula: $CH_3$—NH—C(O)—$CH_2CH_2$—, or $CH_3$—C(O)—NH—$CH_2CH_2$—, etc. If such alkyl groups are further substituted, the substituent can replace any hydrogen atom present on any of the carbon or nitrogen atoms in the group.

As used herein above and throughout this application, "nitrogen" and "sulfur" include any oxidized form of nitrogen and sulfur and the quaternized form of any basic nitrogen, including protonated species and quaternary ammonium salt forms.

The term "compounds of the invention", and equivalent expressions, are meant to embrace compounds of Formula (I) as herein described, including the tautomers, the prodrugs, the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a "carbanion" is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 R, then such group is optionally substituted with up to two R groups and R at each occurrence is selected independently from the defined list of possible R. Such combinations of substituents and/or variables, however, are permissible only if such combinations result in stable compounds.

The yield of each of the chemical reactions described herein is expressed as a percentage of the theoretical yield.

B. Salt, Prodrug, Derivative, and Solvate Terms and Conventions

The terms "prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985); *Prodrugs: Topical and Ocular Drug Delivery*, K. B. Sloan (ed.), Marcel Dekker, 1998; *Methods in Enzymology*, K. Widder et al. (eds.), Vol.42, Academic Press, 1985, particularly pp. 309–396; *Burger's Medicinal Chemistry and Drug Discovery*, 5th Ed., M. Wolff (ed.), John Wiley & Sons, 1995, particularly Vol. 1 and pp. 172–178 and pp. 949–982; *Pro-Drugs as Novel Delivery Systems*, T. Higuchi and V. Stella (eds.), Am. Chem. Soc., 1975; *Bioreversible Carriers in Drug Design*, E. B. Roche (ed.), Elsevier, 1987; each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "salt" means an ionic form of the parent compound or the product of the reaction between the parent compound with a suitable acid or base to make the acid salt or base salt of the parent compound. Salts of the compounds of the present invention can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1–19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic s nontoxic bases are isopropylamine, diethylamine, ethanolamine, trimethylamine, dicyclohexylamine, choline, and caffeine.

The term "solvate" means a physical association of a compound with one or more solvent molecules or a complex of variable stoichiometry formed by a solute (for example, a compound of Formula (I)) and a solvent, for example, water, ethanol, or acetic acid. This physical association involves varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, methanolates, and the like.

The term "hydrate" means a solvate wherein the solvent molecule(s) is/are $H_2O$.

The compounds of the present invention as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

C. Isomer Terms and Conventions

The term "isomers" mean compounds having the same number and kind of atoms, and hence the same molecular weight, but differing in respect to the arrangement or configuration of the atoms in space. The term includes stereoisomers, optical isomers and geometric isomers.

The term "optical isomer" means a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the invention which may give rise to optical isomerism, the invention contemplates optical isomers and mixtures thereof. The compounds of the invention and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure optical isomers, i.e., as individual enantiomers or diastereomers, or as stereoisomer-enriched mixtures. Individual stereoisomers of compounds are prepared by synthesis from optically active starting materials containing the desired chiral centers or by preparation of mixtures of enantiomeric products followed by separation, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of optical isomers that are non-superimposable mirror images of each other.

The term "diastereoisomers" means stereoisomers which are not mirror images of each other.

The term "stereoisomers" means compounds having the same molecular formula and functional groups, but differ in the arrangment of the groups in space. The term includes enantiomers and diastereomers.

The term "racemic mixture" or "racemate" means a mixture containing equal parts of individual enantiomers.

The term "non-racemic mixture" means a mixture containing unequal parts of individual enantiomers .

The term "geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C═N double bonds, cyclic structures, and the like may be present in the compounds of the invention, the invention contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, *Advanced Organic Chemistry: Reactions, Mechanisms, and Structure,* 4th ed., John Wiley & Sons, 1992, which is hereby incorporated by reference in its entirety. Several of the following examples represent single E isomers, single Z isomers and mixtures of E/Z isomers. Determination of the E and Z isomers can be done by analytical methods such as x-ray crystallography, $^1H$ NMR, and $^{13}C$ NMR.

Some of the compounds of the invention can exist in more than one tautomeric form. As mentioned above, the compounds of the invention include all such tautomers.

In general, all tautomeric forms and isomeric forms and mixtures, whether individual geometric isomers or optical isomers or racemic or non-racemic mixtures, of a chemical structure or compound is intended, unless the specific stereochemistry or isomeric form is specifically indicated in the compound name or structure.

D. Pharmaceutical Administration and Treatment Terms and Conventions

The term "patient" includes both human and non-human mammals.

The term "effective amount" means an amount of a compound according to the invention which, in the context of which it is administered or used, is sufficient to achieve the desired effect or result.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "cysteine protease mediated disease" means a disease in which cysteine protease activity contributes to the pathology and/or symptomatology of the disease. Likewise, "cathepsin S [or K] mediated disease" means a disease in which cathepsin S [or K] activity contributes to the pathology and/or symptomatology of the disease.

The terms "treating" or "treatment" mean the treatment of a disease-state in a patient, and include:

(i) preventing the disease-state from occurring in a patient, in particular, when such patient is predisposed to the disease-state but has not yet been diagnosed as having it;

(ii) inhibiting or ameliorating the disease-state, i.e., arresting or slowing its development, such as by inhibiting or ameloirating pathalogic symptoms of the disease state; or (iii) relieving the disease-state, i.e., causing regression or cure of the disease-state.

Embodiments of the Invention

In the broadest generic aspect, the invention provides novel compounds of the formula (I):

(I)

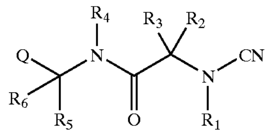

wherein:

$R_1$ is hydrogen, a C1–10 saturated or unsaturated alkyl group wherein one or more C atoms are optionally replaced by O, NH, S(O), $S(O)_2$ or S and wherein said alkyl group is optionally independently substituted with one or more: oxo groups, —$NH_2$, C1–10 alkyl, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, pyrrolyl, pyrazolyl, oxazolyl, isoxazolyl, thiazolyl, imidazolyl pyridinyl, pyrimidinyl, pyrazinyl, indolyl, benzofuranyl, benzothienyl, benzimidazolyl, benzothiazolyl, benzoxazolyl, quinolyl, isoquinolyl, C1–10 alkoxy, aryloxy, C1–10 alkanoyl, aroyl, C1–10 alkoxycarbonyl, aryloxycarbonyl, C1–10 alkanoyloxy, or aroyloxy, or $R_1$ is C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, arylsulfonyl, heteroarylsulfonyl, tetrahydronaphthyl, indenyl, indanyl, tetrahydropyranyl, tetrahydrothiopyranyl, tetrahydrofuranyl, pyrrolidinyl, piperidinyl, morpholinyl, thiomorpholinyl, indolinyl, C3–8cycloalkylsulfonylC1–5alkyl, arylsulfonylC1–5alkyl, aryloxyC1–5alkyl, C1–10alkanoyl, aroyl, C1–10alkoxycarbonyl, arylC1–5alkoxycarbonyl or aryloxycarbonyl, or $R_1$ is carbamoyl wherein the nitrogen atom may be independently mono or di-substituted by C1–10 alkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

each $R_1$ may be further optionally independently substituted by one or more $R_a$;

$R_a$ is a C1–10 saturated or unsaturated alkyl group wherein one or more C atoms are optionally replaced by O, NH, S(O), $S(O)_2$ or S and wherein said alkyl group is optionally independently substituted with one or two oxo groups, or one or more: —$NH_2$, C1–10 alkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_a$ is a C1–10alkoxy, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, C3–8 cycloalkyloxy, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl; C1–10alkanoyl, aroyl, C1–10alkanoyloxy, aryloxy, benzyloxy, C1–10 alkoxycarbonyl, arylC1–3alkoxycarbonyl, aryloxycarbonyl or aroyloxy, or $R_a$ is carbamoyl wherein the nitrogen atom may be independently mono or di-substituted by C1–10 alkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_a$ is ureido wherein either nitrogen atom may be independently substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_a$ is amino wherein the nitrogen atom may be independently mono or di-substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

wherein $R_a$ may be further optionally substituted by one or more $R_b$;

$R_b$ is C3–8 cycloalkyl, tolylsulfonyl, C1–5 alkoxy, aryl, aryloxy, benzyloxy, halogen, hydroxy, oxo, carboxy, cyano, nitro, carboxamide, amidino or guanidino;

or $R_b$ is aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_b$ is amino wherein the nitrogen atom may be independently mono or di-substituted by C1–10 alkyl,C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_b$ is a C1–10 saturated or unsaturated alkyl group wherein one or more C atoms are optionally replaced by O, NH, S(O), $S(O)_2$ or S and wherein said alkyl group is optionally independently substituted with one or two oxo groups, or one or more: $—NH_2$, C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

$R_2$, $R_3$, $R_5$, and $R_6$ independently are hydrogen, or a C1–5 alkyl group;

$R_2$ and $R_3$ together with the carbon to which they are attached, and/or $R_5$ and $R_6$ together with the carbon to which they are attached, each may independently optionally form a nonaromatic 3–6 membered cycloalkyl;

$R_4$ is hydrogen, C2–10alkenyl, C3–8 cycloalkyl, arylC1–10alkyl, aryl or a C1–10 alkyl group wherein one or more of the C atoms are optionally replaced by O, NH, —C(=O)—, S, S(O) or $S(O)_2$; wherein $R_4$ is optionally substituted by one or more $R_e$; or $R_4$ is $R_e$;

$R_e$ is C1–10 alkyl, C3–8 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1]pentanyl, cubanyl, 1,2,3,4-tetrahydronaphthyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl; C1–10 alkoxy, aryloxy, C1–10 alkanoyl, aroyl, C1–10 alkoxycarbonyl, aryloxycarbonyl, C1–10 alkanoyloxy, or aroyloxy;

or $R_a$ is carbamoyl wherein the nitrogen atom may be independently mono or di-substituted by C1–10 alkyl, aryl, indanyl, indenyl, tetrahydronaphthyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_e$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_e$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_e$ is amino, halogen, hydroxy, oxo, carboxy, cyano, amidino or guanidino;

Each $R_a$ may be further optionally substituted by one or more $R_f$;

$R_f$ is C1–5 alkyl, C3–6 cycloalkyl, aryl, arylC1–4-alkyl, C1–5 alkoxy, aryloxy, arylC1–5alkoxy, aroyl, halogen, hydroxy, oxo or cyano;

Q is $R_g$, $C(O)R_g$, $S(O)R_g$ or $S(O)2R_g$;

wherein $R_g$ is C2–10alkenyl, C1–10 alkoxy, aryloxy, C3–8 cycloalkyl, aryl, arylC1–10alkyl, C1–10 alkyl wherein one or more of the C atoms are optionally replaced by O, NH, —C(═O)—, S, S(O) or $S(O)_2$; indenyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, tetrahydronaphthyl, C1–10alkylsulfonylC1–10alkyl, C3–8cycloalkylsulfonylC1–10alkyl, arylsulfonylC1–10alkyl, azetidinyl, pyrrolidinyl, piperidinyl, morpholinyl, thiomorpholinyl, piperazinyl, perhydroazepinyl, perhydrodiazepinyl, indolinyl, isoindolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyrazolyl, pyridinyl, pyrimidinyl, pyrazinyl, pyridazinyl, tetrazolyl, triazolyl, indolyl, benzofuranyl, benzothienyl, dihydrobenzofuranyl, dihydrobenzothienyl, indazolyl, isoindazolyl, benzimidazolyl, benzoxazolyl, benzothiazolyl, benzisoxazolyl, benzisothiazolyl, benzotriazolyl, quinolinyl, tetrahydroquinolinyl, isoquinolinyl, tetrahydroisoquinolinyl, quinazolinyl, tetrahydroquinazolinyl, quinoxalinyl, or amino; wherein $R_g$ is optionally substituted by one or more $R_h$;

$R_h$ is C1–10 alkyl, C3–8 cycloalkyl, aryl, tetrahydronaphthyl, indenyl, indanyl, azetidinyl, pyrrolidinyl, piperidinyl, morpholinyl, thiomorpholinyl, piperazinyl, perhydroazepinyl, perhydrodiazepinyl, indolinyl, isoindolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyrazolyl, pyridinyl, pyrimidinyl, pyrazinyl, pyridazinyl, tetrazolyl, triazolyl, indolyl, benzofuranyl, benzothienyl, dihydrobenzofuranyl, dihydrobenzothienyl, indazolyl, isoindazolyl, benzimidazolyl, benzoxazolyl, benzothiazolyl, benzisoxazolyl, benzisothiazolyl, benzotriazolyl, benzodioxolyl, quinolinyl, tetrahydroquinolinyl, isoquinolinyl, tetrahydroisoquinolinyl, quinazolinyl, tetrahydroquinazolinyl, quinoxalinyl, C1–10 alkoxy, C1–10alkanoyl, C1–10alkanoyloxy, aryloxy, benzyloxy, C1–10 alkoxycarbonyl, aryloxycarbonyl, aroyloxy, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, or cubanyl, or $R_h$ is carbamoyl wherein the nitrogen atom may be independently mono or di-substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, azetidinyl, pyrrolidinyl, piperidinyl, morpholinyl, thiomorpholinyl, piperazinyl, perhydroazepinyl, perhydrodiazepinyl, indolinyl, isoindolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyrazolyl, pyridinyl, pyrimidinyl, pyrazinyl, pyridazinyl, tetrazolyl, triazolyl, indolyl, benzofuranyl, benzothienyl, dihydrobenzofuranyl, dihydrobenzothienyl, indazolyl, isoindazolyl, benzimidazolyl, benzoxazolyl, benzothiazolyl, benzisoxazolyl, benzisothiazolyl, benzotriazolyl, quinolinyl, tetrahydroquinolinyl, isoquinolinyl, tetrahydroisoquinolinyl, quinazolinyl, tetrahydroquinazolinyl, or quinoxalinyl, or $R_h$ is C1–10 alkanoylamino, aroylamino, C1–10 alkylthio, arylthio wherein the sulfur atom may be oxidized to a sulfoxide or sulfone, or $R_h$ is ureido wherein either nitrogen atom may be independently substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, isoindolinyl, azetidinyl, pyrrolidinyl, piperidinyl, morpholinyl, thiomorpholinyl, piperazinyl, perhydroazepinyl, perhydrodiazepinyl, indolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyrazolyl, pyridinyl, pyrimidinyl, pyrazinyl, pyridazinyl, tetrazolyl, triazolyl, indolyl, benzofuranyl, benzothienyl, dihydrobenzofuranyl, dihydrobenzothienyl, indazolyl, isoindazolyl, benzimidazolyl, benzoxazolyl, benzothiazolyl, benzisoxazolyl, benzisothiazolyl, benzotriazolyl, quinolinyl, tetrahydroquinolinyl, isoquinolinyl, tetrahydroisoquinolinyl, quinazolinyl, tetrahydroquinazolinyl, or quinoxalinyl;

or $R_h$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, isoindolinyl, azetidinyl, pyrrolidinyl, piperidinyl, morpholinyl, thiomorpholinyl, piperazinyl, piperazinylcarbonyl, perhydroazepinyl, perhydrodiazepinyl, indolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyrazolyl, pyridinyl, pyrimidinyl, pyrazinyl, pyridazinyl, tetrazolyl, triazolyl, indolyl, benzofuranyl, benzothienyl, dihydrobenzofuranyl, dihydrobenzothienyl, indazolyl, isoindazolyl, benzimidazolyl, benzoxazolyl, benzothiazolyl, benzisoxazolyl, benzisothiazolyl, benzotriazolyl, quinolinyl, tetrahydroquinolinyl, isoquinolinyl, tetrahydroisoquinolinyl, quinazolinyl, tetrahydroquinazolinyl, quinoxalinyl, halogen, hydroxy, oxo, carboxy, cyano, nitro, amidino or guanidino, $R_h$ may be further optionally substituted by one or more $R_i$;

$R_i$ ; is C1–10 alkyl, C3–8 cycloalkyl, aryl, arylC1–10alkyl, heterocyclyl, heterocyclylC1–10alkyl, C1–10 alkoxy, C1–10 alkoxycarbonyl, aryloxy, benzyloxy, halogen, hydroxy, oxo, carboxy, cyano, nitro, amidino or guanidino;

or the pharmaceutically acceptable salts, solvates, tautomers, or prodrugs thereof; with the proviso that when $R_1$ is hydrogen or C1–10alkyl, and $R_2$, $R_3$, $R_5$ and $R_6$ are each independently hydrogen or C1–5alkyl, and $R_4$ is hydrogen or C1–10alkyl, then Q is not C1–10alkyl or C1–10alkoxycarbonyl.

Another embodiment of the invention is directed to the compounds of formula (I) described immediately above, and wherein:

$R_1$ is hydrogen, a C1–7 saturated or unsaturated alkyl group wherein one or more C atoms are optionally replaced by O, NH, S(O), $S(O)_2$ or S and wherein said alkyl group is optionally independently substituted with one or more: oxo groups, C1–4 alkyl, C3–8 cycloalkyl, aryl, pyrrolidinyl, piperidinyl, morpholinyl, thiomorpholinyl, piperazinyl, indolinyl, pyranyl, thiopyranyl, tetrahydropyranyl, tetrahydrothiopyranyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_1$ is C1–7alkoxyC1–7alkyl, C1–7alkylthioC1–7alkyl wherein the sulfur atom may be oxidized to a sulfoxide or sulfone, C3–8 cycloalkyl, aryl, arylsulfonyl, heteroarylsulfonyl, tetrahydronaphthyl, indenyl, indanyl, arylsulfonylC1–5alkyl, aryloxyC1–5alkyl, C1–7alkanoyl, aroyl, tetrahydropyranyl, pyrrolidinyl, piperidinyl, morpholinyl, indolinyl, carbamoyl wherein the nitrogen atom may be independently mono or di-substituted by C1–7 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzothiazolyl, quinolyl or isoquinolyl;

each $R_1$ may be further optionally independently substituted by one or more $R_a$;

$R_a$ is a C1–7 saturated or unsaturated alkyl group wherein one or more C atoms are optionally replaced by O, S(O), $S(O)_2$ or S and wherein said alkyl group is optionally independently substituted with one or two oxo groups, or one or more: —$NH_2$, $C_{1-4}$ alkyl, aryl, pyrrolidinyl, piperidinyl, morpholinyl, thiomorpholinyl, piperazinyl, indolinyl, pyranyl, thiopyranyl, tetrahydropyranyl, tetrahydrothiopyranyl, furanyl, thienyl, pyrrolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_a$ is a C1–7alkoxy, C1–7alkoxyC1–7alkyl, C1–7alkylthioC1–7alkyl wherein the sulfur atom may be oxidized to a sulfoxide or sulfone, C3–8 cycloalkyl, C3–8 cycloalkyloxy, aryl, tetrahydronaphthyl, indenyl, indanyl, pyrrolidinyl, piperidinyl, morpholinyl, thiomorpholinyl, piperazinyl, tetrahydropyranyl, tetrahydrothiopyranyl, furanyl, thienyl, pyrrolyl, pyridinyl, pyrimidinyl, pyrazinyl, indolyl, benzofuranyl, benzothienyl, benzimidazolyl, benzothiazolyl, benzoxazolyl, quinolyl, isoquinolyl, C1–7alkanoyl, aroyl, C1–7alkanoyloxy, aryloxy, benzyloxy, C1–7 alkoxycarbonyl, arylC1–3alkoxycarbonyl, aryloxycarbonyl, aroyloxy, carbamoyl wherein the nitrogen atom may be independently mono or di-substituted by C1–7 alkyl, aryl, pyrrolidinyl, piperidinyl, morpholinyl, thiomorpholinyl, piperazinyl, indolinyl, furanyl, thienyl, pyrrolyl, pyridinyl, pyrimidinyl, pyrazinyl, indolyl, benzofuranyl, benzothienyl, benzimidazolyl, benzothiazolyl, quinolyl or isoquinolyl;

or $R_a$ is ureido wherein either nitrogen atom may be independently substituted by C1–7 alkyl, aryl, pyrrolidinyl, piperidinyl, morpholinyl, thiomorpholinyl, piperazinyl, tetrahydropyranyl, indolinyl, furanyl, thienyl, pyrrolyl, pyridinyl, pyrimidinyl, pyrazinyl, indolyl, benzofuranyl, benzothienyl, benzimidazolyl, benzothiazolyl, quinolyl or isoquinolyl, or $R_a$ is amino wherein the nitrogen atom may be independently mono or di-substituted by C1–7 alkyl, aryl, pyrrolidinyl, piperidinyl, morpholinyl, thiomorpholinyl, piperazinyl, tetrahydropyranyl, indolinyl, furanyl, thienyl, pyrrolyl, pyridinyl, pyrimidinyl, pyrazinyl, indolyl, benzofuranyl, benzothienyl, benzimidazolyl, benzothiazolyl, benzoxazolyl, quinolyl or isoquinolyl, wherein $R_a$ may be further optionally substituted by one or more $R_b$;

$R_b$ is C3–6 cycloalkyl, C1–5 alkoxy, aryl, aryloxy, benzyloxy, halogen, hydroxy, oxo, carboxy, cyano, nitro, carboxamide, amidino or guanidino;

or $R_b$ is aryl, pyrrolidinyl, piperidinyl, morpholinyl, thiomorpholinyl, piperazinyl, tetrahydropyranyl, indolinyl, furanyl, thienyl, pyrrolyl, pyridinyl, pyrimidinyl, pyrazinyl, indolyl, benzofuranyl, benzothienyl, benzimidazolyl, benzothiazolyl, quinolyl or isoquinolyl;

or $R_b$ is amino wherein the nitrogen atom may be independently mono or di-substituted by C1–7 alkyl, aryl, pyrrolidinyl, piperidinyl, morpholinyl, thiomorpholinyl, piperazinyl, tetrahydropyranyl, indolinyl, furanyl, thienyl, pyrrolyl, pyridinyl, pyrimidinyl, pyrazinyl, indolyl, benzofuranyl, benzothienyl, benzimidazolyl, benzothiazolyl, quinolyl or isoquinolyl;

or $R_b$ is a C1–7 saturated or unsaturated alkyl group wherein one or more C atoms are optionally replaced by O, S(O), $S(O)_2$ or S and wherein said alkyl group is optionally independently substituted with one or two oxo groups, or one or more: —$NH_2$, $C_{1-4}$ alkyl, aryl, pyrrolidinyl, piperidinyl, morpholinyl, thiomorpholinyl, piperazinyl, tetrahydropyranyl, indolinyl, furanyl, thienyl, pyrrolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

$R_2$, $R_3$, $R_5$, and $R_6$ independently are hydrogen or a C1–5 alkyl group;

$R_2$ and $R_3$ together with the carbon to which they are attached, and/or $R_5$ and $R_6$ together with the carbon to which they are attached, each may independently optionally form a nonaromatic 3–6 membered cycloalkyl;

$R_4$ is hydrogen, C2–5alkenyl, C3–7 cycloalkyl, arylC1–3alkyl, aryl or a C1–6 alkyl group wherein one or two of the C atoms are optionally replaced by O, —C(═O)—, S, S(O) or $S(O)_2$; wherein $R_4$ is optionally substituted by one or more $R_e$; or $R_4$ is $R_e$;

$R_e$ is C1–5 alkyl, C3–7 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, pyrrolidinyl, piperidinyl, morpholinyl, thiomorpholinyl, piperazinyl, indolinyl, furanyl, tetrahydropyranyl, thienyl, pyrrolyl, oxazolyl, thiazolyl, pyrazolyl, pyridinyl, pyrimidinyl, pyrazinyl, indolyl, benzofuranyl, benzothienyl, benzimidazolyl, benzothiazolyl, quinolinyl, or isoquinolinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl or isoquinolinyl, or $R_e$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, or isoquinolinyl, or $R_e$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl or isoquinolinyl, or $R_e$ is halogen, hydroxy, oxo, carboxy, cyano, amidino or guanidino;

Each $R_e$ may be further optionally substituted by one or more $R_f$, $R_f$ is C1–5 alkyl, C3–6 cycloalkyl, aryl, arylC1–4-alkyl, C1–5 alkoxy, aryloxy, arylC1–5alkoxy, aroyl, halogen, hydroxy, oxo or cyano;

Q is $R_g$, $C(O)R_g$, $S(O)R_g$ or $S(O)_2R_g$;

wherein $R_g$ is C1–5 alkyl wherein one or more C atoms are optionally replaced by O or NH, C1–5 alkoxy, aryloxy, C3–7 cycloalkyl, phenyl, benzyl, naphthyl, tetrahydronaphthyl, C1–5alkylsulfonylC1–5alkyl, C3–7cycloalkylsulfonylC1–5alkyl, arylsulfonylC1–5alkyl, pyrrolidinyl, piperidinyl, morpholinyl, thiomorpholinyl, piperazinyl, indolinyl, isoindolinyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, tetrahydroisoquinolyl, quinoxalinyl or benzoxazolyl, or amino; wherein $R_g$ is optionally substituted by one or more $R_h$;

$R_h$ is C1–5 alkyl, C3–7 cycloalkyl, phenyl, naphthyl, indenyl, indanyl, pyrrolidinyl, piperidinyl, morpholinyl, thiomorpholinyl, piperazinyl, indolinyl, isoindolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, benzoxazolyl, benzisoxazolyl, benzodioxolyl, quinolinyl, isoquinolinyl or tetrahydroisoquinolyl, C1–5 alkoxy, C1–5alkanoyl, C1–5alkanoyloxy, aryloxy, benzyloxy, C1–5 alkoxycarbonyl, aryloxycarbonyl, aroyloxy, carbamoyl wherein the nitrogen atom may be independently mono or di-substituted by C1–6 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl or isoquinolinyl, or $R_h$ is C1–5 alkanoylamino, aroylamino, C1–5 alkylthio, arylthio wherein the sulfur atom may be oxidized to a sulfoxide or sulfone, or $R_h$ is ureido wherein either nitrogen atom may be independently substituted by alkyl, aryl, pyrrolidinyl, piperidinyl, morpholinyl, thiomorpholinyl, piperazinyl, indolinyl, isoindolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, or isoquinolinyl, or $R_h$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, pyrrolidinyl, piperidinyl, morpholinyl, thiomorpholinyl, piperazinyl, piperazinylcarbonyl, indolinyl, isoindolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl or isoquinolinyl, halogen, hydroxy, oxo, carboxy, cyano, nitro, amidino or guanidino, $R_h$ may be further optionally substituted by one or more $R_i$;

$R_i$ is C1–5 alkyl, C3–6 cycloalkyl, aryl, arylC1–5alkyl, pyrrolidinyl, piperidinyl, piperazinyl, morpholinyl, thiomorpholinyl, C1–5 alkoxy, C1–5 alkoxycarbonyl, aryloxy, benzyloxy, halogen, hydroxy, oxo, carboxy, cyano, nitro, amidino or guanidino;

wherein one or more of the amino nitrogens in the amidino or guanidino groups in the compound of formula I may be optionally substituted with $C_{1-3}$alkyl, phenyl$C_{0-3}$alkyl or $C_{1-3}$alkoxy;

or the pharmaceutically acceptable salts, solvates, tautomers or prodrugs thereof.

A further embodiment of the invention is directed to the compounds of formula (I) described immediately above, wherein:

$R_1$ is hydrogen, a C1–6 saturated or unsaturated alkyl group wherein one or more C atoms are optionally replaced by O, NH, S, S(O) or $S(O)_2$ and wherein said alkyl group is optionally independently substituted with one or more: oxo groups, C1–4 alkyl, C3–6 cycloalkyl, aryl, pyrrolidinyl, piperidinyl, morpholinyl, thiomorpholinyl, piperazinyl, indolinyl, pyranyl, thiopyranyl, tetrahydropyranyl, tetrahydrothiopyranyl, pyridinyl, pyrimidinyl, pyrazinyl or indolyl;

or $R_1$ is C1–6alkoxyC1–6alkyl, C1–6alkylthioC1–6alkyl wherein the sulfur atom may be oxidized to a sulfoxide or sulfone, C3–6 cycloalkyl, aryl, arylsulfonyl, arylsulfonylC1–6alkyl, heteroarylsulfonyl, aryloxyC1–6alkyl, C1–6alkanoyl, aroyl, pyrrolidinyl, piperidinyl, morpholinyl, carbamoyl wherein the nitrogen atom may be independently mono or di-substituted by C1–6 alkyl, or aryl;

each $R_1$ may be further optionally independently substituted by one or more $R_a$;

$R_a$ is a C1–6 saturated or unsaturated alkyl group wherein one or more C atoms are optionally replaced by O, S, S(O) or $S(O)_2$ and wherein said alkyl group is optionally independently substituted with one or two oxo groups, or one or more —$NH_2$, $C_{1-4}$ alkyl, or aryl;

or $R_a$ is a C1–6alkoxy, C1–6alkoxyC1–6alkyl, C1–6alkylthioC1–6alkyl, C3–6 cycloalkyl, C3–6 cycloalkyloxy, aryl, pyrrolidinyl, piperidinyl, morpholinyl, thiomorpholinyl, piperazinyl, tetrahydropyranyl, pyridinyl, indolyl, C1–6alkanoyl, aroyl, C1–6alkanoyloxy, aryloxy, benzyloxy, C1–6alkoxycarbonyl, arylC1–3alkoxycarbonyl, aryloxycarbonyl, aroyloxy, carbamoyl wherein the nitrogen atom may be independently mono or di-substituted by C1–6 alkyl, or aryl;

or $R_a$ is ureido wherein either nitrogen atom may be independently substituted by C1–6 alkyl or aryl, or $R_a$ is amino wherein the nitrogen atom may be independently mono or di-substituted by C1–6 alkyl, or aryl, wherein $R_a$ may be further optionally substituted by one or more $R_b$;

$R_b$ is C3–6 cycloalkyl, C1–5 alkoxy, aryl, aryloxy, benzyloxy, halogen, hydroxy, oxo, carboxy, cyano, nitro or carboxamide;

or $R_b$ is amino wherein the nitrogen atom may be independently mono or di-substituted by C1–6 alkyl or aryl;

or $R_b$ is a C1–6 saturated or unsaturated alkyl group wherein one or two C atoms are optionally replaced by O or S and wherein said alkyl group is optionally independently substituted with one or two oxo groups, or one or more: —$NH_2$, $C_{1-4}$ alkyl, or aryl;

$R_2$, $R_3$, $R_5$, and $R_6$ independently are hydrogen or a C1–4 alkyl group;

$R_2$ and $R_3$ together with the carbon to which they are attached, and/or $R_5$ and $R_6$ together with the carbon to which they are attached, each may independently optionally form a nonaromatic 3–6 membered cycloalkyl;

$R_4$ is hydrogen, C2–5alkenyl, C3–6 cycloalkyl, arylC1–3alkyl, aryl or a C1–6 alkyl group wherein one or two of the C atoms are optionally replaced by O, S or $S(O)_2$; wherein $R_4$ is optionally substituted by one or more $R_e$; or $R_4$ is $R_e$;

$R_e$ is C1–5 alkyl, C3–6 cycloalkyl, aryl, indanyl, indenyl, pyridinyl, indolyl, bicyclo[2.2.1]heptanyl, bicyclo[2.2.2]octanyl, bicyclo[4.1.0]heptanyl, bicyclo[3.1.0]hexanyl, bicyclo[1.1.1.]pentanyl, cubanyl, 1,2,3,4-tetrahydronaphthyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl or aryl, or $R_e$ is C1–5 alkanoylamino, aroylamino, C1–5 alkylthio, arylthio wherein the sulfur atom may be oxidized to a sulfoxide or sulfone, ureido wherein either nitrogen atom may be independently substituted by C1–5 alkyl or aryl, or $R_e$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl or aryl, or $R_e$ is halogen, hydroxy, oxo, carboxy, cyano, amidino or guanidino;

Each $R_e$ may be further optionally substituted by one or more $R_f$;

$R_f$ is C1–5 alkyl, C3–6 cycloalkyl, aryl, arylC1–4-alkyl, C1–5 alkoxy, aryloxy, arylC1–5alkoxy, aroyl, halogen, hydroxy, oxo or cyano;

Q is $R_g$, $C(O)R_g$, $S(O)R_g$ or $S(O)_2R_g$;

wherein $R_g$ is C1–5 alkyl wherein one or more C atoms are optionally replaced by O or NH, C1–5 alkoxy, aryloxy, C3–6 cycloalkyl, phenyl, benzyl, naphthyl, tetrahydronaphthyl, C1–5alkylsulfonylC1–5alkyl, C3–6cycloalkylsulfonylC1–5alkyl, arylsulfonylC1–5alkyl, pyrrolidinyl, piperidinyl, morpholinyl, thiomorpholinyl, piperazinyl, isoindolinyl, furanyl, thienyl, oxazolyl, isoxazolyl, thiazolyl, pyridinyl, indolyl, benzofuranyl, benzothienyl, quinolinyl, isoquinolinyl, tetrahydroisoquinolyl, pyrazinyl or quinoxalinyl, or amino; wherein $R_g$ is optionally substituted by one or more $R_h$;

$R_h$ is C1–5 alkyl, C3–6 cycloalkyl, phenyl, naphthyl, indenyl, indanyl, pyrrolidinyl, piperidinyl, morpholinyl, thiomorpholinyl, piperazinyl, pyridinyl, isoindolinyl, quinolinyl, isoquinolinyl, tetrahydroisoquinolyl or benzodioxolyl, C1–5 alkoxy, C1–5alkanoyl, C1–5alkanoyloxy, aryloxy, benzyloxy, C1–5 alkoxycarbonyl, aryloxycarbonyl, aroyloxy, carbamoyl wherein the nitrogen atom may be independently mono or di-substituted by C1–6 alkyl or aryl, or $R_h$ is C1–5 alkanoylamino, aroylamino, C1–5 alkylthio, arylthio wherein the sulfur atom may be oxidized to a sulfoxide or sulfone, or $R_h$ is ureido wherein either nitrogen atom may be independently substituted by alkyl or aryl, or $R_h$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, piperidinyl, morpholinyl, thiomorpholinyl, piperazinyl or piperazinylcarbonyl, halogen, hydroxy, oxo, carboxy, cyano, nitro, amidino or guanidino, $R_h$ may be further optionally substituted by one or more $R_i$;

$R_i$ is C1–5 alkyl, C3–6 cycloalkyl, aryl, arylC1–5alkyl, piperidinyl, piperazinyl, morpholinyl, thiomorpholinyl, C1–5 alkoxy, C1–5 alkoxycarbonyl, aryloxy, benzyloxy, halogen, hydroxy, oxo, carboxy, cyano, nitro, amidino or guanidino;

wherein one or more of the amino nitrogens in the amidino or guanidino groups in the compound of formula I may be optionally substituted with $C_{1-3}$alkyl, phenyl$C_{0-3}$alkyl or $C_{1-3}$alkoxy;

or the pharmaceutically acceptable salts, solvates, tautomers or prodrugs thereof.

A further embodiment of the invention is directed to the compound of formula (I) described immediately above, wherein:

$R_1$ is hydrogen, a C1–6 saturated or unsaturated alkyl group wherein one or two C atoms are optionally replaced by O, NH, S, S(O) or $S(O)_2$, and wherein said alkyl group is optionally independently substituted with one to three: oxo groups, C1–4 alkyl, C3–6 cycloalkyl, aryl, pyrrolidinyl, piperidinyl, piperazinyl, morpholinyl, indolinyl, pyranyl, thiopyranyl, tetrahydropyranyl, tetrahydrothiopyranyl, pyridinyl or indolyl;

or $R_1$ is C1–6alkylthioC1–6alkyl wherein the sulfur atom may be oxidized to a sulfoxide or sulfone, C3–6 cycloalkyl, phenyl, naphthyl, phenylsulfonyl, pyridinylsulfonyl, phenyloxyC1–6alkyl, C1–6alkanoyl, or piperidinyl;

each $R_1$ may be further optionally independently substituted by one or more $R_a$;

$R_a$ is a C1–6 saturated or unsaturated alkyl group wherein one or two C atoms are optionally replaced by O or S;

or $R_a$ is a C1–6alkoxy, C3–6 cycloalkyl, phenyl, naphthyl, pyrrolidinyl, piperidinyl, morpholinyl, thiomorpholinyl, tetrahydropyranyl, piperazinyl, indolyl, or pyridinyl;

wherein $R_a$ may be further optionally substituted by one or more $R_b$;

$R_b$ is C3–6 cycloalkyl, C1–5 alkoxy, halogen, hydroxy, oxo, carboxy, cyano, nitro or carboxamide;

or $R_b$ is phenyl, benzyl or naphthyl;

or $R_b$ is amino wherein the nitrogen atom may be independently mono or di-substituted by C1–6 alkyl, phenyl or naphthyl;

or $R_b$ is a C1–6 saturated or unsaturated alkyl group wherein one or two C atoms are optionally replaced by O or S, and wherein said alkyl group is optionally independently substituted with one or two oxo group;

$R_2$, $R_3$, $R_5$ and R6 independently are hydrogen or a C1–5 alkyl group;

$R_2$ and $R_3$ together with the carbon to which they are attached, and/or $R_5$ and $R_6$ together with the carbon to which they are attached, each may independently optionally form a nonaromatic 3–6 membered cycloalkyl;

$R_4$ is hydrogen, C3–6 cycloalkyl, phenylC1–3alkyl, naphthylC1–3alkyl, phenyl, naphthyl, pyridyl or a C1–6 alkyl group wherein one or two of the C atoms are optionally replaced by O, S or $S(O)_2$; wherein $R_4$ is optionally substituted by one or more $R_e$;

$R_e$ is C1–5 alkyl, C3–6 cycloalkyl, phenyl, naphthyl, indanyl or indolyl, or $R_e$ is halogen, hydroxy, oxo, carboxy, cyano, amidino or guanidino;

Each $R_e$ may be further optionally substituted by one or more $R_f$;

$R_f$ is C1–5 alkyl, C3–6 cycloalkyl, C1–5 alkoxy, halogen, hydroxy, oxo or cyano;

Q is $R_g$, $C(O)R_g$ or $S(O)_2R_g$;

wherein $R_g$ is C1–5 alkyl wherein one or more C atoms are optionally replaced by O or NH, C1–5 alkoxy, phenyl, benzyl, naphthyl, pyrrolidinyl, piperidinyl, morpholinyl, thiomorpholinyl, piperazinyl, furanyl, thienyl, oxazolyl, thiazolyl, pyridinyl, benzofuranyl, benzothienyl, quinolinyl, isoquinolinyl, isoindolinyl, tetrahydroisoquinolyl, pyrazinyl, quinoxalinyl or amino; wherein $R_g$ is optionally substituted by one or more $R_h$;

$R_h$ is C1–5 alkyl, C3–6 cycloalkyl, phenyl, naphthyl, indenyl, indanyl, morpholinyl, thiomorpholinyl, pyridinyl, isoindolinyl, isoquinolinyl, tetrahydroisoquinolinyl or benzodioxolyl, or C1–5alkoxy, or $R_h$ is C1–5 alkylthio, or $R_h$ is amino wherein the nitrogen atom may be independently mono or di-substituted by alkyl, phenyl, naphthyl, piperidinyl, morpholinyl, thiomorpholinyl, piperazinyl or piperazinylcarbonyl, halogen, hydroxy, oxo, carboxy, cyano, nitro, amidino or guanidino, $R_h$ may be further optionally substituted by one or more $R_i$;

$R_i$ is C1–5 alkyl, C3–6 cycloalkyl, aryl, arylC1–5alkyl, morpholinyl, thiomorpholinyl, C1–5 alkoxy, C1–5 alkoxycarbonyl, halogen, hydroxy, oxo, carboxy, cyano, nitro, amidino or guanidino;

wherein one or more of the amino nitrogens in the amidino or guanidino groups in the compound of formula I may be optionally substituted with $C_{1-3}$alkyl, phenyl$C_{0-3}$alkyl or $C_{1-3}$alkoxy;

or the pharmaceutically acceptable salts, solvates, tautomers or prodrugs thereof.

An even further embodiment of the invention is directed to the compounds of formula (I) described immediately above, wherein:

$R_1$ is hydrogen, a C1–6 saturated alkyl group wherein one C atom is optionally replaced by O, S, S(O), $S(O)_2$ or NH and wherein said alkyl group is optionally independently substituted with one or two: oxo groups, phenyl, naphthyl, cyclohexyl, pyrrolidinyl, piperidinyl, piperazinyl, morpholinyl, indolinyl, tetrahyropyranyl, pyridinyl or indolyl;

or $R_1$ is C1–3alkylthioC1–3alkyl wherein the sulfur atom may be oxidized to a sulfoxide, cyclohexyl, phenyl, phenylsulfonyl, pyridinylsulfonyl, phenyloxyC1–4alkyl, C1–6alkanoyl or piperidinyl;

each $R_1$ may be further optionally independently substituted by one or two $R_a$;

$R_a$ is a C1–6 saturated alkyl group;

or $R_a$ is a C1–6alkoxy, cyclohexyl, phenyl, naphthyl, pyrrolidinyl, piperidinyl, indolyl, piperazinyl, pyridinyl or tetrahydropyranyl;

wherein $R_a$ may be further optionally substituted by one or two $R_b$;

$R_b$ is C3–6 cycloalkyl, phenyl, benzyl, C1–5 alkoxy, halogen, hydroxy, oxo, carboxy, cyano, nitro or carboxamide;

or $R_b$ is a C1–6 saturated or unsaturated alkyl group, or is a C1–4alkoxycarbonyl group;

$R_2$, $R_3$, $R_5$, and $R_6$ independently are hydrogen or a C1–5 alkyl group;

$R_2$ and $R_3$ together with the carbon to which they are attached, and/or $R_5$ and $R_6$ together with the carbon to which they are attached, each may independently optionally form a cyclopropyl, cyclobutyl, cyclopentyl or cyclohexyl group;

$R_4$ is hydrogen, cyclopropyl, cyclobutyl, cyclopentyl, cyclohexyl, phenylC1–3alkyl, naphthylC1–3alkyl, phenyl, naphthyl, pyridinyl or a C1–6 alkyl group where a C atom is optionally replaced by $S(O)_2$; wherein $R_4$ is optionally substituted by one or more $R_e$;

$R_e$ is C1–3 alkyl, cyclopropyl, cyclobutyl, cyclopentyl, cyclohexyl, phenyl, naphthyl, indanyl or indolyl, or $R_e$ is hydroxy, halogen, oxo, carboxy or cyano;

Q is $R_g$, $C(O)R_g$ or $S(O)_2R_g$;

wherein $R_g$ is C1–5alkyl wherein one or more C atoms are optionally replaced by O or NH, phenyl, naphthyl, pyrrolidinyl, piperidinyl, morpholinyl, thiomorpholinyl, piperazinyl, furanyl, thienyl, thiazolyl, benzofuranyl, benzothienyl, quinolyl, isoquinolyl, isoindolinyl, tetrahydroisoquinolyl, pyrazinyl or quinoxalinyl, or amino; wherein $R_g$ is optionally substituted by one or more $R_h$;

$R_h$ is C1–5 alkyl, C1–5alkoxy, halogen, phenyl, naphthyl, indenyl, indanyl, morpholinyl, thiomorpholinyl, pyridinyl, isoquinolinyl, isoindolinyl, tetrahydroisoquinolyl benzodioxolyl, piperidinylamino or piperazinylcarbonylamino;

$R_h$ may be further optionally substituted by one or more $R_i$;

$R_i$; is C1–3 alkyl, C3–6 cycloalkyl, phenyl, naphthyl, benzyl, morpholinyl, C1–5 alkoxy, C1–5 alkoxycarbonyl, halogen, hydroxy, oxo, carboxy, cyano or nitro;

or the pharmaceutically acceptable salts, solvates, tautomers or prodrugs thereof.

In yet a further embodiment, the present invention is directed to the compounds of formula (I) described immediately above, wherein:

$R_1$ is hydrogen, C1–6alkyl, C1–6alkanoyl, phenylsulfonyl or pyridylsulfonyl each optionally substituted by cyclohexyl, phenyl, pyrrolidinyl, piperidinyl, indolyl, piperazinyl, pyridinyl, tetrahydropyranyl or naphthyl, or $R_1$ is benzyloxylC1–3alkyl or benzyloxyC1–3alkanoyl;

$R_2$, $R_3$, $R_5$, and $R_6$ independently are hydrogen or C1–3 alkyl;

$R_2$ and $R_3$ together with the carbon to which they are attached, and/or $R_5$ and $R_6$ together with the carbon to which they are attached, each may independently optionally form a cyclopropyl, cyclobutyl, cyclopentyl or cyclohexyl group;

$R_4$ is hydrogen, a C1–6 alkyl group, phenylC1–6alkyl, cyclopropylC1–6alkyl, cyclohexylC1–6alkyl or pyridinyl;

Q is $C(O)R_g$;

wherein $R_g$ is piperidinyl, morpholinyl, thiomorpholinyl, piperazinyl, isoindolinyl, benzofuranyl, tetrahydroisoquinolyl, phenylC1–5alkylamino or naphthylC1–5alkylamino, each optionally substituted by C1–5alkyl, morpholinyl or morpholinylC1–5alkoxy;

or the pharmaceutically acceptable salts, solvates, tautomers or prodrugs thereof.

In yet a further embodiment, the present invention is directed to the compounds of formula (I) described immediately above, wherein:

$R_1$ is C1–6alkanoyl optionally substituted by cyclohexyl or phenyl;

$R_2$, $R_3$, $R_5$, and $R_6$ are hydrogen;

$R_4$ is a C1–6 saturated alkyl group;

Q is $C(O)R_g$;

wherein $R_g$ is morpholinyl, tetrahydroisoquinolyl or phenylC1–3alkylamino;

or the pharmaceutically acceptable salts, solvates, tautomers or prodrugs thereof.

Additional embodiments of the present invention are described below with respect to the individual variables in the compounds of formula (I):

Variable $R_1$

The compounds of formula (I) wherein:

$R_1$ is hydrogen, a C1–6 saturated alkyl group wherein one C atom is optionally replaced by O, S, S(O), $S(O)_2$ or NH and wherein said alkyl group is optionally independently substituted with one or two: oxo groups, phenyl, naphthyl, cyclohexyl, pyrrolidinyl, piperidinyl, piperazinyl, morpholinyl, indolinyl, tetrahydropyranyl, pyridinyl or indolyl;

or $R_1$ is C1–3alkylthioC1–3alkyl wherein the sulfur atom may be oxidized to a sulfoxide, cyclohexyl, phenyl, phenylsulfonyl, pyridinylsulfonyl, phenyloxyC1–4alkyl, C1–6alkanoyl, or piperidinyl;

each $R_1$ may be further optionally independently substituted by one or two $R_a$;

$R_a$, is a C1–6 saturated alkyl group;

or $R_a$ is a C1–6alkoxy, cyclohexyl, phenyl, naphthyl, pyrrolidinyl, piperidinyl, piperazinyl or pyridinyl;

wherein $R_a$ may be further optionally substituted by one or two $R_b$;

$R_b$ is C3–6 cycloalkyl, phenyl, benzyl, C1–5 alkoxy, halogen, hydroxy, oxo, carboxy, cyano, nitro or carboxamide;

or $R_b$ is a C1–6 saturated or unsaturated alkyl group, or is a C1–4alkoxycarbonyl group;

or the pharmaceutically acceptable salts, solvates, tautomers or prodrugs thereof.

In yet another embodiment, the compounds of formula (I) wherein:

$R_1$ is hydrogen, C1–6alkyl or C1–6alkanoyl, each optionally substituted by cyclohexyl, phenyl, or naphthyl, or $R_1$ is benzyloxylC1–3alkyl or benzyloxyC1–3alkanoyl;

or the pharmaceutically acceptable salts, solvates, tautomers or prodrugs thereof.

Variables $R_2$, $R_3$, $R_5$ and $R_6$

The compounds of formula (I) wherein:

$R_2$, $R_3$, $R_5$, and $R_6$ independently are hydrogen or a C1–5 alkyl group;

$R_2$ and $R_3$ together with the carbon to which they are attached, and/or $R_5$ and $R_6$ together with the carbon to which they are attached, each may independently optionally form a cyclopropyl, cyclobutyl, cyclopentyl or cyclohexyl group;

or the pharmaceutically acceptable salts, solvates, tautomers or prodrugs thereof.

In another embodiment, the compounds of formula (I) wherein:

$R_2$, $R_3$, $R_5$, and $R_6$ independently are hydrogen or C1–3 alkyl;

$R_2$ and $R_3$ together with the carbon to which they are attached, and/or $R_5$ and $R_6$ together with the carbon to which they are attached, each may independently optionally form a cyclopropyl, cyclopentyl or cyclohexyl group;

or the pharmaceutically acceptable salts, solvates, tautomers or prodrugs thereof.

Variable $R_4$

The compounds of formula (I) wherein:

$R_4$ is hydrogen, cyclopropyl, cyclopentyl, cyclohexyl, phenylC1–3alkyl, naphthylC1–3alkyl, phenyl, naphthyl, pyridinyl or a C1–6 alkyl group where a C atom is optionally replaced by $S(O)_2$; wherein $R_4$ is optionally substituted by one or more $R_e$;

$R_e$ is C1–3 alkyl, cyclopropyl, cyclobutyl, cyclopentyl, cyclohexyl, phenyl, naphthyl, indanyl or indolyl, or $R_e$ is hydroxy, halogen, oxo, carboxy or cyano;

or the pharmaceutically acceptable salts, solvates, tautomers or prodrugs thereof.

In another embodiment, the compounds of formula (I) wherein:

$R_4$ is hydrogen, a C1–6 alkyl group, phenylC1–6alkyl, cyclopropylC1–6alkyl, cyclohexylC1–6alkyl or pyridinyl;

or the pharmaceutically acceptable salts, solvates, tautomers or prodrugs thereof.

Variable Q

The compounds of formula (I) wherein:

Q is $R_g$, $C(O)R_g$ or $S(O)_2R_g$;

wherein $R_g$ is C1–5alkyl wherein one or more C atoms are optionally replaced by O or NH, phenyl, naphthyl, pyrrolidinyl, piperidinyl, morpholinyl, thiomorpholinyl, piperazinyl, furanyl, thienyl, thiazolyl, benzofuranyl, benzothienyl, quinolyl, isoquinolyl, isoindolinyl, tetrahydroisoquinolyl, pyrazinyl or quinoxalinyl, or amino; wherein $R_g$ is optionally substituted by one or more $R_h$;

$R_h$ is C1–5 alkyl, C1–5alkoxy, halogen, phenyl, naphthyl, indenyl, indanyl, morpholinyl, thiomorpholinyl, pyridinyl, isoquinolinyl, isoindolinyl, tetrahydroisoquinolyl, benzodioxolyl, piperidinylamino or piperazinylcarbonylamino;

$R_h$ may be further optionally substituted by one or more $R_i$;

$R_i$ is C1–3 alkyl, C3–6 cycloalkyl, phenyl, naphthyl, benzyl, morpholinyl, C1–5 alkoxy, C1–5 alkoxycarbonyl, halogen, hydroxy, oxo, carboxy, cyano or nitro;

or the pharmaceutically acceptable salts, solvates, tautomers or prodrugs thereof.

In another embodiment, the compounds of formula (I) wherein:

Q is $C(O)R_g$;

wherein $R_g$ is piperidinyl, morpholinyl, thiomorpholinyl, piperazinyl, isoindolinyl, benzofuranyl, tetrahydroisoquinolyl, phenylC-1–5alkylamino or naphthylC1–5alkylamino, each optionally substituted by C1–5alkyl, morpholinyl or morpholinylC1–5alkoxy;

or the pharmaceutically acceptable salts, solvates, tautomers or prodrugs thereof.

In another embodiment, the present invention is directed to compounds of subgeneric Formula (Ia) as set forth below, wherein Q, $R_4$ and $R_1$ are defined as the A, B and C groups, respectively, in Table I below. Any and all combinations of the A, B, and C groups in Table I within the structural limitations of Formula (Ia), comprise compounds of the invention. That is, Q is independently selected from groups A1 to A34; $R_4$ is independently selected from groups B1 to B26; and $R_1$ is independently selected from groups C1 to C41, from within Table I. For example, the compound:

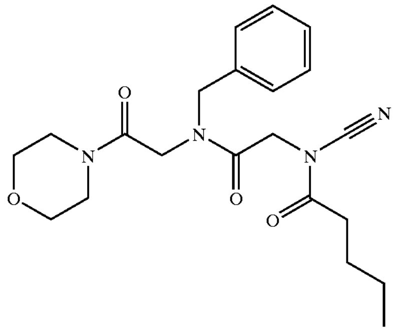

would represent the combination of A6, B17 and C2.

The compound of formula (Ia):

(Ia)

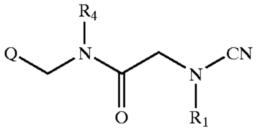

wherein Q is independently selected from groups A1 to A34; $R_4$ is independently selected from groups B1 to B26; and $R_1$ is independently selected from groups C1 to C41; wherein groups A1 to A34, B1 to B26 and C1 to C41 are as defined in the following Table I:

TABLE I

| A | Q | B | $R_4$ | C | $R_1$ |
|---|---|---|---|---|---|
| A1 | 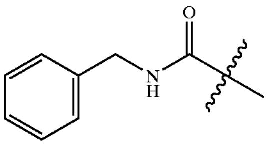 | B1 | —H | C1 | —H |
| A2 | 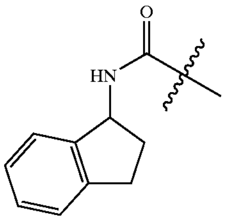 | B2 | $—CH_3$ | C2 | 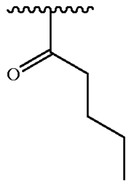 |
| A3 | 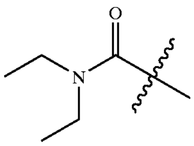 | B3 | 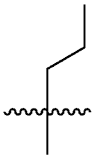 | C3 | 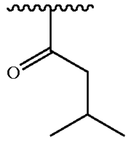 |

TABLE I-continued
| A | Q | B | $R_4$ | C | $R_1$ |
|---|---|---|---|---|---|
| A4 | 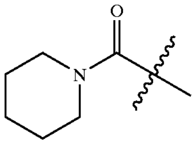 | B4 | 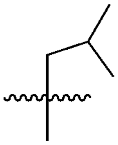 | C4 | 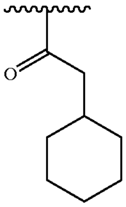 |
| A5 | 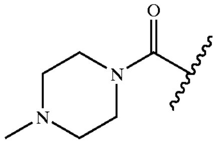 | B5 | 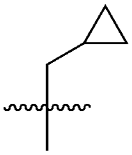 | C5 | 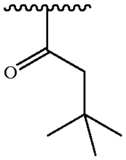 |
| A6 | 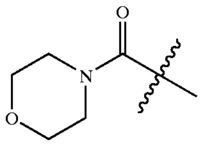 | B6 | 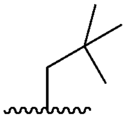 | C6 | 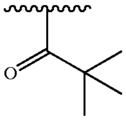 |
| A7 | 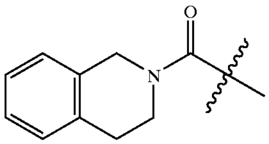 | B7 | 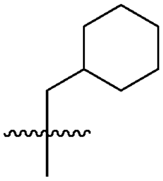 | C7 | 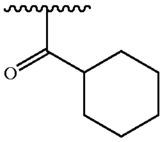 |
| A8 | 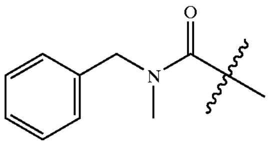 | B8 | 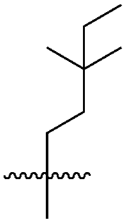 | C8 | 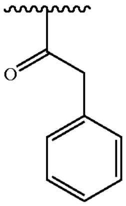 |
| A9 | 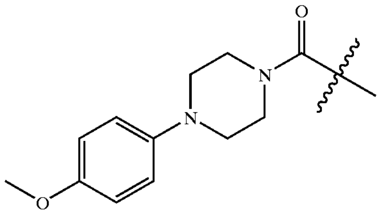 | B9 | 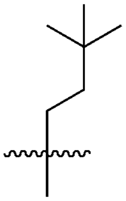 | C9 | 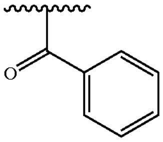 |
| A10 | 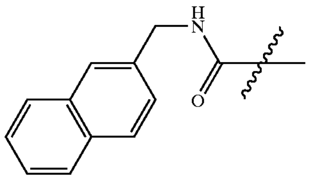 | B10 | 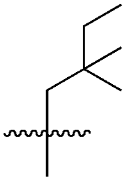 | C10 | 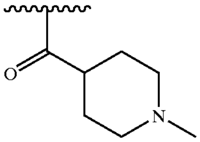 |

TABLE I-continued
| A | Q | B | $R_4$ | C | $R_1$ |
|---|---|---|---|---|---|
| A11 | 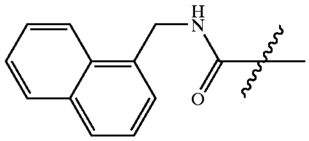 | B11 | 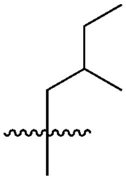 | C11 | 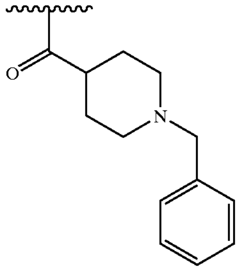 |
| A12 | 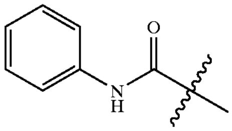 | B12 | 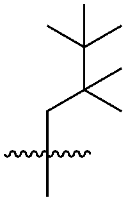 | C12 | 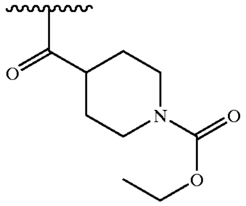 |
| A13 | 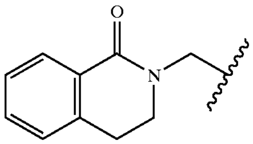 | B13 | 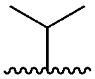 | C13 | 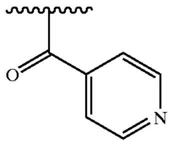 |
| A14 | 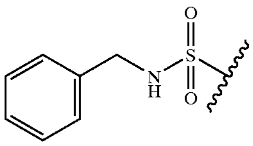 | B14 | 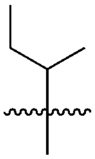 | C14 | 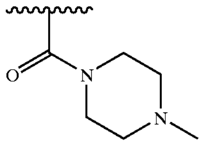 |
| A15 | 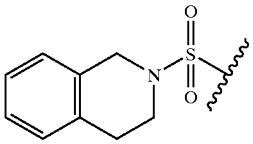 | B15 | 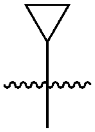 | C15 | 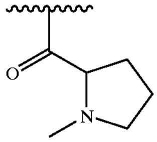 |
| A16 | 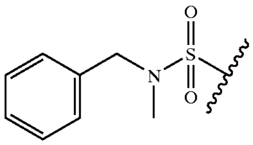 | B16 | 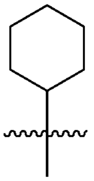 | C16 | 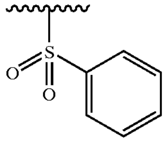 |
| A17 | 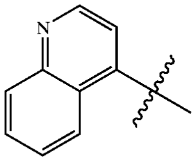 | B17 | 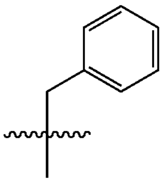 | C17 | 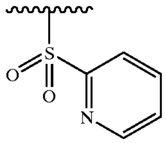 |

TABLE I-continued
| A | Q | B | $R_4$ | C | $R_1$ |
|---|---|---|---|---|---|
| A18 | 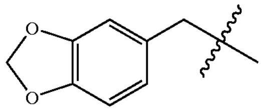 | B18 | 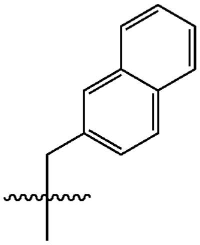 | C18 | $—CH_3$ |
| A19 | 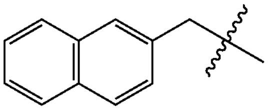 | B19 | 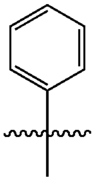 | C19 | 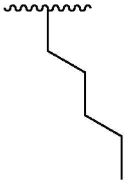 |
| A20 | 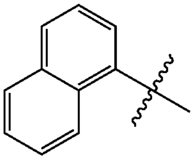 | B20 | 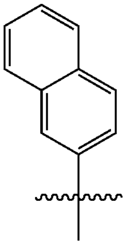 | C20 | 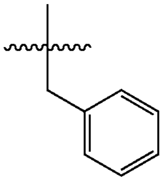 |
| A21 | 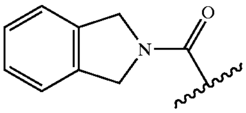 | B21 | 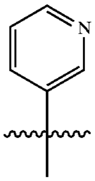 | C21 | 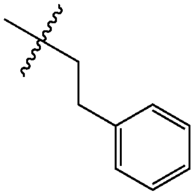 |
| A22 | 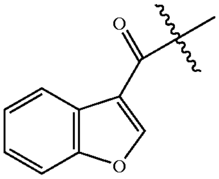 | B22 | 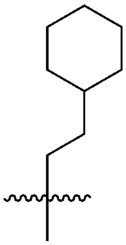 | C22 | 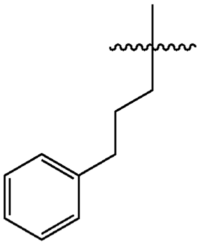 |
| A23 | 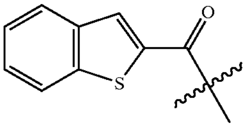 | B23 | 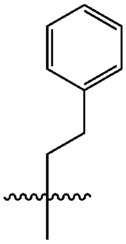 | C23 | 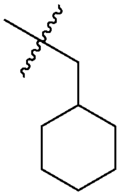 |

TABLE I-continued
| A | Q | B | $R_4$ | C | $R_1$ |
|---|---|---|---|---|---|
| A24 | 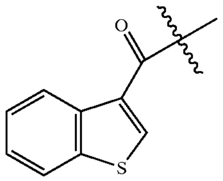 | B24 | 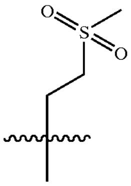 | C24 | 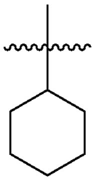 |
| A25 | 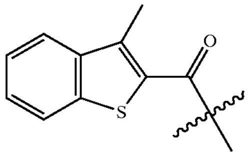 | B25 | 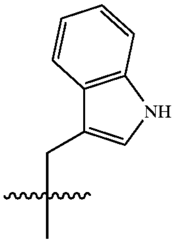 | C25 | 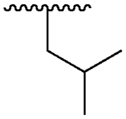 |
| A26 | 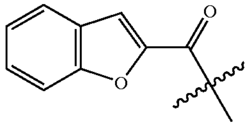 | B26 | 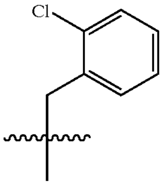 | C26 | 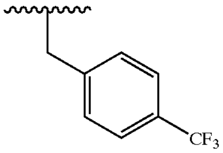 |
| A27 | 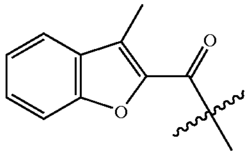 | | | C27 | 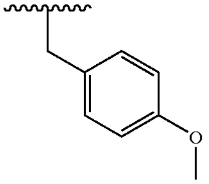 |
| A28 | 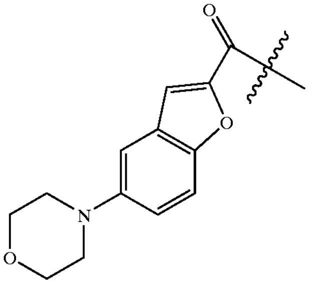 | | | C28 | 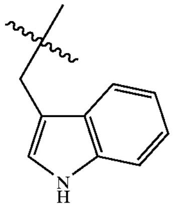 |
| A29 | 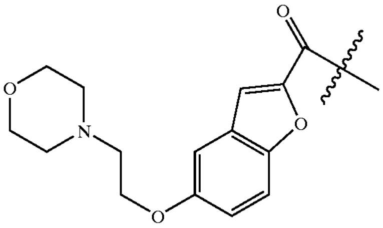 | | | C29 | 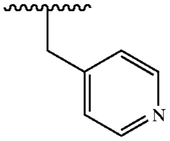 |
| A30 | 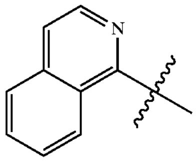 | | | C30 | 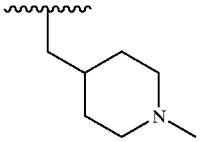 |

TABLE I-continued
| A | Q | B | $R_4$ | C | $R_1$ |
|---|---|---|---|---|---|
| A31 | 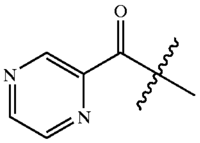 | | | C31 | 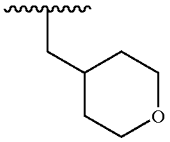 |
| A32 | 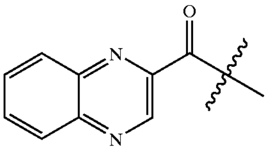 | | | C32 | 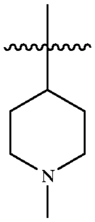 |
| A33 | 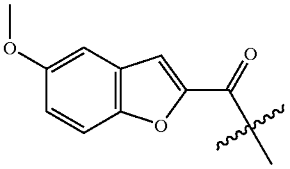 | | | C33 | 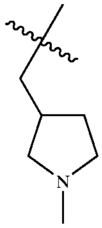 |
| A34 | 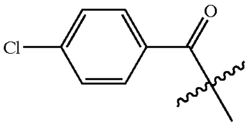 | | | C34 | 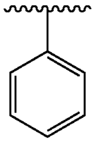 |
| | | | | C35 | 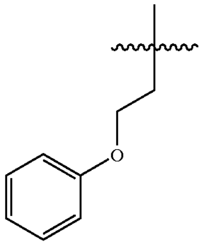 |
| | | | | C36 | 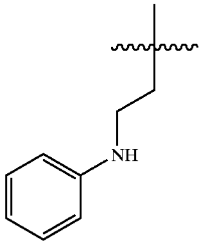 |
| | | | | C37 | 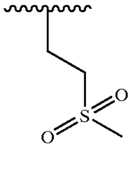 |

TABLE I-continued

| A | Q | B | $R_4$ | C | $R_1$ |
|---|---|---|---|---|---|
| | | | | C38 | 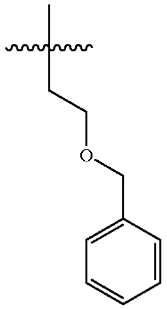 |
| | | | | C39 | 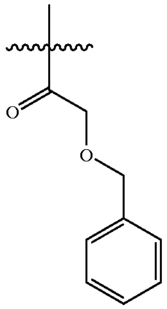 |
| | | | | C40 | 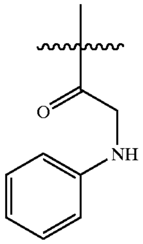 |
| | | | | C41 | 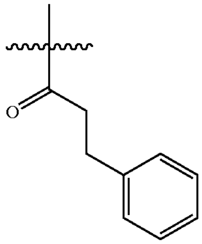 |

or the pharmaceutically acceptable salts, solvates, tautomers or prodrugs thereof. Listed below are specific compounds of the invention falling within the scope of Table I above and postulated to preferably possess Cathepsin K or Cathepsin S activity as indicated. The compounds are listed as specific combinations of the A, B and C groups found in Table I, in which the A, B and C groups listed identify the Q, $R_4$ and $R_1$ groups, respectively, in the compound of formula (Ia) above. For example, the following specific combination: "A6 B4 C8" would represent the following specific compound:

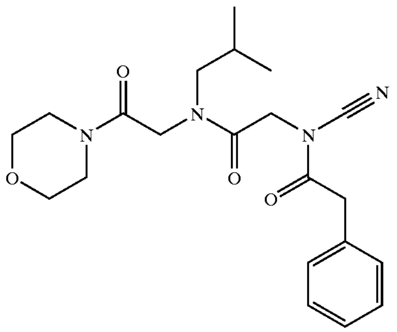

| Specific compounds that are preferred for Cathepsin K inhibitory activity: | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A1 | B4 | C1 | A1 | B5 | C1 | A1 | B6 | C1 | A1 | B7 | C1 | A1 | B11 | C1 | A1 | B13 | C1 | A1 | B14 | C1 | A1 | B15 | C1 | A1 | B16 | C1 | A1 | B17 | C1 |
| A1 | B4 | C2 | A1 | B5 | C2 | A1 | B6 | C2 | A1 | B7 | C2 | A1 | B11 | C2 | A1 | B13 | C2 | A1 | B14 | C2 | A1 | B15 | C2 | A1 | B16 | C2 | A1 | B17 | C2 |
| A1 | B4 | C3 | A1 | B5 | C3 | A1 | B6 | C3 | A1 | B7 | C3 | A1 | B11 | C3 | A1 | B13 | C3 | A1 | B14 | C3 | A1 | B15 | C3 | A1 | B16 | C3 | A1 | B17 | C3 |
| A1 | B4 | C4 | A1 | B5 | C4 | A1 | B6 | C4 | A1 | B7 | C4 | A1 | B11 | C4 | A1 | B13 | C4 | A1 | B14 | C4 | A1 | B15 | C4 | A1 | B16 | C4 | A1 | B17 | C4 |
| A1 | B4 | C5 | A1 | B5 | C5 | A1 | B6 | C5 | A1 | B7 | C5 | A1 | B11 | C5 | A1 | B13 | C5 | A1 | B14 | C5 | A1 | B15 | C5 | A1 | B16 | C5 | A1 | B17 | C5 |
| A1 | B4 | C6 | A1 | B5 | C6 | A1 | B6 | C6 | A1 | B7 | C6 | A1 | B11 | C6 | A1 | B13 | C6 | A1 | B14 | C6 | A1 | B15 | C6 | A1 | B16 | C6 | A1 | B17 | C6 |
| A1 | B4 | C7 | A1 | B5 | C7 | A1 | B6 | C7 | A1 | B7 | C7 | A1 | B11 | C7 | A1 | B13 | C7 | A1 | B14 | C7 | A1 | B15 | C7 | A1 | B16 | C7 | A1 | B17 | C7 |
| A1 | B4 | C8 | A1 | B5 | C8 | A1 | B6 | C8 | A1 | B7 | C8 | A1 | B11 | C8 | A1 | B13 | CB | A1 | B14 | C8 | A1 | B15 | C8 | A1 | B16 | C8 | A1 | B17 | C8 |
| A1 | B4 | C9 | A1 | B5 | C9 | A1 | B6 | C9 | A1 | B7 | C9 | A1 | B11 | C9 | A1 | B13 | C9 | A1 | B14 | C9 | A1 | B15 | C9 | A1 | B16 | C9 | A1 | B17 | C9 |
| A1 | B4 | C10 | A1 | B5 | C10 | A1 | B6 | C10 | A1 | B7 | C10 | A1 | B11 | C10 | A1 | B13 | C10 | A1 | B14 | C10 | A1 | B15 | C10 | A1 | B16 | C10 | A1 | B17 | C10 |
| A1 | B4 | C11 | A1 | B5 | C11 | A1 | B6 | C11 | A1 | B7 | C11 | A1 | B11 | C11 | A1 | B13 | C11 | A1 | B14 | C11 | A1 | B15 | C11 | A1 | B16 | C11 | A1 | B17 | C11 |
| A1 | B4 | C12 | A1 | B5 | C12 | A1 | B6 | C12 | A1 | B7 | C12 | A1 | B11 | C12 | A1 | B13 | C12 | A1 | B14 | C12 | A1 | B15 | C12 | A1 | B16 | C12 | A1 | B17 | C12 |
| A1 | B4 | C13 | A1 | B5 | C13 | A1 | B6 | C13 | A1 | B7 | C13 | A1 | B11 | C13 | A1 | B13 | C13 | A1 | B14 | C13 | A1 | B15 | C13 | A1 | B16 | C13 | A1 | B17 | C13 |
| A1 | B4 | C14 | A1 | B5 | C14 | A1 | B6 | C14 | A1 | B7 | C14 | A1 | B11 | C14 | A1 | B13 | C14 | A1 | B14 | C14 | A1 | B15 | C14 | A1 | B16 | C14 | A1 | B17 | C14 |
| A1 | B4 | C15 | A1 | B5 | C15 | A1 | B6 | C15 | A1 | B7 | C15 | A1 | B11 | C15 | A1 | B13 | C15 | A1 | B14 | C15 | A1 | B15 | C15 | A1 | B16 | C15 | A1 | B17 | C15 |
| A1 | B4 | C16 | A1 | B5 | C16 | A1 | B6 | C16 | A1 | B7 | C16 | A1 | B11 | C16 | A1 | B13 | C16 | A1 | B14 | C16 | A1 | B15 | C16 | A1 | B16 | C16 | A1 | B17 | C16 |
| A1 | B4 | C17 | A1 | B5 | C17 | A1 | B6 | C17 | A1 | B7 | C17 | A1 | B11 | C17 | A1 | Di3 | C17 | A1 | B14 | C17 | A1 | B15 | C17 | A1 | B16 | C17 | A1 | B17 | C17 |
| A1 | B4 | C18 | A1 | B5 | C18 | A1 | B6 | C18 | A1 | B7 | C18 | A1 | B11 | C18 | A1 | B13 | C18 | A1 | B14 | C18 | A1 | B15 | C18 | A1 | B16 | C18 | A1 | B17 | C18 |
| A1 | B4 | C19 | A1 | B5 | C19 | A1 | B6 | C19 | A1 | B7 | C19 | A1 | B11 | C19 | A1 | B13 | C19 | A1 | B14 | C19 | A1 | B15 | C19 | A1 | B16 | C19 | A1 | B17 | C19 |
| A1 | B4 | C20 | A1 | B5 | C20 | A1 | B6 | C20 | A1 | B7 | C20 | A1 | B11 | C20 | A1 | B13 | C20 | A1 | B14 | C20 | A1 | B15 | C20 | A1 | B16 | C20 | A1 | B17 | C20 |
| A1 | B4 | C21 | A1 | B5 | C21 | A1 | B6 | C21 | A1 | B7 | C21 | A1 | B11 | C21 | A1 | B13 | C21 | A1 | B14 | C21 | A1 | B15 | C21 | A1 | B16 | C21 | A1 | B17 | C21 |
| A1 | B4 | C22 | A1 | B5 | C22 | A1 | B6 | C22 | A1 | B7 | C22 | A1 | B11 | C22 | A1 | B13 | C22 | A1 | B14 | C22 | A1 | B15 | C22 | A1 | B16 | C22 | A1 | B17 | C22 |
| A1 | B4 | C23 | A1 | B5 | C23 | A1 | B6 | C23 | A1 | B7 | C23 | A1 | B11 | C23 | A1 | B13 | C23 | A1 | B14 | C23 | A1 | B15 | C23 | A1 | B16 | C23 | A1 | B17 | C23 |
| A1 | B4 | C24 | A1 | B5 | C24 | A1 | B6 | C24 | A1 | B7 | C24 | A1 | B11 | C24 | A1 | B13 | C24 | A1 | B14 | C24 | A1 | B15 | C24 | A1 | B16 | C24 | A1 | B17 | C24 |
| A1 | B4 | C25 | A1 | B5 | C25 | A1 | B6 | C25 | A1 | B7 | C25 | A1 | B11 | C25 | A1 | B13 | C25 | A1 | B14 | C25 | A1 | B15 | C25 | A1 | B16 | C25 | A1 | B17 | C25 |
| A1 | B4 | C26 | A1 | B5 | C26 | A1 | B6 | C26 | A1 | B7 | C26 | A1 | B11 | C26 | A1 | B13 | C26 | A1 | B14 | C26 | A1 | B15 | C26 | A1 | B16 | C26 | A1 | B17 | C26 |
| A1 | B4 | C27 | A1 | B5 | C27 | A1 | B6 | C27 | A1 | B7 | C27 | A1 | B11 | C27 | A1 | B13 | C27 | A1 | B14 | C27 | A1 | B15 | C27 | A1 | B16 | C27 | A1 | B17 | C27 |
| A1 | B4 | C28 | A1 | B5 | C28 | A1 | B6 | C28 | A1 | B7 | C28 | A1 | B11 | C28 | A1 | B13 | C28 | A1 | B14 | C28 | A1 | B15 | C28 | A1 | B16 | C28 | A1 | B17 | C28 |
| A1 | B4 | C29 | A1 | B5 | C29 | A1 | B6 | C29 | A1 | B7 | C29 | A1 | B11 | C29 | A1 | B13 | C29 | A1 | B14 | C29 | A1 | B15 | C29 | A1 | B16 | C29 | A1 | B17 | C29 |
| A1 | B4 | C30 | A1 | B5 | C30 | A1 | B6 | C30 | A1 | B7 | C30 | A1 | B11 | C30 | A1 | B13 | C30 | A1 | B14 | C30 | A1 | B15 | C30 | A1 | B16 | C30 | A1 | B17 | C30 |
| A1 | B4 | C31 | A1 | B5 | C31 | A1 | B6 | C31 | A1 | B7 | C31 | A1 | B11 | C3E | A1 | B13 | C31 | A1 | B14 | C31 | A1 | B15 | C31 | A1 | B16 | C31 | A1 | B17 | C31 |
| A1 | B4 | C32 | A1 | B5 | C32 | A1 | B6 | C32 | A1 | B7 | C32 | A1 | B11 | C32 | A1 | B13 | C32 | A1 | B14 | C32 | A1 | B15 | C32 | A1 | B16 | C32 | A1 | B17 | C32 |
| A1 | B1 | C33 | A1 | B5 | C33 | A1 | B6 | C33 | A1 | B7 | C33 | A1 | B11 | C33 | A1 | B13 | C33 | A1 | B14 | C33 | A1 | B15 | C33 | A1 | B16 | C33 | A1 | B17 | C33 |
| A1 | B1 | C34 | A1 | B5 | C34 | A1 | B6 | C34 | A1 | B7 | C34 | A1 | B11 | C34 | A1 | B13 | C34 | A1 | B14 | C34 | A1 | B15 | C34 | A1 | B16 | C34 | A1 | B17 | C34 |
| A1 | B1 | C35 | A1 | B5 | C35 | A1 | B6 | C35 | A1 | B7 | C35 | A1 | B11 | C35 | A1 | B13 | C35 | A1 | B14 | C35 | A1 | B15 | C35 | A1 | B16 | C35 | A1 | B17 | C35 |
| A1 | B4 | C36 | A1 | B5 | C36 | A1 | B6 | C36 | A1 | B7 | C36 | A1 | B11 | C36 | A1 | B13 | C36 | A1 | B14 | C36 | A1 | B15 | C36 | A1 | B16 | C36 | A1 | B17 | C36 |
| A1 | B4 | C37 | A1 | B5 | C37 | A1 | B6 | C37 | A1 | B7 | C37 | A1 | B11 | C37 | A1 | B13 | C37 | A1 | B14 | C37 | A1 | B15 | C37 | A1 | B16 | C37 | A1 | B17 | C37 |
| A1 | B4 | C38 | A1 | B5 | C38 | A1 | B6 | C38 | A1 | B7 | C38 | A1 | B11 | C38 | A1 | B13 | C38 | A1 | B14 | C38 | A1 | B15 | C38 | A1 | B16 | C38 | A1 | B17 | C38 |
| A1 | B4 | C39 | A1 | B5 | C39 | A1 | B6 | C39 | A1 | B7 | C39 | A1 | B11 | C39 | A1 | B13 | C39 | A1 | B14 | C39 | A1 | B15 | C39 | A1 | B16 | C39 | A1 | B17 | C39 |
| A1 | B4 | C40 | A1 | B5 | C40 | A1 | B6 | C40 | A1 | B7 | C40 | A1 | B11 | C40 | A1 | B13 | C40 | A1 | B14 | C40 | A1 | B15 | C40 | A1 | B16 | C40 | A1 | B17 | C40 |
| A1 | B4 | C41 | A1 | B5 | C41 | A1 | B6 | C41 | A1 | B7 | C41 | A1 | B11 | C41 | A1 | B13 | C41 | A1 | B14 | C41 | A1 | B15 | C41 | A1 | B16 | C41 | A1 | B17 | C41 |
| A5 | B4 | C1 | A5 | B5 | C1 | A5 | B6 | C1 | A5 | B7 | C1 | A5 | B11 | C1 | A5 | B13 | C1 | A5 | B14 | C1 | A5 | B15 | C1 | A5 | B16 | C1 | A5 | B17 | C1 |
| A5 | B4 | C2 | A5 | B5 | C2 | A5 | B6 | C2 | A5 | B7 | C2 | A5 | B11 | C2 | A5 | B13 | C2 | A5 | B14 | C2 | A5 | B15 | C2 | A5 | B16 | C2 | A5 | B17 | C2 |
| A5 | B4 | C3 | A5 | B5 | C3 | A5 | B6 | C3 | A5 | B7 | C3 | A5 | B11 | C3 | A5 | B13 | C3 | A5 | B14 | C3 | A5 | B15 | C3 | A5 | B16 | C3 | A5 | B17 | C3 |
| A5 | B4 | C4 | A5 | B5 | C4 | A5 | B6 | C4 | A5 | B7 | C4 | A5 | B11 | C4 | A5 | B13 | C4 | A5 | B14 | C4 | A5 | B15 | C4 | A5 | B16 | C4 | A5 | B17 | C4 |
| A5 | B4 | C5 | A5 | B5 | C5 | A5 | B6 | C5 | A5 | B7 | C5 | A5 | B11 | C5 | A5 | B13 | C5 | A5 | B14 | C5 | A5 | B15 | C5 | A5 | B16 | C5 | A5 | B17 | C5 |
| A5 | B4 | C6 | A5 | B5 | C6 | A5 | B6 | C6 | A5 | B7 | C6 | A5 | B11 | C6 | A5 | B13 | C6 | A5 | B14 | C6 | A5 | B15 | C6 | A5 | B16 | C6 | A5 | B17 | C6 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A5 | B4 | C7 | A5 | B5 | C7 | A5 | B6 | C7 | A5 | B7 | C7 | A5 | B11 | C7 | A5 | B13 | C7 | A5 | B14 | C7 | A5 | B15 | C7 | A5 | B16 | C7 | A5 | B17 | C7 |
| A5 | B4 | C8 | A5 | B5 | C8 | A5 | B6 | C8 | A5 | B7 | C8 | A5 | B11 | C5 | A5 | B13 | C8 | A5 | B14 | C8 | A5 | B15 | C8 | A5 | B16 | C8 | A5 | B17 | C8 |
| A5 | B4 | C9 | A5 | B5 | C9 | A5 | B6 | C9 | A5 | B7 | C9 | A5 | B11 | C9 | A5 | B13 | C9 | A5 | B14 | C9 | A5 | B15 | C9 | A5 | B16 | C9 | A5 | B17 | C9 |
| A5 | B4 | C10 | A5 | B5 | C10 | A5 | B6 | C10 | A5 | B7 | C10 | A5 | B11 | C10 | A5 | B13 | C10 | A5 | B14 | C10 | A5 | B15 | C10 | A5 | B16 | C10 | A5 | B17 | C10 |
| A5 | B4 | C11 | A5 | B5 | C11 | A5 | B6 | C11 | A5 | B7 | C11 | A5 | B11 | C11 | A5 | B13 | C11 | A5 | B14 | C11 | A5 | B15 | C11 | A5 | B16 | C11 | A5 | B17 | C11 |
| A5 | B4 | C12 | A5 | B5 | C12 | A5 | B6 | C12 | A5 | B7 | C12 | A5 | B11 | C12 | A5 | B13 | C12 | A5 | B14 | C12 | A5 | B15 | C12 | A5 | B16 | C12 | A5 | B17 | C12 |
| A5 | B4 | C13 | A5 | B5 | C13 | A5 | B6 | C13 | A5 | B7 | C13 | A5 | B11 | C13 | A5 | B13 | C13 | A5 | B14 | C13 | A5 | B15 | C13 | A5 | B16 | C13 | A5 | B17 | C13 |
| A5 | B4 | C14 | A5 | B5 | C14 | A5 | B6 | C14 | A5 | B7 | C14 | A5 | B11 | C14 | A5 | B13 | C14 | A5 | B14 | C14 | A5 | B15 | C14 | A5 | B16 | C14 | A5 | B17 | C14 |
| A5 | B4 | C15 | A5 | B5 | C15 | A5 | B6 | C15 | A5 | B7 | C15 | A5 | B11 | C15 | A5 | B13 | C15 | A5 | B14 | C15 | A5 | B15 | C15 | A5 | B16 | C15 | A5 | B17 | C15 |
| A5 | B4 | C16 | A5 | B5 | C16 | A5 | B6 | C16 | A5 | B7 | C16 | A5 | B11 | C16 | A5 | B13 | C16 | A5 | B14 | C16 | A5 | B15 | C16 | A5 | B16 | C16 | A5 | B17 | C16 |
| A5 | B4 | C17 | A5 | B5 | C17 | A5 | B6 | C17 | A5 | B7 | C17 | A5 | B11 | C17 | A5 | B13 | C17 | A5 | B14 | C17 | A5 | B15 | C17 | A5 | B16 | C17 | A5 | B17 | C17 |
| A5 | B4 | C18 | A5 | B5 | C18 | A5 | B6 | C18 | A5 | B7 | C18 | A5 | B11 | C18 | A5 | B13 | C18 | A5 | B14 | C18 | A5 | B15 | C18 | A5 | B16 | C18 | A5 | B17 | C18 |
| A5 | B4 | C19 | A5 | B5 | C19 | A5 | B6 | C19 | A5 | B7 | C19 | A5 | B11 | C19 | A5 | B13 | C19 | A5 | B14 | C19 | A5 | B15 | C19 | A5 | B16 | C19 | A5 | B17 | C19 |
| A5 | B4 | C20 | A5 | B5 | C20 | A5 | B6 | C20 | A5 | B7 | C20 | A5 | B11 | C20 | A5 | B13 | C20 | A5 | B14 | C20 | A5 | B15 | C20 | A5 | B16 | C20 | A5 | B17 | C20 |
| A5 | B4 | C21 | A5 | B5 | C21 | A5 | B6 | C21 | A5 | B7 | C21 | A5 | B11 | C21 | A5 | B13 | C21 | A5 | B14 | C21 | A5 | B15 | C21 | A5 | B16 | C21 | A5 | B17 | C21 |
| A5 | B4 | C22 | A5 | B5 | C22 | A5 | B6 | C22 | A5 | B7 | C22 | A5 | B11 | C22 | A5 | B13 | C22 | A5 | B14 | C22 | A5 | B15 | C22 | A5 | B16 | C22 | A5 | B17 | C22 |
| A5 | B4 | C23 | A5 | B5 | C23 | A5 | B5 | C23 | A5 | B7 | C23 | A5 | B11 | C23 | A5 | B13 | C23 | A5 | B14 | C23 | A5 | B15 | C23 | A5 | B16 | C23 | A5 | B17 | C23 |
| A5 | B4 | C24 | A5 | B5 | C24 | A5 | B6 | C24 | A5 | B7 | C24 | A5 | B11 | C24 | A5 | B13 | C24 | A5 | B14 | C24 | A5 | B15 | C24 | A5 | B16 | C24 | A5 | B17 | C24 |
| A5 | B4 | C25 | A5 | B5 | C25 | A5 | B6 | C25 | A5 | B7 | C25 | A5 | B11 | C25 | A5 | B13 | C25 | A5 | B14 | C25 | A5 | B15 | C25 | A5 | B16 | C25 | A5 | B17 | C25 |
| A5 | B4 | C26 | A5 | B5 | C26 | A5 | B6 | C26 | A5 | B7 | C26 | A5 | B11 | C26 | A5 | B13 | C26 | A5 | B14 | C26 | A5 | B15 | C26 | A5 | B16 | C26 | A5 | B17 | C26 |
| A5 | B4 | C27 | A5 | B5 | C27 | A5 | B6 | C27 | A5 | B7 | C27 | A5 | B11 | C27 | A5 | B13 | C27 | A5 | B14 | C27 | A5 | B15 | C27 | A5 | B16 | C27 | A5 | B17 | C27 |
| A5 | B4 | C28 | A5 | B5 | C28 | A5 | B6 | C28 | A5 | B7 | C28 | A5 | B11 | C28 | A5 | B13 | C28 | A5 | B14 | C28 | A5 | B15 | C28 | A5 | B16 | C28 | A5 | B17 | C28 |
| A5 | B4 | C29 | A5 | B5 | C29 | A5 | B6 | C29 | A5 | B7 | C29 | A5 | B11 | C29 | A5 | B13 | C29 | A5 | B14 | C29 | A5 | B15 | C29 | A5 | B16 | C29 | A5 | B17 | C29 |
| A5 | B4 | C30 | A5 | B5 | C30 | A5 | B6 | C30 | A5 | B7 | C30 | A5 | B11 | C30 | A5 | B13 | C30 | A5 | B14 | C30 | A5 | B15 | C30 | A5 | B16 | C30 | A5 | B17 | C30 |
| A5 | B4 | C31 | A5 | B5 | C31 | A5 | B6 | C31 | A5 | B7 | C31 | A5 | B11 | C31 | A5 | B13 | C31 | A5 | B14 | C31 | A5 | B15 | C31 | A5 | B16 | C31 | A5 | B17 | C31 |
| A5 | B4 | C32 | A5 | B5 | C32 | A5 | B6 | C32 | A5 | B7 | C32 | A5 | B11 | C32 | A5 | B13 | C32 | A5 | B14 | C32 | A5 | B15 | C32 | A5 | B16 | C32 | A5 | B17 | C32 |
| A5 | B4 | C33 | A5 | B5 | C33 | A5 | B6 | C33 | A5 | B7 | C33 | A5 | B11 | C33 | A5 | B13 | C33 | A5 | B14 | C33 | A5 | B15 | C33 | A5 | B16 | C33 | A5 | B17 | C33 |
| A5 | B4 | C34 | A5 | B5 | C34 | A5 | B6 | C34 | A5 | B7 | C34 | A5 | B11 | C34 | A5 | B13 | C34 | A5 | B14 | C34 | A5 | B15 | C34 | A5 | B16 | C34 | A5 | B17 | C34 |
| A5 | B4 | C35 | A5 | B5 | C35 | A5 | B6 | C35 | A5 | B7 | C35 | A5 | B11 | C35 | A5 | B13 | C35 | A5 | B14 | C35 | A5 | B15 | C35 | A5 | B16 | C35 | A5 | B17 | C35 |
| A5 | B4 | C36 | A5 | B5 | C36 | A5 | B6 | C36 | A5 | B7 | C36 | A5 | B11 | C36 | A5 | B13 | C36 | A5 | B14 | C36 | A5 | B15 | C36 | A5 | B16 | C36 | A5 | B17 | C36 |
| A5 | B4 | C37 | A5 | B5 | C37 | A5 | B6 | C37 | A5 | B7 | C37 | A5 | B11 | C37 | A5 | B13 | C37 | A5 | B14 | C37 | A5 | B15 | C37 | A5 | B16 | C37 | A5 | B17 | C37 |
| A5 | B4 | C38 | A5 | B5 | C38 | A5 | B6 | C38 | A5 | B7 | C38 | A5 | B11 | C38 | A5 | B13 | C38 | A5 | B14 | C38 | A5 | B15 | C38 | A5 | B16 | C38 | A5 | B17 | C38 |
| A5 | B4 | C39 | A5 | B5 | C39 | A5 | B6 | C39 | A5 | B7 | C39 | A5 | B11 | C39 | A5 | B13 | C39 | A5 | B14 | C39 | A5 | B15 | C39 | A5 | B16 | C39 | A5 | B17 | C39 |
| A5 | B4 | C40 | A5 | B5 | C40 | A5 | B6 | C40 | A5 | B7 | C40 | A5 | B11 | C40 | A5 | B13 | C40 | A5 | B14 | C40 | A5 | B15 | C40 | A5 | B16 | C40 | A5 | B17 | C40 |
| A5 | B4 | C41 | A5 | B5 | C41 | A5 | B6 | C41 | A5 | B7 | C41 | A5 | B11 | C41 | A5 | B13 | C41 | A5 | B14 | C41 | A5 | B15 | C41 | A5 | B16 | C41 | A5 | B17 | C41 |
| A6 | B4 | C1 | A6 | B5 | C1 | A6 | B6 | C1 | A6 | B7 | C1 | A6 | B11 | C1 | A6 | B13 | C1 | A6 | B14 | C1 | A6 | B15 | C1 | A6 | B16 | C1 | A6 | B17 | C1 |
| A6 | B4 | C2 | A6 | B5 | C2 | A6 | B6 | C2 | A6 | B7 | C2 | A6 | B11 | C2 | A6 | B13 | C2 | A6 | B14 | C2 | A6 | B15 | C2 | A6 | B16 | C2 | A6 | B17 | C2 |
| A6 | B4 | C3 | A6 | B5 | C3 | A6 | B6 | C3 | A6 | B7 | C3 | A6 | B11 | C3 | A6 | B13 | C3 | A6 | B14 | C3 | A6 | B15 | C3 | A6 | B16 | C3 | A6 | B17 | C3 |
| A6 | B4 | C4 | A6 | B5 | C4 | A6 | B6 | C4 | A6 | B7 | C4 | A6 | B11 | C4 | A6 | B13 | C4 | A6 | B14 | C4 | A6 | B15 | C4 | A6 | B16 | C4 | A6 | B17 | C4 |
| A6 | B4 | C5 | A6 | B5 | C5 | A6 | B6 | C5 | A6 | B7 | C5 | A6 | B11 | C5 | A6 | B13 | C5 | A6 | B14 | C5 | A6 | B15 | C5 | A6 | B16 | C5 | A6 | B17 | C5 |
| A6 | B4 | C6 | A6 | B5 | C6 | A6 | B6 | C6 | A6 | B7 | C6 | A6 | B11 | C6 | A6 | B13 | C6 | A6 | B14 | C6 | A6 | B15 | C6 | A6 | B16 | C6 | A6 | B17 | C6 |
| A6 | B4 | C7 | A6 | B5 | C7 | A6 | B6 | C7 | A6 | B7 | C7 | A6 | B11 | C7 | A6 | B13 | C7 | A6 | B14 | C7 | A6 | B15 | C7 | A6 | B16 | C7 | A6 | B17 | C7 |
| A6 | B4 | C8 | A6 | B5 | C8 | A6 | B6 | C8 | A6 | B7 | C8 | A6 | B11 | C8 | A6 | B13 | C8 | A6 | B14 | C8 | A6 | B15 | C8 | A6 | B16 | C8 | A6 | B17 | C8 |
| A6 | B4 | C9 | A6 | B5 | C9 | A6 | B6 | C9 | A6 | B7 | C9 | A6 | B11 | C9 | A6 | B13 | C9 | A6 | B14 | C9 | A6 | B15 | C9 | A6 | B16 | C9 | A6 | B17 | C9 |
| A6 | B4 | C10 | A6 | B5 | C10 | A6 | B6 | C10 | A6 | B7 | C10 | A6 | B11 | C10 | A6 | B13 | C10 | A6 | B14 | C10 | A6 | B15 | C10 | A6 | B16 | C10 | A6 | B17 | C10 |
| A6 | B4 | C11 | A6 | B5 | C11 | A6 | B6 | C11 | A6 | B7 | C11 | A6 | B11 | C11 | A6 | B13 | C11 | A6 | B14 | C11 | A6 | B15 | C11 | A6 | B16 | C11 | A6 | B17 | C11 |
| A6 | B4 | C12 | A6 | B5 | C12 | A6 | B6 | C12 | A6 | B7 | C12 | A6 | B11 | C12 | A6 | B13 | C12 | A6 | B14 | C12 | A6 | B15 | C12 | A6 | B16 | C12 | A6 | B17 | C12 |
| A6 | B4 | C13 | A6 | B5 | C13 | A6 | B6 | C13 | A6 | B7 | C13 | A6 | B11 | C13 | A6 | B13 | C13 | A6 | B14 | C13 | A6 | B15 | C13 | A6 | B16 | C13 | A6 | B17 | C13 |
| A6 | B4 | C14 | A6 | B5 | C14 | A6 | B6 | C14 | A6 | B7 | C14 | A6 | B11 | C14 | A6 | B13 | C14 | A6 | B14 | C14 | A6 | B15 | C14 | A6 | B16 | C14 | A6 | B17 | C14 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A6 | B4 | C15 | A6 | B5 | C15 | A6 | B6 | C15 | A6 | B7 | C15 | A6 | B11 | C15 | A6 | B13 | C15 | A6 | B14 | C15 | A6 | B15 | C15 | A6 | B16 | C15 | A6 | B17 | C15 |
| A6 | B4 | C16 | A6 | B5 | C16 | A6 | B6 | C16 | A6 | B7 | C16 | A6 | B11 | C16 | A6 | B13 | C16 | A6 | B14 | C16 | A6 | B15 | C16 | A6 | B16 | C16 | A6 | B17 | C16 |
| A6 | B4 | C17 | A6 | B5 | C17 | A6 | B6 | C17 | A6 | B7 | C17 | A6 | B11 | C17 | A6 | B13 | C17 | A6 | B14 | C17 | A6 | B15 | C17 | A6 | B16 | C17 | A6 | B17 | C17 |
| A6 | B4 | C15 | A6 | B5 | C18 | A6 | B6 | C18 | A6 | B7 | C18 | A6 | B11 | C18 | A6 | B13 | C18 | A6 | B14 | C18 | A6 | B15 | C18 | A6 | B16 | C18 | A6 | B17 | C18 |
| A6 | B4 | C19 | A6 | B5 | C19 | A6 | B6 | C19 | A6 | B7 | C19 | A6 | B11 | C19 | A6 | B13 | C19 | A6 | B14 | C19 | A6 | B15 | C19 | A6 | B16 | C19 | A6 | B17 | C19 |
| A6 | B4 | C20 | A6 | B5 | C20 | A6 | B6 | C20 | A6 | B7 | C20 | A6 | B11 | C20 | A6 | B13 | C20 | A6 | B14 | C20 | A6 | B15 | C20 | A6 | B16 | C20 | A6 | B17 | C20 |
| A6 | B4 | C21 | A6 | B5 | C21 | A6 | B6 | C21 | A6 | B7 | C21 | A6 | B11 | C21 | A6 | B13 | C21 | A6 | B14 | C21 | A6 | B15 | C21 | A6 | B16 | C21 | A6 | B17 | C21 |
| A6 | B4 | C22 | A6 | B5 | C22 | A6 | B6 | C22 | A6 | B7 | C22 | A6 | B11 | C22 | A6 | B13 | C22 | A6 | B14 | C22 | A6 | B15 | C22 | A6 | B16 | C22 | A6 | B17 | C22 |
| A6 | B4 | C23 | A6 | B5 | C23 | A6 | B6 | C23 | A6 | B7 | C23 | A6 | B11 | C23 | A6 | B13 | C23 | A6 | B14 | C23 | A6 | B15 | C23 | A6 | B16 | C23 | A6 | B17 | C23 |
| A6 | B4 | C24 | A6 | B5 | C24 | A6 | B6 | C24 | A6 | B7 | C24 | A6 | B11 | C24 | A6 | B13 | C24 | A6 | B14 | C24 | A6 | B15 | C24 | A6 | B16 | C24 | A6 | B17 | C24 |
| A6 | B4 | C25 | A6 | B5 | C25 | A6 | B6 | C25 | A6 | B7 | C25 | A6 | B11 | C25 | A6 | B13 | C25 | A6 | B14 | C25 | A6 | B15 | C25 | A6 | B16 | C25 | A6 | B17 | C25 |
| A6 | B4 | C26 | A6 | B5 | C26 | A6 | B6 | C26 | A6 | B7 | C26 | A6 | B11 | C26 | A6 | B13 | C26 | A6 | B14 | C26 | A6 | B15 | C26 | A6 | B16 | C26 | A6 | B17 | C26 |
| A6 | B4 | C27 | A6 | B5 | C27 | A6 | B6 | C27 | A6 | B7 | C27 | A6 | B11 | C27 | A6 | B13 | C27 | A6 | B14 | C27 | A6 | B15 | C27 | A6 | B16 | C27 | A6 | B17 | C27 |
| A6 | B4 | C28 | A6 | B5 | C28 | A6 | B6 | C28 | A6 | B7 | C28 | A6 | B11 | C28 | A6 | B13 | C28 | A6 | B14 | C28 | A6 | B15 | C28 | A6 | B16 | C28 | A6 | B17 | C28 |
| A6 | B4 | C29 | A6 | B5 | C29 | A6 | B6 | C29 | A6 | B7 | C29 | A6 | B11 | C29 | A6 | B13 | C29 | A6 | B14 | C29 | A6 | B15 | C29 | A6 | B16 | C29 | A6 | B17 | C29 |
| A6 | B4 | C30 | A6 | B5 | C30 | A6 | B6 | C30 | A6 | B7 | C30 | A6 | B11 | C30 | A6 | B13 | C30 | A6 | B14 | C30 | A6 | B15 | C30 | A6 | B16 | C30 | A6 | B17 | C30 |
| A6 | B4 | C31 | A6 | B5 | C31 | A6 | B6 | C31 | A6 | B7 | C31 | A6 | B11 | C31 | A6 | B13 | C31 | A6 | B14 | C31 | A6 | B15 | C31 | A6 | B16 | C31 | A6 | B17 | C31 |
| A6 | B4 | C32 | A6 | B5 | C32 | A6 | B6 | C32 | A6 | B7 | C32 | A6 | B11 | C32 | A6 | B13 | C32 | A6 | B14 | C32 | A6 | B15 | C32 | A6 | B16 | C32 | A6 | B17 | C32 |
| A6 | B4 | C33 | A6 | B5 | C33 | A6 | B6 | C33 | A6 | B7 | C33 | A6 | B11 | C33 | A6 | B13 | C33 | A6 | B14 | C33 | A6 | B15 | C33 | A6 | B16 | C33 | A6 | B17 | C33 |
| A6 | B4 | C34 | A6 | B5 | C34 | A6 | B6 | C34 | A6 | B7 | C34 | A6 | B11 | C34 | A6 | B13 | C34 | A6 | B14 | C34 | A6 | B15 | C34 | A6 | B16 | C34 | A6 | B17 | C34 |
| A6 | B4 | C35 | A6 | B5 | C35 | A6 | B6 | C35 | A6 | B7 | C35 | A6 | B11 | C35 | A6 | B13 | C35 | A6 | B14 | C35 | A6 | B15 | C35 | A6 | B16 | C35 | A6 | B17 | C35 |
| A6 | B4 | C36 | A6 | B5 | C36 | A6 | B6 | C36 | A6 | B7 | C36 | A6 | B11 | C36 | A6 | B13 | C36 | A6 | B14 | C36 | A6 | B15 | C36 | A6 | B16 | C36 | A6 | B17 | C36 |
| A6 | B4 | C37 | A6 | B5 | C37 | A6 | B6 | C37 | A6 | B7 | C37 | A6 | B11 | C37 | A6 | B13 | C37 | A6 | B14 | C37 | A6 | B15 | C37 | A6 | B16 | C37 | A6 | B17 | C37 |
| A6 | B4 | C38 | A6 | B5 | C38 | A6 | B6 | C38 | A6 | B7 | C38 | A6 | B11 | C38 | A6 | B13 | C38 | A6 | B14 | C38 | A6 | B15 | C38 | A6 | B16 | C38 | A6 | B17 | C38 |
| A6 | B4 | C39 | A6 | B5 | C39 | A6 | B6 | C39 | A6 | B7 | C39 | A6 | B11 | C39 | A6 | B13 | C39 | A6 | B14 | C39 | A6 | B15 | C39 | A6 | B16 | C39 | A6 | B17 | C39 |
| A6 | B4 | C40 | A6 | B5 | C40 | A6 | B6 | C43 | A6 | B7 | C40 | A6 | B11 | C40 | A6 | B13 | C40 | A6 | B14 | C40 | A6 | B15 | C40 | A6 | B16 | C40 | A6 | B17 | C40 |
| A6 | B4 | C41 | A6 | B5 | C41 | A6 | B6 | C44 | A6 | B7 | C41 | A6 | B11 | C41 | A6 | B13 | C41 | A6 | B14 | C41 | A6 | B15 | C41 | A6 | B16 | C41 | A6 | B17 | C41 |
| A7 | B4 | C1 | A7 | B5 | C1 | A7 | B6 | C1 | A7 | B7 | C1 | A7 | B11 | C1 | A7 | B13 | C1 | A7 | B14 | C1 | A7 | B15 | C1 | A7 | B16 | C1 | A7 | B17 | C1 |
| A7 | B4 | C2 | A7 | B5 | C2 | A7 | B6 | C2 | A7 | B7 | C2 | A7 | B11 | C2 | A7 | B13 | C2 | A7 | B14 | C2 | A7 | B15 | C2 | A7 | B16 | C2 | A7 | B17 | C2 |
| A7 | B4 | C3 | A7 | B5 | C3 | A7 | B6 | C3 | A7 | B7 | C3 | A7 | B11 | C3 | A7 | B13 | C3 | A7 | B14 | C3 | A7 | B15 | C3 | A7 | B16 | C3 | A7 | B17 | C3 |
| A7 | B4 | C4 | A7 | B5 | C4 | A7 | B6 | C4 | A7 | B7 | C4 | A7 | B11 | C4 | A7 | B13 | C4 | A7 | B14 | C4 | A7 | B15 | C4 | A7 | B16 | C4 | A7 | B17 | C4 |
| A7 | B4 | C5 | A7 | B5 | C5 | A7 | B6 | C5 | A7 | B7 | C5 | A7 | B11 | C5 | A7 | B13 | C5 | A7 | B14 | C5 | A7 | B15 | C5 | A7 | B16 | C5 | A7 | B17 | C5 |
| A7 | B4 | C6 | A7 | B5 | C6 | A7 | B6 | C6 | A7 | B7 | C6 | A7 | B11 | C6 | A7 | B13 | C6 | A7 | B14 | C6 | A7 | B15 | C6 | A7 | B16 | C6 | A7 | B17 | C6 |
| A7 | B4 | C7 | A7 | B5 | C7 | A7 | B6 | C7 | A7 | B7 | C7 | A7 | B11 | C7 | A7 | B13 | C7 | A7 | B14 | C7 | A7 | B15 | C7 | A7 | B16 | C7 | A7 | B17 | C7 |
| A7 | B4 | C8 | A7 | B5 | C8 | A7 | B6 | C8 | A7 | B7 | C8 | A7 | B11 | C8 | A7 | B13 | C8 | A7 | B14 | C8 | A7 | B15 | C8 | A7 | B16 | C8 | A7 | B17 | C8 |
| A7 | B4 | C9 | A7 | B5 | C9 | A7 | B6 | C9 | A7 | B7 | C9 | A7 | B11 | C9 | A7 | B13 | C9 | A7 | B14 | C9 | A7 | B15 | C9 | A7 | B16 | C9 | A7 | B17 | C9 |
| A7 | B4 | C10 | A7 | B5 | C10 | A7 | B6 | C10 | A7 | B7 | C10 | A7 | B11 | C10 | A7 | B13 | C10 | A7 | B14 | C10 | A7 | B15 | C10 | A7 | B16 | C10 | A7 | B17 | C10 |
| A7 | B4 | C11 | A7 | B5 | C11 | A7 | B6 | C11 | A7 | B7 | C11 | A7 | B11 | C11 | A7 | B13 | C11 | A7 | B14 | C11 | A7 | B15 | C11 | A7 | B16 | C11 | A7 | B17 | C11 |
| A7 | B4 | C12 | A7 | B5 | C12 | A7 | B6 | C12 | A7 | B7 | C12 | A7 | B11 | C12 | A7 | B13 | C12 | A7 | B14 | C12 | A7 | B15 | C12 | A7 | B16 | C12 | A7 | B17 | C12 |
| A7 | B4 | C13 | A7 | B5 | C13 | A7 | B6 | C13 | A7 | B7 | C13 | A7 | B11 | C13 | A7 | B13 | C13 | A7 | B14 | C13 | A7 | B15 | C13 | A7 | B16 | C13 | A7 | B17 | C13 |
| A7 | B4 | C14 | A7 | B5 | C14 | A7 | B6 | C14 | A7 | B7 | C14 | A7 | B11 | C14 | A7 | B13 | C14 | A7 | B14 | C14 | A7 | B15 | C14 | A7 | B16 | C14 | A7 | B17 | C14 |
| A7 | B4 | C15 | A7 | B5 | C15 | A7 | B6 | C15 | A7 | B7 | C15 | A7 | B11 | C15 | A7 | B13 | C15 | A7 | B14 | C15 | A7 | B15 | C15 | A7 | B16 | C15 | A7 | B17 | C15 |
| A7 | B4 | C16 | A7 | B5 | C16 | A7 | B6 | C16 | A7 | B7 | C16 | A7 | B11 | C16 | A7 | B13 | C16 | A7 | B14 | C16 | A7 | B15 | C16 | A7 | B16 | C16 | A7 | B17 | C16 |
| A7 | B4 | C17 | A7 | B5 | C17 | A7 | B6 | C17 | A7 | B7 | C17 | A7 | B11 | C17 | A7 | B13 | C17 | A7 | B14 | C17 | A7 | B15 | C17 | A7 | B16 | C17 | A7 | B17 | C17 |
| A7 | B4 | C18 | A7 | B5 | C18 | A7 | B6 | C15 | A7 | B7 | C18 | A7 | B11 | C18 | A7 | B13 | C18 | A7 | B14 | C18 | A7 | B15 | C18 | A7 | B16 | C18 | A7 | B17 | C18 |
| A7 | B4 | C19 | A7 | B5 | C19 | A7 | B6 | C19 | A7 | B7 | C19 | A7 | B11 | C19 | A7 | B13 | C19 | A7 | B14 | C19 | A7 | B15 | C19 | A7 | B16 | C19 | A7 | B17 | C19 |
| A7 | B4 | C20 | A7 | B5 | C20 | A7 | B6 | C20 | A7 | B7 | C20 | A7 | B11 | C20 | A7 | B13 | C20 | A7 | B14 | C20 | A7 | B15 | C20 | A7 | B16 | C20 | A7 | B17 | C20 |
| A7 | B4 | C21 | A7 | B5 | C21 | A7 | B6 | C21 | A7 | B7 | C21 | A7 | B11 | C21 | A7 | B13 | C21 | A7 | B14 | C21 | A7 | B15 | C21 | A7 | B16 | C21 | A7 | B17 | C21 |
| A7 | B4 | C22 | A7 | B5 | C22 | A7 | B6 | C22 | A7 | B7 | C22 | A7 | B11 | C22 | A7 | B13 | C22 | A7 | B14 | C22 | A7 | B15 | C22 | A7 | B16 | C22 | A7 | B17 | C22 |
| A7 | B4 | C23 | A7 | B5 | C23 | A7 | B6 | C23 | A7 | B7 | C23 | A7 | B11 | C23 | A7 | B13 | C23 | A7 | B14 | C23 | A7 | B15 | C23 | A7 | B16 | C23 | A7 | B17 | C23 |
| A7 | B4 | C24 | A7 | B5 | C24 | A7 | B6 | C24 | A7 | B7 | C24 | A7 | B11 | C24 | A7 | B13 | C24 | A7 | B14 | C24 | A7 | B15 | C24 | A7 | B16 | C24 | A7 | B17 | C24 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A7 | B4 | C25 | A7 | B5 | C25 | A7 | B6 | C25 | A7 | B7 | C25 | A7 | B11 | C25 | A7 | B13 | C25 | A7 | B14 | C25 | A7 | B15 | C25 | A7 | B16 | C25 | A7 | B17 | C25 |
| A7 | B4 | C26 | A7 | B5 | C26 | A7 | B6 | C26 | A7 | B7 | C26 | A7 | B11 | C26 | A7 | B13 | C26 | A7 | B14 | C26 | A7 | B15 | C26 | A7 | B16 | C26 | A7 | B17 | C26 |
| A7 | B4 | C27 | A7 | B5 | C27 | A7 | B6 | C27 | A7 | B7 | C27 | A7 | B11 | C27 | A7 | B13 | C27 | A7 | B14 | C27 | A7 | B15 | C27 | A7 | B16 | C27 | A7 | B17 | C27 |
| A7 | B4 | C28 | A7 | B5 | C28 | A7 | B6 | C28 | A7 | B7 | C28 | A7 | B11 | C28 | A7 | B13 | C28 | A7 | B14 | C28 | A7 | B15 | C28 | A7 | B16 | C28 | A7 | B17 | C28 |
| A7 | B4 | C29 | A7 | B5 | C29 | A7 | B6 | C29 | A7 | B7 | C29 | A7 | B11 | C29 | A7 | B13 | C29 | A7 | B14 | C29 | A7 | B15 | C29 | A7 | B16 | C29 | A7 | B17 | C29 |
| A7 | B4 | C30 | A7 | B5 | C30 | A7 | B6 | C30 | A7 | B7 | C30 | A7 | B11 | C30 | A7 | B13 | C30 | A7 | B14 | C30 | A7 | B15 | C30 | A7 | B16 | C30 | A7 | B17 | C30 |
| A7 | B4 | C31 | A7 | B5 | C31 | A7 | B6 | C31 | A7 | B7 | C31 | A7 | B11 | C31 | A7 | B13 | C31 | A7 | B14 | C31 | A7 | B15 | C31 | A7 | B16 | C31 | A7 | B17 | C31 |
| A7 | B4 | C32 | A7 | B5 | C32 | A7 | B6 | C32 | A7 | B7 | C32 | A7 | B11 | C32 | A7 | B13 | C32 | A7 | B14 | C32 | A7 | B15 | C32 | A7 | B16 | C32 | A7 | B17 | C32 |
| A7 | B4 | C33 | A7 | B5 | C33 | A7 | B6 | C33 | A7 | B7 | C33 | A7 | B11 | C33 | A7 | B13 | C33 | A7 | B14 | C33 | A7 | B15 | C33 | A7 | B16 | C33 | A7 | B17 | C33 |
| A7 | B4 | C34 | A7 | B5 | C34 | A7 | B6 | C34 | A7 | B7 | C34 | A7 | B11 | C34 | A7 | B13 | C34 | A7 | B14 | C34 | A7 | B15 | C34 | A7 | B16 | C34 | A7 | B17 | C34 |
| A7 | B4 | C35 | A7 | B5 | C35 | A7 | B6 | C35 | A7 | B7 | C35 | A7 | B11 | C35 | A7 | B13 | C35 | A7 | B14 | C35 | A7 | B15 | C35 | A7 | B16 | C35 | A7 | B17 | C35 |
| A7 | B4 | C36 | A7 | B5 | C36 | A7 | B6 | C36 | A7 | B7 | C36 | A7 | B11 | C36 | A7 | B13 | C36 | A7 | B14 | C36 | A7 | B15 | C36 | A7 | B16 | C36 | A7 | B17 | C36 |
| A7 | B4 | C37 | A7 | B5 | C37 | A7 | B6 | C37 | A7 | B7 | C37 | A7 | B11 | C37 | A7 | B13 | C37 | A7 | B14 | C37 | A7 | B15 | C37 | A7 | B16 | C37 | A7 | B17 | C37 |
| A7 | B4 | C38 | A7 | B5 | C38 | A7 | B6 | C38 | A7 | B7 | C38 | A7 | B11 | C38 | A7 | B13 | C38 | A7 | B14 | C38 | A7 | B15 | C38 | A7 | B16 | C38 | A7 | B17 | C38 |
| A7 | B4 | C39 | A7 | B5 | C39 | A7 | B6 | C39 | A7 | B7 | C39 | A7 | B11 | C39 | A7 | B13 | C39 | A7 | B14 | C39 | A7 | B15 | C39 | A7 | B16 | C39 | A7 | B17 | C39 |
| A7 | B4 | C40 | A7 | B5 | C40 | A7 | B6 | C40 | A7 | B7 | C40 | A7 | B11 | C40 | A7 | B13 | C40 | A7 | B14 | C40 | A7 | B15 | C40 | A7 | B16 | C40 | A7 | B17 | C40 |
| A7 | B4 | C41 | A7 | B5 | C41 | A7 | B6 | C41 | A7 | B7 | C41 | A7 | B11 | C41 | A7 | B13 | C41 | A7 | B14 | C41 | A7 | B15 | C41 | A7 | B16 | C41 | A7 | B17 | C41 |
| A8 | B4 | C1 | A8 | B5 | C1 | A8 | B6 | C1 | A8 | B7 | C1 | A8 | B11 | C1 | A8 | B13 | C1 | A5 | B14 | C1 | A8 | B15 | C1 | A8 | B16 | C1 | A8 | B17 | C1 |
| A8 | B4 | C2 | A8 | B5 | C2 | A8 | B6 | C2 | A8 | B7 | C2 | A8 | B11 | C2 | A8 | B13 | C2 | A5 | B14 | C2 | A8 | B15 | C2 | A8 | B16 | C2 | A8 | B17 | C2 |
| A8 | B4 | C3 | A8 | B5 | C3 | A8 | B6 | C3 | A8 | B7 | C3 | A8 | B11 | C3 | A8 | B13 | C3 | A5 | B14 | C3 | A8 | B15 | C3 | A8 | B16 | C3 | A8 | B17 | C3 |
| A8 | B4 | C4 | A8 | B5 | C4 | A8 | B6 | C4 | A8 | B7 | C4 | A8 | B11 | C4 | A8 | B13 | C4 | A5 | B14 | C4 | A8 | B15 | C4 | A8 | B16 | C4 | A8 | B17 | C4 |
| A8 | B4 | C5 | A8 | B5 | C5 | A8 | B6 | C5 | A8 | B7 | C5 | A8 | B11 | C5 | A8 | B13 | C5 | A5 | B14 | C5 | A8 | B15 | C5 | A8 | B16 | C5 | A8 | B17 | C5 |
| A8 | B4 | C6 | A8 | B5 | C6 | A8 | B6 | C6 | A8 | B7 | C6 | A8 | B11 | C6 | A8 | B13 | C6 | A5 | B14 | C6 | A8 | B15 | C6 | A8 | B16 | C6 | A8 | B17 | C6 |
| A8 | B4 | C7 | A8 | B5 | C7 | A8 | B6 | C7 | A8 | B7 | C7 | A8 | B11 | C7 | A8 | B13 | C7 | A5 | B14 | C7 | A8 | B15 | C7 | A8 | B16 | C7 | A8 | B17 | C7 |
| A8 | B4 | C8 | A8 | B5 | C8 | A8 | B6 | C8 | A8 | B7 | C8 | A8 | B11 | C8 | A8 | B13 | C8 | A5 | B14 | C8 | A8 | B15 | C8 | A8 | B16 | C8 | A8 | B17 | C8 |
| A8 | B4 | C9 | A8 | B5 | C9 | A8 | B6 | C9 | A8 | B7 | C9 | A8 | B11 | C9 | A8 | B13 | C9 | A5 | B14 | C9 | A8 | B15 | C9 | A8 | B16 | C9 | A8 | B17 | C9 |
| A8 | B4 | C10 | A8 | B5 | C10 | A8 | B6 | C10 | A8 | B7 | C10 | A8 | B11 | C10 | A8 | B13 | C10 | A5 | B14 | C10 | A8 | B15 | C10 | A8 | B16 | C10 | A8 | B17 | C10 |
| A8 | B4 | C11 | A8 | B5 | C11 | A8 | B6 | C11 | A5 | B7 | C11 | A8 | B11 | C11 | A8 | B13 | C11 | A5 | B14 | C11 | A8 | B15 | C11 | A8 | B16 | C11 | A8 | B17 | C11 |
| A8 | B4 | C12 | A8 | B5 | C12 | A8 | B6 | C12 | A8 | B7 | C12 | A8 | B11 | C12 | A8 | B13 | C12 | A5 | B14 | C12 | A8 | B15 | C12 | A8 | B16 | C12 | A8 | B17 | C12 |
| A8 | B4 | C13 | A8 | B5 | C13 | A8 | B6 | C13 | A8 | B7 | C13 | A8 | B11 | C13 | A8 | B13 | C13 | A5 | B14 | C13 | A8 | B15 | C13 | A8 | B16 | C13 | A8 | B17 | C13 |
| A8 | B4 | C14 | A8 | B5 | C14 | A8 | B6 | C14 | A8 | B7 | C14 | A8 | B11 | C14 | A8 | B13 | C14 | A5 | B14 | C14 | A8 | B15 | C14 | A8 | B16 | C14 | A8 | B17 | C14 |
| A8 | B4 | C15 | A8 | B5 | C15 | A8 | B6 | C15 | A8 | B7 | C15 | A8 | B11 | C15 | A8 | B13 | C15 | A5 | B14 | C15 | A8 | B15 | C15 | A8 | B16 | C15 | A8 | B17 | C15 |
| A8 | B4 | C16 | A8 | B5 | C16 | A8 | B6 | C16 | A8 | B7 | C16 | A8 | B11 | C16 | A8 | B13 | C16 | A5 | B14 | C16 | A8 | B15 | C16 | A8 | B16 | C16 | A8 | B17 | C16 |
| A8 | B4 | C17 | A8 | B5 | C17 | A8 | B6 | C17 | A8 | B7 | C17 | A8 | B11 | C17 | A8 | B13 | C17 | A5 | B14 | C17 | A8 | B15 | C17 | A8 | B16 | C17 | A8 | B17 | C17 |
| A8 | B4 | C18 | A8 | B5 | C18 | A8 | B6 | C18 | A8 | B7 | C18 | A8 | B11 | C18 | A8 | B13 | C18 | A5 | B14 | C18 | A8 | B15 | C18 | A8 | B16 | C18 | A8 | B17 | C18 |
| A8 | B4 | C19 | A8 | B5 | C19 | A8 | B6 | C19 | A8 | B7 | C19 | A8 | B11 | C19 | A8 | B13 | C19 | A5 | B14 | C19 | A8 | B15 | C19 | A8 | B16 | C19 | A8 | B17 | C19 |
| A8 | B4 | C20 | A8 | B5 | C20 | A8 | B6 | C20 | A8 | B7 | C20 | A8 | B11 | C20 | A8 | B13 | C20 | A5 | B14 | C20 | A8 | B15 | C20 | A8 | B16 | C20 | A8 | B17 | C20 |
| A8 | B4 | C21 | A8 | B5 | C21 | A8 | B6 | C21 | A8 | B7 | C21 | A8 | B11 | C21 | A8 | B13 | C21 | A5 | B14 | C21 | A8 | B15 | C21 | A8 | B16 | C21 | A8 | B17 | C21 |
| A8 | B4 | C22 | A8 | B5 | C22 | A8 | B6 | C22 | A8 | B7 | C22 | A8 | B11 | C22 | A8 | B13 | C22 | A5 | B14 | C22 | A8 | B15 | C22 | A8 | B16 | C22 | A8 | B17 | C22 |
| A8 | B4 | C23 | A8 | B5 | C23 | A8 | B6 | C23 | A8 | B7 | C23 | A8 | B11 | C23 | A8 | B13 | C23 | A5 | B14 | C23 | A8 | B15 | C23 | A8 | B16 | C23 | A8 | B17 | C23 |
| A8 | B4 | C24 | A8 | B5 | C24 | A8 | B6 | C24 | A8 | B7 | C24 | A8 | B11 | C24 | A8 | B13 | C24 | A5 | B14 | C24 | A8 | B15 | C24 | A8 | B16 | C24 | A8 | B17 | C24 |
| A8 | B4 | C25 | A8 | B5 | C25 | A8 | B6 | C25 | A8 | B7 | C25 | A8 | B11 | C25 | A8 | B13 | C25 | A5 | B14 | C25 | A8 | B15 | C25 | A8 | B16 | C25 | A8 | B17 | C25 |
| A8 | B4 | C26 | A8 | B5 | C26 | A8 | B6 | C26 | A8 | B7 | C26 | A8 | B11 | C26 | A8 | B13 | C26 | A5 | B14 | C26 | A8 | B15 | C26 | A8 | B16 | C26 | A8 | B17 | C26 |
| A8 | B4 | C27 | A8 | B5 | C27 | A8 | B6 | C27 | A8 | B7 | C27 | A8 | B11 | C27 | A8 | B13 | C27 | A5 | B14 | C27 | A8 | B15 | C27 | A8 | B16 | C27 | A8 | B17 | C27 |
| A8 | B4 | C28 | A8 | B5 | C28 | A8 | B6 | C28 | A8 | B7 | C28 | A8 | B11 | C28 | A8 | B13 | C28 | A5 | B14 | C28 | A8 | B15 | C28 | A8 | B16 | C28 | A8 | B17 | C28 |
| A8 | B4 | C79 | A8 | B5 | C29 | A8 | B6 | C29 | A8 | B7 | C29 | A8 | B11 | C29 | A8 | B13 | C29 | A5 | B14 | C29 | A8 | B15 | C29 | A8 | B16 | C29 | A8 | B17 | C29 |
| A8 | B4 | C30 | A8 | B5 | C30 | A8 | B6 | C30 | A8 | B7 | C30 | A8 | B11 | C30 | A8 | B13 | C30 | A5 | B14 | C30 | A8 | B15 | C30 | A8 | B16 | C30 | A8 | B17 | C30 |
| A8 | B4 | C31 | A8 | B5 | C31 | A8 | B6 | C31 | A8 | B7 | C31 | A8 | B11 | C31 | A8 | B13 | C31 | A5 | B14 | C31 | A8 | B15 | C31 | A8 | B16 | C31 | A8 | B17 | C31 |
| A8 | B4 | C32 | A8 | B5 | C32 | A8 | B6 | C32 | A8 | B7 | C32 | A8 | B11 | C32 | A8 | B13 | C32 | A5 | B14 | C32 | A8 | B15 | C32 | A8 | B16 | C32 | A8 | B17 | C32 |
| A8 | B4 | C33 | A8 | B5 | C33 | A8 | B6 | C33 | A8 | B7 | C33 | A8 | B11 | C33 | A8 | B13 | C33 | A5 | B14 | C33 | A8 | B15 | C33 | A8 | B16 | C33 | A8 | B17 | C33 |
| A8 | B4 | C34 | A8 | B5 | C34 | A8 | B6 | C34 | A8 | B7 | C34 | A8 | B11 | C34 | A8 | B13 | C34 | A5 | B14 | C34 | A8 | B15 | C34 | A8 | B16 | C34 | A8 | B17 | C34 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A8 | B4 | C35 | A8 | B5 | C35 | A8 | B6 | C35 | A8 | B7 | C15 | A8 | B11 | C35 | A8 | B13 | C35 | A5 | B14 | C35 | A8 | B15 | C35 | A8 | B16 | C35 | A8 | B17 | C35 |
| A8 | B4 | C36 | A8 | B5 | C36 | A8 | B6 | C36 | A8 | B7 | C16 | A8 | B11 | C36 | A8 | B13 | C36 | A5 | B14 | C36 | A8 | B15 | C36 | A8 | B16 | C36 | A8 | B17 | C36 |
| A8 | B4 | C37 | A8 | B5 | C37 | A8 | B6 | C37 | A8 | B7 | C37 | A8 | B11 | C37 | A8 | B13 | C37 | A5 | B14 | C37 | A8 | B15 | C37 | A8 | B16 | C37 | A8 | B17 | C37 |
| A8 | B4 | C38 | A8 | B5 | C38 | A8 | B6 | C38 | A8 | B7 | C38 | A8 | B11 | C38 | A8 | B13 | C38 | A5 | B14 | C38 | A8 | B15 | C38 | A8 | B16 | C38 | A8 | B17 | C38 |
| A8 | B4 | C39 | A8 | B5 | C39 | A8 | B6 | C39 | A8 | B7 | C39 | A8 | B11 | C39 | A8 | B13 | C39 | A5 | B14 | C39 | A8 | B15 | C39 | A8 | B16 | C39 | A8 | B17 | C39 |
| A8 | B4 | C40 | A8 | B5 | C40 | A8 | B6 | C40 | A8 | B7 | C40 | A8 | B11 | C40 | A8 | B13 | C40 | A5 | B14 | C40 | A8 | B15 | C40 | A8 | B16 | C40 | A8 | B17 | C40 |
| A8 | B4 | C41 | A8 | B5 | C41 | A8 | B6 | C41 | A8 | B7 | C41 | A8 | B11 | C41 | A8 | B13 | C41 | A5 | B14 | C41 | A8 | B15 | C41 | A8 | B16 | C41 | A8 | B17 | C41 |
| A9 | B4 | C1 | A9 | B5 | C1 | A9 | B6 | C1 | A9 | B7 | C1 | A9 | B11 | C1 | A9 | B13 | C1 | A9 | B14 | C1 | A9 | B15 | C1 | A9 | B16 | C1 | A9 | B17 | C1 |
| A9 | B4 | C2 | A9 | B5 | C2 | A9 | B6 | C2 | A9 | B7 | C2 | A9 | B11 | C2 | A9 | B13 | C2 | A9 | B14 | C2 | A9 | B15 | C2 | A9 | B)6 | C2 | A9 | B17 | C2 |
| A9 | B4 | C3 | A9 | B5 | C3 | A9 | B6 | C3 | A9 | B7 | C3 | A9 | B11 | C3 | A9 | B13 | C3 | A9 | B14 | C3 | A9 | B15 | C3 | A9 | B16 | C3 | A9 | B17 | C3 |
| A9 | B4 | C4 | A9 | B5 | C4 | A9 | B6 | C4 | A9 | B7 | C4 | A9 | B11 | C4 | A9 | B13 | C4 | A9 | B14 | C4 | A9 | B15 | C4 | A9 | B16 | C4 | A9 | B17 | C4 |
| A9 | B4 | C5 | A9 | B5 | C5 | A9 | B6 | C5 | A9 | B7 | C5 | A9 | B11 | C5 | A9 | B13 | C5 | A9 | B14 | C5 | A9 | B15 | C5 | A9 | B16 | C5 | A9 | B17 | C5 |
| A9 | B4 | C6 | A9 | B5 | C6 | A9 | B6 | C6 | A9 | B7 | C6 | A9 | B11 | C6 | A9 | B13 | C6 | A9 | B14 | C6 | A9 | B15 | C6 | A9 | B16 | C6 | A9 | B17 | C6 |
| A9 | B4 | C7 | A9 | B5 | C7 | A9 | B6 | C7 | A9 | B7 | C7 | A9 | B11 | C7 | A9 | B13 | C7 | A9 | B14 | C7 | A9 | B15 | C7 | A9 | B16 | C7 | A9 | B17 | C7 |
| A9 | B4 | C8 | A9 | B5 | C8 | A9 | B6 | C8 | A9 | B7 | C8 | A9 | B11 | C8 | A9 | B13 | C8 | A9 | B14 | C8 | A9 | B15 | C8 | A9 | B16 | C8 | A9 | B17 | C8 |
| A9 | B4 | C9 | A9 | B5 | C9 | A9 | B6 | C9 | A9 | B7 | C9 | A9 | B11 | C9 | A9 | B13 | C9 | A9 | B14 | C9 | A9 | B15 | C9 | A9 | B16 | C9 | A9 | B17 | C9 |
| A9 | B4 | C10 | A9 | B5 | C10 | A9 | B6 | C10 | A9 | B7 | C10 | A9 | B11 | C10 | A9 | B13 | C10 | A9 | B14 | C10 | A9 | B15 | C10 | A9 | B16 | C10 | A9 | B17 | C10 |
| A9 | B4 | C11 | A9 | B5 | C11 | A9 | B6 | C11 | A9 | B7 | C11 | A9 | B11 | C11 | A9 | B13 | C11 | A9 | B14 | C11 | A9 | B15 | C11 | A9 | B16 | C11 | A9 | B17 | C11 |
| A9 | B4 | C12 | A9 | B5 | C12 | A9 | B6 | C12 | A9 | B7 | C12 | A9 | B11 | C12 | A9 | B13 | C12 | A9 | B14 | C12 | A9 | B15 | C12 | A9 | B16 | C12 | A9 | B17 | C12 |
| A9 | B4 | C13 | A9 | B5 | C13 | A9 | B6 | C13 | A9 | B7 | C13 | A9 | B11 | C13 | A9 | B13 | C13 | A9 | B14 | C13 | A9 | B15 | C13 | A9 | B16 | C13 | A9 | B17 | C13 |
| A9 | B4 | C14 | A9 | B5 | C14 | A9 | B6 | C14 | A9 | B7 | C14 | A9 | B11 | C14 | A9 | B13 | C14 | A9 | B14 | C14 | A9 | B15 | C14 | A9 | B16 | C14 | A9 | B17 | C14 |
| A9 | B4 | C15 | A9 | B5 | C15 | A9 | B6 | C15 | A9 | B7 | C15 | A9 | B11 | C15 | A9 | B13 | C15 | A9 | B14 | C15 | A9 | B15 | C15 | A9 | B16 | C15 | A9 | B17 | C15 |
| A9 | B4 | C16 | A9 | B5 | C16 | A9 | B6 | C16 | A9 | B7 | C16 | A9 | B11 | C16 | A9 | B13 | C16 | A9 | B14 | C16 | A9 | B15 | C16 | A9 | B16 | C16 | A9 | B17 | C16 |
| A9 | B4 | C17 | A9 | B5 | C17 | A9 | B6 | C17 | A9 | B7 | C17 | A9 | B11 | C17 | A9 | B13 | C17 | A9 | B14 | C17 | A9 | B15 | C17 | A9 | B16 | C17 | A9 | B17 | C17 |
| A9 | B4 | C18 | A9 | B5 | C18 | A9 | B6 | C18 | A9 | B7 | C18 | A9 | B11 | C18 | A9 | B13 | C18 | A9 | B14 | C18 | A9 | B15 | C18 | A9 | B16 | C18 | A9 | B17 | C18 |
| A9 | B4 | C19 | A9 | B5 | C19 | A9 | B6 | C19 | A9 | B7 | C19 | A9 | B11 | C19 | A9 | B13 | C19 | A9 | B14 | C19 | A9 | B15 | C19 | A9 | B16 | C19 | A9 | B17 | C19 |
| A9 | B4 | C20 | A9 | B5 | C20 | A9 | B6 | C20 | A9 | B7 | C20 | A9 | B11 | C20 | A9 | B13 | C20 | A9 | B14 | C20 | A9 | B15 | C20 | A9 | B16 | C20 | A9 | B17 | C20 |
| A9 | B4 | C21 | A9 | B5 | C21 | A9 | B6 | C21 | A9 | B7 | C21 | A9 | B11 | C21 | A9 | B13 | C21 | A9 | B14 | C21 | A9 | B15 | C21 | A9 | B16 | C21 | A9 | B17 | C21 |
| A9 | B4 | C22 | A9 | B5 | C22 | A9 | B6 | C22 | A9 | B7 | C22 | A9 | B11 | C22 | A9 | B13 | C22 | A9 | B14 | C22 | A9 | B15 | C22 | A9 | B16 | C22 | A9 | B17 | C22 |
| A9 | B4 | C23 | A9 | B5 | C23 | A9 | B6 | C23 | A9 | B7 | C23 | A9 | B11 | C23 | A9 | B13 | C23 | A9 | B14 | C23 | A9 | B15 | C23 | A9 | B16 | C23 | A9 | B17 | C23 |
| A9 | B4 | C24 | A9 | B5 | C24 | A9 | B6 | C24 | A9 | B7 | C24 | A9 | B11 | C24 | A9 | B13 | C24 | A9 | B14 | C24 | A9 | B15 | C24 | A9 | B16 | C24 | A9 | B17 | C24 |
| A9 | B4 | C25 | A9 | B5 | C25 | A9 | B6 | C25 | A9 | B7 | C25 | A9 | B11 | C25 | A9 | B13 | C25 | A9 | B14 | C25 | A9 | B15 | C25 | A9 | B16 | C25 | A9 | B17 | C25 |
| A9 | B4 | C26 | A9 | B5 | C26 | A9 | B6 | C26 | A9 | B7 | C26 | A9 | B11 | C26 | A9 | B13 | C26 | A9 | B14 | C26 | A9 | B15 | C26 | A9 | B16 | C26 | A9 | B17 | C26 |
| A9 | B4 | C27 | A9 | B5 | C27 | A9 | B6 | C27 | A9 | B7 | C27 | A9 | B11 | C27 | A9 | B13 | C27 | A9 | B14 | C27 | A9 | B15 | C27 | A9 | B16 | C27 | A9 | B17 | C27 |
| A9 | B4 | C28 | A9 | B5 | C28 | A9 | B6 | C28 | A9 | B7 | C28 | A9 | B11 | C28 | A9 | B13 | C28 | A9 | B14 | C28 | A9 | B15 | C28 | A9 | B16 | C28 | A9 | B17 | C28 |
| A9 | B4 | C29 | A9 | B5 | C29 | A9 | B6 | C29 | A9 | B7 | C29 | A9 | B11 | C29 | A9 | B13 | C29 | A9 | B14 | C29 | A9 | B15 | C29 | A9 | B16 | C29 | A9 | B17 | C29 |
| A9 | B4 | C30 | A9 | B5 | C30 | A9 | B6 | C30 | A9 | B7 | C30 | A9 | B11 | C30 | A9 | B13 | C30 | A9 | B14 | C30 | A9 | B15 | C30 | A9 | B16 | C30 | A9 | B17 | C30 |
| A9 | B4 | C31 | A9 | B5 | C31 | A9 | B6 | C31 | A9 | B7 | C31 | A9 | B11 | C31 | A9 | B13 | C31 | A9 | B14 | C31 | A9 | B15 | C31 | A9 | B16 | C31 | A9 | B17 | C31 |
| A9 | B4 | C32 | A9 | B5 | C32 | A9 | B6 | C32 | A9 | B7 | C32 | A9 | B11 | C32 | A9 | B13 | C32 | A9 | B14 | C32 | A9 | B15 | C32 | A9 | B16 | C32 | A9 | B17 | C32 |
| A9 | B4 | C33 | A9 | B5 | C33 | A9 | B6 | C33 | A9 | B7 | C33 | A9 | B11 | C33 | A9 | B13 | C33 | A9 | B14 | C33 | A9 | B15 | C33 | A9 | B16 | C33 | A9 | B17 | C33 |
| A9 | B4 | C34 | A9 | B5 | C34 | A9 | B6 | C34 | A9 | B7 | C34 | A9 | B11 | C34 | A9 | B13 | C34 | A9 | B14 | C34 | A9 | B15 | C34 | A9 | B16 | C34 | A9 | B17 | C34 |
| A9 | B4 | C35 | A9 | B5 | C35 | A9 | B6 | C35 | A9 | B7 | C35 | A9 | B11 | C35 | A9 | B13 | C35 | A9 | B14 | C35 | A9 | B15 | C35 | A9 | B16 | C35 | A9 | B17 | C35 |
| A9 | B4 | C36 | A9 | B5 | C36 | A9 | B6 | C36 | A9 | B7 | C36 | A9 | B11 | C36 | A9 | B13 | C36 | A9 | B14 | C36 | A9 | B15 | C36 | A9 | B16 | C36 | A9 | B17 | C36 |
| A9 | B4 | C37 | A9 | B5 | C37 | A9 | B6 | C37 | A9 | B7 | C37 | A9 | B11 | C37 | A9 | B13 | C37 | A9 | B14 | C37 | A9 | B15 | C37 | A9 | B16 | C37 | A9 | B17 | C37 |
| A9 | B4 | C38 | A9 | B5 | C38 | A9 | B6 | C38 | A9 | B7 | C38 | A9 | B11 | C38 | A9 | B13 | C38 | A9 | B14 | C38 | A9 | B15 | C38 | A9 | B16 | C38 | A9 | B17 | C38 |
| A9 | B4 | C39 | A9 | B5 | C39 | A9 | B6 | C39 | A9 | B7 | C39 | A9 | B11 | C39 | A9 | B13 | C39 | A9 | B14 | C39 | A9 | B15 | C39 | A9 | B16 | C39 | A9 | B17 | C39 |
| A9 | B4 | C40 | A9 | B5 | C40 | A9 | B6 | C40 | A9 | B7 | C40 | A9 | B11 | C40 | A9 | B13 | C40 | A9 | B14 | C40 | A9 | B15 | C40 | A9 | B16 | C40 | A9 | B17 | C40 |
| A9 | B4 | C41 | A9 | B5 | C41 | A9 | B6 | C41 | A9 | B7 | C41 | A9 | B11 | C41 | A9 | B13 | C41 | A9 | B14 | C41 | A9 | B15 | C41 | A9 | B16 | C41 | A9 | B17 | C41 |
| A10 | B4 | C1 | A10 | B5 | C1 | A10 | B6 | C1 | A10 | B7 | C1 | A10 | B11 | C1 | A10 | B13 | C1 | A10 | B14 | C1 | A10 | B15 | C1 | A10 | B16 | C1 | A10 | B17 | C1 |
| A10 | B4 | C2 | A10 | B5 | C2 | A10 | B6 | C2 | A10 | B7 | C2 | A10 | B11 | C2 | A10 | B13 | C2 | A10 | B14 | C2 | A10 | B15 | C2 | A10 | B16 | C2 | A10 | B17 | C2 |
| A10 | B4 | C3 | A10 | B5 | C3 | A10 | B6 | C3 | A10 | B7 | C3 | A10 | B11 | C3 | A10 | B13 | C3 | A10 | B14 | C3 | A10 | B15 | C3 | A10 | B16 | C3 | A10 | B17 | C3 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A10 | B4 | C4 | A10 | B5 | C4 | A10 | B6 | C4 | A10 | B7 | C4 | A10 | B11 | C4 | A10 | B13 | C4 | A10 | B14 | C4 | A10 | B15 | C4 | A10 | B16 | C4 | A10 | B17 | C4 |
| A10 | B4 | C5 | A10 | B5 | C5 | A10 | B6 | C5 | A10 | B7 | C5 | A10 | B11 | C5 | A10 | B13 | C5 | A10 | B14 | C5 | A10 | B15 | C5 | A10 | B16 | C5 | A10 | B17 | C5 |
| A10 | B4 | C6 | A10 | B5 | C6 | A10 | B6 | C6 | A10 | B7 | C6 | A10 | B11 | C6 | A10 | B13 | C6 | A10 | B14 | C6 | A10 | B15 | C6 | A10 | B16 | C6 | A10 | B17 | C6 |
| A10 | B4 | C7 | A10 | B5 | C7 | A10 | B6 | C7 | A10 | B7 | C7 | A10 | B11 | C7 | A10 | B13 | C7 | A10 | B14 | C7 | A10 | B15 | C7 | A10 | B16 | C7 | A10 | B17 | C7 |
| A10 | B4 | C8 | A10 | B5 | C8 | A10 | B6 | C8 | A10 | B7 | C8 | A10 | B11 | C8 | A10 | B13 | C8 | A10 | B14 | C8 | A10 | B15 | C8 | A10 | B16 | C8 | A10 | B17 | C8 |
| A10 | B4 | C9 | A10 | B5 | C9 | A10 | B6 | C9 | A10 | B7 | C9 | A10 | B11 | C9 | A10 | B13 | C9 | A10 | B14 | C9 | A10 | B15 | C9 | A10 | B16 | C9 | A10 | B17 | C9 |
| A10 | B4 | C10 | A10 | B5 | C10 | A10 | B6 | C10 | A10 | B7 | C10 | A10 | B11 | C10 | A10 | B13 | C10 | A10 | B14 | C10 | A10 | B15 | C10 | A10 | B16 | C10 | A10 | B17 | C10 |
| A10 | B4 | C11 | A10 | B5 | C11 | A10 | B6 | C11 | A10 | B7 | C11 | A10 | B11 | C11 | A10 | B13 | C11 | A10 | B14 | C11 | A10 | B15 | C11 | A10 | B16 | C11 | A10 | B17 | C11 |
| A10 | B4 | C12 | A10 | B5 | C12 | A10 | B6 | C12 | A10 | B7 | C12 | A10 | B11 | C12 | A10 | B13 | C12 | A10 | B14 | C12 | A10 | B15 | C12 | A10 | B16 | C12 | A10 | B17 | C12 |
| A10 | B4 | C13 | A10 | B5 | C13 | A10 | B6 | C13 | A10 | B7 | C13 | A10 | B11 | C13 | A10 | B13 | C13 | A10 | B14 | C13 | A10 | B15 | C13 | A10 | B16 | C13 | A10 | B17 | C13 |
| A10 | B4 | C14 | A10 | B5 | C14 | A10 | B6 | C14 | A10 | B7 | C14 | A10 | B11 | C14 | A10 | B13 | C14 | A10 | B14 | C14 | A10 | B15 | C14 | A10 | B16 | C14 | A10 | B17 | C14 |
| A10 | B4 | C15 | A10 | B5 | C15 | A10 | B6 | C15 | A10 | B7 | C15 | A10 | B11 | C15 | A10 | B13 | C15 | A10 | B14 | C15 | A10 | B15 | C15 | A10 | B16 | C15 | A10 | B17 | C15 |
| A10 | B4 | C16 | A10 | B5 | C16 | A10 | B6 | C16 | A10 | B7 | C16 | A10 | B11 | C16 | A10 | B13 | C16 | A10 | B14 | C16 | A10 | B15 | C16 | A10 | B16 | C16 | A10 | B17 | C16 |
| A10 | B4 | C17 | A10 | B5 | C17 | A10 | B6 | C17 | A10 | B7 | C17 | A10 | B11 | C17 | A10 | B13 | C17 | A10 | B14 | C17 | A10 | B15 | C17 | A10 | B16 | C17 | A10 | B17 | C17 |
| A10 | B4 | C18 | A10 | B5 | C18 | A10 | B6 | C18 | A10 | B7 | C18 | A10 | B11 | C18 | A10 | B13 | C18 | A10 | B14 | C18 | A10 | B15 | C18 | A10 | B16 | C18 | A10 | B17 | C18 |
| A10 | B4 | C19 | A10 | B5 | C19 | A10 | B6 | C19 | A10 | B7 | C19 | A10 | B11 | C19 | A10 | B13 | C19 | A10 | B14 | C19 | A10 | B15 | C19 | A10 | B16 | C19 | A10 | B17 | C19 |
| A10 | B4 | C20 | A10 | B5 | C20 | A10 | B6 | C20 | A10 | B7 | C20 | A10 | B11 | C20 | A10 | B13 | C20 | A10 | B14 | C20 | A10 | B15 | C20 | A10 | B16 | C20 | A10 | B17 | C20 |
| A10 | B4 | C21 | A10 | B5 | C21 | A10 | B6 | C21 | A10 | B7 | C21 | A10 | B11 | C21 | A10 | B13 | C21 | A10 | B14 | C21 | A10 | B15 | C21 | A10 | B16 | C21 | A10 | B17 | C21 |
| A10 | B4 | C22 | A10 | B5 | C22 | A10 | B6 | C22 | A10 | B7 | C22 | A10 | B11 | C22 | A10 | B13 | C22 | A10 | B14 | C22 | A10 | B15 | C22 | A10 | B16 | C22 | A10 | B17 | C22 |
| A10 | B4 | C23 | A10 | B5 | C23 | A10 | B6 | C23 | A10 | B7 | C23 | A10 | B11 | C23 | A10 | B13 | C23 | A10 | B14 | C23 | A10 | B15 | C23 | A10 | B16 | C23 | A10 | B17 | C23 |
| A10 | B4 | C24 | A10 | B5 | C24 | A10 | B6 | C24 | A10 | B7 | C24 | A10 | B11 | C24 | A10 | B13 | C24 | A10 | B14 | C24 | A10 | B15 | C24 | A10 | B16 | C24 | A10 | B17 | C24 |
| A10 | B4 | C25 | A10 | B5 | C25 | A10 | B6 | C25 | A10 | B7 | C25 | A10 | B11 | C25 | A10 | B13 | C25 | A10 | B14 | C25 | A10 | B15 | C25 | A10 | B16 | C25 | A10 | B17 | C25 |
| A10 | B4 | C26 | A10 | B5 | C26 | A10 | B6 | C26 | A10 | B7 | C26 | A10 | B11 | C26 | A10 | B13 | C26 | A10 | B14 | C26 | A10 | B15 | C26 | A10 | B16 | C26 | A10 | B17 | C26 |
| A10 | B4 | C27 | A10 | B5 | C27 | A10 | B6 | C27 | A10 | B7 | C27 | A10 | B11 | C27 | A10 | B13 | C27 | A10 | B14 | C27 | A10 | B15 | C27 | A10 | B16 | C27 | A10 | B17 | C27 |
| A10 | B4 | C28 | A10 | B5 | C28 | A10 | B6 | C28 | A10 | B7 | C28 | A10 | B11 | C28 | A10 | B13 | C28 | A10 | B14 | C28 | A10 | B15 | C28 | A10 | B16 | C28 | A10 | B17 | C28 |
| A10 | B4 | C29 | A10 | B5 | C29 | A10 | B6 | C29 | A10 | B7 | C29 | A10 | B11 | C29 | A10 | B13 | C29 | A10 | B14 | C29 | A10 | B15 | C29 | A10 | B16 | C29 | A10 | B17 | C29 |
| A10 | B4 | C30 | A10 | B5 | C30 | A10 | B6 | C30 | A10 | B7 | C30 | A10 | B11 | C30 | A10 | B13 | C30 | A10 | B14 | C30 | A10 | B15 | C30 | A10 | B16 | C30 | A10 | B17 | C31 |
| A10 | B4 | C31 | A10 | B5 | C31 | A10 | B6 | C31 | A10 | B7 | C31 | A10 | B11 | C31 | A10 | B13 | C31 | A10 | B14 | C31 | A10 | B15 | C31 | A10 | B16 | C31 | A10 | B17 | C31 |
| A10 | B4 | C32 | A10 | B5 | C32 | A10 | B6 | C32 | A10 | B7 | C32 | A10 | B11 | C32 | A10 | B13 | C32 | A10 | B14 | C32 | A10 | B15 | C32 | A10 | B16 | C32 | A10 | B17 | C32 |
| A10 | B4 | C33 | A10 | B5 | C33 | A10 | B6 | C33 | A10 | B7 | C13 | A10 | B11 | C33 | A10 | B13 | C33 | A10 | B14 | C33 | A10 | B15 | C33 | A10 | B16 | C33 | A10 | B17 | C33 |
| A10 | B4 | C34 | A10 | B5 | C34 | A10 | B6 | C34 | A10 | B7 | C14 | A10 | B11 | C34 | A10 | B13 | C34 | A10 | B14 | C34 | A10 | B15 | C34 | A10 | B16 | C34 | A10 | B17 | C34 |
| A10 | B4 | C35 | A10 | B5 | C35 | A10 | B6 | C35 | A10 | B7 | C35 | A10 | B11 | C35 | A10 | B13 | C35 | A10 | B14 | C35 | A10 | B15 | C35 | A10 | B16 | C35 | A10 | B17 | C35 |
| A10 | B4 | C36 | A10 | B5 | C36 | A10 | B6 | C36 | A10 | B7 | C36 | A10 | B11 | C36 | A10 | B13 | C36 | A10 | B14 | C36 | A10 | B15 | C36 | A10 | B16 | C36 | A10 | B17 | C36 |
| A10 | B4 | C37 | A10 | B5 | C37 | A10 | B6 | C37 | A10 | B7 | C37 | A10 | B11 | C37 | A10 | B13 | C37 | A10 | B14 | C37 | A10 | B15 | C37 | A10 | B16 | C37 | A10 | B17 | C37 |
| A10 | B4 | C38 | A10 | B5 | C38 | A10 | B6 | C38 | A10 | B7 | C38 | A10 | B11 | C38 | A10 | B13 | C38 | A10 | B14 | C38 | A10 | B15 | C38 | A10 | B16 | C38 | A10 | B17 | C38 |
| A10 | B4 | C39 | A10 | B5 | C39 | A10 | B6 | C39 | A10 | B7 | C39 | A10 | B11 | C39 | A10 | B13 | C39 | A10 | B14 | C39 | A10 | B15 | C39 | A10 | B16 | C39 | A10 | B17 | C39 |
| A10 | B4 | C40 | A10 | B5 | C40 | A10 | B6 | C40 | A10 | B7 | C40 | A10 | B11 | C40 | A10 | B13 | C40 | A10 | B14 | C40 | A10 | B15 | C40 | A10 | B16 | C40 | A10 | B17 | C40 |
| A10 | B4 | C41 | A10 | B5 | C41 | A10 | B6 | C41 | A10 | B7 | C41 | A10 | B11 | C41 | A10 | B13 | C41 | A10 | B14 | C41 | A10 | B15 | C41 | A10 | B16 | C41 | A10 | B17 | C41 |
| A11 | B4 | C1 | A11 | B5 | C1 | A11 | B6 | C1 | A11 | B7 | C1 | A11 | B11 | C1 | A11 | B13 | C1 | A11 | B14 | C1 | A11 | B15 | C1 | A11 | B16 | C1 | A11 | B17 | C1 |
| A11 | B4 | C2 | A11 | B5 | C2 | A11 | B6 | C2 | A11 | B7 | C2 | A11 | B11 | C2 | A11 | B13 | C2 | A11 | B14 | C2 | A11 | B15 | C2 | A11 | B16 | C2 | A11 | B17 | C2 |
| A11 | B4 | C3 | A11 | B5 | C3 | A11 | B6 | C3 | A11 | B7 | C3 | A11 | B11 | C3 | A11 | B13 | C3 | A11 | B14 | C3 | A11 | B15 | C3 | A11 | B16 | C3 | A11 | B17 | C3 |
| A11 | B4 | C4 | A11 | B5 | C4 | A11 | B6 | C4 | A11 | B7 | C4 | A11 | B11 | C4 | A11 | B13 | C4 | A11 | B14 | C4 | A11 | B15 | C4 | A11 | B16 | C4 | A11 | B17 | C4 |
| A11 | B4 | C5 | A11 | B5 | C5 | A11 | B6 | C5 | A11 | B7 | C5 | A11 | B11 | C5 | A11 | B13 | C5 | A11 | B14 | C5 | A11 | B15 | C5 | A11 | B16 | C5 | A11 | B17 | C5 |
| A11 | B4 | C6 | A11 | B5 | C6 | A11 | B6 | C6 | A11 | B7 | C6 | A11 | B11 | C6 | A11 | B13 | C6 | A11 | B14 | C6 | A11 | B15 | C6 | A11 | B16 | C6 | A11 | B17 | C6 |
| A11 | B4 | C7 | A11 | B5 | C7 | A11 | B6 | C7 | A11 | B7 | C7 | A11 | B11 | C7 | A11 | B13 | C7 | A11 | B14 | C7 | A11 | B15 | C7 | A11 | B16 | C7 | A11 | B17 | C7 |
| A11 | B4 | C8 | A11 | B5 | C8 | A11 | B6 | C8 | A11 | B7 | C8 | A11 | B11 | C8 | A11 | B13 | C8 | A11 | B14 | C8 | A11 | B15 | C8 | A11 | B16 | C8 | A11 | B17 | C8 |
| A11 | B4 | C9 | A11 | B5 | C9 | A11 | B6 | C9 | A11 | B7 | C9 | A11 | B11 | C9 | A11 | B13 | C9 | A11 | B14 | C9 | A11 | B15 | C9 | A11 | B16 | C9 | A11 | B17 | C9 |
| A11 | B4 | C10 | A11 | B5 | C10 | A11 | B6 | C10 | A11 | B7 | C10 | A11 | B11 | C10 | A11 | B13 | C10 | A11 | B14 | C10 | A11 | B15 | C10 | A11 | B16 | C10 | A11 | B17 | C10 |
| A11 | B4 | C11 | A11 | B5 | C11 | A11 | B6 | C11 | A11 | B7 | C11 | A11 | B11 | C11 | A11 | B13 | C11 | A11 | B14 | C11 | A11 | B15 | C11 | A11 | B16 | C11 | A11 | B17 | C11 |
| A11 | B4 | C12 | A11 | B5 | C12 | A11 | B6 | C12 | A11 | B7 | C12 | A11 | B11 | C12 | A11 | B13 | C12 | A11 | B14 | C12 | A11 | B15 | C12 | A11 | B16 | C12 | A11 | B17 | C12 |
| A11 | B4 | C13 | A11 | B5 | C13 | A11 | B6 | C13 | A11 | B7 | C13 | A11 | B11 | C13 | A11 | B13 | C13 | A11 | B14 | C13 | A11 | B15 | C13 | A11 | B16 | C13 | A11 | B17 | C13 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A11 | B4 | C14 | A11 | B5 | C14 | A11 | B6 | C14 | A11 | B7 | C14 | A11 | B11 | C14 | A11 | B13 | C14 | A11 | B14 | C14 | A11 | B15 | C14 | A11 | B16 | C14 | A11 | B17 | C14 |
| A11 | B4 | C15 | A11 | B5 | C15 | A11 | B6 | C15 | A11 | B7 | C15 | A11 | B11 | C15 | A11 | B13 | C15 | A11 | B14 | C15 | A11 | B15 | C15 | A11 | B16 | C15 | A11 | B17 | C15 |
| A11 | B4 | C16 | A11 | B5 | C16 | A11 | B6 | C16 | A11 | B7 | C16 | A11 | B11 | C16 | A11 | B13 | C16 | A11 | B14 | C16 | A11 | B15 | C16 | A11 | B16 | C16 | A11 | B17 | C16 |
| A11 | B4 | C17 | A11 | B5 | C17 | A11 | B6 | C17 | A11 | B7 | C17 | A11 | B11 | C17 | A11 | B13 | C17 | A11 | B14 | C17 | A11 | B15 | C17 | A11 | B16 | C17 | A11 | B17 | C17 |
| A11 | B4 | C18 | A11 | B5 | C18 | A11 | B6 | C18 | A11 | B7 | C18 | A11 | B11 | C18 | A11 | B13 | C18 | A11 | B14 | C18 | A11 | B15 | C18 | A11 | B16 | C18 | A11 | B17 | C18 |
| A11 | B4 | C19 | A11 | B5 | C19 | A11 | B6 | C19 | A11 | B7 | C19 | A11 | B11 | C19 | A11 | B13 | C19 | A11 | B14 | C19 | A11 | B15 | C19 | A11 | B16 | C19 | A11 | B17 | C19 |
| A11 | B4 | C20 | A11 | B5 | C20 | A11 | B6 | C10 | A11 | B7 | C20 | A11 | B11 | C20 | A11 | B13 | C20 | A11 | B14 | C20 | A11 | B15 | C20 | A11 | B16 | C20 | A11 | B17 | C20 |
| A11 | B4 | C21 | A11 | B5 | C21 | A11 | B6 | C21 | A11 | B7 | C21 | A11 | B11 | C21 | A11 | B13 | C21 | A11 | B14 | C21 | A11 | B15 | C21 | A11 | B16 | C21 | A11 | B17 | C21 |
| A11 | B4 | C22 | A11 | B5 | C22 | A11 | B6 | C22 | A11 | B7 | C22 | A11 | B11 | C22 | A11 | B13 | C22 | A11 | B14 | C22 | A11 | B15 | C22 | A11 | B16 | C22 | A11 | B17 | C22 |
| A11 | B4 | C23 | A11 | B5 | C23 | A11 | B6 | C23 | A11 | B7 | C23 | A11 | B11 | C23 | A11 | B13 | C23 | A11 | B14 | C23 | A11 | B15 | C23 | A11 | B16 | C23 | A11 | B17 | C23 |
| A11 | B4 | C24 | A11 | B5 | C24 | A11 | B6 | C24 | A11 | B7 | C24 | A11 | B11 | C24 | A11 | B13 | C24 | A11 | B14 | C24 | A11 | B15 | C24 | A11 | B16 | C24 | A11 | B17 | C24 |
| A11 | B4 | C25 | A11 | B5 | C25 | A11 | B6 | C25 | A11 | B7 | C25 | A11 | B11 | C25 | A11 | B13 | C25 | A11 | B14 | C25 | A11 | B15 | C25 | A11 | B16 | C25 | A11 | B17 | C25 |
| A11 | B4 | C26 | A11 | B5 | C26 | A11 | B6 | C26 | A11 | B7 | C26 | A11 | B11 | C26 | A11 | B13 | C26 | A11 | B14 | C26 | A11 | B15 | C26 | A11 | B16 | C26 | A11 | B17 | C26 |
| A11 | B4 | C27 | A11 | B5 | C27 | A11 | B6 | C27 | A11 | B7 | C27 | A11 | B11 | C27 | A11 | B13 | C27 | A11 | B14 | C27 | A11 | B15 | C27 | A11 | B16 | C27 | A11 | B17 | C27 |
| A11 | B4 | C28 | A11 | B5 | C28 | A11 | B6 | C28 | A11 | B7 | C28 | A11 | B11 | C28 | A11 | B13 | C28 | A11 | B14 | C28 | A11 | B15 | C28 | A11 | B16 | C28 | A11 | B17 | C28 |
| A11 | B4 | C29 | A11 | B5 | C29 | A11 | B6 | C29 | A11 | B7 | C29 | A11 | B11 | C29 | A11 | B13 | C29 | A11 | B14 | C29 | A11 | B15 | C29 | A11 | B16 | C29 | A11 | B17 | C29 |
| A11 | B4 | C30 | A11 | B5 | C30 | A11 | B6 | C30 | A11 | B7 | C30 | A11 | B11 | C30 | A11 | B13 | C30 | A11 | B14 | C30 | A11 | B15 | C30 | A11 | B16 | C30 | A11 | B17 | C30 |
| A11 | B4 | C31 | A11 | B5 | C31 | A11 | B6 | C31 | A11 | B7 | C31 | A11 | B11 | C31 | A11 | B13 | C31 | A11 | B14 | C31 | A11 | B15 | C31 | A11 | B16 | C31 | A11 | B17 | C31 |
| A11 | B4 | C32 | A11 | B5 | C32 | A11 | B6 | C32 | A11 | B7 | C32 | A11 | B11 | C32 | A11 | B13 | C32 | A11 | B14 | C32 | A11 | B15 | C32 | A11 | B16 | C32 | A11 | B17 | C32 |
| A11 | B4 | C33 | A11 | B5 | C33 | A11 | B6 | C33 | A11 | B7 | C33 | A11 | B11 | C33 | A11 | B13 | C33 | A11 | B14 | C33 | A11 | B15 | C33 | A11 | B16 | C33 | A11 | B17 | C33 |
| A11 | B4 | C34 | A11 | B5 | C34 | A11 | B6 | C34 | A11 | B7 | C34 | A11 | B11 | C34 | A11 | B13 | C34 | A11 | B14 | C34 | A11 | B15 | C34 | A11 | B16 | C34 | A11 | B17 | C34 |
| A11 | B4 | C35 | A11 | B5 | C35 | A11 | B6 | C35 | A11 | B7 | C35 | A11 | B11 | C35 | A11 | B13 | C35 | A11 | B14 | C35 | A11 | B15 | C35 | A11 | B16 | C35 | A11 | B17 | C35 |
| A11 | B4 | C36 | A11 | B5 | C36 | A11 | B6 | C36 | A11 | B7 | C36 | A11 | B11 | C36 | A11 | B13 | C36 | A11 | B14 | C36 | A11 | B15 | C36 | A11 | B16 | C36 | A11 | B17 | C36 |
| A11 | B4 | C37 | A11 | B5 | C37 | A11 | B6 | C37 | A11 | B7 | C37 | A11 | B11 | C37 | A11 | B13 | C37 | A11 | B14 | C37 | A11 | B15 | C37 | A11 | B16 | C37 | A11 | B17 | C37 |
| A11 | B4 | C38 | A11 | B5 | C38 | A11 | B6 | C38 | A11 | B7 | C38 | A11 | B11 | C38 | A11 | B13 | C38 | A11 | B14 | C38 | A11 | B15 | C38 | A11 | B16 | C38 | A11 | B17 | C38 |
| A11 | B4 | C39 | A11 | B5 | C39 | A11 | B6 | C39 | A11 | B7 | C39 | A11 | B11 | C39 | A11 | B13 | C39 | A11 | B14 | C39 | A11 | B15 | C39 | A11 | B16 | C39 | A11 | B17 | C39 |
| A11 | B4 | C40 | A11 | B5 | C40 | A11 | B6 | C40 | A11 | B7 | C40 | A11 | B11 | C40 | A11 | B13 | C40 | A11 | B14 | C40 | A11 | B15 | C40 | A11 | B16 | C40 | A11 | B17 | C40 |
| A11 | B4 | C41 | A11 | B5 | C41 | A11 | B6 | C41 | A11 | B7 | C41 | A11 | B11 | C41 | A11 | B13 | C41 | A11 | B14 | C41 | A11 | B15 | C41 | A11 | B16 | C41 | A11 | B17 | C41 |
| A13 | B4 | C1 | A13 | B5 | C1 | A13 | B6 | C1 | A13 | B7 | C1 | A13 | B11 | C1 | A13 | B13 | C1 | A13 | B14 | C1 | A13 | B15 | C1 | A13 | B16 | C1 | A13 | B17 | C1 |
| A13 | B4 | C2 | A13 | B5 | C2 | A13 | B6 | C2 | A13 | B7 | C2 | A13 | B11 | C2 | A13 | B13 | C2 | A13 | B14 | C2 | A13 | B15 | C2 | A13 | B16 | C2 | A13 | B17 | C2 |
| A13 | B4 | C3 | A13 | B5 | C3 | A13 | B6 | C3 | A13 | B7 | C3 | A13 | B11 | C3 | A13 | B13 | C3 | A13 | B14 | C3 | A13 | B15 | C3 | A13 | B16 | C3 | A13 | B17 | C3 |
| A13 | B4 | C4 | A13 | B5 | C4 | A13 | B6 | C4 | A13 | B7 | C4 | A13 | B11 | C4 | A13 | B13 | C4 | A13 | B14 | C4 | A13 | B15 | C4 | A13 | B16 | C4 | A13 | B17 | C4 |
| A13 | B4 | C5 | A13 | B5 | C5 | A13 | B6 | C5 | A13 | B7 | C5 | A13 | B11 | C5 | A13 | B13 | C5 | A13 | B14 | C5 | A13 | B15 | C5 | A13 | B16 | C5 | A13 | B17 | C5 |
| A13 | B4 | C6 | A13 | B5 | C6 | A13 | B6 | C6 | A13 | B7 | C6 | A13 | B11 | C6 | A13 | B13 | C6 | A13 | B14 | C6 | A13 | B15 | C6 | A13 | B16 | C6 | A13 | B17 | C6 |
| A13 | B4 | C7 | A13 | B5 | C7 | A13 | B6 | C7 | A13 | B7 | C7 | A13 | B11 | C7 | A13 | B13 | C7 | A13 | B14 | C7 | A13 | B15 | C7 | A13 | B16 | C7 | A13 | B17 | C7 |
| A13 | B4 | C8 | A13 | B5 | C8 | A13 | B6 | C8 | A13 | B7 | C8 | A13 | B11 | C8 | A13 | B13 | C8 | A13 | B14 | C8 | A13 | B15 | C8 | A13 | B16 | C8 | A13 | B17 | C8 |
| A13 | B4 | C9 | A13 | B5 | C9 | A13 | B6 | C9 | A13 | B7 | C9 | A13 | B11 | C9 | A13 | B13 | C9 | A13 | B14 | C9 | A13 | B15 | C9 | A13 | B16 | C9 | A13 | B17 | C9 |
| A13 | B4 | C10 | A13 | B5 | C10 | A13 | B6 | C10 | A13 | B7 | C10 | A13 | B11 | C10 | A13 | B13 | C10 | A13 | B14 | C10 | A13 | B15 | C10 | A13 | B16 | C10 | A13 | B17 | C10 |
| A13 | B4 | C11 | A13 | B5 | C11 | A13 | B6 | C11 | A13 | B7 | C11 | A13 | B11 | C11 | A13 | B13 | C11 | A13 | B14 | C11 | A13 | B15 | C11 | A13 | B16 | C11 | A13 | B17 | C11 |
| A13 | B4 | C12 | A13 | B5 | C12 | A13 | B6 | C12 | A13 | B7 | C12 | A13 | B11 | C12 | A13 | B13 | C12 | A13 | B14 | C12 | A13 | B15 | C12 | A13 | B16 | C12 | A13 | B17 | C12 |
| A13 | B4 | C13 | A13 | B5 | C13 | A13 | B6 | C13 | A13 | B7 | C13 | A13 | B11 | C13 | A13 | B13 | C13 | A13 | B14 | C13 | A13 | B15 | C13 | A13 | B16 | C13 | A13 | B17 | C13 |
| A13 | B4 | C14 | A13 | B5 | C14 | A13 | B6 | C14 | A13 | B7 | C14 | A13 | B11 | C14 | A13 | B13 | C14 | A13 | B14 | C14 | A13 | B15 | C14 | A13 | B16 | C14 | A13 | B17 | C14 |
| A13 | B4 | C15 | A13 | B5 | C15 | A13 | B6 | C15 | A13 | B7 | C15 | A13 | B11 | C15 | A13 | B13 | C15 | A13 | B14 | C15 | A13 | B15 | C15 | A13 | B16 | C15 | A13 | B17 | C15 |
| A13 | B4 | C16 | A13 | B5 | C16 | A13 | B6 | C16 | A13 | B7 | C16 | A13 | B11 | C16 | A13 | B13 | C16 | A13 | B14 | C16 | A13 | B15 | C16 | A13 | B16 | C16 | A13 | B17 | C16 |
| A13 | B4 | C17 | A13 | B5 | C17 | A13 | B6 | C17 | A13 | B7 | C17 | A13 | B11 | C17 | A13 | B13 | C17 | A13 | B14 | C17 | A13 | B15 | C17 | A13 | B16 | C17 | A13 | B17 | C17 |
| A13 | B4 | C18 | A13 | B5 | C18 | A13 | B6 | C18 | A13 | B7 | C18 | A13 | B11 | C18 | A13 | B13 | C18 | A13 | B14 | C18 | A13 | B15 | C18 | A13 | B16 | C18 | A13 | B17 | C18 |
| A13 | B4 | C19 | A13 | B5 | C19 | A13 | B6 | C19 | A13 | B7 | C19 | A13 | B11 | C19 | A13 | B13 | C19 | A13 | B14 | C19 | A13 | B15 | C19 | A13 | B16 | C19 | A13 | B17 | C19 |
| A13 | B4 | C20 | A13 | B5 | C20 | A13 | B6 | C20 | A13 | B7 | C20 | A13 | B11 | C20 | A13 | B13 | C20 | A13 | B14 | C20 | A13 | B15 | C20 | A13 | B16 | C20 | A13 | B17 | C20 |
| A13 | B4 | C21 | A13 | B5 | C21 | A13 | B6 | C21 | A13 | B7 | C21 | A13 | B11 | C21 | A13 | B13 | C21 | A13 | B14 | C21 | A13 | B15 | C21 | A13 | B16 | C21 | A13 | B17 | C21 |
| A13 | B4 | C22 | A13 | B5 | C22 | A13 | B6 | C22 | A13 | B7 | C22 | A13 | B11 | C22 | A13 | B13 | C22 | A13 | B14 | C22 | A13 | B15 | C22 | A13 | B16 | C22 | A13 | B17 | C22 |
| A13 | B4 | C23 | A13 | B5 | C23 | A13 | B6 | C23 | A13 | B7 | C23 | A13 | B11 | C23 | A13 | B13 | C23 | A13 | B14 | C23 | A13 | B15 | C23 | A13 | B16 | C23 | A13 | B17 | C23 |

-continued

| | | | | | | | | | | | | | | | | | | | | | | | | | | |
|---|---|---|---|---|---|---|---|---|---|---|---|---|---|---|---|---|---|---|---|---|---|---|---|---|---|---|
| A13 B4 | C24 | A13 B5 | C24 | A13 B6 | C24 | A13 | B7 | C24 | A13 | B11 | C24 | A13 | B13 | C24 | A13 | B14 | C24 | A13 | B15 | C24 | A13 | B16 | C24 | A13 | B17 | C24 |
| A13 B4 | C25 | A13 B5 | C25 | A13 B6 | C25 | A13 | B7 | C25 | A13 | B11 | C25 | A13 | B13 | C25 | A13 | B14 | C25 | A13 | B15 | C25 | A13 | B16 | C25 | A13 | B17 | C25 |
| A13 B4 | C26 | A13 B5 | C26 | A13 B6 | C26 | A13 | B7 | C26 | A13 | B11 | C26 | A13 | B13 | C26 | A13 | B14 | C26 | A13 | B15 | C26 | A13 | B16 | C26 | A13 | B17 | C26 |
| A13 B4 | C27 | A13 B5 | C27 | A13 B6 | C27 | A13 | B7 | C27 | A13 | B11 | C27 | A13 | B13 | C27 | A13 | B14 | C27 | A13 | B15 | C27 | A13 | B16 | C27 | A13 | B17 | C27 |
| A13 B4 | C28 | A13 B5 | C28 | A13 B6 | C28 | A13 | B7 | C28 | A13 | B11 | C28 | A13 | B13 | C28 | A13 | B14 | C28 | A13 | B15 | C28 | A13 | B16 | C28 | A13 | B17 | C28 |
| A13 B4 | C29 | A13 B5 | C29 | A13 B6 | C29 | A13 | B7 | C29 | A13 | B11 | C29 | A13 | B13 | C29 | A13 | B14 | C29 | A13 | B15 | C29 | A13 | B16 | C29 | A13 | B17 | C29 |
| A13 B4 | C30 | A13 B5 | C30 | A13 B6 | C30 | A13 | B7 | C30 | A13 | B11 | C30 | A13 | B13 | C30 | A13 | B14 | C30 | A13 | B15 | C30 | A13 | B16 | C30 | A13 | B17 | C30 |
| A13 B4 | C31 | A13 B5 | C31 | A13 B6 | C31 | A13 | B7 | C31 | A13 | B11 | C31 | A13 | B13 | C31 | A13 | B14 | C31 | A13 | B15 | C31 | A13 | B16 | C31 | A13 | B17 | C31 |
| A13 B4 | C32 | A13 B5 | C32 | A13 B6 | C32 | A13 | B7 | C32 | A13 | B11 | C32 | A13 | B13 | C32 | A13 | B14 | C32 | A13 | B15 | C32 | A13 | B16 | C32 | A13 | B17 | C32 |
| A13 B4 | C33 | A13 B5 | C33 | A13 B6 | C33 | A13 | B7 | C33 | A13 | B11 | C33 | A13 | B13 | C33 | A13 | B14 | C33 | A13 | B15 | C33 | A13 | B16 | C33 | A13 | B17 | C33 |
| A13 B4 | C34 | A13 B5 | C34 | A13 B6 | C34 | A13 | B7 | C34 | A13 | B11 | C34 | A13 | B13 | C34 | A13 | B14 | C34 | A13 | B15 | C34 | A13 | B16 | C34 | A13 | B17 | C34 |
| A13 B4 | C35 | A13 B5 | C35 | A13 B6 | C35 | A13 | B7 | C35 | A13 | B11 | C35 | A13 | B13 | C35 | A13 | B14 | C35 | A13 | B15 | C35 | A13 | B16 | C35 | A13 | B17 | C35 |
| A13 B4 | C36 | A13 B5 | C36 | A13 B6 | C36 | A13 | B7 | C36 | A13 | B11 | C36 | A13 | B13 | C36 | A13 | B14 | C36 | A13 | B15 | C36 | A13 | B16 | C36 | A13 | B17 | C36 |
| A13 B4 | C37 | A13 B5 | C37 | A13 B6 | C37 | A13 | B7 | C37 | A13 | B11 | C37 | A13 | B13 | C37 | A13 | B14 | C37 | A13 | B15 | C37 | A13 | B16 | C37 | A13 | B17 | C37 |
| A13 B4 | C38 | A13 B5 | C38 | A13 B6 | C38 | A13 | B7 | C38 | A13 | B11 | C38 | A13 | B13 | C38 | A13 | B14 | C38 | A13 | B15 | C38 | A13 | B16 | C3S | A13 | B17 | C38 |
| A13 B4 | C39 | A13 B5 | C39 | A13 B6 | C39 | A13 | B7 | C39 | A13 | B11 | C39 | A13 | B13 | C39 | A13 | B14 | C39 | A13 | B15 | C39 | A13 | B16 | C39 | A13 | B17 | C39 |
| A13 B4 | C40 | A13 B5 | C40 | A13 B6 | C40 | A13 | B7 | C40 | A13 | B11 | C40 | A13 | B13 | C40 | A13 | B14 | C40 | A13 | B15 | C40 | A13 | B16 | C40 | A13 | B17 | C40 |
| A13 B4 | C41 | A13 B5 | C41 | A13 B6 | C41 | A13 | B7 | C41 | A13 | B11 | C41 | A13 | B13 | C41 | A13 | B14 | C41 | A13 | B15 | C41 | A13 | B16 | C41 | A13 | B17 | C41 |
| A15 B4 | C1 | A15 B5 | C1 | A15 B6 | C1 | A15 | B7 | C1 | A15 | B11 | C1 | A15 | B13 | C1 | A15 | B14 | C1 | A15 | B15 | C1 | A15 | B16 | C1 | A15 | B17 | C1 |
| A15 B4 | C2 | A15 B5 | C2 | A15 B6 | C1 | A15 | B7 | C2 | A15 | B11 | C2 | A15 | B13 | C2 | A15 | B14 | C2 | A15 | B15 | C2 | A15 | B16 | C2 | A15 | B17 | C2 |
| A15 B4 | C3 | A15 B5 | C3 | A15 B6 | C1 | A15 | B7 | C3 | A15 | B11 | C3 | A15 | B13 | C3 | A15 | B14 | C3 | A15 | B15 | C3 | A15 | B16 | C3 | A15 | B17 | C3 |
| A15 B4 | C4 | A15 B5 | C4 | A15 B6 | C4 | A15 | B7 | C4 | A15 | B11 | C4 | A15 | B13 | C4 | A15 | B14 | C4 | A15 | B15 | C4 | A15 | B16 | C4 | A15 | B17 | C4 |
| A15 B4 | C5 | A15 B5 | C5 | A15 B6 | C5 | A15 | B7 | C5 | A15 | B11 | C5 | A15 | B13 | C5 | A15 | B14 | C5 | A15 | B15 | C5 | A15 | B16 | C5 | A15 | B17 | C5 |
| A15 B4 | C6 | A15 B5 | C6 | A15 B6 | C6 | A15 | B7 | C6 | A15 | B11 | C6 | A15 | B13 | C6 | A15 | B14 | C6 | A15 | B15 | C6 | A15 | B16 | C6 | A15 | B17 | C6 |
| A15 B4 | C7 | A15 B5 | C7 | A15 B6 | C7 | A15 | B7 | C7 | A15 | B11 | C7 | A15 | B13 | C7 | A15 | B14 | C7 | A15 | B15 | C7 | A15 | B16 | C7 | A15 | B17 | C7 |
| A15 B4 | C8 | A15 B5 | C8 | A15 B6 | C8 | A15 | B7 | C8 | A15 | B11 | C8 | A15 | B13 | C8 | A15 | B14 | C5 | A15 | B15 | C8 | A15 | B16 | C8 | A15 | B17 | C8 |
| A15 B4 | C9 | A15 B5 | C9 | A15 B6 | C9 | A15 | B7 | C9 | A15 | B11 | C9 | A15 | B13 | C9 | A15 | B14 | C9 | A15 | B15 | C9 | A15 | B16 | C9 | A15 | B17 | C9 |
| A15 B4 | C10 | A15 B5 | C10 | A15 B6 | C10 | A15 | B7 | C10 | A15 | B11 | C10 | A15 | B13 | C10 | A15 | B14 | C10 | A15 | B15 | C10 | A15 | B16 | C10 | A15 | B17 | C10 |
| A15 B4 | C11 | A15 B5 | C11 | A15 B6 | C11 | A15 | B7 | C11 | A15 | B11 | C11 | A15 | B13 | C11 | A15 | B14 | C11 | A15 | B15 | C11 | A15 | B16 | C11 | A15 | B17 | C11 |
| A15 B4 | C12 | A15 B5 | C12 | A15 B6 | C12 | A15 | B7 | C12 | A15 | B11 | C12 | A15 | B13 | C12 | A15 | B14 | C12 | A15 | B15 | C12 | A15 | B16 | C12 | A15 | B17 | C12 |
| A15 B4 | C13 | A15 B5 | C13 | A15 B6 | C13 | A15 | B7 | C13 | A15 | B11 | C13 | A15 | B13 | C13 | A15 | B14 | C13 | A15 | B15 | C13 | A15 | B16 | C13 | A15 | B17 | C13 |
| A15 B4 | C14 | A15 B5 | C14 | A15 B6 | C14 | A15 | B7 | C14 | A15 | B11 | C14 | A15 | B13 | C14 | A15 | B14 | C14 | A15 | B15 | C14 | A15 | B16 | C14 | A15 | B17 | C14 |
| A15 B4 | C15 | A15 B5 | C15 | A15 B6 | C15 | A15 | B7 | C15 | A15 | B11 | C15 | A15 | B13 | C15 | A15 | B14 | C15 | A15 | B15 | C15 | A15 | B16 | C15 | A15 | B17 | C15 |
| A15 B4 | C16 | A15 B5 | C16 | A15 B6 | C16 | A15 | B7 | C16 | A15 | B11 | C16 | A15 | B13 | C16 | A15 | B14 | C16 | A15 | B15 | C16 | A15 | B16 | C16 | A15 | B17 | C16 |
| A15 B4 | C17 | A15 B5 | C17 | A15 B6 | C17 | A15 | B7 | C17 | A15 | B11 | C17 | A15 | B13 | C17 | A15 | B14 | C17 | A15 | B15 | C17 | A15 | B16 | C17 | A15 | B17 | C17 |
| A15 B4 | C18 | A15 B5 | C18 | A15 B6 | C18 | A15 | B7 | C18 | A15 | B11 | C18 | A15 | B13 | C18 | A15 | B14 | C18 | A15 | B15 | C18 | A15 | B16 | C18 | A15 | B17 | C18 |
| A15 B4 | C19 | A15 B5 | C19 | A15 B6 | C19 | A15 | B7 | C19 | A15 | B11 | C19 | A15 | B13 | C19 | A15 | B14 | C19 | A15 | B15 | C19 | A15 | B16 | C19 | A15 | B17 | C19 |
| A15 B4 | C20 | A15 B5 | C20 | A15 B6 | C20 | A15 | B7 | C20 | A15 | B11 | C20 | A15 | B13 | C20 | A15 | B14 | C20 | A15 | B15 | C20 | A15 | B16 | C20 | A15 | B17 | C20 |
| A15 B4 | C21 | A15 B5 | C21 | A15 B6 | C21 | A15 | B7 | C21 | A15 | B11 | C21 | A15 | B13 | C21 | A15 | B14 | C21 | A15 | B15 | C21 | A15 | B16 | C21 | A15 | B17 | C21 |
| A15 B4 | C22 | A15 B5 | C22 | A15 B6 | C22 | A15 | B7 | C22 | A15 | B11 | C22 | A15 | B13 | C22 | A15 | B14 | C22 | A15 | B15 | C22 | A15 | B16 | C22 | A15 | B17 | C22 |
| A15 B4 | C23 | A15 B5 | C23 | A15 B6 | C23 | A15 | B7 | C23 | A15 | B11 | C23 | A15 | B13 | C23 | A15 | B14 | C23 | A15 | B15 | C23 | A15 | B16 | C23 | A15 | B17 | C23 |
| A15 B4 | C24 | A15 B5 | C24 | A15 B6 | C24 | A15 | B7 | C24 | A15 | B11 | C24 | A15 | B13 | C24 | A15 | B14 | C24 | A15 | B15 | C24 | A15 | B16 | C24 | A15 | B17 | C24 |
| A15 B4 | C25 | A15 B5 | C25 | A15 B6 | C25 | A15 | B7 | C25 | A15 | B11 | C25 | A15 | B13 | C25 | A15 | B14 | C25 | A15 | B15 | C25 | A15 | B16 | C25 | A15 | B17 | C25 |
| A15 B4 | C26 | A15 B5 | C26 | A15 B6 | C26 | A15 | B7 | C26 | A15 | B11 | C26 | A15 | B13 | C26 | A15 | B14 | C26 | A15 | B15 | C26 | A15 | B16 | C26 | A15 | B17 | C26 |
| A15 B4 | C27 | A15 B5 | C27 | A15 B6 | C27 | A15 | B7 | C27 | A15 | B11 | C27 | A15 | B13 | C27 | A15 | B14 | C27 | A15 | B15 | C27 | A15 | B16 | C27 | A15 | B17 | C27 |
| A15 B4 | C28 | A15 B5 | C28 | A15 B6 | C28 | A15 | B7 | C28 | A15 | B11 | C28 | A15 | B13 | C28 | A15 | B14 | C28 | A15 | B15 | C28 | A15 | B16 | C28 | A15 | B17 | C28 |
| A15 B4 | C29 | A15 B5 | C29 | A15 B6 | C29 | A15 | B7 | C29 | A15 | B11 | C29 | A15 | B13 | C29 | A15 | B14 | C29 | A15 | B15 | C29 | A15 | B16 | C29 | A15 | B17 | C29 |
| A15 B4 | C30 | A15 B5 | C30 | A15 B6 | C30 | A15 | B7 | C30 | A15 | B11 | C30 | A15 | B13 | C30 | A15 | B14 | C30 | A15 | B15 | C30 | A15 | B16 | C30 | A15 | B17 | C30 |
| A15 B4 | C31 | A15 B5 | C31 | A15 B6 | C31 | A15 | B7 | C31 | A15 | B11 | C31 | A15 | B13 | C31 | A15 | B14 | C31 | A15 | B15 | C31 | A15 | B16 | C31 | A15 | B17 | C31 |
| A15 B4 | C32 | A15 B5 | C32 | A15 B6 | C32 | A15 | B7 | C32 | A15 | B11 | C32 | A15 | B13 | C32 | A15 | B14 | C32 | A15 | B15 | C32 | A15 | B16 | C32 | A15 | B17 | C32 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A15 | B4 | C33 | A15 | B5 | C33 | A15 | B6 | C33 | A15 | B7 | C33 | A15 | B11 | C33 | A15 | B13 | C33 | A15 | B14 | C33 | A15 | B15 | C33 | A15 | B16 | C33 | A15 | B17 | C33 |
| A15 | B4 | C34 | A15 | B5 | C34 | A15 | B6 | C34 | A15 | B7 | C34 | A15 | B11 | C34 | A15 | B13 | C34 | A15 | B14 | C34 | A15 | B15 | C34 | A15 | B16 | C34 | A15 | B17 | C34 |
| A15 | B4 | C35 | A15 | B5 | C35 | A15 | B6 | C35 | A15 | B7 | C35 | A15 | B11 | C35 | A15 | B13 | C35 | A15 | B14 | C35 | A15 | B15 | C35 | A15 | B16 | C35 | A15 | B17 | C35 |
| A15 | B4 | C36 | A15 | B5 | C36 | A15 | B6 | C36 | A15 | B7 | C36 | A15 | B11 | C36 | A15 | B13 | C36 | A15 | B14 | C36 | A15 | B15 | C36 | A15 | B16 | C36 | A15 | B17 | C36 |
| A15 | B4 | C37 | A15 | B5 | C37 | A15 | B6 | C37 | A15 | B7 | C37 | A15 | B11 | C37 | A15 | B13 | C37 | A15 | B14 | C37 | A15 | B15 | C37 | A15 | B16 | C37 | A15 | B17 | C37 |
| A15 | B4 | C38 | A15 | B5 | C38 | A15 | B6 | C38 | A15 | B7 | C38 | A15 | B11 | C38 | A15 | B13 | C38 | A15 | B14 | C38 | A15 | B15 | C38 | A15 | B16 | C38 | A15 | B17 | C38 |
| A15 | B4 | C39 | A15 | B5 | C39 | A15 | B6 | C39 | A15 | B7 | C39 | A15 | B11 | C39 | A15 | B13 | C39 | A15 | B14 | C39 | A15 | B15 | C39 | A15 | B16 | C39 | A15 | B17 | C39 |
| A15 | B4 | C40 | A15 | B5 | C43 | A15 | B6 | C40 | A15 | B7 | C40 | A15 | B11 | C40 | A15 | B13 | C40 | A15 | B14 | C40 | A15 | B15 | C40 | A15 | B16 | C40 | A15 | B17 | C40 |
| A15 | B4 | C41 | A15 | B5 | C41 | A15 | B6 | C41 | A15 | B7 | C41 | A15 | B11 | C41 | A15 | B13 | C41 | A15 | B14 | C41 | A15 | B15 | C41 | A15 | B16 | C41 | A15 | B17 | C41 |
| A17 | B4 | C1 | A17 | B5 | C1 | A17 | B6 | C1 | A17 | B7 | C1 | A17 | B11 | C1 | A17 | B13 | C1 | A17 | B14 | C1 | A17 | B15 | C1 | A17 | B16 | C1 | A17 | B17 | C1 |
| A17 | B4 | C2 | A17 | B5 | C2 | A17 | B6 | C2 | A17 | B7 | C2 | A17 | B11 | C2 | A17 | B13 | C2 | A17 | B14 | C2 | A17 | B15 | C2 | A17 | B16 | C2 | A17 | B17 | C2 |
| A17 | B4 | C3 | A17 | B5 | C3 | A17 | B6 | C3 | A17 | B7 | C3 | A17 | B11 | C3 | A17 | B13 | C3 | A17 | B14 | C3 | A17 | B15 | C3 | A17 | B16 | C3 | A17 | B17 | C3 |
| A17 | B4 | C4 | A17 | B5 | C4 | A17 | B6 | C4 | A17 | B7 | C4 | A17 | B11 | C4 | A17 | B13 | C4 | A17 | B14 | C4 | A17 | B15 | C4 | A17 | B16 | C4 | A17 | B17 | C4 |
| A17 | B4 | C5 | A17 | B5 | C5 | A17 | B6 | C5 | A17 | B7 | C5 | A17 | B11 | C5 | A17 | B13 | C5 | A17 | B14 | C5 | A17 | B15 | C5 | A17 | B16 | C5 | A17 | B17 | C5 |
| A17 | B4 | C6 | A17 | B5 | C6 | A17 | B6 | C6 | A17 | B7 | C6 | A17 | B11 | C6 | A17 | B13 | C6 | A17 | B14 | C6 | A17 | B15 | C6 | A17 | B16 | C6 | A17 | B17 | C6 |
| A17 | B4 | C7 | A17 | B5 | C7 | A17 | B6 | C7 | A17 | B7 | C7 | A17 | B11 | C7 | A17 | B13 | C7 | A17 | B14 | C7 | A17 | B15 | C7 | A17 | B16 | C7 | A17 | B17 | C7 |
| A17 | B4 | C8 | A17 | B5 | C8 | A17 | B6 | C8 | A17 | B7 | C8 | A17 | B11 | C8 | A17 | B13 | C8 | A17 | B14 | C8 | A17 | B15 | C8 | A17 | B16 | C8 | A17 | B17 | C8 |
| A17 | B4 | C9 | A17 | B5 | C9 | A17 | B6 | C9 | A17 | B7 | C9 | A17 | B11 | C9 | A17 | B13 | C9 | A17 | B14 | C9 | A17 | B15 | C9 | A17 | B16 | C9 | A17 | B17 | C9 |
| A17 | B4 | C10 | A17 | B5 | C10 | A17 | B6 | C10 | A17 | B7 | C10 | A17 | B11 | C10 | A17 | B13 | C10 | A17 | B14 | C10 | A17 | B15 | C10 | A17 | B16 | C10 | A17 | B17 | C10 |
| A17 | B4 | C11 | A17 | B5 | C11 | A17 | B6 | C11 | A17 | B7 | C11 | A17 | B11 | C11 | A17 | B13 | C11 | A17 | B14 | C11 | A17 | B15 | C11 | A17 | B16 | C11 | A17 | B17 | C11 |
| A17 | B4 | C12 | A17 | B5 | C12 | A17 | B6 | C12 | A17 | B7 | C12 | A17 | B11 | C12 | A17 | B13 | C12 | A17 | B14 | C12 | A17 | B15 | C12 | A17 | B16 | C12 | A17 | B17 | C12 |
| A17 | B4 | C13 | A17 | B5 | C13 | A17 | B6 | C13 | A17 | B7 | C13 | A17 | B11 | C13 | A17 | B13 | C13 | A17 | B14 | C13 | A17 | B15 | C13 | A17 | B16 | C13 | A17 | B17 | C13 |
| A17 | B4 | C14 | A17 | B5 | C14 | A17 | B6 | C14 | A17 | B7 | C14 | A17 | B11 | C14 | A17 | B13 | C14 | A17 | B14 | C14 | A17 | B15 | C14 | A17 | B16 | C14 | A17 | B17 | C14 |
| A17 | B4 | C15 | A17 | B5 | C15 | A17 | B6 | C15 | A17 | B7 | C15 | A17 | B11 | C15 | A17 | B13 | C15 | A17 | B14 | C15 | A17 | B15 | C15 | A17 | B16 | C15 | A17 | B17 | C15 |
| A17 | B4 | C16 | A17 | B5 | C16 | A17 | B6 | C16 | A17 | B7 | C16 | A17 | B11 | C16 | A17 | B13 | C16 | A17 | B14 | C16 | A17 | B15 | C16 | A17 | B16 | C16 | A17 | B17 | C16 |
| A17 | B4 | C17 | A17 | B5 | C17 | A17 | B6 | C17 | A17 | B7 | C17 | A17 | B11 | C17 | A17 | B13 | C17 | A17 | B14 | C17 | A17 | B15 | C17 | A17 | B16 | C17 | A17 | B17 | C17 |
| A17 | B4 | C18 | A17 | B5 | C18 | A17 | B6 | C18 | A17 | B7 | C18 | A17 | B11 | C18 | A17 | B13 | C18 | A17 | B14 | C18 | A17 | B15 | C18 | A17 | B16 | C18 | A17 | B17 | C18 |
| A17 | B4 | C19 | A17 | B5 | C19 | A17 | B6 | C19 | A17 | B7 | C19 | A17 | B11 | C19 | A17 | B13 | C19 | A17 | B14 | C19 | A17 | B15 | C19 | A17 | B16 | C19 | A17 | B17 | C19 |
| A17 | B4 | C20 | A17 | B5 | C20 | A17 | B6 | C20 | A17 | B7 | C20 | A17 | B11 | C20 | A17 | B13 | C20 | A17 | B14 | C20 | A17 | B15 | C20 | A17 | B16 | C20 | A17 | B17 | C20 |
| A17 | B4 | C21 | A17 | B5 | C21 | A17 | B6 | C21 | A17 | B7 | C21 | A17 | B11 | C21 | A17 | B13 | C21 | A17 | B14 | C21 | A17 | B15 | C21 | A17 | B16 | C21 | A17 | B17 | C21 |
| A17 | B4 | C22 | A17 | B5 | C22 | A17 | B6 | C22 | A17 | B7 | C22 | A17 | B11 | C22 | A17 | B13 | C22 | A17 | B14 | C22 | A17 | B15 | C22 | A17 | B16 | C22 | A17 | B17 | C22 |
| A17 | B4 | C23 | A17 | B5 | C23 | A17 | B6 | C23 | A17 | B7 | C23 | A17 | B11 | C23 | A17 | B13 | C23 | A17 | B14 | C23 | A17 | B15 | C23 | A17 | B16 | C23 | A17 | B17 | C23 |
| A17 | B4 | C24 | A17 | B5 | C24 | A17 | B6 | C24 | A17 | B7 | C24 | A17 | B11 | C24 | A17 | B13 | C24 | A17 | B14 | C24 | A17 | B15 | C24 | A17 | B16 | C24 | A17 | B17 | C24 |
| A17 | B4 | C25 | A17 | B5 | C25 | A17 | B6 | C25 | A17 | B7 | C25 | A17 | B11 | C25 | A17 | B13 | C25 | A17 | B14 | C25 | A17 | B15 | C25 | A17 | B16 | C25 | A17 | B17 | C25 |
| A17 | B4 | C26 | A17 | B5 | C26 | A17 | B6 | C26 | A17 | B7 | C26 | A17 | B11 | C26 | A17 | B13 | C26 | A17 | B14 | C26 | A17 | B15 | C26 | A17 | B16 | C26 | A17 | B17 | C26 |
| A17 | B4 | C27 | A17 | B5 | C27 | A17 | B6 | C27 | A17 | B7 | C27 | A17 | B11 | C27 | A17 | B13 | C27 | A17 | B14 | C27 | A17 | B15 | C27 | A17 | B16 | C27 | A17 | B17 | C27 |
| A17 | B4 | C28 | A17 | B5 | C28 | A17 | B6 | C28 | A17 | B7 | C28 | A17 | B11 | C28 | A17 | B13 | C28 | A17 | B14 | C28 | A17 | B15 | C28 | A17 | B16 | C28 | A17 | B17 | C28 |
| A17 | B4 | C29 | A17 | B5 | C29 | A17 | B6 | C29 | A17 | B7 | C29 | A17 | B11 | C29 | A17 | B13 | C29 | A17 | B14 | C29 | A17 | B15 | C29 | A17 | B16 | C29 | A17 | B17 | C29 |
| A17 | B4 | C30 | A17 | B5 | C30 | A17 | B6 | C30 | A17 | B7 | C30 | A17 | B11 | C30 | A17 | B13 | C30 | A17 | B14 | C30 | A17 | B15 | C30 | A17 | B16 | C30 | A17 | B17 | C30 |
| A17 | B4 | C31 | A17 | B5 | C31 | A17 | B6 | C31 | A17 | B7 | C31 | A17 | B11 | C31 | A17 | B13 | C31 | A17 | B14 | C31 | A17 | B15 | C31 | A17 | B16 | C31 | A17 | B17 | C31 |
| A17 | B4 | C32 | A17 | B5 | C32 | A17 | B6 | C32 | A17 | B7 | C32 | A17 | B11 | C32 | A17 | B13 | C32 | A17 | B14 | C32 | A17 | B15 | C32 | A17 | B16 | C32 | A17 | B17 | C32 |
| A17 | B4 | C33 | A17 | B5 | C33 | A17 | B6 | C33 | A17 | B7 | C33 | A17 | B11 | C33 | A17 | B13 | C33 | A17 | B14 | C33 | A17 | B15 | C33 | A17 | B16 | C33 | A17 | B17 | C33 |
| A17 | B4 | C34 | A17 | B5 | C34 | A17 | B6 | C34 | A17 | B7 | C34 | A17 | B11 | C34 | A17 | B13 | C34 | A17 | B14 | C34 | A17 | B15 | C34 | A17 | B16 | C34 | A17 | B17 | C34 |
| A17 | B4 | C35 | A17 | B5 | C35 | A17 | B6 | C35 | A17 | B7 | C35 | A17 | B11 | C35 | A17 | B13 | C35 | A17 | B14 | C35 | A17 | B15 | C35 | A17 | B16 | C35 | A17 | B17 | C35 |
| A17 | B4 | C36 | A17 | B5 | C36 | A17 | B6 | C36 | A17 | B7 | C36 | A17 | B11 | C36 | A17 | B13 | C36 | A17 | B14 | C36 | A17 | B15 | C36 | A17 | B16 | C36 | A17 | B17 | C16 |
| A17 | B4 | C37 | A17 | B5 | C37 | A17 | B6 | C37 | A17 | B7 | C37 | A17 | B11 | C37 | A17 | B13 | C37 | A17 | B14 | C37 | A17 | B15 | C37 | A17 | B16 | C37 | A17 | B17 | C37 |
| A17 | B4 | C38 | A17 | B5 | C38 | A17 | B6 | C38 | A17 | B7 | C38 | A17 | B11 | C38 | A17 | B13 | C38 | A17 | B14 | C38 | A17 | B15 | C38 | A17 | B16 | C38 | A17 | B17 | C38 |
| A17 | B4 | C39 | A17 | B5 | C39 | A17 | B6 | C39 | A17 | B7 | C39 | A17 | B11 | C39 | A17 | B13 | C39 | A17 | B14 | C39 | A17 | B15 | C39 | A17 | B16 | C39 | A17 | B17 | C39 |
| A17 | B4 | C40 | A17 | B5 | C40 | A17 | B6 | C40 | A17 | B7 | C40 | A17 | B11 | C40 | A17 | B13 | C40 | A17 | B14 | C40 | A17 | B15 | C40 | A17 | B16 | C40 | A17 | B17 | C10 |
| A17 | B4 | C41 | A17 | B5 | C41 | A17 | B6 | C41 | A17 | B7 | C41 | A17 | B11 | C41 | A17 | B13 | C41 | A17 | B14 | C41 | A17 | B15 | C41 | A17 | B16 | C41 | A17 | B17 | C41 |
| A26 | B4 | C1 | A26 | B5 | C1 | A26 | B6 | C1 | A26 | B7 | C1 | A26 | B11 | C1 | A26 | B13 | C1 | A26 | B14 | C1 | A26 | B15 | C1 | A26 | B16 | C1 | A26 | B17 | C1 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A26 | B4 | C2 | A26 | B5 | C2 | A26 | B6 | C2 | A26 | B7 | C2 | A26 | B11 | C2 | A26 | B13 | C2 | A26 | B14 | C2 | A26 | B15 | C2 | A26 | B16 | C2 | A26 | B17 | C2 |
| A26 | B4 | C3 | A26 | B5 | C3 | A26 | B6 | C3 | A26 | B7 | C3 | A26 | B11 | C3 | A26 | B13 | C3 | A26 | B14 | C3 | A26 | B15 | C3 | A26 | B16 | C3 | A26 | B17 | C3 |
| A26 | B4 | C4 | A26 | B5 | C4 | A26 | B6 | C4 | A26 | B7 | C4 | A26 | B11 | C4 | A26 | B13 | C4 | A26 | B14 | C4 | A26 | B15 | C4 | A26 | B16 | C4 | A26 | B17 | C4 |
| A26 | B4 | C5 | A26 | B5 | C5 | A26 | B6 | C5 | A26 | B7 | C5 | A26 | B11 | C5 | A26 | B13 | C5 | A26 | B14 | C5 | A26 | B15 | C5 | A26 | B16 | C5 | A26 | B17 | C5 |
| A26 | B4 | C6 | A26 | B5 | C6 | A26 | B6 | C6 | A26 | B7 | C6 | A26 | B11 | C6 | A26 | B13 | C6 | A26 | B14 | C6 | A26 | B15 | C6 | A26 | B16 | C6 | A26 | B17 | C6 |
| A26 | B4 | C7 | A26 | B5 | C7 | A26 | B6 | C7 | A26 | B7 | C7 | A26 | B11 | C7 | A26 | B13 | C7 | A26 | B14 | C7 | A26 | B15 | C7 | A26 | B16 | C7 | A26 | B17 | C7 |
| A26 | B4 | C8 | A26 | B5 | C8 | A26 | B6 | C8 | A26 | B7 | C8 | A26 | B11 | C8 | A26 | B13 | C8 | A26 | B14 | C8 | A26 | B15 | C8 | A26 | B16 | C8 | A26 | B17 | C8 |
| A26 | B4 | C9 | A26 | B5 | C9 | A26 | B6 | C9 | A26 | B7 | C9 | A26 | B11 | C9 | A26 | B13 | C9 | A26 | B14 | C9 | A26 | B15 | C9 | A26 | B16 | C9 | A26 | B17 | C9 |
| A26 | B4 | C10 | A26 | B5 | C10 | A26 | B6 | C10 | A26 | B7 | C10 | A26 | B11 | C10 | A26 | B13 | C10 | A26 | B14 | C10 | A26 | B15 | C10 | A26 | B16 | C10 | A26 | B17 | C10 |
| A26 | B4 | C11 | A26 | B5 | C11 | A26 | B6 | C11 | A26 | B7 | C11 | A26 | B11 | C11 | A26 | B13 | C11 | A26 | B14 | C11 | A26 | B15 | C11 | A26 | B16 | C11 | A26 | B17 | C11 |
| A26 | B4 | C12 | A26 | B5 | C12 | A26 | B6 | C12 | A26 | B7 | C12 | A26 | B11 | C12 | A26 | B13 | C12 | A26 | B14 | C12 | A26 | B15 | C12 | A26 | B16 | C12 | A26 | B17 | C12 |
| A26 | B4 | C13 | A26 | B5 | C13 | A26 | B6 | C13 | A26 | B7 | C13 | A26 | B11 | C13 | A26 | B13 | C13 | A26 | B14 | C13 | A26 | B15 | C13 | A26 | B16 | C13 | A26 | B17 | C13 |
| A26 | B4 | C14 | A26 | B5 | C14 | A26 | B6 | C14 | A26 | B7 | C14 | A26 | B11 | C14 | A26 | B13 | C14 | A26 | B14 | C14 | A26 | B15 | C14 | A26 | B16 | C14 | A26 | B17 | C14 |
| A26 | B4 | C15 | A26 | B5 | C15 | A26 | B6 | C15 | A26 | B7 | C15 | A26 | B11 | C15 | A26 | B13 | C15 | A26 | B14 | C15 | A26 | B15 | C15 | A26 | B16 | C15 | A26 | B17 | C15 |
| A26 | B4 | C16 | A26 | B5 | C16 | A26 | B6 | C16 | A26 | B7 | C16 | A26 | B11 | C16 | A26 | B13 | C16 | A26 | B14 | C16 | A26 | B15 | C16 | A26 | B16 | C16 | A26 | B17 | C16 |
| A26 | B4 | C17 | A26 | B5 | C17 | A26 | B6 | C17 | A26 | B7 | C17 | A26 | B11 | C17 | A26 | B13 | C17 | A26 | B14 | C17 | A26 | B15 | C17 | A26 | B16 | C17 | A26 | B17 | C17 |
| A26 | B4 | C18 | A26 | B5 | C18 | A26 | B6 | C18 | A26 | B7 | C15 | A26 | B11 | C18 | A26 | B13 | C18 | A26 | B14 | C18 | A26 | B15 | C18 | A26 | B16 | C18 | A26 | B17 | C18 |
| A26 | B4 | C19 | A26 | B5 | C19 | A26 | B6 | C19 | A26 | B7 | C19 | A26 | B11 | C19 | A26 | B13 | C19 | A26 | B14 | C19 | A26 | B15 | C19 | A26 | B16 | C19 | A26 | B17 | C19 |
| A26 | B4 | C20 | A26 | B5 | C20 | A26 | B6 | C20 | A26 | B7 | C20 | A26 | B11 | C20 | A26 | B13 | C20 | A26 | B14 | C20 | A26 | B15 | C20 | A26 | B16 | C20 | A26 | B17 | C20 |
| A26 | B4 | C21 | A26 | B5 | C21 | A26 | B6 | C21 | A26 | B7 | C21 | A26 | B11 | C21 | A26 | B13 | C21 | A26 | B14 | C21 | A26 | B15 | C21 | A26 | B16 | C21 | A26 | B17 | C21 |
| A26 | B4 | C22 | A26 | B5 | C22 | A26 | B6 | C22 | A26 | B7 | C22 | A26 | B11 | C22 | A26 | B13 | C22 | A26 | B14 | C22 | A26 | B15 | C22 | A26 | B16 | C22 | A26 | B17 | C22 |
| A26 | B4 | C23 | A26 | B5 | C23 | A26 | B6 | C23 | A26 | B7 | C23 | A26 | B11 | C23 | A26 | B13 | C23 | A26 | B14 | C23 | A26 | B15 | C23 | A26 | B16 | C23 | A26 | B17 | C23 |
| A26 | B4 | C24 | A26 | B5 | C24 | A26 | B6 | C24 | A26 | B7 | C24 | A26 | B11 | C24 | A26 | B13 | C24 | A26 | B14 | C24 | A26 | B15 | C24 | A26 | B16 | C24 | A26 | B17 | C24 |
| A26 | B4 | C25 | A26 | B5 | C25 | A26 | B6 | C25 | A26 | B7 | C25 | A26 | B11 | C25 | A26 | B13 | C25 | A26 | B14 | C25 | A26 | B15 | C25 | A26 | B16 | C25 | A26 | B17 | C25 |
| A26 | B4 | C26 | A26 | B5 | C26 | A26 | B6 | C26 | A26 | B7 | C26 | A26 | B11 | C26 | A26 | B13 | C26 | A26 | B14 | C26 | A26 | B15 | C26 | A26 | B16 | C26 | A26 | B17 | C26 |
| A26 | B4 | C27 | A26 | B5 | C27 | A26 | B6 | C27 | A26 | B7 | C27 | A26 | B11 | C27 | A26 | B13 | C27 | A26 | B14 | C27 | A26 | B15 | C27 | A26 | B16 | C27 | A26 | B17 | C27 |
| A26 | B4 | C28 | A26 | B5 | C28 | A26 | B6 | C28 | A26 | B7 | C28 | A26 | B11 | C28 | A26 | B13 | C28 | A26 | B14 | C28 | A26 | B15 | C28 | A26 | B16 | C28 | A26 | B17 | C28 |
| A26 | B4 | C29 | A26 | B5 | C29 | A26 | B6 | C29 | A26 | B7 | C29 | A26 | B11 | C29 | A26 | B13 | C29 | A26 | B14 | C29 | A26 | B15 | C29 | A26 | B16 | C29 | A26 | B17 | C29 |
| A26 | B4 | C30 | A26 | B5 | C30 | A26 | B6 | C30 | A26 | B7 | C30 | A26 | B11 | C30 | A26 | B13 | C30 | A26 | B14 | C30 | A26 | B15 | C30 | A26 | B16 | C30 | A26 | B17 | C30 |
| A26 | B4 | C31 | A26 | B5 | C31 | A26 | B6 | C31 | A26 | B7 | C31 | A26 | B11 | C31 | A26 | B13 | C31 | A26 | B14 | C31 | A26 | B15 | C31 | A26 | B16 | C31 | A26 | B17 | C31 |
| A26 | B4 | C32 | A26 | B5 | C32 | A26 | B6 | C32 | A26 | B7 | C32 | A26 | B11 | C32 | A26 | B13 | C32 | A26 | B14 | C32 | A26 | B15 | C32 | A26 | B16 | C32 | A26 | B17 | C32 |
| A26 | B4 | C33 | A26 | B5 | C33 | A26 | B6 | C33 | A26 | B7 | C33 | A26 | B11 | C33 | A26 | B13 | C33 | A26 | B14 | C33 | A26 | B15 | C33 | A26 | B16 | C33 | A26 | B17 | C33 |
| A26 | B4 | C34 | A26 | B5 | C34 | A26 | B6 | C34 | A26 | B7 | C34 | A26 | B11 | C34 | A26 | B13 | C34 | A26 | B14 | C34 | A26 | B15 | C34 | A26 | B16 | C34 | A26 | B17 | C34 |
| A26 | B4 | C35 | A26 | B5 | C35 | A26 | B6 | C35 | A26 | B7 | C35 | A26 | B11 | C35 | A26 | B13 | C35 | A26 | B14 | C35 | A26 | B15 | C35 | A26 | B16 | C35 | A26 | B17 | C35 |
| A26 | B4 | C36 | A26 | B5 | C36 | A26 | B6 | C36 | A26 | B7 | C36 | A26 | B11 | C36 | A26 | B13 | C36 | A26 | B14 | C36 | A26 | B15 | C36 | A26 | B16 | C36 | A26 | B17 | C36 |
| A26 | B4 | C37 | A26 | B5 | C37 | A26 | B6 | C37 | A26 | B7 | C37 | A26 | B11 | C37 | A26 | B13 | C37 | A26 | B14 | C37 | A26 | B15 | C37 | A26 | B16 | C37 | A26 | B17 | C37 |
| A26 | B4 | C38 | A26 | B5 | C38 | A26 | B6 | C38 | A26 | B7 | C38 | A26 | B11 | C38 | A26 | B13 | C38 | A26 | B14 | C38 | A26 | B15 | C38 | A26 | B16 | C38 | A26 | B17 | C38 |
| A26 | B4 | C39 | A26 | B5 | C39 | A26 | B6 | C39 | A26 | B7 | C39 | A26 | B11 | C39 | A26 | B13 | C39 | A26 | B14 | C39 | A26 | B15 | C39 | A26 | B16 | C39 | A26 | B17 | C39 |
| A26 | B4 | C40 | A26 | B5 | C40 | A26 | B6 | C40 | A26 | B7 | C40 | A26 | B11 | C40 | A26 | B13 | C40 | A26 | B14 | C40 | A26 | B15 | C40 | A26 | B16 | C40 | A26 | B17 | C43 |
| A26 | B4 | C41 | A26 | B5 | C41 | A26 | B6 | C41 | A26 | B7 | C41 | A26 | B11 | C41 | A26 | B13 | C41 | A26 | B14 | C41 | A26 | B15 | C41 | A26 | B16 | C41 | A26 | B17 | C41 |
| A26 | B4 | C1 | A27 | B5 | C1 | A27 | B6 | C1 | A27 | B7 | C1 | A27 | B11 | C1 | A27 | B13 | C1 | A27 | B14 | C1 | A27 | B15 | C1 | A27 | B16 | C1 | A27 | B17 | C1 |
| A27 | B4 | C2 | A27 | B5 | C2 | A27 | B6 | C2 | A27 | B7 | C2 | A27 | B11 | C2 | A27 | B13 | C2 | A27 | B14 | C2 | A27 | B15 | C2 | A27 | B16 | C2 | A27 | B17 | C2 |
| A27 | B4 | C3 | A27 | B5 | C3 | A27 | B6 | C3 | A27 | B7 | C3 | A27 | B11 | C3 | A27 | B13 | C3 | A27 | B14 | C3 | A27 | B15 | C3 | A27 | B16 | C3 | A27 | B17 | C3 |
| A27 | B4 | C4 | A27 | B5 | C4 | A27 | B6 | C4 | A27 | B7 | C4 | A27 | B11 | C4 | A27 | B13 | C4 | A27 | B14 | C4 | A27 | B15 | C4 | A27 | B16 | C4 | A27 | B17 | C4 |
| A27 | B4 | C5 | A27 | B5 | C5 | A27 | B6 | C5 | A27 | B7 | C5 | A27 | B11 | C5 | A27 | B13 | C5 | A27 | B14 | C5 | A27 | B15 | C5 | A27 | B16 | C5 | A27 | B17 | C5 |
| A27 | B4 | C6 | A27 | B5 | C6 | A27 | B6 | C6 | A27 | B7 | C6 | A27 | B11 | C6 | A27 | B13 | C6 | A27 | B14 | C6 | A27 | B15 | C6 | A27 | B16 | C6 | A27 | B17 | C6 |
| A27 | B4 | C7 | A27 | B5 | C7 | A27 | B6 | C7 | A27 | B7 | C7 | A27 | B11 | C7 | A27 | B13 | C7 | A27 | B14 | C7 | A27 | B15 | C7 | A27 | B16 | C7 | A27 | B17 | C7 |
| A27 | B4 | C8 | A27 | B5 | C8 | A27 | B6 | C8 | A27 | B7 | C8 | A27 | B11 | C8 | A27 | B13 | C8 | A27 | B14 | C8 | A27 | B15 | C8 | A27 | B16 | C8 | A27 | B17 | C8 |
| A27 | B4 | C9 | A27 | B5 | C9 | A27 | B6 | C9 | A27 | B7 | C9 | A27 | B11 | C9 | A27 | B13 | C9 | A27 | B14 | C9 | A27 | B15 | C9 | A27 | B16 | C9 | A27 | B17 | C9 |
| A27 | B4 | C10 | A27 | B5 | C10 | A27 | B6 | C10 | A27 | B7 | C10 | A27 | B11 | C10 | A27 | B13 | C10 | A27 | B14 | C10 | A27 | B15 | C10 | A27 | B16 | C10 | A27 | B17 | C10 |
| A27 | B4 | C11 | A27 | B5 | C11 | A27 | B6 | C11 | A27 | B7 | C11 | A27 | B11 | C11 | A27 | B13 | C11 | A27 | B14 | C11 | A27 | B15 | C11 | A27 | B16 | C11 | A27 | B17 | C11 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A27 | B4 | C12 | A27 | B5 | C12 | A27 | B6 | C12 | A27 | B7 | C12 | A27 | B11 | C12 | A27 | B13 | C12 | A27 | B14 | C12 | A27 | B15 | C12 | A27 | B16 | C12 | A27 | B17 | C12 |
| A27 | B4 | C13 | A27 | B5 | C13 | A27 | B6 | C13 | A27 | B7 | C13 | A27 | B11 | C13 | A27 | B13 | C13 | A27 | B14 | C13 | A27 | B15 | C13 | A27 | B16 | C13 | A27 | B17 | C13 |
| A27 | B4 | C14 | A27 | B5 | C14 | A27 | B6 | C14 | A27 | B7 | C14 | A27 | B11 | C14 | A27 | B13 | C14 | A27 | B14 | C14 | A27 | B15 | C14 | A27 | B16 | C14 | A27 | B17 | C14 |
| A27 | B4 | C15 | A27 | B5 | C15 | A27 | B6 | C15 | A27 | B7 | C15 | A27 | B11 | C15 | A27 | B13 | C15 | A27 | B14 | C15 | A27 | B15 | C15 | A27 | B16 | C15 | A27 | B17 | C15 |
| A27 | B4 | C16 | A27 | B5 | C16 | A27 | B6 | C16 | A27 | B7 | C16 | A27 | B11 | C16 | A27 | B13 | C16 | A27 | B14 | C16 | A27 | B15 | C16 | A27 | B16 | C16 | A27 | B17 | C16 |
| A27 | B4 | C17 | A27 | B5 | C17 | A27 | B6 | C17 | A27 | B7 | C17 | A27 | B11 | C17 | A27 | B13 | C17 | A27 | B14 | C17 | A27 | B15 | C17 | A27 | B16 | C17 | A27 | B17 | C17 |
| A27 | B4 | C18 | A27 | B5 | C18 | A27 | B6 | C18 | A27 | B7 | C18 | A27 | B11 | C18 | A27 | B13 | C18 | A27 | B14 | C18 | A27 | B15 | C18 | A27 | B16 | C18 | A27 | B17 | C18 |
| A27 | B4 | C19 | A27 | B5 | C19 | A27 | B6 | C19 | A27 | B7 | C19 | A27 | B11 | C19 | A27 | B13 | C19 | A27 | B14 | C19 | A27 | B15 | C19 | A27 | B16 | C19 | A27 | B17 | C19 |
| A27 | B4 | C20 | A27 | B5 | C20 | A27 | B6 | C20 | A27 | B7 | C20 | A27 | B11 | C20 | A27 | B13 | C20 | A27 | B14 | C20 | A27 | B15 | C20 | A27 | B16 | C20 | A27 | B17 | C20 |
| A27 | B4 | C21 | A27 | B5 | C21 | A27 | B6 | C21 | A27 | B7 | C21 | A27 | B11 | C21 | A27 | B13 | C21 | A27 | B14 | C21 | A27 | B15 | C21 | A27 | B16 | C21 | A27 | B17 | C21 |
| A27 | B4 | C22 | A27 | B5 | C22 | A27 | B6 | C22 | A27 | B7 | C22 | A27 | B11 | C22 | A27 | B13 | C22 | A27 | B14 | C22 | A27 | B15 | C22 | A27 | B16 | C22 | A27 | B17 | C22 |
| A27 | B4 | C23 | A27 | B5 | C23 | A27 | B6 | C23 | A27 | B7 | C23 | A27 | B11 | C23 | A27 | B13 | C23 | A27 | B14 | C23 | A27 | B15 | C23 | A27 | B16 | C23 | A27 | B17 | C23 |
| A27 | B4 | C24 | A27 | B5 | C24 | A27 | B6 | C24 | A27 | B7 | C24 | A27 | B11 | C24 | A27 | B13 | C24 | A27 | B14 | C24 | A27 | B15 | C24 | A27 | B16 | C24 | A27 | B17 | C24 |
| A27 | B4 | C25 | A27 | B5 | C25 | A27 | B6 | C25 | A27 | B7 | C25 | A27 | B11 | C25 | A27 | B13 | C25 | A27 | B14 | C25 | A27 | B15 | C25 | A27 | B16 | C25 | A27 | B17 | C25 |
| A27 | B4 | C26 | A27 | B5 | C26 | A27 | B6 | C26 | A27 | B7 | C26 | A27 | B11 | C26 | A27 | B13 | C26 | A27 | B14 | C26 | A27 | B15 | C26 | A27 | B16 | C26 | A27 | B17 | C26 |
| A27 | B4 | C27 | A27 | B5 | C27 | A27 | B6 | C27 | A27 | B7 | C27 | A27 | B11 | C27 | A27 | B13 | C27 | A27 | B14 | C27 | A27 | B15 | C27 | A27 | B16 | C27 | A27 | B17 | C27 |
| A27 | B4 | C28 | A27 | B5 | C28 | A27 | B6 | C28 | A27 | B7 | C28 | A27 | B11 | C28 | A27 | B13 | C28 | A27 | B14 | C28 | A27 | B15 | C28 | A27 | B16 | C28 | A27 | B17 | C28 |
| A27 | B4 | C29 | A27 | B5 | C29 | A27 | B6 | C29 | A27 | B7 | C29 | A27 | B11 | C29 | A27 | B13 | C29 | A27 | B14 | C29 | A27 | B15 | C29 | A27 | B16 | C29 | A27 | B17 | C29 |
| A27 | B4 | C30 | A27 | B5 | C30 | A27 | B6 | C30 | A27 | B7 | C30 | A27 | B11 | C30 | A27 | B13 | C30 | A27 | B14 | C30 | A27 | B15 | C30 | A27 | B16 | C30 | A27 | B17 | C30 |
| A27 | B4 | C31 | A27 | B5 | C31 | A27 | B6 | C31 | A27 | B7 | C31 | A27 | B11 | C31 | A27 | B13 | C31 | A27 | B14 | C31 | A27 | B15 | C31 | A27 | B16 | C31 | A27 | B17 | C31 |
| A27 | B4 | C32 | A27 | B5 | C32 | A27 | B6 | C32 | A27 | B7 | C32 | A27 | B11 | C32 | A27 | B13 | C32 | A27 | B14 | C32 | A27 | B15 | C32 | A27 | B16 | C32 | A27 | B17 | C32 |
| A27 | B4 | C33 | A27 | B5 | C33 | A27 | B6 | C33 | A27 | B7 | C33 | A27 | B11 | C33 | A27 | B13 | C33 | A27 | B14 | C33 | A27 | B15 | C33 | A27 | B16 | C33 | A27 | B17 | C33 |
| A27 | B4 | C34 | A27 | B5 | C34 | A27 | B6 | C34 | A27 | B7 | C34 | A27 | B11 | C34 | A27 | B13 | C34 | A27 | B14 | C34 | A27 | B15 | C34 | A27 | B16 | C34 | A27 | B17 | C34 |
| A27 | B4 | C35 | A27 | B5 | C35 | A27 | B6 | C35 | A27 | B7 | C35 | A27 | B11 | C35 | A27 | B13 | C35 | A27 | B14 | C35 | A27 | B15 | C35 | A27 | B16 | C35 | A27 | B17 | C35 |
| A27 | B4 | C36 | A27 | B5 | C36 | A27 | B6 | C36 | A27 | B7 | C36 | A27 | B11 | C36 | A27 | B13 | C36 | A27 | B14 | C36 | A27 | B15 | C36 | A27 | B16 | C36 | A27 | B17 | C36 |
| A27 | B4 | C37 | A27 | B5 | C37 | A27 | B6 | C37 | A27 | B7 | C37 | A27 | B11 | C37 | A27 | B13 | C37 | A27 | B14 | C37 | A27 | B15 | C37 | A27 | B16 | C37 | A27 | B17 | C37 |
| A27 | B4 | C38 | A27 | B5 | C38 | A27 | B6 | C38 | A27 | B7 | C38 | A27 | B11 | C38 | A27 | B13 | C38 | A27 | B14 | C38 | A27 | B15 | C38 | A27 | B16 | C38 | A27 | B17 | C38 |
| A27 | B4 | C39 | A27 | B5 | C39 | A27 | B6 | C39 | A27 | B7 | C39 | A27 | B11 | C39 | A27 | B13 | C39 | A27 | B14 | C39 | A27 | B15 | C39 | A27 | B16 | C39 | A27 | B17 | C39 |
| A27 | B4 | C40 | A27 | B5 | C40 | A27 | B6 | C40 | A27 | B7 | C40 | A27 | B11 | C40 | A27 | B13 | C40 | A27 | B14 | C40 | A27 | B15 | C40 | A27 | B16 | C40 | A27 | B17 | C40 |
| A27 | B4 | C41 | A27 | B5 | C41 | A27 | B6 | C41 | A27 | B7 | C41 | A27 | B11 | C41 | A27 | B13 | C41 | A27 | B14 | C41 | A27 | B15 | C41 | A27 | B16 | C41 | A27 | B17 | C41 |
| A29 | B4 | C1 | A29 | B5 | C1 | A29 | B6 | C1 | A29 | B7 | C1 | A29 | B11 | C1 | A29 | B13 | C1 | A29 | B14 | C1 | A29 | B15 | C1 | A29 | B16 | C1 | A29 | B17 | C1 |
| A29 | B4 | C2 | A29 | B5 | C2 | A29 | B6 | C2 | A29 | B7 | C2 | A29 | B11 | C2 | A29 | B13 | C2 | A29 | B14 | C2 | A29 | B15 | C2 | A29 | B16 | C2 | A29 | B17 | C2 |
| A29 | B4 | C3 | A29 | B5 | C3 | A29 | B6 | C3 | A29 | B7 | C3 | A29 | B11 | C3 | A29 | B13 | C3 | A29 | B14 | C3 | A29 | B15 | C3 | A29 | B16 | C3 | A29 | B17 | C3 |
| A29 | B4 | C4 | A29 | B5 | C4 | A29 | B6 | C4 | A29 | B7 | C4 | A29 | B11 | C4 | A29 | B13 | C4 | A29 | B14 | C4 | A29 | B15 | C4 | A29 | B16 | C4 | A29 | B17 | C4 |
| A29 | B4 | C5 | A29 | B5 | C5 | A29 | B6 | C5 | A29 | B7 | C5 | A29 | B11 | C5 | A29 | B13 | C5 | A29 | B14 | C5 | A29 | B15 | C5 | A29 | B16 | C5 | A29 | B17 | C5 |
| A29 | B4 | C6 | A29 | B5 | C6 | A29 | B6 | C6 | A29 | B7 | C6 | A29 | B11 | C6 | A29 | B13 | C6 | A29 | B14 | C6 | A29 | B15 | C6 | A29 | B16 | C6 | A29 | B17 | C6 |
| A29 | B4 | C7 | A29 | B5 | C7 | A29 | B6 | C7 | A29 | B7 | C7 | A29 | B11 | C7 | A29 | B13 | C7 | A29 | B14 | C7 | A29 | B15 | C7 | A29 | B16 | C7 | A29 | B17 | C7 |
| A29 | B4 | C8 | A29 | B5 | C8 | A29 | B6 | C8 | A29 | B7 | C8 | A29 | B11 | C8 | A29 | B13 | C8 | A29 | B14 | C8 | A29 | B15 | C8 | A29 | B16 | C8 | A29 | B17 | C8 |
| A29 | B4 | C9 | A29 | B5 | C9 | A29 | B6 | C9 | A29 | B7 | C9 | A29 | B11 | C9 | A29 | B13 | C9 | A29 | B14 | C9 | A29 | B15 | C9 | A29 | B16 | C9 | A29 | B17 | C9 |
| A29 | B4 | C10 | A29 | B5 | C10 | A29 | B6 | C10 | A29 | B7 | C10 | A29 | B11 | C10 | A29 | B13 | C10 | A29 | B14 | C10 | A29 | B15 | C10 | A29 | B16 | C10 | A29 | B17 | C10 |
| A29 | B4 | C11 | A29 | B5 | C11 | A29 | B6 | C11 | A29 | B7 | C11 | A29 | B11 | C11 | A29 | B13 | C11 | A29 | B14 | C11 | A29 | B15 | C11 | A29 | B16 | C11 | A29 | B17 | C11 |
| A29 | B4 | C12 | A29 | B5 | C12 | A29 | B6 | C12 | A29 | B7 | C12 | A29 | B11 | C12 | A29 | B13 | C12 | A29 | B14 | C12 | A29 | B15 | C12 | A29 | B16 | C12 | A29 | B17 | C12 |
| A29 | B4 | C13 | A29 | B5 | C13 | A29 | B6 | C13 | A29 | B7 | C13 | A29 | B11 | C13 | A29 | B13 | C13 | A29 | B14 | C13 | A29 | B15 | C13 | A29 | B16 | C13 | A29 | B17 | C13 |
| A29 | B4 | C14 | A29 | B5 | C14 | A29 | B6 | C14 | A29 | B7 | C14 | A29 | B11 | C14 | A29 | B13 | C14 | A29 | B14 | C14 | A29 | B15 | C14 | A29 | B16 | C14 | A29 | B17 | C14 |
| A29 | B4 | C15 | A29 | B5 | C15 | A29 | B6 | C15 | A29 | B7 | C15 | A29 | B11 | C15 | A29 | B13 | C15 | A29 | B14 | C15 | A29 | B15 | C15 | A29 | B16 | C15 | A29 | B17 | C15 |
| A29 | B4 | C16 | A29 | B5 | C16 | A29 | B6 | C16 | A29 | B7 | C16 | A29 | B11 | C16 | A29 | B13 | C16 | A29 | B14 | C16 | A29 | B15 | C16 | A29 | B16 | C16 | A29 | B17 | C16 |
| A29 | B4 | C17 | A29 | B5 | C17 | A29 | B6 | C17 | A29 | B7 | C17 | A29 | B11 | C17 | A29 | B13 | C17 | A29 | B14 | C17 | A29 | B15 | C17 | A29 | B16 | C17 | A29 | B17 | C17 |
| A29 | B4 | C18 | A29 | B5 | C18 | A29 | B6 | C18 | A29 | B7 | C18 | A29 | B11 | C18 | A29 | B13 | C18 | A29 | B14 | C18 | A29 | B15 | C18 | A29 | B16 | C18 | A29 | B17 | C18 |
| A29 | B4 | C19 | A29 | B5 | C19 | A29 | B6 | C19 | A29 | B7 | C19 | A29 | B11 | C19 | A29 | B13 | C19 | A29 | B14 | C19 | A29 | B15 | C19 | A29 | B16 | C19 | A29 | B17 | C19 |
| A29 | B4 | C20 | A29 | B5 | C20 | A29 | B6 | C20 | A29 | B7 | C20 | A29 | B11 | C20 | A29 | B13 | C20 | A29 | B14 | C20 | A29 | B15 | C20 | A29 | B16 | C20 | A29 | B17 | C20 |
| A29 | B4 | C21 | A29 | B5 | C21 | A29 | B6 | C21 | A29 | B7 | C21 | A29 | B11 | C21 | A29 | B13 | C21 | A29 | B11 | C21 | A29 | B15 | C21 | A29 | B16 | C21 | A29 | B17 | C21 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A29 | B4 | C22 | A29 | B5 | C22 | A29 | B6 | C22 | A29 | B7 | C22 | A29 | B11 | C22 | A29 | B13 | C22 | A29 | B14 | C22 | A29 | B15 | C22 | A29 | B16 | C22 | A29 | B17 | C22 |
| A29 | B4 | C23 | A29 | B5 | C23 | A29 | B6 | C23 | A29 | B7 | C23 | A29 | B11 | C23 | A29 | B13 | C23 | A29 | B14 | C23 | A29 | B15 | C23 | A29 | B16 | C23 | A29 | B17 | C23 |
| A29 | B4 | C24 | A29 | B5 | C24 | A29 | B6 | C24 | A29 | B7 | C24 | A29 | B11 | C24 | A29 | B13 | C24 | A29 | B14 | C24 | A29 | B15 | C24 | A29 | B16 | C24 | A29 | B17 | C24 |
| A29 | B4 | C25 | A29 | B5 | C25 | A29 | B6 | C25 | A29 | B7 | C25 | A29 | B11 | C25 | A29 | B13 | C25 | A29 | B14 | C25 | A29 | B15 | C25 | A29 | B16 | C25 | A29 | B17 | C25 |
| A29 | B4 | C26 | A29 | B5 | C26 | A29 | B6 | C26 | A29 | B7 | C26 | A29 | B11 | C26 | A29 | B13 | C26 | A29 | B14 | C26 | A29 | B15 | C26 | A29 | B16 | C26 | A29 | B17 | C26 |
| A29 | B4 | C27 | A29 | B5 | C27 | A29 | B6 | C27 | A29 | B7 | C27 | A29 | B11 | C27 | A29 | B13 | C27 | A29 | B14 | C27 | A29 | B15 | C27 | A29 | B16 | C27 | A29 | B17 | C27 |
| A29 | B4 | C28 | A29 | B5 | C28 | A29 | B6 | C28 | A29 | B7 | C28 | A29 | B11 | C28 | A29 | B13 | C28 | A29 | B14 | C28 | A29 | B15 | C28 | A29 | B16 | C28 | A29 | B17 | C28 |
| A29 | B4 | C29 | A29 | B5 | C29 | A29 | B6 | C29 | A29 | B7 | C29 | A29 | B11 | C29 | A29 | B13 | C29 | A29 | B14 | C29 | A29 | B15 | C29 | A29 | B16 | C29 | A29 | B17 | C29 |
| A29 | B4 | C30 | A29 | B5 | C30 | A29 | B6 | C30 | A29 | B7 | C30 | A29 | B11 | C30 | A29 | B13 | C30 | A29 | B14 | C30 | A29 | B15 | C30 | A29 | B16 | C30 | A29 | B17 | C30 |
| A29 | B4 | C31 | A29 | B5 | C31 | A29 | B6 | C31 | A29 | B7 | C31 | A29 | B11 | C31 | A29 | B13 | C31 | A29 | B14 | C31 | A29 | B15 | C31 | A29 | B16 | C31 | A29 | B17 | C31 |
| A29 | B4 | C32 | A29 | B5 | C32 | A29 | B6 | C32 | A29 | B7 | C32 | A29 | B11 | C32 | A29 | B13 | C32 | A29 | B14 | C32 | A29 | B15 | C32 | A29 | B16 | C32 | A29 | B17 | C32 |
| A29 | B4 | C33 | A29 | B5 | C33 | A29 | B6 | C33 | A29 | B7 | C33 | A29 | B11 | C33 | A29 | B13 | C33 | A29 | B14 | C33 | A29 | B15 | C33 | A29 | B16 | C33 | A29 | B17 | C33 |
| A29 | B4 | C34 | A29 | B5 | C34 | A29 | B6 | C34 | A29 | B7 | C34 | A29 | B11 | C34 | A29 | B13 | C34 | A29 | B14 | C34 | A29 | B15 | C34 | A29 | B16 | C34 | A29 | B17 | C34 |
| A29 | B4 | C35 | A29 | B5 | C35 | A29 | B6 | C35 | A29 | B7 | C35 | A29 | B11 | C35 | A29 | B13 | C35 | A29 | B14 | C35 | A29 | B15 | C35 | A29 | B16 | C35 | A29 | B17 | C35 |
| A29 | B4 | C36 | A29 | B5 | C36 | A29 | B6 | C36 | A29 | B7 | C36 | A29 | B11 | C36 | A29 | B13 | C36 | A29 | B14 | C36 | A29 | B15 | C36 | A29 | B16 | C36 | A29 | B17 | C36 |
| A29 | B4 | C37 | A29 | B5 | C37 | A29 | B6 | C37 | A29 | B7 | C37 | A29 | B11 | C37 | A29 | B13 | C37 | A29 | B14 | C37 | A29 | B15 | C37 | A29 | B16 | C37 | A29 | B17 | C37 |
| A29 | B4 | C38 | A29 | B5 | C38 | A29 | B6 | C38 | A29 | B7 | C38 | A29 | B11 | C38 | A29 | B13 | C38 | A29 | B14 | C38 | A29 | B15 | C38 | A29 | B16 | C38 | A29 | B17 | C38 |
| A29 | B4 | C39 | A29 | B5 | C39 | A29 | B6 | C39 | A29 | B7 | C39 | A29 | B11 | C39 | A29 | B13 | C39 | A29 | B14 | C39 | A29 | B15 | C39 | A29 | B16 | C39 | A29 | B17 | C39 |
| A29 | B4 | C40 | A29 | B5 | C40 | A29 | B6 | C40 | A29 | B7 | C40 | A29 | B11 | C40 | A29 | B13 | C40 | A29 | B14 | C40 | A29 | B15 | C40 | A29 | B16 | C40 | A29 | B17 | C40 |
| A29 | B4 | C41 | A29 | B5 | C41 | A29 | B6 | C41 | A29 | B7 | C41 | A29 | B11 | C41 | A29 | B13 | C41 | A29 | B14 | C41 | A29 | B15 | C41 | A29 | B16 | C41 | A29 | B17 | C41 |
| A30 | B4 | C1 | A30 | B5 | C1 | A30 | B6 | C1 | A30 | B7 | C1 | A30 | B11 | C1 | A30 | B13 | C1 | A30 | B14 | C1 | A30 | B15 | C1 | A30 | B16 | C1 | A30 | B17 | C1 |
| A30 | B4 | C2 | A30 | B5 | C2 | A30 | B6 | C2 | A30 | B7 | C2 | A30 | B11 | C2 | A30 | B13 | C2 | A30 | B14 | C2 | A30 | B15 | C2 | A30 | B16 | C2 | A30 | B17 | C2 |
| A30 | B4 | C3 | A30 | B5 | C3 | A30 | B6 | C3 | A30 | B7 | C3 | A30 | B11 | C3 | A30 | B13 | C3 | A30 | B14 | C3 | A30 | B15 | C3 | A30 | B16 | C3 | A30 | B17 | C3 |
| A30 | B4 | C4 | A30 | B5 | C4 | A30 | B6 | C4 | A30 | B7 | C4 | A30 | B11 | C4 | A30 | B13 | C4 | A30 | B14 | C4 | A30 | B15 | C4 | A30 | B16 | C4 | A30 | B17 | C4 |
| A30 | B4 | C5 | A30 | B5 | C5 | A30 | B6 | C5 | A30 | B7 | C5 | A30 | B11 | C5 | A30 | B13 | C5 | A30 | B14 | C5 | A30 | B15 | C5 | A30 | B16 | C5 | A30 | B17 | C5 |
| A30 | B4 | C6 | A30 | B5 | C6 | A30 | B6 | C6 | A30 | B7 | C6 | A30 | B11 | C6 | A30 | B13 | C6 | A30 | B14 | C6 | A30 | B15 | C6 | A30 | B16 | C6 | A30 | B17 | C6 |
| A30 | B4 | C7 | A30 | B5 | C7 | A30 | B6 | C7 | A30 | B7 | C7 | A30 | B11 | C7 | A30 | B13 | C7 | A30 | B14 | C7 | A30 | B15 | C7 | A30 | B16 | C7 | A30 | B17 | C7 |
| A30 | B4 | C8 | A30 | B5 | C8 | A30 | B6 | C8 | A30 | B7 | C8 | A30 | B11 | C8 | A30 | B13 | C8 | A30 | B14 | C8 | A30 | B15 | C8 | A30 | B16 | C8 | A30 | B17 | C8 |
| A30 | B4 | C9 | A30 | B5 | C9 | A30 | B6 | C9 | A30 | B7 | C9 | A30 | B11 | C9 | A30 | B13 | C9 | A30 | B14 | C9 | A30 | B15 | C9 | A30 | B16 | C9 | A30 | B17 | C9 |
| A30 | B4 | C10 | A30 | B5 | C10 | A30 | B6 | C10 | A30 | B7 | C10 | A30 | B11 | C10 | A30 | B13 | C10 | A30 | B14 | C10 | A30 | B15 | C10 | A30 | B16 | C10 | A30 | B17 | C10 |
| A30 | B4 | C11 | A30 | B5 | C11 | A30 | B6 | C11 | A30 | B7 | C11 | A30 | B11 | C11 | A30 | B13 | C11 | A30 | B14 | C11 | A30 | B15 | C11 | A30 | B16 | C11 | A30 | B17 | C11 |
| A30 | B4 | C12 | A30 | B5 | C12 | A30 | B6 | C12 | A30 | B7 | C12 | A30 | B11 | C12 | A30 | B13 | C12 | A30 | B14 | C12 | A30 | B15 | C12 | A30 | B16 | C12 | A30 | B17 | C12 |
| A30 | B4 | C13 | A30 | B5 | C13 | A30 | B6 | C13 | A30 | B7 | C13 | A30 | B11 | C13 | A30 | B13 | C13 | A30 | B14 | C13 | A30 | B15 | C13 | A30 | B16 | C13 | A30 | B17 | C13 |
| A30 | B4 | C14 | A30 | B5 | C14 | A30 | B6 | C14 | A30 | B7 | C14 | A30 | B11 | C14 | A30 | B13 | C14 | A30 | B14 | C14 | A30 | B15 | C14 | A30 | B16 | C14 | A30 | B17 | C14 |
| A30 | B4 | C15 | A30 | B5 | C15 | A30 | B6 | C15 | A30 | B7 | C15 | A30 | B11 | C15 | A30 | B13 | C15 | A30 | B14 | C15 | A30 | B15 | C15 | A30 | B16 | C15 | A30 | B17 | C15 |
| A30 | B4 | C16 | A30 | B5 | C16 | A30 | B6 | C16 | A30 | B7 | C16 | A30 | B11 | C16 | A30 | B13 | C16 | A30 | B14 | C16 | A30 | B15 | C16 | A30 | B16 | C16 | A30 | B17 | C16 |
| A30 | B4 | C17 | A30 | B5 | C17 | A30 | B6 | C17 | A30 | B7 | C17 | A30 | B11 | C17 | A30 | B13 | C17 | A30 | B14 | C17 | A30 | B15 | C17 | A30 | B16 | C17 | A30 | B17 | C17 |
| A30 | B4 | C18 | A30 | B5 | C18 | A30 | B6 | C18 | A30 | B7 | C18 | A30 | B11 | C18 | A30 | B13 | C18 | A30 | B14 | C18 | A30 | B15 | C18 | A30 | B16 | C18 | A30 | B17 | C18 |
| A30 | B4 | C19 | A30 | B5 | C19 | A30 | B6 | C19 | A30 | B7 | C19 | A30 | B11 | C19 | A30 | B13 | C19 | A30 | B14 | C19 | A30 | B15 | C19 | A30 | B16 | C19 | A30 | B17 | C19 |
| A30 | B4 | C20 | A30 | B5 | C20 | A30 | B6 | C20 | A30 | B7 | C20 | A30 | B11 | C20 | A30 | B13 | C20 | A30 | B14 | C20 | A30 | B15 | C20 | A30 | B16 | C20 | A30 | B17 | C20 |
| A30 | B4 | C21 | A30 | B5 | C21 | A30 | B6 | C21 | A30 | B7 | C21 | A30 | B11 | C21 | A30 | B13 | C21 | A30 | B14 | C21 | A30 | B15 | C21 | A30 | B16 | C21 | A30 | B17 | C21 |
| A30 | B4 | C22 | A30 | B5 | C22 | A30 | B6 | C22 | A30 | B7 | C22 | A30 | B11 | C22 | A30 | B13 | C22 | A30 | B14 | C22 | A30 | B15 | C22 | A30 | B16 | C22 | A30 | B17 | C22 |
| A30 | B4 | C23 | A30 | B5 | C23 | A30 | B6 | C23 | A30 | B7 | C23 | A30 | B11 | C23 | A30 | B13 | C23 | A30 | B14 | C23 | A30 | B15 | C23 | A30 | B16 | C23 | A30 | B17 | C23 |
| A30 | B4 | C24 | A30 | B5 | C24 | A30 | B6 | C24 | A30 | B7 | C24 | A30 | B11 | C24 | A30 | B13 | C24 | A30 | B14 | C24 | A30 | B15 | C24 | A30 | B16 | C24 | A30 | B17 | C24 |
| A30 | B4 | C25 | A30 | B5 | C25 | A30 | B6 | C25 | A30 | B7 | C25 | A30 | B11 | C25 | A30 | B13 | C25 | A30 | B14 | C25 | A30 | B15 | C25 | A30 | B16 | C25 | A30 | B17 | C25 |
| A30 | B4 | C26 | A30 | B5 | C26 | A30 | B6 | C26 | A30 | B7 | C26 | A30 | B11 | C26 | A30 | B13 | C26 | A30 | B14 | C26 | A30 | B15 | C26 | A30 | B16 | C26 | A30 | B17 | C26 |
| A30 | B4 | C27 | A30 | B5 | C27 | A30 | B6 | C27 | A30 | B7 | C27 | A30 | B11 | C27 | A30 | B13 | C27 | A30 | B14 | C27 | A30 | B15 | C27 | A30 | B16 | C27 | A30 | B17 | C27 |
| A30 | B4 | C28 | A30 | B5 | C28 | A30 | B6 | C28 | A30 | B7 | C28 | A30 | B11 | C28 | A30 | B13 | C28 | A30 | B14 | C28 | A30 | B15 | C28 | A30 | B16 | C28 | A30 | B17 | C28 |
| A30 | B4 | C29 | A30 | B5 | C29 | A30 | B6 | C29 | A30 | B7 | C29 | A30 | B11 | C29 | A30 | B13 | C29 | A30 | B14 | C29 | A30 | B15 | C29 | A30 | B16 | C29 | A30 | B17 | C29 |
| A30 | B4 | C30 | A30 | B5 | C30 | A30 | B6 | C30 | A30 | B7 | C30 | A30 | B11 | C30 | A10 | B13 | C30 | A30 | B14 | C30 | A30 | B15 | C30 | A30 | B16 | C30 | A30 | B17 | C30 |

-continued

| | | | | | | | | | | | | | | | | | | | | | | | | | | |
|---|---|---|---|---|---|---|---|---|---|---|---|---|---|---|---|---|---|---|---|---|---|---|---|---|---|---|
| A30 B4 | C31 | A30 B5 | C31 | A30 B6 | C31 | A30 | B7 | C31 | A30 | B11 | C31 | A30 | B13 | C31 | A30 | B14 | C31 | A30 | B15 | C31 | A30 | B16 | C31 | A30 | B17 | C31 |
| A30 B4 | C32 | A30 B5 | C32 | A30 B6 | C32 | A30 | B7 | C32 | A30 | B11 | C32 | A30 | B13 | C32 | A30 | B14 | C32 | A30 | B15 | C32 | A30 | B16 | C32 | A30 | B17 | C32 |
| A30 B4 | C33 | A30 B5 | C33 | A30 B6 | C33 | A30 | B7 | C33 | A30 | B11 | C33 | A30 | B13 | C33 | A30 | B14 | C33 | A30 | B15 | C33 | A30 | B16 | C33 | A30 | B17 | C33 |
| A30 B4 | C34 | A30 B5 | C34 | A30 B6 | C34 | A30 | B7 | C34 | A30 | B11 | C34 | A30 | B13 | C34 | A30 | B14 | C34 | A30 | B15 | C34 | A30 | B16 | C34 | A30 | B17 | C34 |
| A30 B4 | C35 | A30 B5 | C35 | A30 B6 | C35 | A30 | B7 | C35 | A30 | B11 | C35 | A30 | B13 | C35 | A30 | B14 | C35 | A30 | B15 | C35 | A30 | B16 | C35 | A30 | B17 | C35 |
| A30 B4 | C36 | A30 B5 | C36 | A30 B6 | C36 | A30 | B7 | C36 | A30 | B11 | C36 | A30 | B13 | C36 | A30 | B14 | C36 | A30 | B15 | C36 | A30 | B16 | C36 | A30 | B17 | C36 |
| A30 B4 | C37 | A30 B5 | C37 | A30 B6 | C37 | A30 | B7 | C37 | A30 | B11 | C37 | A30 | B13 | C37 | A30 | B14 | C37 | A30 | B15 | C37 | A30 | B16 | C37 | A30 | B17 | C37 |
| A30 B4 | C38 | A30 B5 | C38 | A30 B6 | C38 | A30 | B7 | C38 | A30 | B11 | C38 | A30 | B13 | C38 | A30 | B14 | C38 | A30 | B15 | C38 | A30 | B16 | C38 | A30 | B17 | C38 |
| A30 B4 | C39 | A30 B5 | C39 | A30 B6 | C39 | A30 | B7 | C39 | A30 | B11 | C39 | A30 | B13 | C39 | A30 | B14 | C39 | A30 | B15 | C39 | A30 | B16 | C39 | A30 | B17 | C39 |
| A30 B4 | C40 | A30 B5 | C40 | A30 B6 | C40 | A30 | B7 | C40 | A30 | B11 | C40 | A30 | B13 | C40 | A30 | B14 | C40 | A30 | B15 | C40 | A30 | B16 | C40 | A30 | B17 | C40 |
| A30 B4 | C41 | A30 B5 | C41 | A30 B6 | C41 | A30 | B7 | C41 | A30 | B11 | C41 | A30 | B13 | C41 | A30 | B14 | C41 | A30 | B15 | C41 | A30 | B16 | C41 | A30 | B17 | C41 |
| A32 B4 | C1 | A32 B5 | C1 | A32 B6 | C1 | A32 | B7 | C1 | A32 | B11 | C1 | A32 | B13 | C1 | A32 | B14 | C1 | A32 | B15 | C1 | A32 | B16 | C1 | A32 | B17 | C1 |
| A32 B4 | C2 | A32 B5 | C2 | A32 B6 | C2 | A32 | B7 | C2 | A32 | B11 | C2 | A32 | B13 | C2 | A32 | B14 | C2 | A32 | B15 | C2 | A32 | B16 | C2 | A32 | B17 | C2 |
| A32 B4 | C3 | A32 B5 | C3 | A32 B6 | C3 | A32 | B7 | C3 | A32 | B11 | C3 | A32 | B13 | C3 | A32 | B14 | C3 | A32 | B15 | C3 | A32 | B16 | C3 | A32 | B17 | C3 |
| A32 B4 | C4 | A32 B5 | C4 | A32 B6 | C4 | A32 | B7 | C4 | A32 | B11 | C4 | A32 | B13 | C4 | A32 | B14 | C4 | A32 | B15 | C4 | A32 | B16 | C4 | A32 | B17 | C4 |
| A32 B4 | C5 | A32 B5 | C5 | A32 B6 | C5 | A32 | B7 | C5 | A32 | B11 | C5 | A32 | B13 | C5 | A32 | B14 | C5 | A32 | B15 | C5 | A32 | B16 | C5 | A32 | B17 | C5 |
| A32 B4 | C6 | A32 B5 | C6 | A32 B6 | C6 | A32 | B7 | C6 | A32 | B11 | C6 | A32 | B13 | C6 | A32 | B14 | C6 | A32 | B15 | C6 | A32 | B16 | C6 | A32 | B17 | C6 |
| A32 B4 | C7 | A32 B5 | C7 | A32 B6 | C7 | A32 | B7 | C7 | A32 | B11 | C7 | A32 | B13 | C7 | A32 | B14 | C7 | A32 | B15 | C7 | A32 | B16 | C7 | A32 | B17 | C7 |
| A32 B4 | C8 | A32 B5 | C8 | A32 B6 | C8 | A32 | B7 | C8 | A32 | B11 | C8 | A32 | B13 | C8 | A32 | B14 | C8 | A32 | B15 | C8 | A32 | B16 | C8 | A32 | B17 | C8 |
| A32 B4 | C9 | A32 B5 | C9 | A32 B6 | C9 | A32 | B7 | C9 | A32 | B11 | C9 | A32 | B13 | C9 | A32 | B14 | C9 | A32 | B15 | C9 | A32 | B16 | C9 | A32 | B17 | C9 |
| A32 B4 | C10 | A32 B5 | C10 | A32 B6 | C10 | A32 | B7 | C10 | A32 | B11 | C10 | A32 | B13 | C10 | A32 | B14 | C10 | A32 | B15 | C10 | A32 | B16 | C10 | A32 | B17 | C10 |
| A32 B4 | C11 | A32 B5 | C11 | A32 B6 | C11 | A32 | B7 | C11 | A32 | B11 | C11 | A32 | B13 | C11 | A32 | B14 | C11 | A32 | B15 | C11 | A32 | B16 | C11 | A32 | B17 | C11 |
| A32 B4 | C12 | A32 B5 | C12 | A32 B6 | C12 | A32 | B7 | C12 | A32 | B11 | C12 | A32 | B13 | C12 | A32 | B14 | C12 | A32 | B15 | C12 | A32 | B16 | C12 | A32 | B17 | C12 |
| A32 B4 | C13 | A32 B5 | C13 | A32 B6 | C13 | A32 | B7 | C13 | A32 | B11 | C13 | A32 | B13 | C13 | A32 | B14 | C13 | A32 | B15 | C13 | A32 | B16 | C13 | A32 | B17 | C13 |
| A32 B4 | C14 | A32 B5 | C14 | A32 B6 | C14 | A32 | B7 | C14 | A32 | B11 | C14 | A32 | B13 | C14 | A32 | B14 | C14 | A32 | B15 | C14 | A32 | B16 | C14 | A32 | B17 | C14 |
| A32 B4 | C15 | A32 B5 | C15 | A32 B6 | C15 | A32 | B7 | C15 | A32 | B11 | C15 | A32 | B13 | C15 | A32 | B14 | C15 | A32 | B15 | C15 | A32 | B16 | C15 | A32 | B17 | C15 |
| A32 B4 | C16 | A32 B5 | C16 | A32 B6 | C16 | A32 | B7 | C16 | A32 | B11 | C16 | A32 | B13 | C16 | A32 | B14 | C16 | A32 | B15 | C16 | A32 | B16 | C16 | A32 | B17 | C16 |
| A32 B4 | C17 | A32 B5 | C17 | A32 B6 | C17 | A32 | B7 | C17 | A32 | B11 | C17 | A32 | B13 | C17 | A32 | B14 | C17 | A32 | B15 | C17 | A32 | B16 | C17 | A32 | B17 | C17 |
| A32 B4 | C18 | A32 B5 | C18 | A32 B6 | C18 | A32 | B7 | C18 | A32 | B11 | C18 | A32 | B13 | C18 | A32 | B14 | C18 | A32 | B15 | C18 | A32 | B16 | C18 | A32 | B17 | C18 |
| A32 B4 | C19 | A32 B5 | C19 | A32 B6 | C19 | A32 | B7 | C19 | A32 | B11 | C19 | A32 | B13 | C19 | A32 | B14 | C19 | A32 | B15 | C19 | A32 | B16 | C19 | A32 | B17 | C19 |
| A32 B4 | C20 | A32 B5 | C20 | A32 B6 | C20 | A32 | B7 | C20 | A32 | B11 | C20 | A32 | B13 | C20 | A32 | B14 | C20 | A32 | B15 | C20 | A32 | B16 | C20 | A32 | B17 | C20 |
| A32 B4 | C21 | A32 B5 | C21 | A32 B6 | C21 | A32 | B7 | C21 | A32 | B11 | C21 | A32 | B13 | C21 | A32 | B14 | C21 | A32 | B15 | C21 | A32 | B16 | C21 | A32 | B17 | C21 |
| A32 B4 | C22 | A32 B5 | C22 | A32 B6 | C22 | A32 | B7 | C22 | A32 | B11 | C22 | A32 | B13 | C22 | A32 | B14 | C22 | A32 | B15 | C22 | A32 | B16 | C22 | A32 | B17 | C22 |
| A32 B4 | C23 | A32 B5 | C23 | A32 B6 | C23 | A32 | B7 | C23 | A32 | B11 | C23 | A32 | B13 | C23 | A32 | B14 | C23 | A32 | B15 | C23 | A32 | B16 | C23 | A32 | B17 | C23 |
| A32 B4 | C24 | A32 B5 | C24 | A32 B6 | C24 | A32 | B7 | C24 | A32 | B11 | C24 | A32 | B13 | C24 | A32 | B14 | C24 | A32 | B15 | C24 | A32 | B16 | C24 | A32 | B17 | C24 |
| A32 B4 | C25 | A32 B5 | C25 | A32 B6 | C25 | A32 | B7 | C25 | A32 | B11 | C25 | A32 | B13 | C25 | A32 | B14 | C25 | A32 | B15 | C25 | A32 | B16 | C25 | A32 | B17 | C25 |
| A32 B4 | C26 | A32 B5 | C26 | A32 B6 | C26 | A32 | B7 | C26 | A32 | B11 | C26 | A32 | B13 | C26 | A32 | B14 | C26 | A32 | B15 | C26 | A32 | B16 | C26 | A32 | B17 | C26 |
| A32 B4 | C27 | A32 B5 | C27 | A32 B6 | C27 | A32 | B7 | C27 | A32 | B11 | C27 | A32 | B13 | C27 | A32 | B14 | C27 | A32 | B15 | C27 | A32 | B16 | C27 | A32 | B17 | C27 |
| A32 B4 | C28 | A32 B5 | C28 | A32 B6 | C28 | A32 | B7 | C28 | A32 | B11 | C28 | A32 | B13 | C28 | A32 | B14 | C28 | A32 | B15 | C28 | A32 | B16 | C28 | A32 | B17 | C28 |
| A32 B4 | C29 | A32 B5 | C29 | A32 B6 | C29 | A32 | B7 | C29 | A32 | B11 | C29 | A32 | B13 | C29 | A32 | B14 | C29 | A32 | B15 | C29 | A32 | B16 | C29 | A32 | B17 | C29 |
| A32 B4 | C30 | A32 B5 | C30 | A32 B6 | C30 | A32 | B7 | C30 | A32 | B11 | C30 | A32 | B13 | C30 | A32 | B14 | C30 | A32 | B15 | C30 | A32 | B16 | C30 | A32 | B17 | C30 |
| A32 B4 | C31 | A32 B5 | C31 | A32 B6 | C31 | A32 | B7 | C31 | A32 | B11 | C31 | A32 | B13 | C31 | A32 | B14 | C31 | A32 | B15 | C31 | A32 | B16 | C31 | A32 | B17 | C31 |
| A32 B4 | C32 | A32 B5 | C32 | A32 B6 | C32 | A32 | B7 | C32 | A32 | B11 | C32 | A32 | B13 | C32 | A32 | B14 | C32 | A32 | B15 | C32 | A32 | B16 | C32 | A32 | B17 | C32 |
| A32 B4 | C33 | A32 B5 | C33 | A32 B6 | C33 | A32 | B7 | C33 | A32 | B11 | C33 | A32 | B13 | C33 | A32 | B14 | C33 | A32 | B15 | C33 | A32 | B16 | C33 | A32 | B17 | C33 |
| A32 B4 | C34 | A32 B5 | C34 | A32 B6 | C34 | A32 | B7 | C34 | A32 | B11 | C34 | A32 | B13 | C34 | A32 | B14 | C34 | A32 | B15 | C34 | A32 | B16 | C34 | A32 | B17 | C34 |
| A32 B4 | C35 | A32 B5 | C35 | A32 B6 | C35 | A32 | B7 | C35 | A32 | B11 | C35 | A32 | B13 | C35 | A32 | B14 | C35 | A32 | B15 | C35 | A32 | B16 | C35 | A32 | B17 | C35 |
| A32 B4 | C36 | A32 B5 | C36 | A32 B6 | C36 | A32 | B7 | C36 | A32 | B11 | C36 | A32 | B13 | C36 | A32 | B14 | C36 | A32 | B15 | C36 | A32 | B16 | C36 | A32 | B17 | C36 |
| A32 B4 | C37 | A32 B5 | C37 | A32 B6 | C37 | A32 | B7 | C37 | A32 | B11 | C37 | A32 | B13 | C37 | A32 | B14 | C37 | A32 | B15 | C37 | A32 | B16 | C37 | A32 | B17 | C37 |
| A32 B4 | C38 | A32 B5 | C38 | A32 B6 | C38 | A32 | B7 | C38 | A32 | B11 | C38 | A32 | B13 | C38 | A32 | B14 | C38 | A32 | B15 | C38 | A32 | B16 | C38 | A32 | B17 | C38 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A32 | B4 | C39 | A32 | B5 | C39 | A32 | B6 | C39 | A32 | B7 | C39 | A32 | B11 | C39 | A32 | B13 | C39 | A32 | B14 | C39 | A32 | B15 | C39 | A32 | B16 | C39 | A32 | B17 | C39 |
| A32 | B4 | C40 | A32 | B5 | C40 | A32 | B6 | C40 | A32 | B7 | C40 | A32 | B11 | C40 | A32 | B13 | C40 | A32 | B14 | C40 | A32 | B15 | C40 | A32 | B16 | C40 | A32 | B17 | C40 |
| A32 | B4 | C41 | A32 | B5 | C41 | A32 | B6 | C41 | A32 | B7 | C41 | A32 | B11 | C41 | A32 | B13 | C41 | A32 | B14 | C41 | A32 | B15 | C41 | A32 | B16 | C41 | A32 | B17 | C41 |

Specific compounds that are preferred for Calhepsin S inhibitory activity:

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A4 | B6 | C1 | A4 | B7 | C1 | A4 | B5 | C1 | A4 | B9 | C1 | A4 | B10 | C1 | A4 | B12 | C1 | A4 | B18 | C1 | A4 | B22 | C1 | A4 | B23 | C1 | A4 | B25 | C1 |
| A4 | B6 | C2 | A4 | B7 | C2 | A4 | B8 | C2 | A4 | B9 | C2 | A4 | B10 | C2 | A4 | B12 | C2 | A4 | B18 | C2 | A4 | B22 | C2 | A4 | B23 | C2 | A4 | B25 | C2 |
| A4 | B6 | C3 | A4 | B7 | C3 | A4 | B8 | C3 | A4 | B9 | C3 | A4 | B10 | C3 | A4 | B12 | C3 | A4 | B18 | C3 | A4 | B22 | C3 | A4 | B23 | C3 | A4 | B25 | C3 |
| A4 | B6 | C4 | A4 | B7 | C4 | A4 | B8 | C4 | A4 | B9 | C4 | A4 | B10 | C4 | A4 | B12 | C4 | A4 | B18 | C4 | A4 | B22 | C4 | A4 | B23 | C4 | A4 | B25 | C4 |
| A4 | B6 | C5 | A4 | B7 | C5 | A4 | B8 | C5 | A4 | B9 | C5 | A4 | B10 | C5 | A4 | B12 | C5 | A4 | B18 | C5 | A4 | B22 | C5 | A4 | B23 | C5 | A4 | B25 | C5 |
| A4 | B6 | C6 | A4 | B7 | C6 | A4 | B8 | C6 | A4 | B9 | C6 | A4 | B10 | C6 | A4 | B12 | C6 | A4 | B18 | C6 | A4 | B22 | C6 | A4 | B23 | C6 | A4 | B25 | C6 |
| A4 | B6 | C7 | A4 | B7 | C7 | A4 | B8 | C7 | A4 | B9 | C7 | A4 | B10 | C7 | A4 | B12 | C7 | A4 | B18 | C7 | A4 | B22 | C7 | A4 | B23 | C7 | A4 | B25 | C7 |
| A4 | B6 | C5 | A4 | B7 | C8 | A4 | B8 | C8 | A4 | B9 | C8 | A4 | B10 | C8 | A4 | B12 | C8 | A4 | B18 | C8 | A4 | B22 | C8 | A4 | B23 | C8 | A4 | B25 | C8 |
| A4 | B6 | C9 | A4 | B7 | C9 | A4 | B8 | C9 | A4 | B9 | C9 | A4 | B10 | C9 | A4 | B12 | C9 | A4 | B18 | C9 | A4 | B22 | C9 | A4 | B23 | C9 | A4 | B25 | C9 |
| A4 | B6 | C10 | A4 | B7 | C10 | A4 | B8 | C10 | A4 | B9 | C10 | A4 | B10 | C10 | A4 | B12 | C10 | A4 | B18 | C10 | A4 | B22 | C10 | A4 | B23 | C10 | A4 | B25 | C10 |
| A4 | B6 | C11 | A4 | B7 | C11 | A4 | B8 | C11 | A4 | B9 | C11 | A4 | B10 | C11 | A4 | B12 | C11 | A4 | B18 | C11 | A4 | B22 | C11 | A4 | B23 | C11 | A4 | B25 | C11 |
| A4 | B6 | C12 | A4 | B7 | C12 | A4 | B8 | C12 | A4 | B9 | C12 | A4 | B10 | C12 | A4 | B12 | C12 | A4 | B18 | C12 | A4 | B22 | C12 | A4 | B23 | C12 | A4 | B25 | C12 |
| A4 | B6 | C13 | A4 | B7 | C13 | A4 | B8 | C13 | A4 | B9 | C13 | A4 | B10 | C13 | A4 | B12 | C13 | A4 | B18 | C13 | A4 | B22 | C13 | A4 | B23 | C13 | A4 | B25 | C13 |
| A4 | B6 | C14 | A4 | B7 | C14 | A4 | B8 | C14 | A4 | B9 | C14 | A4 | B10 | C14 | A4 | B12 | C14 | A4 | B18 | C14 | A4 | B22 | C14 | A4 | B23 | C14 | A4 | B25 | C14 |
| A4 | B6 | C15 | A4 | B7 | C15 | A4 | B8 | C15 | A4 | B9 | C15 | A4 | B10 | C15 | A4 | B12 | C15 | A4 | B18 | C15 | A4 | B22 | C15 | A4 | B23 | C15 | A4 | B25 | C15 |
| A4 | B6 | C16 | A4 | B7 | C16 | A4 | B8 | C16 | A4 | B9 | C16 | A4 | B10 | C16 | A4 | B12 | C16 | A4 | B18 | C16 | A4 | B22 | C16 | A4 | B23 | C16 | A4 | B25 | C16 |
| A4 | B6 | C17 | A4 | B7 | C17 | A4 | B8 | C17 | A4 | B9 | C17 | A4 | B10 | C17 | A4 | B12 | C17 | A4 | B18 | C17 | A4 | B22 | C17 | A4 | B23 | C17 | A4 | B25 | C17 |
| A4 | B6 | C18 | A4 | B7 | C18 | A4 | B8 | C18 | A4 | B9 | C18 | A4 | B10 | C18 | A4 | B12 | C18 | A4 | B18 | C18 | A4 | B22 | C18 | A4 | B23 | C18 | A4 | B25 | C18 |
| A4 | B6 | C19 | A4 | B7 | C19 | A4 | B8 | C19 | A4 | B9 | C19 | A4 | B10 | C19 | A4 | B12 | C19 | A4 | B18 | C19 | A4 | B22 | C19 | A4 | B23 | C19 | A4 | B25 | C19 |
| A4 | B6 | C20 | A4 | B7 | C20 | A4 | B8 | C20 | A4 | B9 | C20 | A4 | B10 | C20 | A4 | B12 | C20 | A4 | B18 | C20 | A4 | B22 | C20 | A4 | B23 | C20 | A1 | B25 | C20 |
| A4 | B6 | C21 | A4 | B7 | C21 | A4 | B8 | C21 | A4 | B9 | C21 | A4 | B10 | C21 | A4 | B12 | C21 | A4 | B18 | C21 | A4 | B22 | C21 | A4 | B23 | C21 | A4 | B25 | C21 |
| A4 | B6 | C22 | A4 | B7 | C22 | A4 | B8 | C22 | A4 | B9 | C22 | A4 | B10 | C22 | A4 | B12 | C22 | A4 | B18 | C22 | A4 | B22 | C22 | A4 | B23 | C22 | A4 | B25 | C22 |
| A4 | B6 | C23 | A4 | B7 | C23 | A4 | B8 | C23 | A4 | B9 | C23 | A4 | B10 | C23 | A4 | B12 | C23 | A4 | B18 | C23 | A4 | B22 | C23 | A4 | B23 | C23 | A4 | B25 | C23 |
| A4 | B6 | C24 | A4 | B7 | C24 | A4 | B8 | C24 | A4 | B9 | C24 | A4 | B10 | C24 | A4 | B12 | C24 | A4 | B18 | C24 | A4 | B22 | C24 | A4 | B23 | C24 | A4 | B25 | C24 |
| A4 | B6 | C25 | A4 | B7 | C25 | A4 | B8 | C25 | A4 | B9 | C25 | A4 | B10 | C25 | A4 | B12 | C25 | A4 | B18 | C25 | A4 | B22 | C25 | A4 | B23 | C25 | A4 | B25 | C25 |
| A4 | B6 | C26 | A4 | B7 | C26 | A4 | B8 | C26 | A4 | B9 | C26 | A4 | B10 | C26 | A4 | B12 | C26 | A4 | B18 | C26 | A4 | B22 | C26 | A4 | B23 | C26 | A4 | B25 | C26 |
| A4 | B6 | C27 | A4 | B7 | C27 | A4 | B8 | C27 | A4 | B9 | C27 | A4 | B10 | C27 | A4 | B12 | C27 | A4 | B18 | C27 | A4 | B22 | C27 | A4 | B23 | C27 | A4 | B25 | C27 |
| A4 | B6 | C28 | A4 | B7 | C28 | A4 | B8 | C28 | A4 | B9 | C28 | A4 | B10 | C28 | A4 | B12 | C28 | A4 | B18 | C28 | A4 | B22 | C28 | A4 | B23 | C28 | A4 | B25 | C28 |
| A4 | B6 | C29 | A4 | B7 | C29 | A4 | B8 | C29 | A4 | B9 | C29 | A4 | B10 | C29 | A4 | B12 | C29 | A4 | B18 | C29 | A4 | B22 | C29 | A4 | B23 | C29 | A4 | B25 | C29 |
| A4 | B6 | C30 | A4 | B7 | C30 | A4 | B8 | C30 | A4 | B9 | C30 | A4 | B10 | C30 | A4 | B12 | C30 | A4 | B18 | C30 | A4 | B22 | C30 | A4 | B23 | C30 | A4 | B25 | C30 |
| A4 | B6 | C31 | A4 | B7 | C31 | A4 | B8 | C31 | A4 | B9 | C31 | A4 | B10 | C31 | A4 | B12 | C31 | A4 | B18 | C31 | A4 | B22 | C31 | A4 | B23 | C31 | A4 | B25 | C31 |
| A4 | B6 | C32 | A4 | B7 | C32 | A4 | B8 | C32 | A4 | B9 | C32 | A4 | B10 | C32 | A4 | B12 | C32 | A4 | B18 | C32 | A4 | B22 | C32 | A4 | B23 | C32 | A4 | B25 | C32 |
| A4 | B6 | C33 | A4 | B7 | C33 | A4 | B8 | C33 | A4 | B9 | C33 | A4 | B10 | C33 | A4 | B12 | C33 | A4 | B18 | C33 | A4 | B22 | C33 | A4 | B23 | C33 | A4 | B25 | C33 |
| A4 | B6 | C34 | A4 | B7 | C34 | A4 | B8 | C34 | A4 | B9 | C34 | A4 | B10 | C34 | A4 | B12 | C34 | A4 | B18 | C34 | A4 | B22 | C34 | A4 | B23 | C34 | A4 | B25 | C34 |
| A4 | B6 | C35 | A4 | B7 | C35 | A4 | B8 | C35 | A4 | B9 | C35 | A4 | B10 | C35 | A4 | B12 | C35 | A4 | B18 | C35 | A4 | B22 | C35 | A4 | B23 | C35 | A4 | B25 | C35 |
| A4 | B6 | C36 | A4 | B7 | C36 | A4 | B8 | C36 | A4 | B9 | C36 | A4 | B10 | C36 | A4 | B12 | C36 | A4 | B18 | C36 | A4 | B22 | C36 | A4 | B23 | C36 | A4 | B25 | C36 |
| A4 | B6 | C37 | A4 | B7 | C37 | A4 | B8 | C37 | A4 | B9 | C37 | A4 | B10 | C37 | A4 | B12 | C37 | A4 | B18 | C37 | A4 | B22 | C37 | A4 | B23 | C37 | A4 | B25 | C37 |
| A4 | B6 | C38 | A4 | B7 | C38 | A4 | B8 | C38 | A4 | B9 | C38 | A4 | B10 | C38 | A4 | B12 | C38 | A4 | B18 | C38 | A4 | B22 | C38 | A4 | B23 | C38 | A4 | B25 | C35 |
| A4 | B6 | C39 | A4 | B7 | C39 | A4 | B8 | C39 | A4 | B9 | C39 | A4 | B10 | C39 | A4 | B12 | C39 | A4 | B18 | C39 | A4 | B22 | C39 | A4 | B23 | C39 | A4 | B25 | C39 |
| A4 | B6 | C40 | A4 | B7 | C40 | A4 | B8 | C40 | A4 | B9 | C40 | A4 | B10 | C40 | A4 | B12 | C40 | A4 | B18 | C40 | A4 | B22 | C40 | A4 | B23 | C40 | A4 | B25 | C40 |
| A4 | B6 | C41 | A4 | B7 | C41 | A4 | B5 | C41 | A4 | B9 | C41 | A4 | B10 | C41 | A4 | B12 | C41 | A4 | B18 | C41 | A4 | B22 | C41 | A4 | B23 | C4 | A4 | B25 | C41 |
| A5 | B6 | C1 | A5 | B7 | C1 | A5 | B5 | C1 | A5 | B9 | C1 | A5 | B10 | C1 | A5 | B12 | C1 | A5 | B18 | C1 | A5 | B22 | C1 | A5 | B23 | C1 | A5 | B25 | C1 |
| A5 | B6 | C2 | A5 | B7 | C2 | A5 | B5 | C2 | A5 | B9 | C2 | A5 | B10 | C2 | A5 | B12 | C2 | A5 | B18 | C2 | A5 | B22 | C2 | A5 | B23 | C2 | A5 | B25 | C2 |
| A5 | B6 | C3 | A5 | B7 | C3 | A5 | B5 | C3 | A5 | B9 | C3 | A5 | B10 | C3 | A5 | B12 | C3 | A5 | B18 | C3 | A5 | B22 | C3 | A5 | B23 | C3 | A5 | B25 | C3 |
| A5 | B6 | C4 | A5 | B7 | C4 | A5 | B8 | C4 | A5 | B9 | C4 | A5 | B10 | C4 | A5 | B12 | C4 | A5 | B18 | C4 | A5 | B22 | C4 | A5 | B23 | C4 | A5 | B25 | C4 |
| A5 | B6 | C5 | A5 | B7 | C5 | A5 | B8 | C5 | A5 | B9 | C5 | A5 | B10 | C5 | A5 | B12 | C5 | A5 | B18 | C5 | A5 | B22 | C5 | A5 | B23 | C5 | A5 | B25 | C5 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A5 | B6 | C6 | A5 | B7 | C6 | A5 | B8 | C6 | A5 | B9 | C6 | A5 | B10 | C6 | A5 | B12 | C6 | A5 | B18 | C6 | A5 | B22 | C6 | A5 | B23 | C6 | A5 | B25 | C6 |
| A5 | B6 | C7 | A5 | B7 | C7 | A5 | B8 | C7 | A5 | B9 | C7 | A5 | B10 | C7 | A5 | B12 | C7 | A5 | B18 | C7 | A5 | B22 | C7 | A5 | B23 | C7 | A5 | B25 | C7 |
| A5 | B6 | C8 | A5 | B7 | C8 | A5 | B8 | C8 | A5 | B9 | C8 | A5 | B10 | C8 | A5 | B12 | C8 | A5 | B18 | C8 | A5 | B22 | C8 | A5 | B23 | C8 | A5 | B25 | C8 |
| A5 | B6 | C9 | A5 | B7 | C9 | A5 | B8 | C9 | A5 | B9 | C9 | A5 | B10 | C9 | A5 | B12 | C9 | A5 | B18 | C9 | A5 | B22 | C9 | A5 | B23 | C9 | A5 | B25 | C9 |
| A5 | B6 | C10 | A5 | B7 | C10 | A5 | B8 | C10 | A5 | B9 | C10 | A5 | B10 | C10 | A5 | B12 | C10 | A5 | B18 | C10 | A5 | B22 | C10 | A5 | B23 | C10 | A5 | B25 | C10 |
| A5 | B6 | C11 | A5 | B7 | C11 | A5 | B8 | C11 | A5 | B9 | C11 | A5 | B10 | C11 | A5 | B12 | C11 | A5 | B18 | C11 | A5 | B22 | C11 | A5 | B23 | C11 | A5 | B25 | C11 |
| A5 | B6 | C12 | A5 | B7 | C12 | A5 | B8 | C12 | A5 | B9 | C12 | A5 | B10 | C12 | A5 | B12 | C12 | A5 | B18 | C12 | A5 | B22 | C12 | A5 | B23 | C12 | A5 | B25 | C12 |
| A5 | B6 | C13 | A5 | B7 | C13 | A5 | B8 | C13 | A5 | B9 | C13 | A5 | B10 | C13 | A5 | B12 | C13 | A5 | B18 | C13 | A5 | B22 | C13 | A5 | B23 | C13 | A5 | B25 | C13 |
| A5 | B6 | C14 | A5 | B7 | C14 | A5 | B8 | C14 | A5 | B9 | C14 | A5 | B10 | C14 | A5 | B12 | C14 | A5 | B18 | C14 | A5 | B22 | C14 | A5 | B23 | C14 | A5 | B25 | C14 |
| A5 | B6 | C15 | A5 | B7 | C15 | A5 | B8 | C15 | A5 | B9 | C15 | A5 | B10 | C15 | A5 | B12 | C15 | A5 | B18 | C15 | A5 | B22 | C15 | A5 | B23 | C15 | A5 | B25 | C15 |
| A5 | B6 | C16 | A5 | B7 | C16 | A5 | B8 | C16 | A5 | B9 | C16 | A5 | B10 | C16 | A5 | B12 | C16 | A5 | B18 | C16 | A5 | B22 | C16 | A5 | B23 | C16 | A5 | B25 | C16 |
| A5 | B6 | C17 | A5 | B7 | C17 | A5 | B8 | C17 | A5 | B9 | C17 | A5 | B10 | C17 | A5 | B12 | C17 | A5 | B18 | C17 | A5 | B22 | C17 | A5 | B23 | C17 | A5 | B25 | C17 |
| A5 | B6 | C18 | A5 | B7 | C18 | A5 | B8 | C18 | A5 | B9 | C18 | A5 | B10 | C18 | A5 | B12 | C18 | A5 | B18 | C18 | A5 | B22 | C18 | A5 | B23 | C18 | A5 | B25 | C15 |
| A5 | B6 | C19 | A5 | B7 | C19 | A5 | B8 | C19 | A5 | B9 | C19 | A5 | B10 | C19 | A5 | B12 | C19 | A5 | B18 | C19 | A5 | B22 | C19 | A5 | B23 | C19 | A5 | B25 | C19 |
| A5 | B6 | C20 | A5 | B7 | C20 | A5 | B8 | C20 | A5 | B9 | C20 | A5 | B10 | C20 | A5 | B12 | C20 | A5 | B18 | C20 | A5 | B22 | C20 | A5 | B23 | C20 | A5 | B25 | C20 |
| A5 | B6 | C21 | A5 | B7 | C21 | A5 | B8 | C21 | A5 | B9 | C21 | A5 | B10 | C21 | A5 | B12 | C21 | A5 | B18 | C21 | A5 | B22 | C21 | A5 | B23 | C21 | A5 | B25 | C21 |
| A5 | B6 | C22 | A5 | B7 | C22 | A5 | B8 | C22 | A5 | B9 | C22 | A5 | B10 | C22 | A5 | B12 | C22 | A5 | B18 | C22 | A5 | B22 | C22 | A5 | B23 | C22 | A5 | B25 | C22 |
| A5 | B6 | C23 | A5 | B7 | C23 | A5 | B8 | C23 | A5 | B9 | C23 | A5 | B10 | C23 | A5 | B12 | C23 | A5 | B18 | C23 | A5 | B22 | C23 | A5 | B23 | C23 | A5 | B25 | C23 |
| A5 | B6 | C24 | A5 | B7 | C24 | A5 | B8 | C24 | A5 | B9 | C24 | A5 | B10 | C24 | A5 | B12 | C24 | A5 | B18 | C24 | A5 | B22 | C24 | A5 | B23 | C24 | A5 | B25 | C24 |
| A5 | B6 | C25 | A5 | B7 | C25 | A5 | B8 | C25 | A5 | B9 | C25 | A5 | B10 | C25 | A5 | B12 | C25 | A5 | B18 | C25 | A5 | B22 | C25 | A5 | B23 | C25 | A5 | B25 | C25 |
| A5 | B6 | C26 | A5 | B7 | C26 | A5 | B8 | C26 | A5 | B9 | C26 | A5 | B10 | C26 | A5 | B12 | C26 | A5 | B18 | C26 | A5 | B22 | C26 | A5 | B23 | C26 | A5 | B25 | C26 |
| A5 | B6 | C27 | A5 | B7 | C27 | A5 | B8 | C27 | A5 | B9 | C27 | A5 | B10 | C27 | A5 | B12 | C27 | A5 | B18 | C27 | A5 | B22 | C27 | A5 | B23 | C27 | A5 | B25 | C27 |
| A5 | B6 | C28 | A5 | B7 | C28 | A5 | B8 | C28 | A5 | B9 | C28 | A5 | B10 | C28 | A5 | B12 | C28 | A5 | B18 | C28 | A5 | B22 | C28 | A5 | B23 | C28 | A5 | B25 | C28 |
| A5 | B6 | C29 | A5 | B7 | C29 | A5 | B8 | C29 | A5 | B9 | C29 | A5 | B10 | C29 | A5 | B12 | C29 | A5 | B18 | C29 | A5 | B22 | C29 | A5 | B23 | C29 | A5 | B25 | C29 |
| A5 | B6 | C30 | A5 | B7 | C30 | A5 | B8 | C30 | A5 | B9 | C30 | A5 | B10 | C30 | A5 | B12 | C30 | A5 | B18 | C30 | A5 | B22 | C30 | A5 | B23 | C30 | A5 | B25 | C30 |
| A5 | B6 | C31 | A5 | B7 | C31 | A5 | B8 | C31 | A5 | B9 | C31 | A5 | B10 | C31 | A5 | B12 | C31 | A5 | B18 | C31 | A5 | B22 | C31 | A5 | B23 | C31 | A5 | B25 | C31 |
| A5 | B6 | C32 | A5 | B7 | C32 | A5 | B8 | C32 | A5 | B9 | C32 | A5 | B10 | C32 | A5 | B12 | C32 | A5 | B18 | C32 | A5 | B22 | C32 | A5 | B23 | C32 | A5 | B25 | C32 |
| A5 | B6 | C33 | A5 | B7 | C33 | A5 | B8 | C33 | A5 | B9 | C33 | A5 | B10 | C33 | A5 | B12 | C33 | A5 | B18 | C33 | A5 | B22 | C33 | A5 | B23 | C33 | A5 | B25 | C33 |
| A5 | B6 | C34 | A5 | B7 | C34 | A5 | B8 | C34 | A5 | B9 | C34 | A5 | B10 | C34 | A5 | B12 | C34 | A5 | B18 | C34 | A5 | B22 | C34 | A5 | B23 | C34 | A5 | B25 | C34 |
| A5 | B6 | C35 | A5 | B7 | C35 | A5 | B8 | C35 | A5 | B9 | C35 | A5 | B10 | C35 | A5 | B12 | C35 | A5 | B18 | C35 | A5 | B22 | C35 | A5 | B23 | C35 | A5 | B25 | C35 |
| A5 | B6 | C36 | A5 | B7 | C36 | A5 | B8 | C36 | A5 | B9 | C36 | A5 | B10 | C36 | A5 | B12 | C36 | A5 | B18 | C36 | A5 | B22 | C36 | A5 | B23 | C36 | A5 | B25 | C36 |
| A5 | B6 | C37 | A5 | B7 | C37 | A5 | B8 | C37 | A5 | B9 | C37 | A5 | B10 | C37 | A5 | B12 | C37 | A5 | B18 | C37 | A5 | B22 | C37 | A5 | B23 | C37 | A5 | B25 | C37 |
| A5 | B6 | C38 | A5 | B7 | C38 | A5 | B8 | C38 | A5 | B9 | C38 | A5 | B10 | C38 | A5 | B12 | C38 | A5 | B18 | C38 | A5 | B22 | C38 | A5 | B23 | C38 | A5 | B25 | C38 |
| A5 | B6 | C39 | A5 | B7 | C39 | A5 | B8 | C39 | A5 | B9 | C39 | A5 | B10 | C39 | A5 | B12 | C39 | A5 | B18 | C39 | A5 | B22 | C39 | A5 | B23 | C39 | A5 | B25 | C39 |
| A5 | B6 | C40 | A5 | B7 | C40 | A5 | B8 | C40 | A5 | B9 | C40 | A5 | B10 | C40 | A5 | B12 | C40 | A5 | B18 | C40 | A5 | B22 | C40 | A5 | B23 | C40 | A5 | B25 | C40 |
| A5 | B6 | C41 | A5 | B7 | C41 | A5 | B8 | C41 | A5 | B9 | C41 | A5 | B10 | C41 | A5 | B12 | C41 | A5 | B18 | C41 | A5 | B22 | C41 | A5 | B23 | C41 | A5 | B25 | C41 |
| A6 | B6 | C1 | A6 | B7 | C1 | A6 | B8 | C1 | A6 | B9 | C1 | A6 | B10 | C1 | A6 | B12 | C1 | A6 | B18 | C1 | A6 | B22 | C1 | A6 | B23 | C1 | A6 | B25 | C1 |
| A6 | B6 | C2 | A6 | B7 | C2 | A6 | B8 | C2 | A6 | B9 | C2 | A6 | B10 | C2 | A6 | B12 | C2 | A6 | B18 | C2 | A6 | B22 | C2 | A6 | B23 | C2 | A6 | B25 | C2 |
| A6 | B6 | C3 | A6 | B7 | C3 | A6 | B8 | C3 | A6 | B9 | C3 | A6 | B10 | C3 | A6 | B12 | C3 | A6 | B18 | C3 | A6 | B22 | C3 | A6 | B23 | C3 | A6 | B25 | C3 |
| A6 | B6 | C4 | A6 | B7 | C4 | A6 | B8 | C4 | A6 | B9 | C4 | A6 | B10 | C4 | A6 | B12 | C4 | A6 | B18 | C4 | A6 | B22 | C4 | A6 | B23 | C4 | A6 | B25 | C4 |
| A6 | B6 | C5 | A6 | B7 | C5 | A6 | B8 | C5 | A6 | B9 | C5 | A6 | B10 | C5 | A6 | B12 | C5 | A6 | B18 | C5 | A6 | B22 | C5 | A6 | B23 | C5 | A6 | B25 | C5 |
| A6 | B6 | C6 | A6 | B7 | C6 | A6 | B8 | C6 | A6 | B9 | C6 | A6 | B10 | C6 | A6 | B12 | C6 | A6 | B18 | C6 | A6 | B22 | C6 | A6 | B23 | C6 | A6 | B25 | C6 |
| A6 | B6 | C7 | A6 | B7 | C7 | A6 | B8 | C7 | A6 | B9 | C7 | A6 | B10 | C7 | A6 | B12 | C7 | A6 | B18 | C7 | A6 | B22 | C7 | A6 | B23 | C7 | A6 | B25 | C7 |
| A6 | B6 | C8 | A6 | B7 | C8 | A6 | B8 | C8 | A6 | B9 | C8 | A6 | B10 | C8 | A6 | B12 | C8 | A6 | B18 | C8 | A6 | B22 | C8 | A6 | B23 | C8 | A6 | B25 | C8 |
| A6 | B6 | C9 | A6 | B7 | C9 | A6 | B8 | C9 | A6 | B9 | C9 | A6 | B10 | C9 | A6 | B12 | C9 | A6 | B18 | C9 | A6 | B22 | C9 | A6 | B23 | C9 | A6 | B25 | C9 |
| A6 | B6 | C10 | A6 | B7 | C10 | A6 | B8 | C10 | A6 | B9 | C10 | A6 | B10 | C10 | A6 | B12 | C10 | A6 | B18 | C10 | A6 | B22 | C10 | A6 | B23 | C10 | A6 | B25 | C10 |
| A6 | B6 | C11 | A6 | B7 | C11 | A6 | B8 | C11 | A6 | B9 | C11 | A6 | B10 | C11 | A6 | B12 | C11 | A6 | B18 | C11 | A6 | B22 | C11 | A6 | B23 | C11 | A6 | B25 | C11 |
| A6 | B6 | C12 | A6 | B7 | C12 | A6 | B8 | C12 | A6 | B9 | C12 | A6 | B10 | C12 | A6 | B12 | C12 | A6 | B18 | C12 | A6 | B22 | C12 | A6 | B23 | C12 | A6 | B25 | C12 |
| A6 | B6 | C13 | A6 | B7 | C13 | A6 | B8 | C13 | A6 | B9 | C13 | A6 | B10 | C13 | A6 | B12 | C13 | A6 | B18 | C13 | A6 | B22 | C13 | A6 | B23 | C13 | A6 | B25 | C13 |
| A6 | B6 | C14 | A6 | B7 | C14 | A6 | B8 | C14 | A6 | B9 | C14 | A6 | B10 | C14 | A6 | B12 | C14 | A6 | B18 | C14 | A6 | B22 | C14 | A6 | B23 | C14 | A6 | B25 | C14 |
| A6 | B6 | C15 | A6 | B7 | C15 | A6 | B8 | C15 | A6 | B9 | C15 | A6 | B10 | C15 | A6 | B12 | C15 | A6 | B18 | C15 | A6 | B22 | C15 | A6 | B23 | C15 | A6 | B25 | C15 |
| A6 | B6 | C16 | A6 | B7 | C16 | A6 | B8 | C16 | A6 | B9 | C16 | A6 | B10 | C16 | A6 | B12 | C16 | A6 | B18 | C16 | A6 | B22 | C16 | A6 | B23 | C16 | A6 | B25 | C16 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A6 | B6 | C17 | A6 | B7 | C17 | A6 | B8 | C17 | A6 | B9 | C17 | A6 | B10 | C17 | A6 | B12 | C17 | A6 | B18 | C17 | A6 | B22 | C17 | A6 | B23 | C17 | A6 | B25 | C17 |
| A6 | B6 | C18 | A6 | B7 | C18 | A6 | B8 | C18 | A6 | B9 | C18 | A6 | B10 | C18 | A6 | B12 | C18 | A6 | B18 | C18 | A6 | B22 | C18 | A6 | B23 | C18 | A6 | B25 | C18 |
| A6 | B6 | C19 | A6 | B7 | C19 | A6 | B8 | C19 | A6 | B9 | C19 | A6 | B10 | C19 | A6 | B12 | C19 | A6 | B18 | C19 | A6 | B22 | C19 | A6 | B23 | C19 | A6 | B25 | C19 |
| A6 | B6 | C20 | A6 | B7 | C20 | A6 | B8 | C20 | A6 | B9 | C20 | A6 | B10 | C20 | A6 | B12 | C20 | A6 | B18 | C20 | A6 | B22 | C20 | A6 | B23 | C20 | A6 | B25 | C20 |
| A6 | B6 | C21 | A6 | B7 | C21 | A6 | B8 | C21 | A6 | B9 | C21 | A6 | B10 | C21 | A6 | B12 | C21 | A6 | B18 | C21 | A6 | B22 | C21 | A6 | B23 | C21 | A6 | B25 | C21 |
| A6 | B6 | C22 | A6 | B7 | C22 | A6 | B8 | C22 | A6 | B9 | C22 | A6 | B10 | C22 | A6 | B12 | C22 | A6 | B18 | C22 | A6 | B22 | C22 | A6 | B23 | C22 | A6 | B25 | C22 |
| A6 | B6 | C23 | A6 | B7 | C23 | A6 | B8 | C23 | A6 | B9 | C23 | A6 | B10 | C23 | A6 | B12 | C23 | A6 | B18 | C23 | A6 | B22 | C23 | A6 | B23 | C23 | A6 | B25 | C23 |
| A6 | B6 | C24 | A6 | B7 | C24 | A6 | B8 | C24 | A6 | B9 | C24 | A6 | B10 | C24 | A6 | B12 | C24 | A6 | B18 | C24 | A6 | B22 | C24 | A6 | B23 | C24 | A6 | B25 | C24 |
| A6 | B6 | C25 | A6 | B7 | C25 | A6 | B8 | C25 | A6 | B9 | C25 | A6 | B10 | C25 | A6 | B12 | C25 | A6 | B15 | C25 | A6 | B22 | C25 | A6 | B23 | C25 | A6 | B25 | C25 |
| A6 | B6 | C26 | A6 | B7 | C26 | A6 | B8 | C26 | A6 | B9 | C26 | A6 | B10 | C26 | A6 | B12 | C26 | A6 | B18 | C26 | A6 | B22 | C26 | A6 | B23 | C26 | A6 | B25 | C26 |
| A6 | B6 | C27 | A6 | B7 | C27 | A6 | B8 | C27 | A6 | B9 | C27 | A6 | B10 | C27 | A6 | B12 | C27 | A6 | B18 | C27 | A6 | B22 | C27 | A6 | B23 | C27 | A6 | B25 | C27 |
| A6 | B6 | C28 | A6 | B7 | C28 | A6 | B8 | C28 | A6 | B9 | C28 | A6 | B10 | C28 | A6 | B12 | C28 | A6 | B18 | C28 | A6 | B22 | C28 | A6 | B23 | C28 | A6 | B25 | C28 |
| A6 | B6 | C29 | A6 | B7 | C29 | A6 | B8 | C29 | A6 | B9 | C29 | A6 | B10 | C29 | A6 | B12 | C29 | A6 | B18 | C29 | A6 | B22 | C29 | A6 | B23 | C29 | A6 | B25 | C29 |
| A6 | B6 | C30 | A6 | B7 | C30 | A6 | B8 | C30 | A6 | B9 | C30 | A6 | B10 | C30 | A6 | B12 | C30 | A6 | B18 | C30 | A6 | B22 | C30 | A6 | B23 | C30 | A6 | B25 | C30 |
| A6 | B6 | C31 | A6 | B7 | C31 | A6 | B8 | C31 | A6 | B9 | C31 | A6 | B10 | C31 | A6 | B12 | C31 | A6 | B18 | C31 | A6 | B22 | C31 | A6 | B23 | C31 | A6 | B25 | C31 |
| A6 | B6 | C32 | A6 | B7 | C32 | A6 | B8 | C32 | A6 | B9 | C32 | A6 | B10 | C32 | A6 | B12 | C32 | A6 | B18 | C32 | A6 | B22 | C32 | A6 | B23 | C32 | A6 | B25 | C32 |
| A6 | B6 | C33 | A6 | B7 | C33 | A6 | B8 | C33 | A6 | B9 | C33 | A6 | B10 | C33 | A6 | B12 | C33 | A6 | B18 | C33 | A6 | B22 | C33 | A6 | B23 | C33 | A6 | B25 | C33 |
| A6 | B6 | C34 | A6 | B7 | C34 | A6 | B8 | C34 | A6 | B9 | C34 | A6 | B10 | C34 | A6 | B12 | C34 | A6 | B18 | C34 | A6 | B22 | C34 | A6 | B23 | C34 | A6 | B25 | C34 |
| A6 | B6 | C35 | A6 | B7 | C35 | A6 | B8 | C35 | A6 | B9 | C35 | A6 | B10 | C35 | A6 | B12 | C35 | A6 | B18 | C35 | A6 | B22 | C35 | A6 | B23 | C35 | A6 | B25 | C35 |
| A6 | B6 | C36 | A6 | B7 | C36 | A6 | B8 | C36 | A6 | B9 | C36 | A6 | B10 | C36 | A6 | B12 | C36 | A6 | B18 | C36 | A6 | B22 | C36 | A6 | B23 | C36 | A6 | B25 | C36 |
| A6 | B6 | C37 | A6 | B7 | C37 | A6 | B8 | C37 | A6 | B9 | C37 | A6 | B10 | C37 | A6 | B12 | C37 | A6 | B18 | C37 | A6 | B22 | C37 | A6 | B23 | C37 | A6 | B25 | C37 |
| A6 | B6 | C38 | A6 | B7 | C38 | A6 | B8 | C38 | A6 | B9 | C38 | A6 | B10 | C38 | A6 | B12 | C38 | A6 | B18 | C38 | A6 | B22 | C38 | A6 | B23 | C38 | A6 | B25 | C38 |
| A6 | B6 | C39 | A6 | B7 | C39 | A6 | B8 | C39 | A6 | B9 | C39 | A6 | B10 | C39 | A6 | B12 | C39 | A6 | B18 | C39 | A6 | B22 | C39 | A6 | B23 | C39 | A6 | B25 | C39 |
| A6 | B6 | C40 | A6 | B7 | C40 | A6 | B8 | C40 | A6 | B9 | C40 | A6 | B10 | C40 | A6 | B12 | C40 | A6 | B18 | C40 | A6 | B22 | C40 | A6 | B23 | C40 | A6 | B25 | C40 |
| A6 | B6 | C41 | A6 | B7 | C41 | A6 | B8 | C41 | A6 | B9 | C41 | A6 | B10 | C41 | A6 | B12 | C41 | A6 | B18 | C41 | A6 | B22 | C41 | A6 | B23 | C41 | A6 | B25 | C41 |
| A8 | B6 | C1 | A8 | B7 | C1 | A8 | B8 | C1 | A8 | B9 | C1 | A8 | B10 | C1 | A8 | B12 | C1 | A8 | B18 | C1 | A8 | B22 | C1 | A8 | B23 | C1 | A8 | B25 | C1 |
| A8 | B6 | C2 | A8 | B7 | C2 | A8 | B8 | C2 | A8 | B9 | C1 | A8 | B10 | C2 | A8 | B12 | C2 | A8 | B18 | C2 | A8 | B22 | C2 | A8 | B23 | C2 | A8 | B25 | C2 |
| A8 | B6 | C3 | A8 | B7 | C3 | A8 | B8 | C3 | A8 | B9 | C3 | A8 | B10 | C3 | A8 | B12 | C3 | A8 | B18 | C3 | A8 | B22 | C3 | A8 | B23 | C3 | A8 | B25 | C3 |
| A8 | B6 | C4 | A8 | B7 | C4 | A8 | B8 | C4 | A8 | B9 | C4 | A8 | B10 | C4 | A8 | B12 | C4 | A8 | B18 | C4 | A8 | B22 | C4 | A8 | B23 | C4 | A8 | B25 | C4 |
| A8 | B6 | C5 | A8 | B7 | C5 | A8 | B8 | C5 | A8 | B9 | C5 | A8 | B10 | C5 | A8 | B12 | C5 | A8 | B18 | C5 | A8 | B22 | C5 | A8 | B23 | C5 | A8 | B25 | C5 |
| A8 | B6 | C6 | A8 | B7 | C6 | A8 | B8 | C6 | A8 | B9 | C6 | A8 | B10 | C6 | A8 | B12 | C6 | A8 | B18 | C6 | A8 | B22 | C6 | A8 | B23 | C6 | A8 | B25 | C6 |
| A8 | B6 | C7 | A8 | B7 | C7 | A8 | B8 | C7 | A8 | B9 | C7 | A8 | B10 | C7 | A8 | B12 | C7 | A8 | B18 | C7 | A8 | B22 | C7 | A8 | B23 | C7 | A8 | B25 | C7 |
| A8 | B6 | C5 | A8 | B7 | C8 | A8 | B8 | C8 | A8 | B9 | C8 | A8 | B10 | C8 | A8 | B12 | C5 | A8 | B18 | C8 | A8 | B22 | C5 | A8 | B23 | C8 | A8 | B25 | C8 |
| A8 | B6 | C9 | A8 | B7 | C9 | A8 | B8 | C9 | A8 | B9 | C9 | A8 | B10 | C9 | A8 | B12 | C9 | A8 | B18 | C9 | A8 | B22 | C9 | A8 | B23 | C9 | A8 | B25 | C9 |
| A8 | B6 | C10 | A8 | B7 | C10 | A8 | B8 | C10 | A8 | B9 | C10 | A8 | B10 | C10 | A8 | B12 | C10 | A8 | B18 | C10 | A8 | B22 | C10 | A8 | B23 | C10 | A8 | B25 | C10 |
| A8 | B6 | C11 | A8 | B7 | C11 | A8 | B8 | C11 | A8 | B9 | C11 | A8 | B10 | C11 | A8 | B12 | C11 | A8 | B18 | C11 | A8 | B22 | C11 | A8 | B23 | C11 | A8 | B25 | C11 |
| A8 | B6 | C12 | A8 | B7 | C12 | A8 | B8 | C12 | A8 | B9 | C12 | A8 | B10 | C12 | A8 | B12 | C12 | A8 | B18 | C12 | A8 | B22 | C12 | A8 | B23 | C12 | A8 | B25 | C12 |
| A8 | B6 | C13 | A8 | B7 | C13 | A8 | B8 | C13 | A8 | B9 | C13 | A8 | B10 | C13 | A8 | B12 | C13 | A8 | B18 | C13 | A8 | B22 | C13 | A8 | B23 | C13 | A8 | B25 | C13 |
| A8 | B6 | C14 | A8 | B7 | C14 | A8 | B8 | C14 | A8 | B9 | C14 | A8 | B10 | C14 | A8 | B12 | C14 | A8 | B18 | C14 | A8 | B22 | C14 | A8 | B23 | C14 | A8 | B25 | C14 |
| A8 | B6 | C15 | A8 | B7 | C15 | A8 | B8 | C15 | A8 | B9 | C15 | A8 | B10 | C15 | A8 | B12 | C15 | A8 | B18 | C15 | A8 | B22 | C15 | A8 | B23 | C15 | A8 | B25 | C15 |
| A8 | B6 | C16 | A8 | B7 | C16 | A8 | B8 | C16 | A8 | B9 | C16 | A8 | B10 | C16 | A8 | B12 | C16 | A8 | B18 | C16 | A8 | B22 | C16 | A8 | B23 | C16 | A8 | B25 | C16 |
| A8 | B6 | C17 | A8 | B7 | C17 | A8 | B8 | C17 | A8 | B9 | C17 | A8 | B10 | C17 | A8 | B12 | C17 | A8 | B18 | C17 | A8 | B22 | C17 | A8 | B23 | C17 | A8 | B25 | C17 |
| A8 | B6 | C18 | A8 | B7 | C18 | A8 | B8 | C18 | A8 | B9 | C18 | A8 | B10 | C18 | A8 | B12 | C18 | A8 | B18 | C18 | A8 | B22 | C18 | A8 | B23 | C18 | A8 | B25 | C18 |
| A8 | B6 | C19 | A8 | B7 | C19 | A8 | B8 | C19 | A8 | B9 | C19 | A8 | B10 | C19 | A8 | B12 | C19 | A8 | B18 | C19 | A8 | B22 | C19 | A8 | B23 | C19 | A8 | B25 | C19 |
| A8 | B6 | C20 | A8 | B7 | C20 | A8 | B8 | C20 | A8 | B9 | C20 | A8 | B10 | C20 | A8 | B12 | C20 | A8 | B18 | C20 | A8 | B22 | C20 | A8 | B23 | C20 | A8 | B25 | C20 |
| A8 | B6 | C21 | A8 | B7 | C21 | A8 | B8 | C21 | A8 | B9 | C21 | A8 | B10 | C21 | A8 | B12 | C21 | A8 | B18 | C21 | A8 | B22 | C21 | A8 | B23 | C21 | A8 | B25 | C21 |
| A8 | B6 | C22 | A8 | B7 | C22 | A8 | B8 | C22 | A8 | B9 | C22 | A8 | B10 | C22 | A8 | B12 | C22 | A8 | B18 | C22 | A8 | B22 | C22 | A8 | B23 | C22 | A8 | B25 | C22 |
| A8 | B6 | C23 | A8 | B7 | C23 | A8 | B8 | C23 | A8 | B9 | C23 | A8 | B10 | C23 | A8 | B12 | C23 | A8 | B18 | C23 | A8 | B22 | C23 | A8 | B23 | C23 | A8 | B25 | C23 |
| A8 | B6 | C24 | A8 | B7 | C24 | A8 | B8 | C24 | A8 | B9 | C24 | A8 | B10 | C24 | A8 | B12 | C24 | A8 | B18 | C24 | A8 | B22 | C24 | A8 | B23 | C24 | A8 | B25 | C24 |
| A8 | B6 | C25 | A8 | B7 | C25 | A8 | B8 | C25 | A8 | B9 | C25 | A8 | B10 | C25 | A8 | B12 | C25 | A8 | B18 | C25 | A8 | B22 | C25 | A8 | B23 | C25 | A8 | B25 | C25 |
| A8 | B6 | C26 | A8 | B7 | C26 | A8 | B8 | C26 | A8 | B9 | C26 | A8 | B10 | C26 | A8 | B12 | C26 | A8 | B18 | C26 | A8 | B22 | C26 | A8 | B23 | C26 | A8 | B25 | C26 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A8 | B6 | C27 | A8 | B7 | C27 | A8 | B8 | C27 | A8 | B9 | C27 | A8 | B10 | C27 | A8 | B12 | C27 | A8 | B18 | C27 | A8 | B22 | C27 | A8 | B23 | C27 | A8 | B25 | C27 |
| A8 | B6 | C28 | A8 | B7 | C28 | A8 | B8 | C28 | A8 | B9 | C28 | A8 | B10 | C28 | A8 | B12 | C28 | A8 | B18 | C28 | A8 | B22 | C28 | A8 | B23 | C28 | A8 | B25 | C28 |
| A8 | B6 | C29 | A8 | B7 | C29 | A8 | B8 | C29 | A8 | B9 | C29 | A8 | B10 | C29 | A8 | B12 | C29 | A8 | B18 | C29 | A8 | B22 | C29 | A8 | B23 | C29 | A8 | B25 | C29 |
| A8 | B6 | C30 | A8 | B7 | C30 | A8 | B8 | C30 | A8 | B9 | C30 | A8 | B10 | C30 | A8 | B12 | C30 | A8 | B18 | C30 | A8 | B22 | C30 | A8 | B23 | C30 | A8 | B25 | C30 |
| A8 | B6 | C31 | A8 | B7 | C31 | A8 | B8 | C31 | A8 | B9 | C31 | A8 | B10 | C31 | A8 | B12 | C31 | A8 | B18 | C31 | A8 | B22 | C31 | A8 | B23 | C31 | A8 | B25 | C31 |
| A8 | B6 | C32 | A8 | B7 | C32 | A8 | B8 | C32 | A8 | B9 | C32 | A8 | B10 | C32 | A8 | B12 | C32 | A8 | B18 | C32 | A8 | B22 | C32 | A8 | B23 | C32 | A8 | B25 | C32 |
| A8 | B6 | C33 | A8 | B7 | C33 | A8 | B8 | C33 | A8 | B9 | C33 | A8 | B10 | C33 | A8 | B12 | C33 | A8 | B18 | C33 | A8 | B22 | C33 | A8 | B23 | C33 | A8 | B25 | C33 |
| A8 | B6 | C34 | A8 | B7 | C34 | A8 | B8 | C34 | A8 | B9 | C34 | A8 | B10 | C34 | A8 | B12 | C34 | A8 | B18 | C34 | A8 | B22 | C34 | A8 | B23 | C34 | A8 | B25 | C34 |
| A8 | B6 | C33 | A8 | B7 | C35 | A8 | B8 | C35 | A8 | B9 | C35 | A8 | B10 | C35 | A8 | B12 | C35 | A8 | B18 | C35 | A8 | B22 | C35 | A8 | B23 | C35 | A8 | B25 | C35 |
| A8 | B6 | C36 | A8 | B7 | C36 | A8 | B8 | C36 | A8 | B9 | C36 | A8 | B10 | C36 | A8 | B12 | C36 | A8 | B18 | C36 | A8 | B22 | C36 | A8 | B23 | C36 | A8 | B25 | C36 |
| A8 | B6 | C37 | A8 | B7 | C37 | A8 | B8 | C37 | A8 | B9 | C37 | A8 | B10 | C37 | A8 | B12 | C37 | A8 | B18 | C37 | A8 | B22 | C37 | A8 | B23 | C37 | A8 | B25 | C37 |
| A8 | B6 | C38 | A8 | B7 | C38 | A8 | B8 | C38 | A8 | B9 | C38 | A8 | B10 | C38 | A8 | B12 | C38 | A8 | B18 | C38 | A8 | B22 | C38 | A8 | B23 | C38 | A8 | B25 | C38 |
| A8 | B6 | C39 | A8 | B7 | C39 | A8 | B8 | C39 | A8 | B9 | C39 | A8 | B10 | C39 | A8 | B12 | C39 | A8 | B18 | C39 | A8 | B22 | C39 | A8 | B23 | C39 | A8 | B25 | C39 |
| A8 | B6 | C40 | A8 | B7 | C40 | A8 | B8 | C40 | A8 | B9 | C40 | A8 | B10 | C40 | A8 | B12 | C40 | A8 | B18 | C40 | A8 | B22 | C40 | A8 | B23 | C40 | A8 | B25 | C40 |
| A8 | B6 | C41 | A8 | B7 | C41 | A8 | B8 | C41 | A8 | B9 | C41 | A8 | B10 | C41 | A8 | B12 | C41 | A8 | B18 | C41 | A8 | B22 | C41 | A8 | B23 | C41 | A8 | B25 | C41 |
| A17 | B6 | C1 | A17 | B7 | C1 | A17 | B8 | C1 | A17 | B9 | C1 | A17 | B10 | C1 | A17 | B12 | C1 | A17 | B18 | C1 | A17 | B22 | C1 | A17 | B23 | C1 | A17 | B25 | C1 |
| A17 | B6 | C2 | A17 | B7 | C2 | A17 | B8 | C2 | A17 | B9 | C2 | A17 | B10 | C2 | A17 | B12 | C2 | A17 | B18 | C2 | A17 | B22 | C2 | A17 | B23 | C2 | A17 | B25 | C2 |
| A17 | B6 | C3 | A17 | B7 | C3 | A17 | B8 | C3 | A17 | B9 | C3 | A17 | B10 | C3 | A17 | B12 | C3 | A17 | B18 | C3 | A17 | B22 | C3 | A17 | B23 | C3 | A17 | B25 | C3 |
| A17 | B6 | C4 | A17 | B7 | C4 | A17 | B8 | C4 | A17 | B9 | C4 | A17 | B10 | C4 | A17 | B12 | C4 | A17 | B18 | C4 | A17 | B22 | C4 | A17 | B23 | C4 | A17 | B25 | C4 |
| A17 | B6 | C5 | A17 | B7 | C5 | A17 | B8 | C5 | A17 | B9 | C5 | A17 | B10 | C5 | A17 | B12 | C5 | A17 | B18 | C5 | A17 | B22 | C5 | A17 | B23 | C5 | A17 | B25 | C5 |
| A17 | B6 | C6 | A17 | B7 | C6 | A17 | B8 | C6 | A17 | B9 | C6 | A17 | B10 | C6 | A17 | B12 | C6 | A17 | B18 | C6 | A17 | B22 | C6 | A17 | B23 | C6 | A17 | B25 | C6 |
| A17 | B6 | C7 | A17 | B7 | C7 | A17 | B8 | C7 | A17 | B9 | C7 | A17 | B10 | C7 | A17 | B12 | C7 | A17 | B18 | C7 | A17 | B22 | C7 | A17 | B23 | C7 | A17 | B25 | C7 |
| A17 | B6 | C8 | A17 | B7 | C8 | A17 | B8 | C8 | A17 | B9 | C8 | A17 | B10 | C8 | A17 | B12 | C8 | A17 | B18 | C5 | A17 | B22 | C8 | A17 | B23 | C5 | A17 | B25 | C8 |
| A17 | B6 | C9 | A17 | B7 | C9 | A17 | B8 | C9 | A17 | B9 | C9 | A17 | B10 | C9 | A17 | B12 | C9 | A17 | B18 | C9 | A17 | B22 | C9 | A17 | B23 | C9 | A17 | B25 | C9 |
| A17 | B6 | C10 | A17 | B7 | C10 | A17 | B8 | C10 | A17 | B9 | C10 | A17 | B10 | C10 | A17 | B12 | C10 | A17 | B18 | C10 | A17 | B22 | C10 | A17 | B23 | C10 | A17 | B25 | C10 |
| A17 | B6 | C11 | A17 | B7 | C11 | A17 | B8 | C11 | A17 | B9 | C11 | A17 | B10 | C11 | A17 | B12 | C11 | A17 | B18 | C11 | A17 | B22 | C11 | A17 | B23 | C11 | A17 | B25 | C11 |
| A17 | B6 | C12 | A17 | B7 | C12 | A17 | B8 | C12 | A17 | B9 | C12 | A17 | B10 | C12 | A17 | B12 | C12 | A17 | B18 | C12 | A17 | B22 | C12 | A17 | B23 | C12 | A17 | B25 | C12 |
| A17 | B6 | C13 | A17 | B7 | C13 | A17 | B8 | C13 | A17 | B9 | C13 | A17 | B10 | C13 | A17 | B12 | C13 | A17 | B18 | C13 | A17 | B22 | C13 | A17 | B23 | C13 | A17 | B25 | C13 |
| A17 | B6 | C14 | A17 | B7 | C14 | A17 | B8 | C14 | A17 | B9 | C14 | A17 | B10 | C14 | A17 | B12 | C14 | A17 | B18 | C14 | A17 | B22 | C14 | A17 | B23 | C14 | A17 | B25 | C14 |
| A17 | B6 | C15 | A17 | B7 | C15 | A17 | B8 | C15 | A17 | B9 | C15 | A17 | B10 | C15 | A17 | B12 | C15 | A17 | B18 | C15 | A17 | B22 | C15 | A17 | B23 | C15 | A17 | B25 | C15 |
| A17 | B6 | C16 | A17 | B7 | C16 | A17 | B8 | C16 | A17 | B9 | C16 | A17 | B10 | C16 | A17 | B12 | C16 | A17 | B18 | C16 | A17 | B22 | C16 | A17 | B23 | C16 | A17 | B25 | C16 |
| A17 | B6 | C17 | A17 | B7 | C17 | A17 | B8 | C17 | A17 | B9 | C17 | A17 | B10 | C17 | A17 | B12 | C17 | A17 | B18 | C17 | A17 | B22 | C17 | A17 | B23 | C17 | A17 | B25 | C17 |
| A17 | B6 | C18 | A17 | B7 | C18 | A17 | B8 | C18 | A17 | B9 | C18 | A17 | B10 | C18 | A17 | B12 | C18 | A17 | B18 | C18 | A17 | B22 | C18 | A17 | B23 | C18 | A17 | B25 | C18 |
| A17 | B6 | C19 | A17 | B7 | C19 | A17 | B8 | C19 | A17 | B9 | C19 | A17 | B10 | C19 | A17 | B12 | C19 | A17 | B18 | C19 | A17 | B22 | C19 | A17 | B23 | C19 | A17 | B25 | C19 |
| A17 | B6 | C20 | A17 | B7 | C20 | A17 | B8 | C20 | A17 | B9 | C20 | A17 | B10 | C20 | A17 | B12 | C20 | A17 | B18 | C21 | A17 | B22 | C20 | A17 | B23 | C20 | A17 | B25 | C20 |
| A17 | B6 | C21 | A17 | B7 | C21 | A17 | B8 | C21 | A17 | B9 | C21 | A17 | B10 | C21 | A17 | B12 | C21 | A17 | B18 | C21 | A17 | B22 | C21 | A17 | B23 | C21 | A17 | B25 | C21 |
| A17 | B6 | C22 | A17 | B7 | C22 | A17 | B8 | C22 | A17 | B9 | C22 | A17 | B10 | C22 | A17 | B12 | C22 | A17 | B18 | C22 | A17 | B22 | C22 | A17 | B23 | C22 | A17 | B25 | C22 |
| A17 | B6 | C23 | A17 | B7 | C23 | A17 | B8 | C23 | A17 | B9 | C23 | A17 | B10 | C23 | A17 | B12 | C23 | A17 | B18 | C23 | A17 | B22 | C23 | A17 | B23 | C23 | A17 | B25 | C23 |
| A17 | B6 | C24 | A17 | B7 | C24 | A17 | B8 | C24 | A17 | B9 | C24 | A17 | B10 | C24 | A17 | B12 | C24 | A17 | B18 | C24 | A17 | B22 | C24 | A17 | B23 | C24 | A17 | B25 | C24 |
| A17 | B6 | C25 | A17 | B7 | C25 | A17 | B8 | C25 | A17 | B9 | C25 | A17 | B10 | C25 | A17 | B12 | C25 | A17 | B18 | C25 | A17 | B22 | C25 | A17 | B23 | C25 | A17 | B25 | C25 |
| A17 | B6 | C26 | A17 | B7 | C26 | A17 | B8 | C26 | A17 | B9 | C26 | A17 | B10 | C26 | A17 | B12 | C26 | A17 | B18 | C26 | A17 | B22 | C26 | A17 | B23 | C26 | A17 | B25 | C26 |
| A17 | B6 | C27 | A17 | B7 | C27 | A17 | B8 | C27 | A17 | B9 | C27 | A17 | B10 | C27 | A17 | B12 | C27 | A17 | B18 | C27 | A17 | B22 | C27 | A17 | B23 | C27 | A17 | B25 | C27 |
| A17 | B6 | C28 | A17 | B7 | C28 | A17 | B8 | C28 | A17 | B9 | C28 | A17 | B10 | C28 | A17 | B12 | C28 | A17 | B18 | C28 | A17 | B22 | C28 | A17 | B23 | C28 | A17 | B25 | C28 |
| A17 | B6 | C29 | A17 | B7 | C29 | A17 | B8 | C29 | A17 | B9 | C29 | A17 | B10 | C29 | A17 | B12 | C29 | A17 | B18 | C29 | A17 | B22 | C29 | A17 | B23 | C29 | A17 | B25 | C29 |
| A17 | B6 | C30 | A17 | B7 | C30 | A17 | B8 | C30 | A17 | B9 | C30 | A17 | B10 | C30 | A17 | B12 | C30 | A17 | B18 | C30 | A17 | B22 | C30 | A17 | B23 | C30 | A17 | B25 | C30 |
| A17 | B6 | C31 | A17 | B7 | C31 | A17 | B8 | C31 | A17 | B9 | C31 | A17 | B10 | C31 | A17 | B12 | C31 | A17 | B18 | C31 | A17 | B22 | C31 | A17 | B23 | C31 | A17 | B25 | C31 |
| A17 | B6 | C32 | A17 | B7 | C32 | A17 | B8 | C32 | A17 | B9 | C32 | A17 | B10 | C32 | A17 | B12 | C32 | A17 | B18 | C32 | A17 | B22 | C32 | A17 | B23 | C32 | A17 | B25 | C32 |
| A17 | B6 | C33 | A17 | B7 | C33 | A17 | B8 | C33 | A17 | B9 | C33 | A17 | B10 | C33 | A17 | B12 | C33 | A17 | B18 | C33 | A17 | B22 | C33 | A17 | B23 | C33 | A17 | B25 | C33 |
| A17 | B6 | C34 | A17 | B7 | C34 | A17 | B8 | C34 | A17 | B9 | C34 | A17 | B10 | C34 | A17 | B12 | C34 | A17 | B18 | C34 | A17 | B22 | C34 | A17 | B23 | C34 | A17 | B25 | C34 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A17 | B6 | C35 | A17 | B7 | C35 | A17 | B8 | C35 | A17 | B9 | C35 | A17 | B10 | C35 | A17 | B12 | C35 | A17 | B18 | C35 | A17 | B22 | C35 | A17 | B23 | C35 | A17 | B25 | C35 |
| A17 | B6 | C36 | A17 | B7 | C36 | A17 | B8 | C36 | A17 | B9 | C36 | A17 | B10 | C36 | A17 | B12 | C36 | A17 | B18 | C36 | A17 | B22 | C36 | A17 | B23 | C36 | A17 | B25 | C36 |
| A17 | B6 | C37 | A17 | B7 | C37 | A17 | B8 | C37 | A17 | B9 | C37 | A17 | B10 | C37 | A17 | B12 | C37 | A17 | B15 | C37 | A17 | B22 | C37 | A17 | B23 | C37 | A17 | B25 | C37 |
| A17 | B6 | C38 | A17 | B7 | C38 | A17 | B8 | C38 | A17 | B9 | C38 | A17 | B10 | C38 | A17 | B12 | C38 | A17 | B15 | C38 | A17 | B22 | C38 | A17 | B23 | C38 | A17 | B25 | C38 |
| A17 | B6 | C39 | A17 | B7 | C39 | A17 | B8 | C39 | A17 | B9 | C39 | A17 | B10 | C39 | A17 | B12 | C39 | A17 | B15 | C39 | A17 | B22 | C39 | A17 | B23 | C39 | A17 | B25 | C39 |
| A17 | B6 | C40 | A17 | B7 | C40 | A17 | B8 | C40 | A17 | B9 | C40 | A17 | B10 | C40 | A17 | B12 | C40 | A17 | B15 | C40 | A17 | B22 | C40 | A17 | B23 | C40 | A17 | B25 | C40 |
| A17 | B6 | C41 | A17 | B7 | C41 | A17 | B8 | C41 | A17 | B9 | C41 | A17 | B10 | C41 | A17 | B12 | C41 | A17 | B15 | C41 | A17 | B22 | C41 | A17 | B23 | C41 | A17 | B25 | C41 |
| A26 | B6 | C1 | A26 | B7 | C1 | A26 | B8 | C1 | A26 | B9 | C1 | A26 | B10 | C1 | A26 | B12 | C1 | A26 | B18 | C1 | A26 | B22 | C1 | A26 | B23 | C1 | A26 | B25 | C1 |
| A26 | B6 | C2 | A26 | B7 | C2 | A26 | B8 | C2 | A26 | B9 | C2 | A26 | B10 | C2 | A26 | B12 | C2 | A26 | B18 | C2 | A26 | B22 | C2 | A26 | B23 | C2 | A26 | B25 | C2 |
| A26 | B6 | C3 | A26 | B7 | C3 | A26 | B8 | C3 | A26 | B9 | C3 | A26 | B10 | C3 | A26 | B12 | C3 | A26 | B15 | C3 | A26 | B22 | C3 | A26 | B23 | C3 | A26 | B25 | C3 |
| A26 | B6 | C4 | A26 | B7 | C4 | A26 | B8 | C4 | A26 | B9 | C4 | A26 | B10 | C4 | A26 | B12 | C4 | A26 | B18 | C4 | A26 | B22 | C4 | A26 | B23 | C4 | A26 | B25 | C4 |
| A26 | B6 | C5 | A26 | B7 | C5 | A26 | B8 | C5 | A26 | B9 | C5 | A26 | B10 | C5 | A26 | B12 | C5 | A26 | B18 | C5 | A26 | B22 | C5 | A26 | B23 | C5 | A26 | B25 | C5 |
| A26 | B6 | C6 | A26 | B7 | C6 | A26 | B8 | C6 | A26 | B9 | C6 | A26 | B10 | C6 | A26 | B12 | C6 | A26 | B18 | C6 | A26 | B22 | C6 | A26 | B23 | C6 | A26 | B25 | C6 |
| A26 | B6 | C7 | A26 | B7 | C7 | A26 | B8 | C7 | A26 | B9 | C7 | A26 | B10 | C7 | A26 | B12 | C7 | A26 | B18 | C7 | A26 | B22 | C7 | A26 | B23 | C7 | A26 | B25 | C7 |
| A26 | B6 | C8 | A26 | B7 | C8 | A26 | B8 | C8 | A26 | B9 | C8 | A26 | B10 | C8 | A26 | B12 | C8 | A26 | B18 | C8 | A26 | B22 | C5 | A26 | B23 | C8 | A26 | B25 | C8 |
| A26 | B6 | C9 | A26 | B7 | C9 | A26 | B8 | C9 | A26 | B9 | C9 | A26 | B10 | C9 | A26 | B12 | C9 | A26 | B18 | C9 | A26 | B22 | C9 | A26 | B23 | C9 | A26 | B25 | C9 |
| A26 | B6 | C10 | A26 | B7 | C10 | A26 | B8 | C10 | A26 | B9 | C10 | A26 | B10 | C10 | A26 | B12 | C10 | A26 | B18 | C10 | A26 | B22 | C10 | A26 | B23 | C10 | A26 | B25 | C10 |
| A26 | B6 | C11 | A26 | B7 | C11 | A26 | B8 | C11 | A26 | B9 | C11 | A26 | B10 | C11 | A26 | B12 | C11 | A26 | B18 | C11 | A26 | B22 | C11 | A26 | B23 | C11 | A26 | B25 | C11 |
| A26 | B6 | C12 | A26 | B7 | C12 | A26 | B8 | C12 | A26 | B9 | C12 | A26 | B10 | C12 | A26 | B12 | C12 | A26 | B18 | C12 | A26 | B22 | C12 | A26 | B23 | C12 | A26 | B25 | C12 |
| A26 | B6 | C13 | A26 | B7 | C13 | A26 | B8 | C13 | A26 | B9 | C13 | A26 | B10 | C13 | A26 | B12 | C13 | A26 | B18 | C13 | A26 | B22 | C13 | A26 | B23 | C13 | A26 | B25 | C13 |
| A26 | B6 | C14 | A26 | B7 | C14 | A26 | B8 | C14 | A26 | B9 | C14 | A26 | B10 | C14 | A26 | B12 | C14 | A26 | B18 | C14 | A26 | B22 | C14 | A26 | B23 | C14 | A26 | B25 | C14 |
| A26 | B6 | C15 | A26 | B7 | C15 | A26 | B8 | C15 | A26 | B9 | C15 | A26 | B10 | C15 | A26 | B12 | C15 | A26 | B18 | C15 | A26 | B22 | C15 | A26 | B23 | C15 | A26 | B25 | C15 |
| A26 | B6 | C16 | A26 | B7 | C16 | A26 | B8 | C16 | A26 | B9 | C16 | A26 | B10 | C16 | A26 | B12 | C16 | A26 | B18 | C16 | A26 | B22 | C16 | A26 | B23 | C16 | A26 | B25 | C16 |
| A26 | B6 | C17 | A26 | B7 | C17 | A26 | B8 | C17 | A26 | B9 | C17 | A26 | B10 | C17 | A26 | B12 | C17 | A26 | B18 | C17 | A26 | B22 | C17 | A26 | B23 | C17 | A26 | B25 | C17 |
| A26 | B6 | C18 | A26 | B7 | C18 | A26 | B8 | C18 | A26 | B9 | C18 | A26 | B10 | C18 | A26 | B12 | C18 | A26 | B18 | C18 | A26 | B22 | C18 | A26 | B23 | C18 | A26 | B25 | C18 |
| A26 | B6 | C19 | A26 | B7 | C19 | A26 | B8 | C19 | A26 | B9 | C19 | A26 | B10 | C19 | A26 | B12 | C19 | A26 | B18 | C19 | A26 | B22 | C19 | A26 | B23 | C19 | A26 | B25 | C19 |
| A26 | B6 | C20 | A26 | B7 | C20 | A26 | B8 | C20 | A26 | B9 | C20 | A26 | B10 | C20 | A26 | B12 | C20 | A26 | B18 | C20 | A26 | B22 | C20 | A26 | B23 | C20 | A26 | B25 | C20 |
| A26 | B6 | C21 | A26 | B7 | C21 | A26 | B8 | C21 | A26 | B9 | C21 | A26 | B10 | C21 | A26 | B12 | C21 | A26 | B18 | C21 | A26 | B22 | C21 | A26 | B23 | C21 | A26 | B25 | C21 |
| A26 | B6 | C22 | A26 | B7 | C22 | A26 | B8 | C22 | A26 | B9 | C22 | A26 | B10 | C22 | A26 | B12 | C22 | A26 | B18 | C22 | A26 | B22 | C22 | A26 | B23 | C22 | A26 | B25 | C22 |
| A26 | B6 | C23 | A26 | B7 | C23 | A26 | B8 | C23 | A26 | B9 | C23 | A26 | B10 | C23 | A26 | B12 | C23 | A26 | B18 | C23 | A26 | B22 | C23 | A26 | B23 | C23 | A26 | B25 | C23 |
| A26 | B6 | C24 | A26 | B7 | C24 | A26 | B8 | C24 | A26 | B9 | C24 | A26 | B10 | C24 | A26 | B12 | C24 | A26 | B18 | C24 | A26 | B22 | C24 | A26 | B23 | C24 | A26 | B25 | C24 |
| A26 | B6 | C25 | A26 | B7 | C25 | A26 | B8 | C25 | A26 | B9 | C25 | A26 | B10 | C25 | A26 | B12 | C25 | A26 | B18 | C25 | A26 | B22 | C25 | A26 | B23 | C25 | A26 | B25 | C25 |
| A26 | B6 | C26 | A26 | B7 | C26 | A26 | B8 | C26 | A26 | B9 | C26 | A26 | B10 | C26 | A26 | B12 | C26 | A26 | B18 | C26 | A26 | B22 | C26 | A26 | B23 | C26 | A26 | B25 | C26 |
| A26 | B6 | C27 | A26 | B7 | C27 | A26 | B8 | C27 | A26 | B9 | C27 | A26 | B10 | C27 | A26 | B12 | C27 | A26 | B18 | C27 | A26 | B22 | C27 | A26 | B23 | C27 | A26 | B25 | C27 |
| A26 | B6 | C28 | A26 | B7 | C28 | A26 | B8 | C28 | A26 | B9 | C28 | A26 | B10 | C28 | A26 | B12 | C28 | A26 | B18 | C28 | A26 | B22 | C28 | A26 | B23 | C28 | A26 | B25 | C28 |
| A26 | B6 | C29 | A26 | B7 | C29 | A26 | B8 | C29 | A26 | B9 | C29 | A26 | B10 | C29 | A26 | B12 | C29 | A26 | B18 | C29 | A26 | B22 | C29 | A26 | B23 | C29 | A26 | B25 | C29 |
| A26 | B6 | C30 | A26 | B7 | C30 | A26 | B8 | C30 | A26 | B9 | C30 | A26 | B10 | C30 | A26 | B12 | C30 | A26 | B18 | C30 | A26 | B22 | C30 | A26 | B23 | C30 | A26 | B25 | C30 |
| A26 | B6 | C31 | A26 | B7 | C31 | A26 | B8 | C31 | A26 | B9 | C31 | A26 | B10 | C31 | A26 | B12 | C31 | A26 | B18 | C31 | A26 | B22 | C31 | A26 | B23 | C31 | A26 | B25 | C31 |
| A26 | B6 | C32 | A26 | B7 | C32 | A26 | B8 | C32 | A26 | B9 | C32 | A26 | B10 | C32 | A26 | B12 | C32 | A26 | B18 | C32 | A26 | B22 | C32 | A26 | B23 | C32 | A26 | B25 | C32 |
| A26 | B6 | C33 | A26 | B7 | C33 | A26 | B8 | C33 | A26 | B9 | C33 | A26 | B10 | C33 | A26 | B12 | C13 | A26 | B18 | C33 | A26 | B22 | C33 | A26 | B23 | C33 | A26 | B25 | C33 |
| A26 | B6 | C34 | A26 | B7 | C34 | A26 | B8 | C34 | A26 | B9 | C34 | A26 | B10 | C34 | A26 | B12 | C34 | A26 | B18 | C34 | A26 | B22 | C34 | A26 | B23 | C34 | A26 | B25 | C34 |
| A26 | B6 | C35 | A26 | B7 | C35 | A26 | B8 | C35 | A26 | B9 | C35 | A26 | B10 | C35 | A26 | B12 | C35 | A26 | B18 | C35 | A26 | B22 | C35 | A26 | B23 | C35 | A26 | B25 | C35 |
| A26 | B6 | C36 | A26 | B7 | C36 | A26 | B8 | C36 | A26 | B9 | C36 | A26 | B10 | C36 | A26 | B12 | C36 | A26 | B18 | C36 | A26 | B22 | C36 | A26 | B23 | C36 | A26 | B25 | C36 |
| A26 | B6 | C37 | A26 | B7 | C37 | A26 | B8 | C37 | A26 | B9 | C37 | A26 | B10 | C37 | A26 | B12 | C37 | A26 | B18 | C37 | A26 | B22 | C37 | A26 | B23 | C37 | A26 | B25 | C37 |
| A26 | B6 | C38 | A26 | B7 | C38 | A26 | B8 | C38 | A26 | B9 | C38 | A26 | B10 | C38 | A26 | B12 | C38 | A26 | B18 | C38 | A26 | B22 | C38 | A26 | B23 | C38 | A26 | B25 | C38 |
| A26 | B6 | C39 | A26 | B7 | C39 | A26 | B8 | C39 | A26 | B9 | C39 | A26 | B10 | C39 | A26 | B12 | C39 | A26 | B18 | C39 | A26 | B22 | C39 | A26 | B23 | C39 | A26 | B25 | C39 |
| A26 | B6 | C40 | A26 | B7 | C40 | A26 | B8 | C40 | A26 | B9 | C40 | A26 | B10 | C40 | A26 | B12 | C40 | A26 | B18 | C40 | A26 | B22 | C40 | A26 | B23 | C40 | A26 | B25 | C40 |
| A26 | B6 | C41 | A26 | B7 | C41 | A26 | B8 | C41 | A26 | B9 | C41 | A26 | B10 | C41 | A26 | B12 | C41 | A26 | B18 | C41 | A26 | B22 | C41 | A26 | B23 | C41 | A26 | B25 | C41 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A30 | B6 | C1 | A30 | B7 | C1 | A30 | B8 | C1 | A30 | B9 | C1 | A30 | B10 | C1 | A30 | B12 | C1 | A30 | B18 | C1 | A30 | B22 | C1 | A30 | B23 | C1 | A30 | B25 | C1 |
| A30 | B6 | C2 | A30 | B7 | C2 | A30 | B8 | C2 | A30 | B9 | C2 | A30 | B10 | C2 | A30 | B12 | C2 | A30 | B18 | C2 | A30 | B22 | C2 | A30 | B23 | C2 | A30 | B25 | C2 |
| A30 | B6 | C3 | A30 | B7 | C3 | A30 | B8 | C3 | A30 | B9 | C3 | A30 | B10 | C3 | A30 | B12 | C3 | A30 | B18 | C3 | A30 | B22 | C3 | A30 | B23 | C3 | A30 | B25 | C3 |
| A30 | B6 | C4 | A30 | B7 | C4 | A30 | B8 | C4 | A30 | B9 | C4 | A30 | B10 | C4 | A30 | B12 | C4 | A30 | B18 | C4 | A30 | B22 | C4 | A30 | B23 | C4 | A30 | B25 | C4 |
| A30 | B6 | C5 | A30 | B7 | C5 | A30 | B8 | C5 | A30 | B9 | C5 | A30 | B10 | C5 | A30 | B12 | C5 | A30 | B18 | C5 | A30 | B22 | C5 | A30 | B23 | C5 | A30 | B25 | C5 |
| A30 | B6 | C6 | A30 | B7 | C6 | A30 | B8 | C6 | A30 | B9 | C6 | A30 | B10 | C6 | A30 | B12 | C6 | A30 | B18 | C6 | A30 | B22 | C6 | A30 | B23 | C6 | A30 | B25 | C6 |
| A30 | B6 | C7 | A30 | B7 | C7 | A30 | B8 | C7 | A30 | B9 | C7 | A30 | B10 | C7 | A30 | B12 | C7 | A30 | B18 | C7 | A30 | B22 | C7 | A30 | B23 | C7 | A30 | B25 | C7 |
| A30 | B6 | C8 | A30 | B7 | C8 | A30 | B8 | C8 | A30 | B9 | C8 | A30 | B10 | C8 | A30 | B12 | C8 | A30 | B18 | C8 | A30 | B22 | C8 | A30 | B23 | C8 | A30 | B25 | C5 |
| A30 | B6 | C9 | A30 | B7 | C9 | A30 | B8 | C9 | A30 | B9 | C9 | A30 | B10 | C9 | A30 | B12 | C9 | A30 | B18 | C9 | A30 | B22 | C9 | A30 | B23 | C9 | A30 | B25 | C9 |
| A30 | B6 | C10 | A30 | B7 | C10 | A30 | B8 | C10 | A30 | B9 | C10 | A30 | B10 | C10 | A30 | B12 | C10 | A30 | B18 | C10 | A30 | B22 | C10 | A30 | B23 | C10 | A30 | B25 | C10 |
| A30 | B6 | C11 | A30 | B7 | C11 | A30 | B8 | C11 | A30 | B9 | C11 | A30 | B10 | C11 | A30 | B12 | C11 | A30 | B18 | C11 | A30 | B22 | C11 | A30 | B23 | C11 | A30 | B25 | C11 |
| A30 | B6 | C12 | A30 | B7 | C12 | A30 | B8 | C12 | A30 | B9 | C12 | A30 | B10 | C12 | A30 | B12 | C12 | A30 | B18 | C12 | A30 | B22 | C12 | A30 | B23 | C12 | A30 | B25 | C12 |
| A30 | B6 | C13 | A30 | B7 | C13 | A30 | B8 | C13 | A30 | B9 | C13 | A30 | B10 | C13 | A30 | B12 | C13 | A30 | B18 | C13 | A30 | B22 | C13 | A30 | B23 | C13 | A30 | B25 | C13 |
| A30 | B6 | C14 | A30 | B7 | C14 | A30 | B8 | C14 | A30 | B9 | C14 | A30 | B10 | C14 | A30 | B12 | C14 | A30 | B18 | C14 | A30 | B22 | C14 | A30 | B23 | C14 | A30 | B25 | C14 |
| A30 | B6 | C15 | A30 | B7 | C15 | A30 | B8 | C15 | A30 | B9 | C15 | A30 | B10 | C15 | A30 | B12 | C15 | A30 | B18 | C15 | A30 | B22 | C15 | A30 | B23 | C15 | A30 | B25 | C15 |
| A30 | B6 | C16 | A30 | B7 | C16 | A30 | B8 | C16 | A30 | B9 | C16 | A30 | B10 | C16 | A30 | B12 | C16 | A30 | B18 | C16 | A30 | B22 | C16 | A30 | B23 | C16 | A30 | B25 | C16 |
| A30 | B6 | C17 | A30 | B7 | C17 | A30 | B8 | C17 | A30 | B9 | C17 | A30 | B10 | C17 | A30 | B12 | C17 | A30 | B18 | C17 | A30 | B22 | C17 | A30 | B23 | C17 | A30 | B25 | C17 |
| A30 | B6 | C18 | A30 | B7 | C18 | A30 | B8 | C18 | A30 | B9 | C18 | A30 | B10 | C18 | A30 | B12 | C18 | A30 | B18 | C18 | A30 | B22 | C18 | A30 | B23 | C18 | A30 | B25 | C18 |
| A30 | B6 | C19 | A30 | B7 | C19 | A30 | B8 | C19 | A30 | B9 | C19 | A30 | B10 | C19 | A30 | B12 | C19 | A30 | B18 | C19 | A30 | B22 | C19 | A30 | B23 | C19 | A30 | B25 | C19 |
| A30 | B6 | C20 | A30 | B7 | C20 | A30 | B8 | C20 | A30 | B9 | C20 | A30 | B10 | C20 | A30 | B12 | C20 | A30 | B18 | C20 | A30 | B22 | C20 | A30 | B23 | C20 | A30 | B25 | C20 |
| A30 | B6 | C21 | A30 | B7 | C2i | A30 | B8 | C21 | A30 | B9 | C21 | A30 | B10 | C21 | A30 | B12 | C21 | A30 | B18 | C21 | A30 | B22 | C21 | A30 | B23 | C21 | A30 | B25 | C21 |
| A30 | B6 | C22 | A30 | B7 | C22 | A30 | B8 | C22 | A30 | B9 | C22 | A30 | B10 | C22 | A30 | B12 | C22 | A30 | B18 | C22 | A30 | B22 | C22 | A30 | B23 | C22 | A30 | B25 | C22 |
| A30 | B6 | C23 | A30 | B7 | C23 | A30 | B8 | C23 | A30 | B9 | C23 | A30 | B10 | C23 | A30 | B12 | C23 | A30 | B18 | C23 | A30 | B22 | C23 | A30 | B23 | C23 | A30 | B25 | C23 |
| A30 | B6 | C24 | A30 | B7 | C24 | A30 | B8 | C24 | A30 | B9 | C24 | A30 | B10 | C24 | A30 | B12 | C24 | A30 | B18 | C24 | A30 | B22 | C24 | A30 | B23 | C24 | A30 | B25 | C24 |
| A30 | B6 | C25 | A30 | B7 | C25 | A30 | B8 | C25 | A30 | B9 | C25 | A30 | B10 | C25 | A30 | B12 | C25 | A30 | B18 | C25 | A30 | B22 | C25 | A30 | B23 | C25 | A30 | B25 | C25 |
| A30 | B6 | C26 | A30 | B7 | C26 | A30 | B8 | C2E | A30 | B9 | C26 | A30 | B10 | C26 | A30 | B12 | C26 | A30 | B18 | C26 | A30 | B22 | C26 | A30 | B23 | C26 | A30 | B25 | C26 |
| A30 | B6 | C27 | A30 | B7 | C27 | A30 | B8 | C27 | A30 | B9 | C27 | A30 | B10 | C27 | A30 | B12 | C27 | A30 | B18 | C27 | A30 | B22 | C27 | A30 | B23 | C27 | A30 | B25 | C27 |
| A30 | B6 | C28 | A30 | B7 | C28 | A30 | B8 | C28 | A30 | B9 | C28 | A30 | B10 | C28 | A30 | B12 | C28 | A30 | B18 | C28 | A30 | B22 | C28 | A30 | B23 | C28 | A30 | B25 | C28 |
| A30 | B6 | C29 | A30 | B7 | C29 | A30 | B8 | C29 | A30 | B9 | C29 | A30 | B10 | C29 | A30 | B12 | C29 | A30 | B18 | C29 | A30 | B22 | C29 | A30 | B23 | C29 | A30 | B25 | C29 |
| A30 | B6 | C30 | A30 | B7 | C30 | A30 | B8 | C30 | A30 | B9 | C30 | A30 | B10 | C30 | A30 | B12 | C30 | A30 | B18 | C30 | A30 | B22 | C30 | A30 | B23 | C30 | A30 | B25 | C30 |
| A30 | B6 | C31 | A30 | B7 | C31 | A30 | B8 | C31 | A30 | B9 | C31 | A30 | B10 | C31 | A30 | B12 | C31 | A30 | B18 | C31 | A30 | B22 | C31 | A30 | B23 | C31 | A30 | B25 | C31 |
| A30 | B6 | C32 | A30 | B7 | C32 | A10 | B8 | C32 | A30 | B9 | C32 | A30 | B10 | C32 | A30 | B12 | C32 | A30 | B18 | C32 | A30 | B22 | C32 | A10 | B23 | C32 | A30 | B25 | C32 |
| A30 | B6 | C33 | A30 | B7 | C33 | A30 | B8 | C33 | A30 | B9 | C33 | A30 | B10 | C33 | A30 | B12 | C33 | A30 | B18 | C33 | A30 | B22 | C33 | A30 | B23 | C33 | A30 | B25 | C33 |
| A30 | B6 | C34 | A30 | B7 | C34 | A10 | B8 | C34 | A30 | B9 | C34 | A30 | B10 | C34 | A30 | B12 | C34 | A30 | B18 | C34 | A30 | B22 | C34 | A30 | B23 | C34 | A30 | B25 | C34 |
| A30 | B6 | C35 | A30 | B7 | C35 | A30 | B8 | C35 | A30 | B9 | C35 | A30 | B10 | C35 | A30 | B12 | C35 | A30 | B18 | C35 | A30 | B22 | C35 | A30 | B23 | C35 | A30 | B25 | C35 |
| A30 | B6 | C36 | A30 | B7 | C36 | A30 | B8 | C36 | A30 | B9 | C36 | A30 | B10 | C36 | A30 | B12 | C36 | A30 | B18 | C36 | A30 | B22 | C36 | A30 | B23 | C36 | A30 | B25 | C36 |
| A30 | B6 | C37 | A30 | B7 | C37 | A30 | B8 | C37 | A30 | B9 | C37 | A30 | B10 | C37 | A30 | B12 | C37 | A30 | B18 | C37 | A30 | B22 | C37 | A30 | B23 | C37 | A30 | B25 | C37 |
| A30 | B6 | C38 | A30 | B7 | C38 | A30 | B8 | C38 | A30 | B9 | C38 | A30 | B10 | C38 | A30 | B12 | C38 | A30 | B18 | C38 | A30 | B22 | C38 | A30 | B23 | C38 | A30 | B25 | C38 |
| A30 | B6 | C39 | A30 | B7 | C39 | A30 | B8 | C39 | A30 | B9 | C39 | A30 | B10 | C39 | A30 | B12 | C39 | A30 | B18 | C39 | A30 | B22 | C39 | A30 | B23 | C39 | A30 | B25 | C39 |
| A30 | B6 | C40 | A30 | B7 | C40 | A30 | B8 | C40 | A30 | B9 | C40 | A30 | B10 | C40 | A30 | B12 | C40 | A30 | B18 | C40 | A30 | B22 | C40 | A30 | B23 | C40 | A30 | B25 | C40 |
| A30 | B6 | C41 | A30 | B7 | C41 | A30 | B8 | C41 | A30 | B9 | C41 | A30 | B10 | C41 | A10 | B12 | C41 | A30 | B18 | C41 | A30 | B22 | C41 | A30 | B23 | C41 | A30 | B25 | C41 |
| A31 | B6 | C1 | A31 | B7 | C1 | A31 | B8 | C1 | A31 | B9 | C1 | A31 | B10 | C1 | A31 | B12 | C1 | A31 | B18 | C1 | A31 | B22 | C1 | A31 | B23 | C1 | A31 | B25 | C1 |
| A31 | B6 | C7 | A31 | B7 | C2 | A31 | B8 | C2 | A31 | B9 | C2 | A31 | B10 | C2 | A31 | B12 | C2 | A31 | B18 | C2 | A31 | B22 | C2 | A31 | B23 | C2 | A31 | B25 | C2 |
| A31 | B6 | C3 | A31 | B7 | C3 | A31 | B8 | C3 | A31 | B9 | C3 | A31 | B10 | C3 | A31 | B12 | C3 | A31 | B18 | C3 | A31 | B22 | C3 | A31 | B23 | C3 | A31 | B25 | C3 |
| A31 | B6 | C4 | A31 | B7 | C4 | A31 | B8 | C4 | A31 | B9 | C4 | A31 | B10 | C4 | A31 | B12 | C4 | A31 | B18 | C4 | A31 | B22 | C4 | A31 | B23 | C4 | A31 | B25 | C4 |
| A31 | B6 | C5 | A31 | B7 | C5 | A31 | B8 | C5 | A31 | B9 | C5 | A31 | B10 | C5 | A31 | B12 | C5 | A31 | B18 | C5 | A31 | B22 | C5 | A31 | B23 | C5 | A31 | B25 | C5 |
| A31 | B6 | C6 | A31 | B7 | C6 | A31 | B8 | C6 | A31 | B9 | C6 | A31 | B10 | C6 | A31 | B12 | C6 | A31 | B18 | C6 | A31 | B22 | C6 | A31 | B23 | C6 | A31 | B25 | C6 |
| A31 | B6 | C7 | A31 | B7 | C7 | A31 | B8 | C7 | A31 | B9 | C7 | A31 | B10 | C7 | A31 | B12 | C7 | A31 | B18 | C7 | A31 | B22 | C7 | A31 | B23 | C7 | A31 | B25 | C7 |

-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| A31 | B6 | C8 | A31 | B7 | C8 | A31 | B8 | C8 | A31 | B9 | C8 | A31 | B10 | C8 | A31 | B12 | C8 | A31 | B18 | C8 | A31 | B22 | C8 | A31 | B23 | C8 | A31 | B25 | C8 |
| A31 | B6 | C9 | A31 | B7 | C9 | A31 | B8 | C9 | A31 | B9 | C9 | A31 | B10 | C9 | A31 | B12 | C9 | A31 | B18 | C9 | A31 | B22 | C9 | A31 | B23 | C9 | A31 | B25 | C9 |
| A31 | B6 | C10 | A31 | B7 | C10 | A31 | B8 | C10 | A31 | B9 | C10 | A31 | B10 | C10 | A31 | B12 | C10 | A31 | B18 | C10 | A31 | B22 | C10 | A31 | B23 | C10 | A31 | B25 | C10 |
| A31 | B6 | C11 | A31 | B7 | C11 | A31 | B8 | C11 | A31 | B9 | C11 | A31 | B10 | C11 | A31 | B12 | C11 | A31 | B18 | C11 | A31 | B22 | C11 | A31 | B23 | C11 | A31 | B25 | C11 |
| A31 | B6 | C12 | A31 | B7 | C12 | A31 | B8 | C12 | A31 | B9 | C12 | A31 | B10 | C12 | A31 | B12 | C12 | A31 | B18 | C12 | A31 | B22 | C12 | A31 | B23 | C12 | A31 | B25 | C12 |
| A31 | B6 | C13 | A31 | B7 | C13 | A31 | B8 | C13 | A31 | B9 | C13 | A31 | B10 | C13 | A31 | B12 | C13 | A31 | B18 | C13 | A31 | B22 | C13 | A31 | B23 | C13 | A31 | B25 | C13 |
| A31 | B6 | C14 | A31 | B7 | C14 | A31 | B8 | C14 | A31 | B9 | C14 | A31 | B10 | C14 | A31 | B12 | C14 | A31 | B18 | C14 | A31 | B22 | C14 | A31 | B23 | C14 | A31 | B25 | C14 |
| A31 | B6 | C15 | A31 | B7 | C15 | A31 | B8 | C15 | A31 | B9 | C15 | A31 | B10 | C15 | A31 | B12 | C15 | A31 | B18 | C15 | A31 | B22 | C15 | A31 | B23 | C15 | A31 | B25 | C15 |
| A31 | B6 | C16 | A31 | B7 | C16 | A31 | B8 | C16 | A31 | B9 | C16 | A31 | B10 | C16 | A31 | B12 | C16 | A31 | B18 | C16 | A11 | B22 | C16 | A31 | B23 | C16 | A31 | B25 | C16 |
| A31 | B6 | C17 | A31 | B7 | C17 | A31 | B8 | C17 | A31 | B9 | C17 | A31 | B10 | C17 | A31 | B12 | C17 | A31 | B18 | C17 | A31 | B22 | C17 | A31 | B23 | C17 | A31 | B25 | C17 |
| A31 | B6 | C18 | A31 | B7 | C18 | A31 | B8 | C18 | A31 | B9 | C18 | A31 | B10 | C18 | A31 | B12 | C18 | A31 | B18 | C18 | A31 | B22 | C18 | A31 | B23 | C15 | A31 | B25 | C18 |
| A31 | B6 | C19 | A31 | B7 | C19 | A31 | B8 | C19 | A31 | B9 | C19 | A31 | B10 | C19 | A31 | B12 | C19 | A31 | B18 | C19 | A31 | B22 | C19 | A31 | B23 | C19 | A31 | B25 | C19 |
| A31 | B6 | C20 | A31 | B7 | C20 | A31 | B8 | C20 | A31 | B9 | C20 | A31 | B10 | C20 | A31 | B12 | C20 | A31 | B18 | C20 | A31 | B22 | C20 | A31 | B23 | C20 | A31 | B25 | C20 |
| A31 | B6 | C21 | A31 | B7 | C21 | A31 | B8 | C21 | A31 | B9 | C21 | A31 | B10 | C21 | A31 | B12 | C21 | A31 | B18 | C21 | A31 | B22 | C21 | A31 | B23 | C21 | A31 | B25 | C21 |
| A31 | B6 | C22 | A31 | B7 | C22 | A31 | B8 | C22 | A31 | B9 | C22 | A31 | B10 | C22 | A31 | B12 | C22 | A31 | B18 | C22 | A31 | B22 | C22 | A31 | B23 | C22 | A31 | B25 | C22 |
| A31 | B6 | C23 | A31 | B7 | C23 | A31 | B8 | C23 | A31 | B9 | C23 | A31 | B10 | C23 | A31 | B12 | C23 | A31 | B18 | C23 | A31 | B22 | C23 | A31 | B23 | C23 | A31 | B25 | C23 |
| A31 | B6 | C24 | A31 | B7 | C24 | A31 | B8 | C24 | A31 | B9 | C24 | A31 | B10 | C24 | A31 | B12 | C24 | A31 | B18 | C24 | A31 | B22 | C24 | A31 | B23 | C24 | A31 | B25 | C24 |
| A31 | B6 | C25 | A31 | B7 | C25 | A31 | B8 | C25 | A31 | B9 | C25 | A31 | B10 | C25 | A31 | B12 | C25 | A31 | B18 | C25 | A31 | B22 | C25 | A31 | B23 | C25 | A31 | B25 | C25 |
| A31 | B6 | C26 | A31 | B7 | C26 | A31 | B8 | C26 | A31 | B9 | C26 | A31 | B10 | C26 | A31 | B12 | C26 | A31 | B18 | C26 | A31 | B22 | C26 | A31 | B23 | C26 | A31 | B25 | C26 |
| A31 | B6 | C27 | A31 | B7 | C27 | A31 | B8 | C27 | A31 | B9 | C27 | A31 | B10 | C27 | A31 | B12 | C27 | A31 | B18 | C27 | A31 | B22 | C27 | A31 | B23 | C27 | A31 | B25 | C27 |
| A31 | B6 | C28 | A31 | B7 | C28 | A31 | B8 | C28 | A31 | B9 | C28 | A31 | B10 | C28 | A31 | B12 | C28 | A31 | B18 | C28 | A31 | B22 | C28 | A31 | B23 | C28 | A31 | 825 | C28 |
| A31 | B6 | C29 | A31 | B7 | C29 | A31 | B8 | C29 | A31 | B9 | C29 | A31 | B10 | C29 | A31 | B12 | C29 | A31 | B18 | C29 | A31 | B22 | C29 | A31 | B23 | C29 | A31 | B25 | C29 |
| A31 | B6 | C30 | A31 | B7 | C30 | A31 | B8 | C30 | A31 | B9 | C30 | A31 | B10 | C30 | A31 | B12 | C30 | A31 | B18 | C30 | A31 | B22 | C30 | A31 | B23 | C30 | A31 | B25 | C30 |
| A31 | B6 | C31 | A31 | B7 | C31 | A31 | B8 | C31 | A31 | B9 | C31 | A31 | B10 | C31 | A31 | B12 | C31 | A31 | B18 | C31 | A31 | B22 | C31 | A31 | B23 | C31 | A31 | B25 | C31 |
| A31 | B6 | C32 | A31 | B7 | C32 | A31 | B8 | C32 | A31 | B9 | C32 | A31 | B10 | C32 | A31 | B12 | C32 | A31 | B18 | C32 | A31 | B22 | C32 | A31 | B23 | C32 | A31 | B25 | C32 |
| A31 | B6 | C33 | A31 | B7 | C33 | A31 | B8 | C33 | A31 | B9 | C33 | A31 | B10 | C33 | A31 | B12 | C33 | A31 | B18 | C33 | A31 | B22 | C33 | A31 | B23 | C33 | A31 | B25 | C33 |
| A31 | B6 | C34 | A31 | B7 | C34 | A31 | B8 | C34 | A31 | B9 | C34 | A31 | B10 | C34 | A31 | B12 | C34 | A31 | B18 | C34 | A31 | B22 | C34 | A31 | B23 | C34 | A31 | B25 | C34 |
| A31 | B6 | C35 | A31 | B7 | C35 | A31 | B8 | C35 | A31 | B9 | C35 | A31 | B10 | C35 | A31 | B12 | C35 | A31 | B18 | C35 | A31 | B22 | C35 | A31 | B23 | C35 | A31 | B25 | C35 |
| A31 | B6 | C36 | A31 | B7 | C36 | A31 | B8 | C36 | A31 | B9 | C36 | A31 | B10 | C36 | A31 | B12 | C36 | A31 | B18 | C36 | A31 | B22 | C36 | A31 | B23 | C36 | A31 | B25 | C36 |
| A31 | B6 | C37 | A31 | B7 | C37 | A31 | B8 | C37 | A31 | B9 | C37 | A31 | B10 | C37 | A31 | B12 | C37 | A31 | B18 | C37 | A31 | B22 | C37 | A31 | B23 | C37 | A31 | B25 | C37 |
| A31 | B6 | C38 | A31 | B7 | C38 | A31 | B8 | C38 | A31 | B9 | C38 | A31 | B10 | C38 | A31 | B12 | C38 | A31 | B18 | C38 | A31 | B22 | C38 | A31 | B23 | C38 | A31 | B25 | C38 |
| A31 | B6 | C39 | A31 | B7 | C39 | A31 | B8 | C39 | A31 | B9 | C39 | A31 | B10 | C39 | A31 | B12 | C39 | A31 | B18 | C39 | A31 | B22 | C39 | A31 | B23 | C39 | A31 | B25 | C39 |
| A31 | B6 | C40 | A31 | B7 | C40 | A31 | B8 | C40 | A31 | B9 | C40 | A31 | B10 | C40 | A31 | B12 | C40 | A31 | B18 | C40 | A31 | B22 | C40 | A31 | B23 | C40 | A31 | B25 | C40 |
| A31 | B6 | C41 | A31 | B7 | C41 | A31 | B8 | C41 | A31 | B9 | C41 | A31 | B10 | C41 | A31 | B12 | C41 | A31 | B18 | C41 | A31 | B22 | C41 | A31 | B23 | C41 | A31 | B25 | C41 |

or the pharmaceutically acceptable salts, solvates, tautomers or prodrugs of any of the above compounds.

Even more preferred embodiments of the compounds of the present invention are directed to the compounds of formula (Ia) below, postulated to preferably possess Cathepsin K activity:

(Ia)

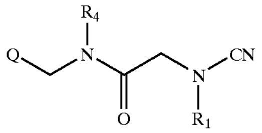

wherein:

$R_1$ is selected from the following groups:

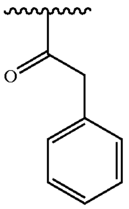
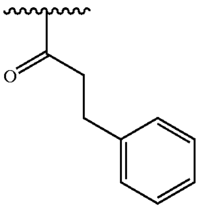
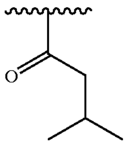

and

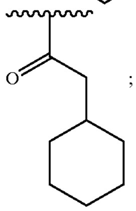

;

$R_4$ is selected from the following groups:

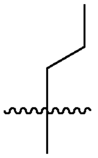
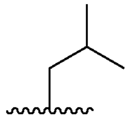

and

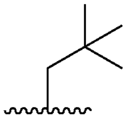

;

and Q is selected from the following groups:

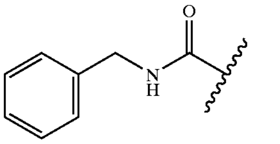
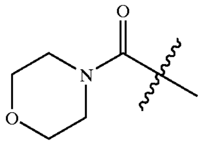

and

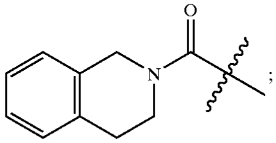

;

or the pharmaceutically acceptable salts, solvates, tautomers or prodrugs thereof.

The compounds described above can be synthesized by the General schemes and methods described in the experimental section of this document and analogous methods known to those skilled in the art without undue experimentation.

GENERAL SYNTHETIC METHODS

The invention also provides processes of making the present novel compounds. Compounds of the invention may be prepared by methods described below. In the following schemes, the variables $R_1$, $R_2$, $R_3$, $R_4$, $R_5$, $R_6$ and Q are as defined previously for the compounds of formula (I) except where indicated. Intermediates used in the preparation of the compounds of the invention are either commercially available or readily prepared by methods known to those skilled in the art.

I

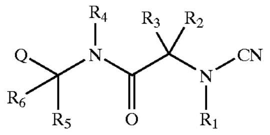

The synthesis of the compounds of formula (I) may be carried out as illustrated in the following Scheme I:

Scheme I

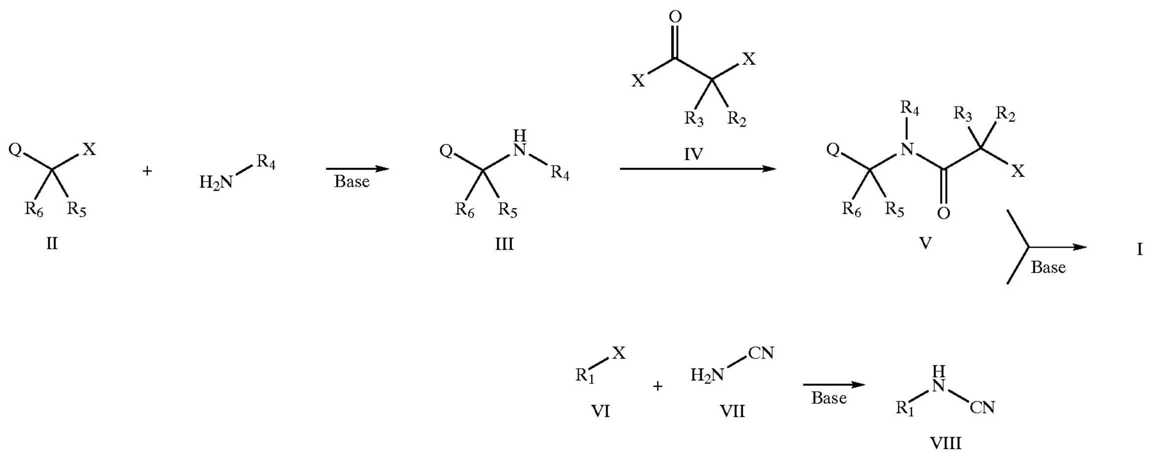

As shown in Scheme I, an amine bearing $R_4$ is reacted with II, where X is a suitable leaving group such as a halogen, mesylate, triflate or tosylate, in a suitable solvent such as THF. The reaction may be done in the presence of a suitable base such as triethylamine, or alternatively in the presence of excess $R_4NH_2$. Intermediate III is then reacted with IV, where X is defined as above, in a suitable solvent such as THF, optionally in the presence of a suitable base such as triethylamine, to provide V. Intermediate V is reacted with cyanamide VIII in a suitable solvent such as DMF, in the presence of a suitable base such as potassium t-butoxide to give the desired compound of formula I. Intermediate VIII may be prepared by reacting $R_1X$, where X is defined as above with cyanamide (VII) in a suitable solvent such as acetone, in the presence of a suitable base, for example aqueous sodium hydroxide. Intermediates II, $R_4$ $NH_2$, IV, and VI are either commercially available or easily prepared by methods described in the literature and known to those skilled in the art.

An alternate synthesis of intermediate III is illustrated in the following Scheme II:

Scheme II

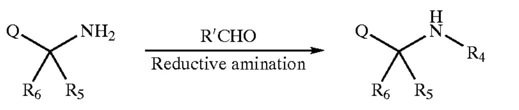

IX

III $R_4$ = R'$CH_2$

In this method an amine bearing Q, $R_5$, and $R_6$ (IX) is reacted with an aldehyde (R'CHO) under reductive amination conditions to provide an intermediate III in which $R_4$=R'$CH_2$. This method is therefore useful to prepare intermediates of formula III as shown in Scheme I wherein the $R_4$ group is selected from an $R_4$ group as defined previously having a —$CH_2$— group bonded to the nitrogen atom in the backbone of formula (III), and R' is that terminal portion of that $R_4$ group which is bonded to said —$CH_2$— group which, in turn, is bonded to the nitrogen atom in the backbone of formula (III).

Compounds of formula I may also be prepared as described in the following Scheme III:

Scheme III

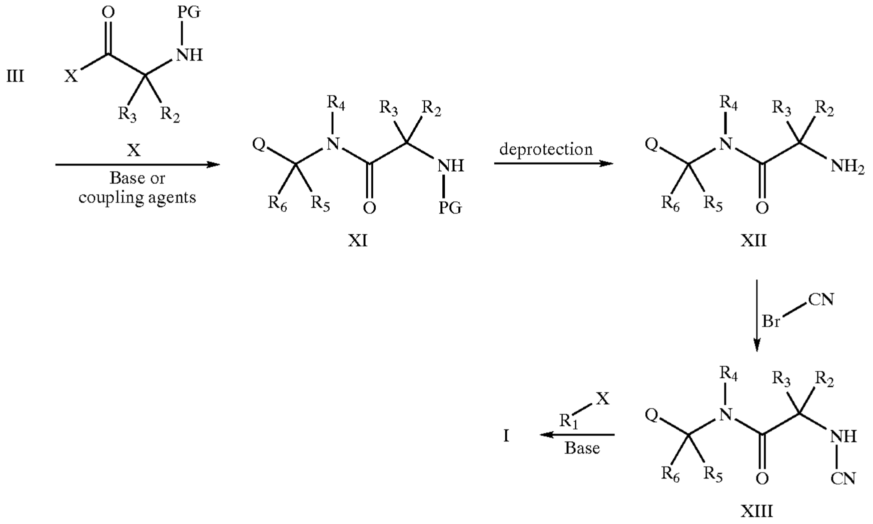

In this method, intermediate III (Scheme I or Scheme II) is reacted with intermediate X, where PG is a suitable protecting group such as a t-butoxycarbonyl (Boc) group, and substituent X is defined as above, in a suitable solvent such as THF and optionally in the presence of a suitable base, such as triethylamine, or a suitable coupling agent, such as EDC to provide XI. Deprotection of XI by standard methods that depend on the group PG used provides XII. Reaction of XII with cyanogen bromide, optionally in the presence of a suitable base such as triethylamine, provides XIII. Reaction of XIII with $R_1$ bearing a leaving group X defined as above, in the presence of a suitable base such as potassium t-butoxide provides the desired compound of formula I.

In order for this invention to be more fully understood, the following examples are set forth. These examples are for the purpose of illustrating embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

SYNTHETIC EXAMPLES

Example 1

N-cyano-N-{[isobutyl-(2-morpholin-4-yl-2-oxo-ethyl)-carbamoyl]-methyl}-2-phenyl-acetamide

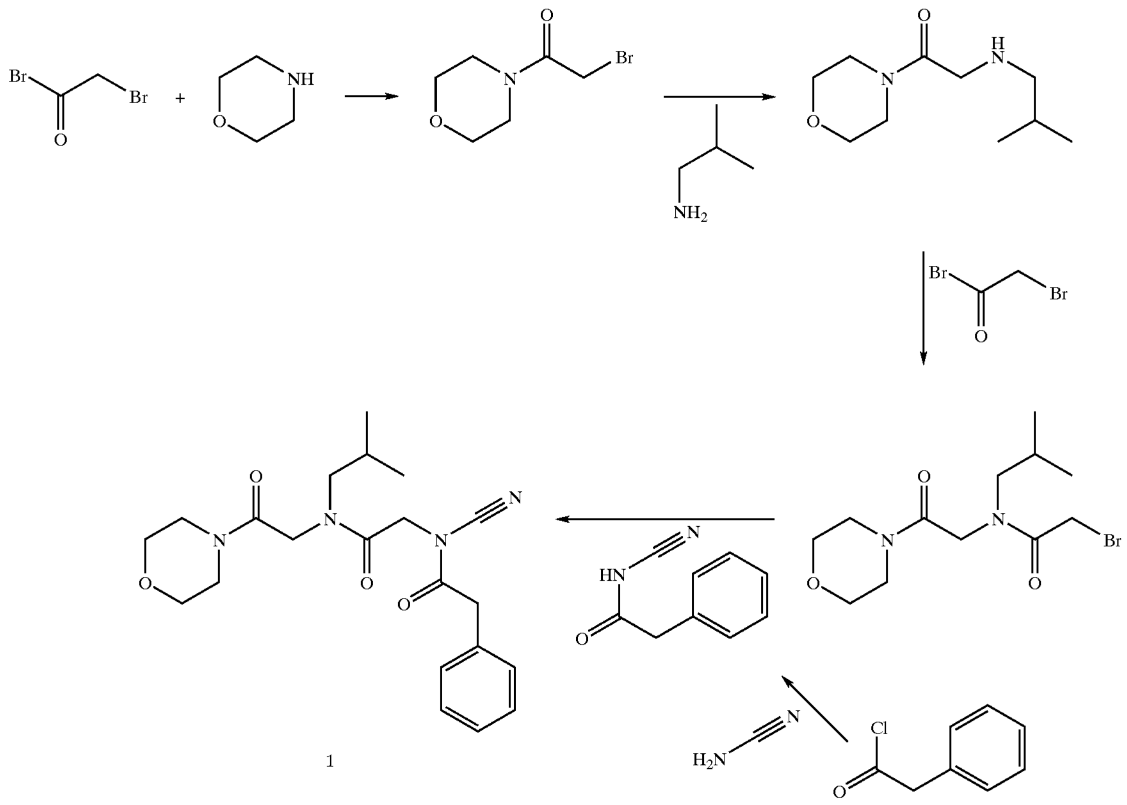

1

Bromoacetyl bromide (6.0 mL, 68.9 mmol) was dissolved in 30 mL of ether. Morpholine (7.0 mL, 80.3 mmol) was added dropwise to the above solution at −78° C. The reaction mixture was warmed to room temperature in 30 min. The resulting white solid was removed by filtration and washed with ether. The filtrate was washed with saturated sodium bicarbonate (20 mL×2). The combined aqueous phase was extracted with ether (20 mL×4). The combined organic extracts were washed with brine and dried over sodium sulfate. The solvent was removed in vacuo to give N-bromoacetyl-morpholine (3.73 g, 45%) as a clear oil.

N-Bromoacetyl-morpholine (3.73 g, 18 mmol) was dissolved in 20 mL of THF. Isobutylamine (5.40 mL, 54.0 mmol) was added. The reaction mixture was stirred at room temperature for 24 h. Solvent and excess reagent were removed in vacuo. The residue was treated with ether. The resulting solid was removed by filtration and washed with ether. The filtrate was concentrated under reduced pressure to give 2-isobutylamino-1-morpholin-4-yl-ethanone (1.43 g, 40%) as a clear oil.

2-Isobutylamino-1 -morpholin-4-yl-ethanone (1.43 g, 7.13 mmol) was dissolved in 15 mL of THF. To this solution at −78° C. was added a solution of bromoacetyl bromide (1.24 mL, 14.3 mmol) in 15 mL of THF. The mixture was warmed to room temperature and stirred for 2 h. Solvent was removed in vacuo. The residue was dissolved in 30 mL of methylene chloride, washed with saturated sodium bicarbonate, and brine, then dried over sodium sulfate. The solvent was removed in vacuo and the residue was purified by silica gel flash chromatography eluting with 2% MeOH in methylene chloride to give 2-bromo-N-isobutyl-N-(2-morpholin-4-yl-2-oxo-ethyl)-acetamide (1.37 g, 60%) as a clear oil.

Cyanamide (5.04 g, 120 mmol) was dissolved in 40 mL of 40% sodium hydroxide. To this solution at 0° C., phenylacetyl chloride (3.97 mL, 30 mmol) in 30 mL of acetone was added over 1 h. After stirring at room temperature for 2 h, the reaction mixture as acidified with concentrated HCl to pH 2. Acetone was removed in vacuo. The resulting suspension was extracted with methylene chloride (30 mL×4). The combined organic extracts were washed with brine and dried over magnesium sulfate. Solvent was removed in vacuo to give N-cyano-2-phenylacetamide (3.96 g, 82%) as a yellow oil.

N-Cyano-2-phenylacetamide (160 mg, 1.00 mmol) was dissolved in 5 mL of dry DMF. Potassium t-butoxide (112 mg, 1.00 mmol) was added. This mixture was stirred at room temperature for 30 min. The 2-bromo-N-isobutyl-N-(2-morpholin-4-yl-2-oxo-ethyl)-acetamide (321 mg, 1.00 mmol) from above was dissolved in 5 mL of dry DMF and added to the reaction mixture. The reaction mixture was stirred at room temperature for 2 h and then heated at 70° C. for 6 h. Solvent was removed in vacuo and residue was purified by HPLC to give the title compound (87 mg, 22%) as a clear oil.

Example 2

Synthesis of N-({[2-(3,4-dihydro-1H-isoquinolin-2-yl)-2-oxo-ethyl]-isobutyl-carbamoyl}-methyl)-N-cyano-2-phenyl-acetamide

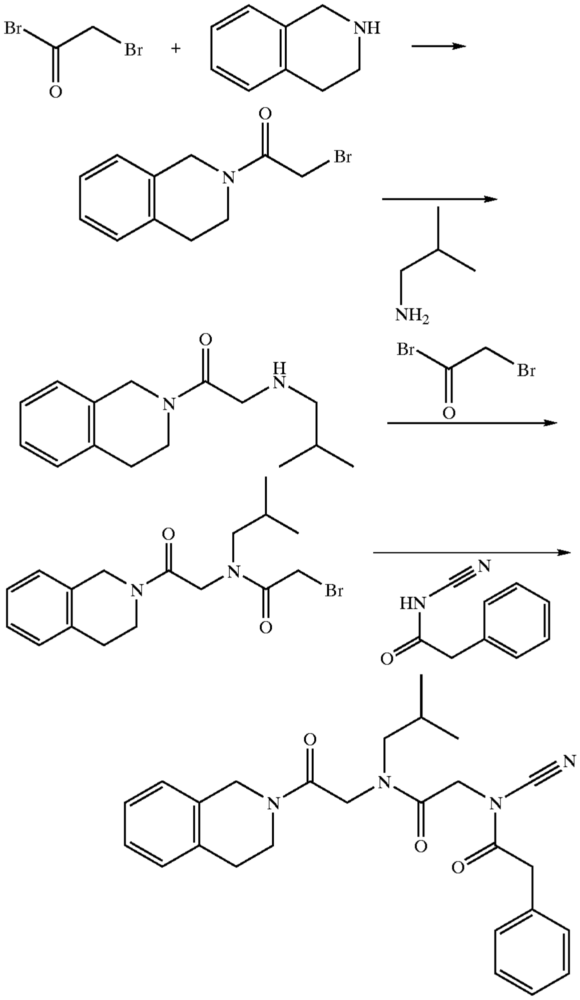

2

To a stirred solution of bromoacetyl bromide (0.57 mL, 6.4 mmol) in THF (4.0 mL) was added 1,2,3,4-tetrahydroisoquinoline (1.0 g, 7.5 mmol) at −78° C., under argon. Upon complete addition, the cooling bath was removed and the reaction mixture was stirred at ambient temperature for 1 h. After this time, the precipitated solids were removed via filtration and washed with EtOAc. The combined filtrates were washed with saturated $NaHCO_3$ (2×), then once with brine. Concentration of the organic phase gave an orange oil which was used without further purification.

To a stirred solution of the above intermediate in THF (4.0 mL) was added isobutylamine (2.0 mL, 20.1 mmol) at room temperature. After 0.5 h the reaction was poured into saturated $NaHCO_3$ and EtOAc. The layers were separated and the organic phase was concentrated to give the crude product. Purification by silica gel flash chromatography, eluting with 0–5% MeOH/EtOAc, 30 mL/min, gave 0.45 g (25%) of 1-(3,4-dihydro-1H-isoquinolin-2-yl)-2-isobutylamino-ethanone.

To a stirred solution of 1-(3,4-dihydro-1H-isoquinolin-2-yl)-2-isobutylamino-ethanone (0.45 g, 1.8 mmol) in THF (4.0 mL), a solution of bromoacetyl bromide (0.32 mL, 3.6 mmol) in 4.0 mL THF was added dropwise at −78° C., under argon. After 3 h (the temperature gradually rose to 10° C.) the reaction was concentrated and the remaining residue was diluted with methylene chloride and saturated $NaHCO_3$. The layers were separated and the organic phase was washed with brine and then dried ($MgSO_4$). Filtration and concentration gave the crude product which was purified via silica gel flash chromatography (0–5% MeOH/methylene chloride, 30 mL/min.) to give 0.34 g (51%) of 2-bromo-N-[2-(3,4-dihydro-1H-isoquinolin-2-yl)-2-oxo-ethyl]-N-isobutyl-acetamide.

To a stirred solution of N-cyano-2-phenyl-acetamide (0.15 g, 0.9 mmol) (see Example 1) in DMF (5.0 mL), potassium tert-butoxide (0.9 mL of a 1.0 M THF solution, 0.9 mmol) was added dropwise at 0° C., under argon. The resulting mixture was stirred at 0° C. for 20 min, then at ambient temperature for 15 min. After this time, the resulting anion was added dropwise to a stirred solution of the 2-bromo-N-[2-(3,4-dihydro-1H-isoquinolin-2-yl)-2-oxo-ethyl]-N-isobutyl-acetamide (0.34 g, 0.9 mmol) from above in DMF (5.0 mL) at room temperature, under argon. Upon complete addition, the reaction was stirred at room temperature for 1.5 h, then warmed to 40° C. for 6 h. The reaction was cooled to room temperature and stirred for 48 h after which time it was concentrated to dryness. The resulting residue was dissolved in EtOAc and washed with 5% citric acid (aqueous). The layers were separated and the aqueous phase was extracted with EtOAc (2×). The combined organics were dried ($MgSO_4$), filtered and concentrated to give the crude product which was purified via reverse phase HPLC (C18 column, 20–100% $CH_3CN/H_2O$ over 20 min at a flow rate of 20 mL/min, UV detection was at 220 nm). Retention time of the product was 16 min. Product-containing fractions were concentrated to give 49 mg (12%) of the title compound.

Example 3

Synthesis of N-{[(2,2-dimethyl-propyl)-(2-morpholin-4-yl-2-oxo-ethyl)-carbamoyl]-methyl}-N-cyano-2-phenyl-acetamide

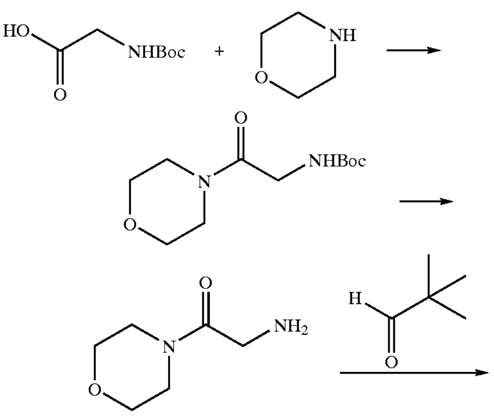

-continued

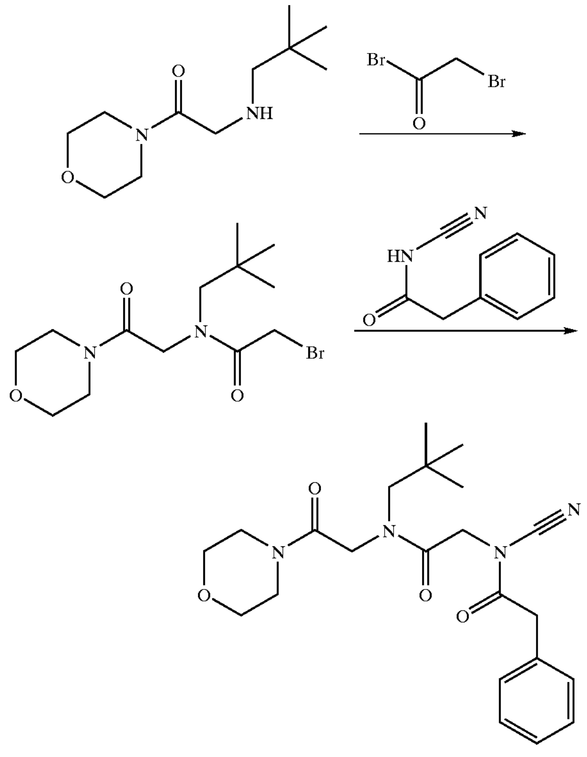

3

To a stirred solution of N-(tert-butoxycarbonyl)glycine (3.0 g, 17.1 mmol) in DMF (75 mL), N,N-diisopropylethylamine (14.9 mL, 85.5 mmol) was added, followed by EDC (3.6 g, 18.8 mmol) and HOBT (2.5 g, 18.8 mmol) at 0° C., under argon. The resulting mixture was stirred for 0.5 h after which time morpholine (3.0 mL, 34.2 mmol) was introduced in a dropwise manner. Upon complete addition, the reaction was warmed to ambient temperature, stirred overnight and concentrated. The resulting residue was diluted with EtOAc and saturated $NaHCO_3$. The layers were separated and the aqueous phase was extracted with EtOAc. The combined organics were dried (MgSO4), filtered and concentrated to give 2.3 g (55%) of (2-morpholin-4-yl-2-oxo-ethyl)-carbamic acid tert-butyl ester which was used without further purification.

To a stirred solution of the above (2-morpholin-4-yl-2-oxo-ethyl)-carbamic acid tert-butyl ester (0.44 g, 1.8 mmol) in 1,4-dioxane (4.0 mL), HCl (4.0 mL of a 4 M solution in 1,4-dioxane) was added at room temperature. After one h, the precipitated product was collected via filtration and washed with EtOAc. The solid was dried under high vacuum to give 0.23 g (76%) of 2-amino-1-morpholin-4-yl-ethanone hydrochloride which was used without further purification.

To a stirred solution of the above 2-amino-1-morpholin-4-yl-ethanone hydrochloride (0.23 g, 1.3 mmol) in methylene chloride (4.0 mL) and triethylamine (0.19 mL, 1.4 mmol), 4 angstrom sieves (10 beads, pulverized to a powder) were added, followed by trimethylacetaldehyde (0.35 mL, 3.3 mmol) at room temperature, under argon. The resulting mixture was stirred at room temperature overnight after which time sodium triacetoxyborohydride (0.54 g, 2.6 mmol) was added. After 6 h, the solids were removed via filtration and washed with methylene chloride. The combined filtrates were concentrated and the remaining residue was diluted with EtOAc and water. The aqueous phase was lyophilized to give a white solid that was diluted with EtOAc. The solids were removed via filtration and washed with EtOAc. The combined organics were concentrated to give the crude product which was purified via silica gel flash chromatography eluting with 100% EtOAc, then 0.5% $NH_4OH$/10% MeOH/EtOAc, flow rate 30 mL/min. The product-containing fractions were concentrated to give 0.18 g (67%) of 2-(2,2-dimethyl-propylamino)-1-morpholin-4yl-ethanone.

To a stirred solution of the above 2-(2,2-dimethyl-propylamino)-1-morpholin-4-yl-ethanone (0.18 g, 0.8 mmol) in THF (2.0 mL), a solution of bromoacetyl bromide (0.15 mL, 1.6mmol) in THF (2.0 mL) was added, dropwise at −78° C., under nitrogen. After 3 h the reaction was concentrated and the resulting residue was diluted with methylene chloride and saturated $NaHCO_3$. The layers were separated and the aqueous phase was extracted with methylene chloride. The combined organic layers were dried ($MgSO_4$), filtered and concentrated to give the crude product. Purification via silica gel flash chromatography, eluting with EtOAc, flow rate 30 mL/min, gave 0.10 g (36%) of 2-bromo-N-(2,2-dimethyl-propyl)-N-(2-morpholin-4-yl-2-oxo-ethyl)-acetamide.

To a stirred solution of N-cyano-2-phenyl-acetamide (35 mg, 0.2 mmol) (see Example 1) in DMF (1.25 mL), potassium tert-butoxide (0.22 mL of a 1.0 M THF solution, 0.22 mmol) was added, dropwise at 0° C., under nitrogen. Upon complete addition, the cooling bath was removed and the reaction was stirred for 0.5 h. After this time, the resulting anion was added dropwise to a stirred solution of the above 2-bromo-N-(2,2-dimethyl-propyl)-N-(2-morpholin-4-yl-2-oxo-ethyl)-acetamide (88 mg, 0.24 mmol) in DMF (1.25 mL) at room temperature, under nitrogen. Upon complete addition, the reaction was stirred at room temperature for 0.5 h, then warmed to 45° C. for 15 h. The reaction was cooled to room temperature and concentrated to dryness. The remaining residue was dissolved in EtOAc and washed with 5% citric acid (aqueous). The layers were separated and the aqueous phase was extracted with EtOAc (2×). The combined organics were dried ($MgSO_4$), filtered and concentrated to give the crude product which was purified via reverse phase HPLC (C18 column, 20–100% $CH_3CN/H_2O$ over 20 min at a flow rate of 20 mL/minute, UV detection was at 220 nm). Retention time of the product was 14.7 min. Product-containing fractions were concentrated to give 14 mg (15%) of the title compound.

The following compounds were also made by methods analogous to those described in Examples 1–3:

| Example | Structure | Name |
|---|---|---|
| 4 | 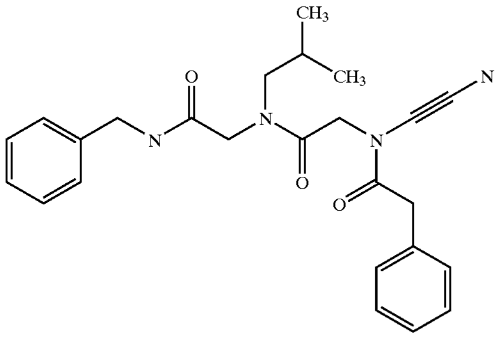 | N-{[(Benzylcarbamoyl-methyl)-isobutyl-carbamoyl]-methyl}-N-cyano-2-phenyl-acetamide |
| 5 | 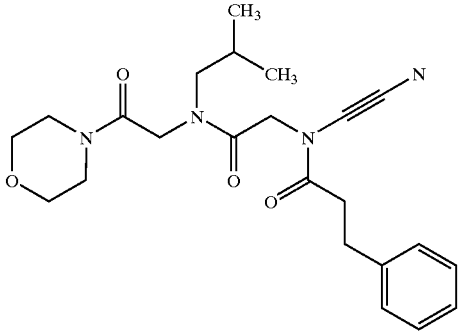 | N-{[Isobutyl-(2-morpholin-4-yl-2-oxo-ethyl)-carbamoyl]-methyl}-N-cyano-3-phenyl-propionamide |
| 6 | 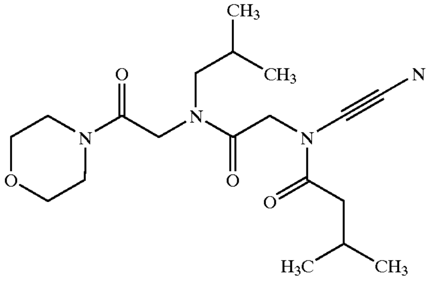 | N-{[Isobutyl-(2-morpholin-4-yl-2-oxo-ethyl)-carbamoyl]-methyl}-3-methyl-N-cyano-butyramide |
| 7 | 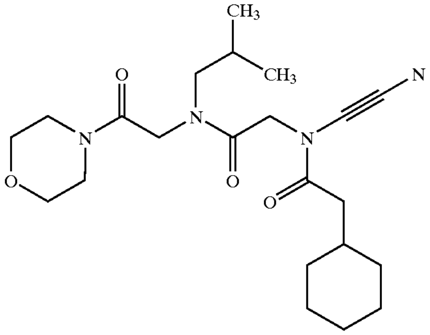 | 2-Cyclohexyl-N-{[isobutyl-(2-morpholin-4-yl-2-oxo-ethyl)-carbamoyl]-methyl}-N-cyano-acetamide |

-continued

| Example | Structure | Name |
|---|---|---|
| 8 | 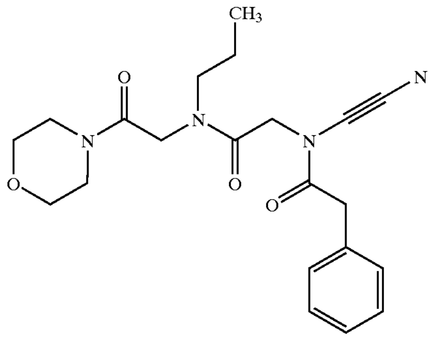 | N-Cyano-N-{[(2-morpholin-4-yl-2-oxo-ethyl)-propyl-carbamoyl]-methyl}-2-phenyl-acetamide |

METHODS OF THERAPEUTIC USE

The compounds of the invention are useful in inhibiting the activity of cysteine proteases, such as cathepsins S, K, F, L and B. In doing so, these compounds-are useful in blocking disease processes mediated by these cysteine proteases. Accordingly, the compounds of the present invention are useful in treating cysteine protease mediated disease states, i.e., those diseases in which cysteine protease activity contributes to the pathology and/or symptomatology of the disease. A variety of such cysteine protease mediated disease states are known in the art and are disclosed, for example, in the references cited in the "Background of the Invention" section above.

Compounds of this invention effectively block degradation of the invariant chain to CLIP by cathepsin S, and thus inhibit antigen presentation and antigen-specific immune responses. Control of antigen specific immune responses is an attractive means for treating autoimmune diseases and other undesirable T-cell mediated immune responses. Thus, there is provided methods of treatment using the compounds of this invention for such conditions. These encompass autoimmune diseases and other diseases involving inappropriate antigen specific immune responses including, but not limited to, rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, endometriosis, glomerulonephritis, atopic dermatitis, insulin-dependent diabetes mellitus and asthma. The compounds of the invention can also be used to treat other disorders associated with extracellular proteolysis such as Alzheimer's disease and atherosclerosis. The compounds of the invention can also be used to treat other disorders associated with inappropriate autoimmune responses, T-cell mediated immune responses, or extracellular proteolysis mediated by cathepsin S, unrelated to those listed above or discussed in the Background of the Invention. Therefore, the invention also provides methods of modulating an autoimmune disease comprising administering to a patient in need of such treatment a pharmaceutically effect amount of a compound according to the invention.

Accordingly, in one embodiment the present invention is directed to a method of treating a disease mediated by cathepsin S comprising adminstering to a patient in need of such treatment a therapeutically effective amount of a compound according to claim 1, or a pharmaceutically acceptable salt, solvate, tautomer or prodrug thereof. Examples of diseases mediated by cathepsin S that may be treated include: autoimmune diseases (such as rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, atopic dermatitis and insulin-dependent diabetes mellitus); Alzheimer's disease, atherosclerosis, endometriosis and asthma.

Compounds of the invention also inhibit cathepsin K. In doing so, they may block bone resorption, bone loss and inappropriate degradation of bone collagen and other bone matrix proteases. Thus, there is provided a method for treating diseases characterized by bone resporption, bone loss or excessive cartilage or bone matrix degradation such as osteoporosis, Paget's disease, Gaucher disease, gingivitis, periodontitis, and rheumatoid arthritis, or diseases characterized by increases in bone resporption and demineralization of bone. In view of their Cathepsin K inhibitory activity, the compounds of the invention may also be useful for treating disorders associated with excessive elastin degradation such as lymphangiomyomatosis, vascular inflammation, and cardiovascular diseases such as atherosclerosis. Inhibition of cathepsins F, L, and B are also within the scope of the invention due to similarity of the active sites in cysteine proteases as described above.

Accordingly, in another embodiment the present invention is directed to a method of treating a disease mediated by cathepsin K comprising adminstering to a patient in need of such treatment a therapeutically effective amount of a compound according to claim 1, or a pharmaceutically acceptable salt, solvate, tautomer or prodrug thereof. Examples of diseases mediated by cathepsin K that may be treated include: a disease characterized by bone resporption, bone loss or excessive cartilage or bone matrix degradation, such as osteoporosis, Paget's disease, Gaucher disease, gingivitis, periodontitis, and rheumatoid arthritis, or diseases characterized by increases in bone resporption and demineralization of bone, such as those associated with many cancers and with bone metastases of breast and prostate tumors, or disorders associated with excessive elastin degradation such as lymphangiomyomatosis, vascular inflammation, and cardiovascular diseases such as atherosclerosis.

In addition, the compounds according to the invention can be used for the treatment of any other specific disease-state or condition not specifically mentioned above which have been treated, are being treated or will in the future be treated with compounds that are inhibitors of cathepsins S, K, F, L or B.

The activity of particular compounds disclosed herein against the various cathepsins, for example, cathepsin S and K, may be determined without undue experimentation by one of ordinary skill in the art in view of the knowledge in the art, the guidance provided throughout this specification and by the screens described in the section below entitled "ASSESMENT OF BIOLOGICAL PROPERTIES."

In general, it is expected that compounds within formula (I) having less bulky groups at the $R_4$ position would be more active as inhibitors of cathepsin K, for example, compounds where $R_4$=B3 to B6 or B11 from the above Table I. On the other hand, it is expected in general that compounds within formula (I) having bulkier groups at the $R_4$ position would be more active as inhibitors of cathepsin S, for example, where $R_4$=B7 to B10, B12, B18 or B22 to B26 from the above Table I. In particular, Examples 1 to 8 set forth above have been tested and have demonstrated cathepsin S and/or K inhibitory activity in one or more of the screens described below. Specifically, Examples 1 to 8 were tested for and demonstrated cathepsin K inhibitory activity and Examples 1–3 and 5–8 were tested for and demonstrated inhibitory activity against cathepsin S.

For therapeutic use, the compounds of the invention may be administered in any conventional dosage form in any conventional manner to a patient, e.g. a mammal, in need of such treatment. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, pharmaceutical dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician. Some degree of routine dose optimization may be required to determine an optimal dosing level and pattern.

ASSESSMENT OF BIOLOGICAL PROPERTIES

Expression and Purification of Recombinant Human Cathepsin S

Expression and Purification of recombinant human Cathepsin S may be done as described in U.S. Pat. No. 6,313,117, which is herein incorporated by reference.

Inhibition of Cathepsin S

Human recombinant cathepsin S expressed in Baculovirus is used at a final concentration of 10 nM in buffer. Buffer is 50 mM sodium acetate, pH 6.5, 2.5 mM EDTA, 2.5 mM TCEP. Enzyme is incubated with either compound or DMSO for 10 min at 37° C. Substrate 7-amino-4-methylcoumarin, CBZ-L-valyl-L-valyl-L-arginineamide (custom synthesis by Molecular Probes) is diluted to 20 uM in water (final concentration of 5 uM), added to assay and incubated for additional 10 minutes at 37° C. Compound activity is measured by diminished fluorescence compared to DMSO control when read at 360 nm excitation and 460 nm emission.

Another assay for Cathepsin S inhibitory activity is the cell based assay described in Riese, R. J. et al., Immunity, 1996, 4, 357–366, incorporated herein by reference.

Preferred compounds for the inhibition of Cathepsin S are those that will exhibit an $IC_{50}$ of 10 micromolar or below in the above assays.

Inhibition of Cathepsin K, F, L and B:

Inhibition of these enzymes by particular compounds of the invention may be determined without undue experimentation by using methods as provided in the references cited hereinbelow each of which is incorporated herein by reference:

1. S. K. Lee, S. R. Goldring, and J. A. Lorenzo. (1995) Endocrinology 136: 4572.
2. N. Takahashi et al. (1988) Endocrinology 122: 1373.
3. N. Takahashi et al. (1988) Endocrinology 123:1504.
4. T. Akatsu et al. (1992) J. Bone Miner. Res. 7: 1297.
5. T. Akatsu et al. (1989) J. Bone Miner. Res. 4: 29.
6. T. Shuto et al. (1994) Endocrinology 134:1121.
7. A. Boyde, N. N. Ali, and S. J. Jones. (1984) Br. Dent. J. 156: 216.
8. D. W. Dempster et al. (1987) J. Bone Miner. Res. 2: 443.
9. R. J. Murrills et al. (1989) J. Bone Miner. Res. 4: 259.
10. N. T. Foged et al. (1996) J. Bone Miner. Res. I1: 226.

A Cathepsin K bone resporption cellular assay can be carried out as follows:

In vitro culturing of murine osteoclasts can be accomplished by a modification of previous published protocols (1–6). Briefly, tibiae and femur are removed from 6–10 week-old C57BL/6 male mice. Marrow is flushed from the bones and placed into MEM-alpha media (Gibco) supplemented with 10% FCS (Gibco). After washing, 100 mm tissue culture dishes is seeded at $1\times10^6$ cells/$cm^2$ (at $2\times10^6$cells/mL) and supplemented with 10 nM 1,25- dihydroxyvitamin D3 (Sigma) and cultured at 37° C. and 5% $CO_2$. Cultures are fed every 3 days by removing 80% of the media and replacement with fresh media and vitamin $D_3$. In vitro bone resorption assays can be carried out similar to those previously described (1, 7–9) with modifications: After 7 days in culture, osteoclasts are trypsinized and scraped off 100 mm dishes and split into 96 well plates containing bovine cortical bone slices. After 2 hours at 37° C., non-adherent cells are removed by washing and MEM-alpha media containing 0.7 g sodium bicarbonate/liter is added to the wells and media is supplemented with 100 ng/mL sRANKL (R&D Systems). After 3–4 days, supernatants are removed and analyzed for the presence of C-terminal peptides from type I collagen using a one-step ELISA (Osteometer Biotech) originally described by Foged et al. (10).

Preferred compounds for the inhibition of Cathepsin K are those that will exhibit an $IC_{50}$ of 50 micromolar or below in the above cellular assay.

A Cathepsin K enzymatic assay is disclosed in the following reference:

Bromme, D., Okamoto, K., Wang, B. B., and Biroc, S. (1996) J. Biol. Chem. 271, 2126–2132.

Preferred compounds for the inhibition of Cathepsin K are those that will exhibit an $IC_{50}$ of 10 micromolar or below in the above enzymatic assay.

Cathepsins B and L assays are to be found in the following reference:

Methods in Enzymology, Vol. 244, Proteolytic Enzymes: Serine and Cysteine Peptidases, Alan J. Barrett, ed.

Cathepsin F assays are to be found in the following references:

Wang, B., Shi, G. P., Yao, P. M., Li, Z., Chapman, H. A., and Bromme, D. (1998) J. Biol. Chem. 273, 32000–32008.

Santamaria, I., Velasco, G., Pendas, A. M., Paz, A., and Lopez-Otin, C (1999) J. Biol. Chem. 274, 13800–13809.

Preferred compounds for the inhibition of Cathepsins B, L and F are those that will Is exhibit an $IC_{50}$ of 10 micromolar or below in the above assays.

We claim:

1. A compound of formula (I):

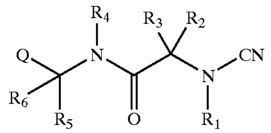

(I)

wherein:

$R_1$ is hydrogen, a C1–10 saturated or unsaturated alkyl group wherein one or more C atoms are optionally replaced by O, NH, S(O), $S(O)_2$ or S and wherein said alkyl group is optionally independently substituted with one or more: oxo groups, —$NH_2$, C1–10 alkyl, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, pyrrolyl, pyrazolyl, oxazolyl, isoxazolyl, thiazolyl, imidazolyl pyridinyl, pyrimidinyl, pyrazinyl, indolyl, benzofuranyl, benzothienyl, benzimidazolyl, benzothiazolyl, benzoxazolyl, quinolyl, isoquinolyl, C1–10 alkoxy, aryloxy, C1–10 alkanoyl, aroyl, C1–10 alkoxycarbonyl, aryloxycarbonyl, C1–10 alkanoyloxy, or aroyloxy, or $R_1$ is C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, arylsulfonyl, heteroarylsulfonyl, tetrahydronaphthyl, indenyl, indanyl, tetrahydropyranyl, tetrahydrothiopyranyl, tetrahydrofuranyl, pyrrolidinyl, piperidinyl, morpholinyl, thiomorpholinyl, indolinyl, C3–8cycloalkylsulfonylC1–5alkyl, arylsulfonylC1–5alkyl, aryloxyC1–5alkyl, C1–10alkanoyl, aroyl, C1–10alkoxycarbonyl, arylC1–5alkoxycarbonyl or aryloxycarbonyl, or $R_1$ is carbamoyl wherein the nitrogen atom may be independently mono or di-substituted by C1–10 alkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

each $R_1$ may be further optionally independently substituted by one or more $R_a$;

$R_a$ is a C1–10 saturated or unsaturated alkyl group wherein one or more C atoms are optionally replaced by O, NH, S(O), $S(O)_2$ or S and wherein said alkyl group is optionally independently substituted with one or two oxo groups, or one or more: —$NH_2$, C1–10 alkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_a$ is a C1–10alkoxy, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, C3–8 cycloalkyloxy, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl; C1–10alkanoyl, aroyl, C1–10alkanoyloxy, aryloxy, benzyloxy, C1–10 alkoxycarbonyl, arylC1–3alkoxycarbonyl, aryloxycarbonyl or aroyloxy, or $R_a$ is carbamoyl wherein the nitrogen atom may be independently mono or di-substituted by C1–10 alkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_a$ is ureido wherein either nitrogen atom may be independently substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_a$ is amino wherein the nitrogen atom may be independently mono or di-substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

wherein $R_a$ may be further optionally substituted by one or more $R_b$;

$R_b$ is C3–8 cycloalkyl, tolylsulfonyl, C1–5 alkoxy, aryl, aryloxy, benzyloxy, halogen, hydroxy, oxo, carboxy, cyano, nitro, carboxamide, amidino or guanidino;

or $R_b$ is aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_b$ is amino wherein the nitrogen atom may be independently mono or di-substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_b$ is a C1–10 saturated or unsaturated alkyl group wherein one or more C atoms are optionally replaced by O, NH, S(O), $S(O)_2$ or S and wherein said alkyl group is optionally independently substituted with one or two oxo groups, or one or more: $—NH_2$, C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

$R_2$, $R_3$, $R_5$, and $R_6$ independently are hydrogen, or a C1–5 alkyl group;

$R_2$ and $R_3$ together with the carbon to which they are attached, and/or $R_5$ and $R_6$ together with the carbon to which they are attached, each may independently optionally form a nonaromatic 3–6 membered cycloalkyl;

$R_4$ is hydrogen, C2–10alkenyl, C3–8 cycloalkyl, arylC1–10alkyl, aryl or a C1–10 alkyl group wherein one or more of the C atoms are optionally replaced by O, NH, —C(═O)—, S, S(O) or $S(O)_2$; wherein $R_4$ is optionally substituted by one or more $R_e$; or $R_4$ is $R_c$;

$R_c$ is C1–10 alkyl, C3–8 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl; C1–10 alkoxy, aryloxy, C1–10 alkanoyl, aroyl, C1–10 alkoxycarbonyl, aryloxycarbonyl, C1–10 alkanoyloxy, or aroyloxy;

or $R_e$ is carbamoyl wherein the nitrogen atom may be independently mono or di-substituted by C1–10 alkyl, aryl, indanyl, indenyl, tetrahydronaphthyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_e$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, C1–10alkoxyC1–10alkyl, C1–10alkylaminoC1–10alkyl, C1–10alkylthioC1–10 alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_e$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, pyrrolidinyl, piperidinyl, morpholinyl, thiomorpholinyl, piperazinyl, indolinyl, pyranyl, thiopyranyl, furanyl, tetrahydropyranyl, tetrahydrothiopyranyl, tetrahydrofuranyl, thienyl, pyrrolyl, pyrazolyl, imidazolyl, oxazolyl, isoxazolyl, thiazolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_e$ is amino, halogen, hydroxy, oxo, carboxy, cyano, amidino or guanidino;

Each $R_e$ may be further optionally substituted by one or more $R_f$;

$R_f$ is C1–5 alkyl, C3–6 cycloalkyl, aryl, arylC1–4-alkyl, C1–5 alkoxy, aryloxy, arylC1–5alkoxy, aroyl, halogen, hydroxy, oxo or cyano;

Q is $R_g$, $C(O)R_g$, $S(O)R_g$, or $S(O)_2R_g$;

wherein $R_g$ is C2–10alkenyl, C1–10 alkoxy, aryloxy, C3–8 cycloalkyl, aryl, arylC1–10alkyl, C1–10 alkyl wherein one or more of the C atoms are optionally replaced by O, NH, —C(═O)—, S, S(O) or $S(O)_2$; indenyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, tetrahydronaphthyl, C1–10alkylsulfonylC1–10alkyl, C3–8cycloalkylsulfonylC1–10alkyl, arylsulfonylC1–10alkyl, azetidinyl, pyrrolidinyl, piperidinyl, morpholinyl, thiomorpholinyl, piperazinyl, perhydroazepinyl, perhydrodiazepinyl, indolinyl, isoindolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyrazolyl, pyridinyl, pyrimidinyl, pyrazinyl, pyridazinyl, tetrazolyl, triazolyl, indolyl, benzofuranyl, benzothienyl, dihydrobenzofuranyl, dihydrobenzothienyl, indazolyl, isoindazolyl, benzimidazolyl, benzoxazolyl, benzothiazolyl, benzisoxazolyl, benzisothiazolyl, benzotriazolyl, quinolinyl, tetrahydroquinolinyl, isoquinolinyl, tetrahydroisoquinolinyl, quinazolinyl, tetrahydroquinazolinyl, quinoxalinyl, or amino;

wherein $R_g$ is optionally substituted by one or more $R_h$;

$R_h$ is C1–10 alkyl, C3–8 cycloalkyl, aryl, tetrahydronaphthyl, indenyl, indanyl, azetidinyl, pyrrolidinyl, piperidinyl, morpholinyl, thiomorpholinyl, piperazinyl, perhydroazepinyl, perhydrodiazepinyl, indolinyl, isoindolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyrazolyl, pyridinyl, pyrimidinyl, pyrazinyl, pyridazinyl, tetrazolyl, triazolyl, indolyl, benzofuranyl, benzothienyl, dihydrobenzofuranyl, dihydrobenzothienyl, indazolyl, isoindazolyl, benzimidazolyl, benzoxazolyl, benzothiazolyl, benzisoxazolyl, benzisothiazolyl, benzotriazolyl, benzodioxolyl, quinolinyl, tetrahydroquinolinyl, isoquinolinyl, tetrahydroisoquinolinyl, quinazolinyl, tetrahydroquinazolinyl, quinoxalinyl, C1–10 alkoxy, C1–10alkanoyl, C1–10alkanoyloxy, aryloxy, benzyloxy, C1–10 alkoxycarbonyl, aryloxycarbonyl, aroyloxy, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, or cubanyl, or $R_h$ is carbamoyl wherein the nitrogen atom may be independently mono or di-substituted by C1–10 alkyl, C1–10alkoxyC1–10alkyl, C1– alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, azetidinyl, pyrrolidinyl, piperidinyl, morpholinyl, thiomorpholinyl, piperazinyl, perhydroazepinyl, perhydrodiazepinyl, indolinyl, isoindolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyrazolyl, pyridinyl, pyrimidinyl, pyrazinyl, pyridazinyl, tetrazolyl, triazolyl, indolyl, benzofuranyl, benzothienyl, dihydrobenzofuranyl, dihydrobenzothienyl, indazolyl, isoindazolyl, benzimidazolyl, benzoxazolyl, benzothiazolyl, benzisoxazolyl, benzisothiazolyl, benzotriazolyl, quinolinyl, tetrahydroquinolinyl, isoquinolinyl, tetrahydroisoquinolinyl, quinazolinyl, tetrahydroquinazolinyl, or quinoxalinyl, or $R_h$ is C1–10 alkanoylamino, aroylamino, C1–10 alkylthio, arylthio wherein the sulfur atom may be oxidized to a sulfoxide or sulfone, or $R_h$ is ureido wherein either nitrogen atom may be independently substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, isoindolinyl, azetidinyl, pyrrolidinyl, piperidinyl, morpholinyl, thiomorpholinyl, piperazinyl, perhydroazepinyl, perhydrodiazepinyl, indolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyrazolyl, pyridinyl, pyrimidinyl, pyrazinyl, pyridazinyl, tetrazolyl, triazolyl, indolyl, benzofuranyl, benzothienyl, dihydrobenzofuranyl, dihydrobenzothienyl, indazolyl, isoindazolyl, benzimidazolyl, benzoxazolyl, benzothiazolyl, benzisoxazolyl, benzisothiazolyl, benzotriazolyl, quinolinyl, tetrahydroquinolinyl, isoquinolinyl, tetrahydroisoquinolinyl, quinazolinyl, tetrahydroquinazolinyl, or quinoxalinyl;

or $R_h$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, isoindolinyl, azetidinyl, pyrrolidinyl, piperidinyl, morpholinyl, thiomorpholinyl, piperazinyl, piperazinylcarbonyl, perhydroazepinyl, perhydrodiazepinyl, indolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyrazolyl, pyridinyl, pyrimidinyl, pyrazinyl, pyridazinyl, tetrazolyl, triazolyl, indolyl, benzofuranyl, benzothienyl, dihydrobenzofuranyl, dihydrobenzothienyl, indazolyl, isoindazolyl, benzimidazolyl, benzoxazolyl, benzothiazolyl, benzisoxazolyl, benzisothiazolyl, benzotriazolyl, quinolinyl, tetrahydroquinolinyl, isoquinolinyl, tetrahydroisoquinolinyl, quinazolinyl, tetrahydroquinazolinyl, quinoxalinyl, halogen, hydroxy, oxo, carboxy, cyano, nitro, amidino or guanidino, $R_h$ may be further optionally substituted by one or more $R_i$;

$R_i$ is C1–10 alkyl, C3–8 cycloalkyl, aryl, arylC1–10alkyl, heterocyclyl, heterocyclylC1–10alkyl, C1–10 alkoxy, C1–10 alkoxycarbonyl, aryloxy, benzyloxy, halogen, hydroxy, oxo, carboxy, cyano, nitro, amidino or guanidino;

or a pharmaceutically acceptable salt, tautomer, prodrug ester or prodrug amide thereof;

with the proviso that when $R_1$ is hydrogen or C1–10alkyl, and $R_2$, $R_3$, $R_5$ and $R_6$ are each independently hydrogen or C1–5alkyl, and $R_4$ is hydrogen or C1–10alkyl, then Q is not C1–10alkyl or C1–10alkoxycarbonyl.

2. A compound according to claim 1, wherein:

$R_1$ is hydrogen, a C1–7 saturated or unsaturated alkyl group wherein one or more C atoms are optionally replaced by O, NH, S(O), $S(O)_2$ or S and wherein said alkyl group is optionally independently substituted with one or more: oxo groups, C1–4 alkyl, C3–8 cycloalkyl, aryl, pyrrolidinyl, piperidinyl, morpholinyl, thiomorpholinyl, piperazinyl, indolinyl, pyranyl, thiopyranyl, tetrahydropyranyl, tetrahydrothiopyranyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_1$ is C1–7alkoxyC1–7alkyl, C1–7alkylthioC1–7alkyl wherein the sulfur atom may be oxidized to a sulfoxide or sulfone, C3–8 cycloalkyl, aryl, arylsulfonyl, heteroarylsulfonyl, tetrahydronaphthyl, indenyl, indanyl, arylsulfonylC1–5alkyl, aryloxyC1–5alkyl, C1–7alkanoyl, aroyl, tetrahydropyranyl, pyrrolidinyl, piperidinyl, morpholinyl, indolinyl, carbamoyl wherein the nitrogen atom may be independently mono or di-substituted by C1–7 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzothiazolyl, quinolyl or isoquinolyl;

each $R_1$ may be further optionally independently substituted by one or more $R_a$;

$R_a$ is a C1–7 saturated or unsaturated alkyl group wherein one or more C atoms are optionally replaced by O, S(O), $S(O)_2$ or S and wherein said alkyl group is optionally independently substituted with one or two oxo groups, or one or more: —$NH_2$, $C_{1-4}$ alkyl, aryl, pyrrolidinyl, piperidinyl, morpholinyl, thiomorpholinyl, piperazinyl, indolinyl, pyranyl, thiopyranyl, tetrahydropyranyl, tetrahydrothiopyranyl, furanyl, thienyl, pyrrolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

or $R_a$ is a C1–7alkoxy, C1–7alkoxyC1–7alkyl, C1–7alkylthioC1–7alkyl wherein the sulfur atom may be oxidized to a sulfoxide or sulfone, C3–8 cycloalkyl, C3–8 cycloalkyloxy, aryl, tetrahydronaphthyl, indenyl, indanyl, pyrrolidinyl, piperidinyl, morpholinyl, thiomorpholinyl, piperazinyl, tetrahydropyranyl, tetrahydrothiopyranyl, furanyl, thienyl, pyrrolyl, pyridinyl, pyrimidinyl, pyrazinyl, indolyl, benzofuranyl, benzothienyl, benzimidazolyl, benzothiazolyl, benzoxazolyl, quinolyl, isoquinolyl, C1–7alkanoyl, aroyl, C1–7alkanoyloxy, aryloxy, benzyloxy, C1 –7 alkoxycarbonyl, arylC1–3alkoxycarbonyl, aryloxycarbonyl, aroyloxy, carbamoyl wherein the nitrogen atom may be independently mono or di-substituted by C1–7 alkyl, aryl, pyrrolidinyl, piperidinyl, morpholinyl, thiomorpholinyl, piperazinyl, indolinyl, furanyl, thienyl, pyrrolyl, pyridinyl, pyrimidinyl, pyrazinyl, indolyl, benzofuranyl, benzothienyl, benzimidazolyl, benzothiazolyl, quinolyl or isoquinolyl;

or $R_a$ is ureido wherein either nitrogen atom may be independently substituted by C1–7 alkyl, aryl, pyrrolidinyl, piperidinyl, morpholinyl, thiomorpholinyl, piperazinyl, tetrahydropyranyl, indolinyl, furanyl, thienyl, pyrrolyl, pyridinyl, pyrimidinyl, pyrazinyl, indolyl, benzofuranyl, benzothienyl, benzimidazolyl, benzothiazolyl, quinolyl or isoquinolyl, or $R_a$ is amino wherein the nitrogen atom may be independently mono or di-substituted by C1–7 alkyl, aryl, pyrrolidinyl, piperidinyl, morpholinyl, thiomorpholinyl, piperazinyl, tetrahydropyranyl, indolinyl, furanyl, thienyl, pyrrolyl, pyridinyl, pyrimidinyl, pyrazinyl, indolyl, benzofuranyl, benzothienyl, benzimidazolyl, benzothiazolyl, benzoxazolyl, quinolyl or isoquinolyl, wherein $R_a$ may be further optionally substituted by one or more $R_b$;

$R_b$ is C3–6 cycloalkyl, C1–5 alkoxy, aryl, aryloxy, benzyloxy, halogen, hydroxy, oxo, carboxy, cyano, nitro, carboxamide, amidino or guanidino;

or $R_b$ is aryl, pyrrolidinyl, piperidinyl, morpholinyl, thiomorpholinyl, piperazinyl, tetrahydropyranyl, indolinyl, furanyl, thienyl, pyrrolyl, pyridinyl, pyrimidinyl, pyrazinyl, indolyl, benzofuranyl, benzothienyl, benzimidazolyl, benzothiazolyl, quinolyl or isoquinolyl;

or $R_b$ is amino wherein the nitrogen atom may be independently mono or di-substituted by C1–7 alkyl, aryl, pyrrolidinyl, piperidinyl, morpholinyl, thiomorpholinyl, piperazinyl, tetrahydropyranyl, indolinyl, furanyl, thienyl, pyrrolyl, pyridinyl, pyrimidinyl, pyrazinyl, indolyl, benzofuranyl, benzothienyl, benzimidazolyl, benzothiazolyl, quinolyl or isoquinolyl;

or $R_b$ is a C1–7 saturated or unsaturated alkyl group wherein one or more C atoms are optionally replaced by O, S(O), $S(O)_2$ or S and wherein said alkyl group is optionally independently substituted with one or two oxo groups, or one or more: —$NH_2$, $C_{1-4}$ alkyl, aryl, pyrrolidinyl, piperidinyl, morpholinyl, thiomorpholinyl, piperazinyl, tetrahydropyranyl, indolinyl, furanyl, thienyl, pyrrolyl, pyridinyl, pyrimidinyl, pyrazinyl, indolyl, benzofuranyl, benzothienyl, benzimidazolyl, benzothiazolyl, benzoxazolyl, quinolyl or isoquinolyl;

$R_2$, $R_3$, $R_5$, and $R_6$ independently are hydrogen or a C1–5 alkyl group;

$R_2$ and $R_3$ together with the carbon to which they are attached, and/or $R_5$ and $R_6$ together with the carbon to which they are attached, each may independently optionally form a nonaromatic 3–6 membered cycloalkyl;

$R_4$ is hydrogen, C2–5alkenyl, C3–7 cycloalkyl, arylC1–3alkyl, aryl or a C1–6 alkyl group wherein one or two of the C atoms are optionally replaced by O, —C(=O)—, S, S(O) or $S(O)_2$; wherein $R_4$ is optionally substituted by one or more $R_e$; or $R_4$ is $R_e$;

$R_a$ is C1–5 alkyl, C3–7 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, pyrrolidinyl, piperidinyl, morpholinyl, thiomorpholinyl, piperazinyl, indolinyl, furanyl, tetrahydropyranyl, thienyl, pyrrolyl, oxazolyl, thiazolyl, pyrazolyl, pyridinyl, pyrimidinyl, pyrazinyl, indolyl, benzofuranyl, benzothienyl, benzimidazolyl, benzothiazolyl, quinolinyl, or isoquinolinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl or isoquinolinyl, or $R_e$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, or isoquinolinyl, or $R_e$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl or isoquinolinyl, or $R_e$ is halogen, hydroxy, oxo, carboxy, cyano, amidino or guanidino;

Each $R_e$ may be further optionally substituted by one or more $R_f$;

$R_f$ is C1–5 alkyl, C3–6 cycloalkyl, aryl, arylC1–4-alkyl, C1–5 alkoxy, aryloxy, arylC1–5alkoxy, aroyl, halogen, hydroxy, oxo or cyano;

Q is $R_g$, $C(O)R_g$, $S(O)R_g$ or $S(O)_2R_g$;

wherein $R_g$ is C1–5 alkyl wherein one or more C atoms are optionally replaced by O or NH, C1–5 alkoxy, aryloxy, C3–7 cycloalkyl, phenyl, benzyl, naphthyl, tetrahydronaphthyl, C1–5alkylsulfonylC1–5alkyl, C3–7cycloalkylsulfonylC1–5alkyl, arylsulfonylC1–5alkyl, pyrrolidinyl, piperidinyl, morpholinyl, thiomorpholinyl, piperazinyl, indolinyl, isoindolinyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, tetrahydroisoquinolyl, quinoxalinyl or benzoxazolyl, or amino; wherein $R_g$ is optionally substituted by one or more $R_h$;

$R_h$ is C1–5 alkyl, C3–7 cycloalkyl, phenyl, naphthyl, indenyl, indanyl, pyrrolidinyl, piperidinyl, morpholinyl, thiomorpholinyl, piperazinyl, indolinyl, isoindolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, benzoxazolyl, benzisoxazolyl, benzodioxolyl, quinolinyl, isoquinolinyl or tetrahydroisoquinolyl, C1–5 alkoxy, C1–5alkanoyl, C1–5alkanoyloxy, aryloxy, benzyloxy, C1–5 alkoxycarbonyl, aryloxycarbonyl, aroyloxy, carbamoyl wherein the nitrogen atom may be independently mono or di-substituted by C1–6 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl or isoquinolinyl, or $R_h$ is C1–5 alkanoylamino, aroylamino, C1–5 alkylthio, arylthio wherein the sulfur atom may be oxidized to a sulfoxide or sulfone, or $R_h$ is ureido wherein either nitrogen atom may be independently substituted by alkyl, aryl, pyrrolidinyl, piperidinyl, morpholinyl, thiomorpholinyl, piperazinyl, indolinyl, isoindolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, or isoquinolinyl, or $R_h$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, pyrrolidinyl, piperidinyl, morpholinyl, thiomorpholinyl, piperazinyl, piperazinylcarbonyl, indolinyl, isoindolinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl or isoquinolinyl, halogen, hydroxy, oxo, carboxy, cyano, nitro, amidino or guanidino, $R_h$ may be further optionally substituted by one or more $R_i$;

$R_i$ is C1–5 alkyl, C3–6 cycloalkyl, aryl, arylC1–5alkyl, pyrrolidinyl, piperidinyl, piperazinyl, morpholinyl, thiomorpholinyl, C1–5 alkoxy, C1–5 alkoxycarbonyl, aryloxy, benzyloxy, halogen, hydroxy, oxo, carboxy, cyano, nitro, amidino or guanidino;

wherein one or more of the amino nitrogens in the amidino or guanidino groups in the compound of formula I may be optionally substituted with $C_{1-3}$alkyl, phenyl$C_{0-3}$alkyl or $C_{1-3}$alkoxy;

or a pharmaceutically acceptable salt, tautomer, prodrug ester or prodrug amide thereof.

3. A compound according to claim 1, wherein:

$R_1$ is hydrogen, a C1–6 saturated or unsaturated alkyl group wherein one or more C atoms are optionally replaced by O, NH, S, S(O) or $S(O)_2$ and wherein said alkyl group is optionally independently substituted with one or more: oxo groups, C1–4 alkyl, C3–6 cycloalkyl, aryl, pyrrolidinyl, piperidinyl, morpholinyl, thiomorpholinyl, piperazinyl, indolinyl, pyranyl, thiopyranyl, tetrahydropyranyl, tetrahydrothiopyranyl, pyridinyl, pyrimidinyl, pyrazinyl or indolyl;

or $R_1$ is C1–6alkoxyC1–6alkyl, C1–6alkylthioC1–6alkyl wherein the sulfur atom may be oxidized to a sulfoxide or sulfone, C3–6 cycloalkyl, aryl, arylsulfonyl, arylsulfonylC1–6alkyl, heteroarylsulfonyl, aryloxyC1–6alkyl, C1–6alkanoyl, aroyl, pyrrolidinyl, piperidinyl, morpholinyl, carbamoyl wherein the nitrogen atom may be independently mono or di-substituted by C1–6 alkyl, or aryl;

each $R_1$ may be further optionally independently substituted by one or more $R_a$;

$R_a$ is a C1–6 saturated or unsaturated alkyl group wherein one or more C atoms are optionally replaced by O, S, S(O) or $S(O)_2$ and wherein said alkyl group is optionally independently substituted with one or two oxo groups, or one or more: —$NH_2$, $C_{1-4}$ alkyl, or aryl;

or $R_a$ is a C1–6alkoxy, C1–6alkoxyC1–6alkyl, C1–6alkylthioC1–6alkyl, C3–6 cycloalkyl, C3–6 cycloalkyloxy, aryl, pyrrolidinyl, piperidinyl, morpholinyl, thiomorpholinyl, piperazinyl, tetrahydropyranyl, pyridinyl, indolyl, C1–6alkanoyl, aroyl, C1–6alkanoyloxy, aryloxy, benzyloxy, C1–6alkoxycarbonyl, arylC1–3alkoxycarbonyl, aryloxycarbonyl, aroyloxy, carbamoyl wherein the nitrogen atom may be independently mono or di-substituted by C1–6 alkyl, or aryl;

or $R_a$ is ureido wherein either nitrogen atom may be independently substituted by C1–6 alkyl or aryl, or $R_a$ is amino wherein the nitrogen atom may be independently mono or di-substituted by C1–6 alkyl, or aryl, wherein $R_a$ may be further optionally substituted by one or more $R_b$;

$R_b$ is C3–6 cycloalkyl, C1–5 alkoxy, aryl, aryloxy, benzyloxy, halogen, hydroxy, oxo, carboxy, cyano, nitro or carboxamide;

or $R_b$ is amino wherein the nitrogen atom may be independently mono or di-substituted by C1–6 alkyl or aryl;

or $R_b$ is a C1–6 saturated or unsaturated alkyl group wherein one or two C atoms are optionally replaced by O or S and wherein said alkyl group is optionally independently substituted with one or two oxo groups, or one or more: —$NH_2$, $C_{1-4}$ alkyl, or aryl;

$R_2$, $R_3$, $R_5$, and $R_6$ independently are hydrogen or a C1–4 alkyl group;

$R_2$ and $R_3$ together with the carbon to which they are attached, and/or $R_5$ and $R_6$ together with the carbon to which they are attached, each may independently optionally form a nonaromatic 3–6 membered cycloalkyl;

$R_4$ is hydrogen, C2–5alkenyl, C3–6 cycloalkyl, arylC1–3alkyl, aryl or a C1–6 alkyl group wherein one or two of the C atoms are optionally replaced by O, S or $S(O)_2$; wherein $R_4$ is optionally substituted by one or more $R_e$; or $R_4$ is $R_e$;

$R_e$ is C1–5 alkyl, C3–6 cycloalkyl, aryl, indanyl, indenyl, pyridinyl, indolyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl or aryl, or $R_e$ is C1–5 alkanoylamino, aroylamino, C1–5 alkylthio, arylthio wherein the sulfur atom may be oxidized to a sulfoxide or sulfone, ureido wherein either nitrogen atom may be independently substituted by C1–5 alkyl or aryl, or $R_e$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl or aryl, or $R_e$ is halogen, hydroxy, oxo, carboxy, cyano, amidino or guanidino;

Each $R_e$ may be further optionally substituted by one or more $R_f$;

$R_f$ is C1–5 alkyl, C3–6 cycloalkyl, aryl, arylC1–4-alkyl, C1–5 alkoxy, aryloxy, arylC1–5alkoxy, aroyl, halogen, hydroxy, oxo or cyano;

Q is $R_g$, C(O)$R_g$, S(O)$R_g$ or $S(O)_2R_g$;

wherein $R_g$ is C1–5 alkyl wherein one or more C atoms are optionally replaced by O or NH, C1–5 alkoxy, aryloxy, C3–6 cycloalkyl, phenyl, benzyl, naphthyl, tetrahydronaphthyl, C1–5alkylsulfonylC1–5alkyl, C3–6cycloalkylsulfonylC1–5alkyl, arylsulfonylC1–5alkyl, pyrrolidinyl, piperidinyl, morpholinyl, thiomorpholinyl, piperazinyl, isoindolinyl, furanyl, thienyl, oxazolyl, isoxazolyl, thiazolyl, pyridinyl, indolyl, benzofuranyl, benzothienyl, quinolinyl, isoquinolinyl, tetrahydroisoquinolyl, pyrazinyl or quinoxalinyl, or amino;

wherein $R_g$ is optionally substituted by one or more $R_h$;

$R_h$ is C1–5 alkyl, C3–6 cycloalkyl, phenyl, naphthyl, indenyl, indanyl, pyrrolidinyl, piperidinyl, morpholinyl, thiomorpholinyl, piperazinyl, pyridinyl, isoindolinyl, quinolinyl, isoquinolinyl, tetrahydroisoquinolyl or benzodioxolyl, C1–5 alkoxy, C1–5alkanoyl, C1–5alkanoyloxy, aryloxy, benzyloxy, C1–5 alkoxycarbonyl, aryloxycarbonyl, aroyloxy, carbamoyl wherein the nitrogen atom may be independently mono or di-substituted by C1–6 alkyl or aryl, or $R_h$ is C1–5 alkanoylamino, aroylamino, C1–5 alkylthio, arylthio wherein the sulfur atom may be oxidized to a sulfoxide or sulfone, or $R_h$ is ureido wherein either nitrogen atom may be independently substituted by alkyl or aryl, or $R_h$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, piperidinyl, morpholinyl, thiomorpholinyl, piperazinyl or piperazinylcarbonyl, halogen, hydroxy, oxo, carboxy, cyano, nitro, amidino or guanidino, $R_h$ may be further optionally substituted by one or more $R_i$;

$R_i$ is C1–5 alkyl, C3–6 cycloalkyl, aryl, arylC1–5alkyl, piperidinyl, piperazinyl, morpholinyl, thiomorpholinyl, C1–5 alkoxy, C1–5 alkoxycarbonyl, aryloxy, benzyloxy, halogen, hydroxy, oxo, carboxy, cyano, nitro, amidino or guanidino;

wherein one or more of the amino nitrogens in the amidino or guanidino groups in the compound of formula I may be optionally substituted with $C_{1-3}$alkyl, phenyl$C_{0-3}$alkyl or $C_{1-3}$alkoxy;

or a pharmaceutically acceptable salt, tautomer, prodrug ester or prodrug amide thereof.

4. A compound according to claim 1, wherein:

$R_1$ is hydrogen, a C1–6 saturated or unsaturated alkyl group wherein one or two C atoms are optionally replaced by O, NH, S, S(O) or $S(O)_2$, and wherein said alkyl group is optionally independently substituted with one to three: oxo groups, C1–4 alkyl, C3–6 cycloalkyl, aryl, pyrrolidinyl, piperidinyl, piperazinyl, morpholinyl, indolinyl, pyranyl, thiopyranyl, tetrahydropyranyl, tetrahydrothiopyranyl, pyridinyl or indolyl;

or $R_1$ is C1–6alkylthioC1–6alkyl wherein the sulfur atom may be oxidized to a sulfoxide or sulfone, C3–6 cycloalkyl, phenyl, naphthyl, phenylsulfonyl, pyridinylsulfonyl, phenyloxyC1–6alkyl, C1–6alkanoyl, or piperidinyl;

each $R_1$ may be further optionally independently substituted by one or more $R_a$;

$R_a$ is a C1–6 saturated or unsaturated alkyl group wherein one or two C atoms are optionally replaced by O or S;

or $R_a$ is a C1–6alkoxy, C3–6 cycloalkyl, phenyl, naphthyl, pyrrolidinyl, piperidinyl, morpholinyl, thiomorpholinyl, tetrahydropyranyl, piperazinyl, indolyl, or pyridinyl;

wherein $R_a$ may be further optionally substituted by one or more $R_b$;

$R_b$ is C3–6 cycloalkyl, C1–5 alkoxy, halogen, hydroxy, oxo, carboxy, cyano, nitro or carboxamide;

or $R_b$ is phenyl, benzyl or naphthyl;

or $R_b$ is amino wherein the nitrogen atom may be independently mono or di-substituted by C1–6 alkyl, phenyl or naphthyl;

or $R_b$ is a C1–6 saturated or unsaturated alkyl group wherein one or two C atoms are optionally replaced by O or S, and wherein said alkyl group is optionally independently substituted with one or two oxo group;

$R_2$, $R_3$, $R_5$, and $R_6$ independently are hydrogen or a C1–5 alkyl group;

$R_2$ and $R_3$ together with the carbon to which they are attached, and/or $R_5$ and $R_6$ together with the carbon to which they are attached, each may independently optionally form a nonaromatic 3–6 membered cycloalkyl;

$R_4$ is hydrogen, C3–6 cycloalkyl, phenylC1–3alkyl, naphthylC1–3alkyl, phenyl, naphthyl, pyridyl or a C1–6 alkyl group wherein one or two of the C atoms are optionally replaced by O, S or $S(O)_2$; wherein $R_4$ is optionally substituted by one or more $R_e$;

$R_e$ is C1–5 alkyl, C3–6 cycloalkyl, phenyl, naphthyl, indanyl or indolyl, or $R_e$ is halogen, hydroxy, oxo, carboxy, cyano, amidino or guanidino;

Each $R_e$ may be further optionally substituted by one or more $R_f$;

$R_f$ is C1–5 alkyl, C3–6 cycloalkyl, C1–5 alkoxy, halogen, hydroxy, oxo or cyano;

Q is $R_g$, $C(O)R_g$ or $S(O)_2R_g$;

wherein $R_g$ is C1–5 alkyl wherein one or more C atoms are optionally replaced by O or NH, C1–5 alkoxy, phenyl, benzyl, naphthyl, pyrrolidinyl, piperidinyl, morpholinyl, thiomorpholinyl, piperazinyl, furanyl, thienyl, oxazolyl, thiazolyl, pyridinyl, benzofuranyl, benzothienyl, quinolinyl, isoquinolinyl, isoindolinyl, tetrahydroisoquinolyl, pyrazinyl, quinoxalinyl or amino; wherein $R_g$ is optionally substituted by one or more $R_h$;

$R_h$ is C1–5 alkyl, C3–6 cycloalkyl, phenyl, naphthyl, indenyl, indanyl, morpholinyl, thiomorpholinyl, pyridinyl, isoindolinyl, isoquinolinyl, tetrahydroisoquinolinyl or benzodioxolyl, or C1–5alkoxy, or $R_h$ is C1–5 alkylthio, or $R_h$ is amino wherein the nitrogen atom may be independently mono or di-substituted by alkyl, phenyl, naphthyl, piperidinyl, morpholinyl, thiomorpholinyl, piperazinyl or piperazinylcarbonyl, halogen, hydroxy, oxo, carboxy, cyano, nitro, amidino or guanidino, $R_h$ may be further optionally substituted by one or more $R_i$;

$R_i$ is C1–5 alkyl, C3–6 cycloalkyl, aryl, arylC1–5alkyl, morpholinyl, thiomorpholinyl, C1–5 alkoxy, C1–5 alkoxycarbonyl, halogen, hydroxy, oxo, carboxy, cyano, nitro, amidino or guanidino;

wherein one or more of the amino nitrogens in the amidino or guanidino groups in the compound of formula I may be optionally substituted with $C_{1-3}$alkyl, phenyl$C_{0-3}$alkyl or $C_{1-3}$alkoxy;

or a pharmaceutically acceptable salt, tautomer, prodrug ester or prodrug amide thereof.

5. A compound according to claim 1, wherein:

$R_1$ is hydrogen, a C1–6 saturated alkyl group wherein one C atom is optionally replaced by O, S, S(O), $S(O)_2$ or NH and wherein said alkyl group is optionally independently substituted with one or two: oxo groups, phenyl, naphthyl, cyclohexyl, pyrrolidinyl, piperidinyl, piperazinyl, morpholinyl, indolinyl, tetrahyropyranyl, pyridinyl or indolyl;

or $R_1$ is C1–3alkylthioC1–3alkyl wherein the sulfur atom may be oxidized to a sulfoxide, cyclohexyl, phenyl, phenylsulfonyl, pyridinylsulfonyl, phenyloxyC1–4alkyl, C1–6alkanoyl or piperidinyl;

each $R_1$ may be further optionally independently substituted by one or two $R_a$;

$R_a$ is a C1–6 saturated alkyl group;

or $R_a$ is a C1–6alkoxy, cyclohexyl, phenyl, naphthyl, pyrrolidinyl, piperidinyl, indolyl, piperazinyl, pyridinyl or tetrahydropyranyl;

wherein $R_a$ may be further optionally substituted by one or two $R_b$;

$R_b$ is C3–6 cycloalkyl, phenyl, benzyl, C1–5 alkoxy, halogen, hydroxy, oxo, carboxy, cyano, nitro or carboxamide;

or $R_b$ is a C1–6 saturated or unsaturated alkyl group, or is a C1–4alkoxycarbonyl group;

$R_2$, $R_3$, $R_5$, and $R_6$ independently are hydrogen or a C1–5 alkyl group;

$R_2$ and $R_3$ together with the carbon to which they are attached, and/or $R_5$ and $R_6$ together with the carbon to which they are attached, each may independently optionally form a cyclopropyl, cyclobutyl, cyclopentyl or cyclohexyl group;

$R_4$ is hydrogen, cyclopropyl, cyclobutyl, cyclopentyl, cyclohexyl, phenylC1–3alkyl, naphthylC1–3alkyl, phenyl, naphthyl, pyridinyl or a C1–6 alkyl group where a C atom is optionally replaced by $S(O)_2$; wherein $R_4$ is optionally substituted by one or more $R_e$;

$R_e$ is C1–3 alkyl, cyclopropyl, cyclobutyl, cyclopentyl, cyclohexyl, phenyl, naphthyl, indanyl or indolyl, or $R_e$ is hydroxy, halogen, oxo, carboxy or cyano;

Q is $R_g$, $C(O)R_g$ or $S(O)_2R_g$;

wherein $R_g$ is C1–5alkyl wherein one or more C atoms are optionally replaced by O or NH, phenyl, naphthyl, pyrrolidinyl, piperidinyl, morpholinyl, thiomorpholinyl, piperazinyl, furanyl, thienyl, thiazolyl, benzofuranyl, benzothienyl, quinolyl, isoquinolyl, isoindolinyl, tetrahydroisoquinolyl, pyrazinyl or quinoxalinyl, or amino; wherein $R_g$ is optionally substituted by one or more $R_h$;

$R_h$ is C1–5 alkyl, C1–5alkoxy, halogen, phenyl, naphthyl, indenyl, indanyl, morpholinyl, thiomorpholinyl, pyridinyl, isoquinolinyl, isoindolinyl, tetrahydroisoquinolyl benzodioxolyl, piperidinylamino or piperazinylcarbonylamino;

$R_h$ may be further optionally substituted by one or more $R_i$;

$R_i$ is C1–3 alkyl, C3–6 cycloalkyl, phenyl, naphthyl, benzyl, morpholinyl, C1–5 alkoxy, C1–5 alkoxycarbonyl, halogen, hydroxy, oxo, carboxy, cyano or nitro;

or a pharmaceutically acceptable salt, tautomer, prodrug ester or prodrug amide thereof.

6. A compound according to claim 1, wherein:

$R_1$ is hydrogen, C1–6alkyl, C1–6alkanoyl, phenylsulfonyl or pyridylsulfonyl each optionally substituted by cyclohexyl, phenyl, pyrrolidinyl, piperidinyl, indolyl, piperazinyl, pyridinyl, tetrahydropyranyl or naphthyl, or $R_1$ is benzyloxylC1–3alkyl or benzyloxyC1–3alkanoyl;

$R_2$, $R_3$, $R_5$, and $R_6$ independently are hydrogen or C1–3 alkyl;

$R_2$ and $R_3$ together with the carbon to which they are attached, and/or $R_5$ and $R_6$ together with the carbon to which they are attached, each may independently optionally form a cyclopropyl, cyclobutyl, cyclopentyl or cyclohexyl group;

$R_4$ is hydrogen, a C1–6 alkyl group, phenylC1–6alkyl, cyclopropylC1–6alkyl, cyclohexylC1–6alkyl or pyridinyl;

Q is $C(O)R_g$;

wherein $R_g$ is piperidinyl, morpholinyl, thiomorpholinyl, piperazinyl, isoindolinyl, benzofuranyl, tetrahydroisoquinolyl, phenylC1–5alkylamino or naphthylC1–5alkylamino, each optionally substituted by C1–5alkyl, morpholinyl or morpholinylC1–5alkoxy;

or a pharmaceutically acceptable salt, tautomer, prodrug ester or prodrug amide thereof.

7. A compound according to claim 1, wherein:

$R_1$ is C1–6alkanoyl optionally substituted by cyclohexyl or phenyl;

$R_2$, $R_3$, $R_5$, and $R_6$ are hydrogen;

$R_4$ is a C1–6 saturated alkyl group;

Q is $C(O)R_g$;

wherein $R_a$ is morpholinyl, tetrahydroisoquinolyl or phenylC1–3alkylamino;

or a pharmaceutically acceptable salt, tautomer, prodrug ester or prodrug amide thereof.

8. A compound according to claim 1 wherein:

$R_1$ is hydrogen, a C1–6 saturated alkyl group wherein one C atom is optionally replaced by O, S, S(O), $S(O)_2$ or NH and wherein said alkyl group is optionally independently substituted with one or two: oxo groups, phenyl, naphthyl, cyclohexyl, pyrrolidinyl, piperidinyl, piperazinyl, morpholinyl, indolinyl, tetrahydropyranyl, pyridinyl or indolyl;

or $R_1$ is C1–3alkylthioC1–3alkyl wherein the sulfur atom may be oxidized to a sulfoxide, cyclohexyl, phenyl, phenylsulfonyl, pyridinylsulfonyl, phenyloxyC1–4alkyl, C1–6alkanoyl, or piperidinyl;

each $R_1$ may be further optionally independently substituted by one or two $R_a$;

$R_a$ is a C1–6 saturated alkyl group;

or $R_a$ is a C1–6alkoxy, cyclohexyl, phenyl, naphthyl, pyrrolidinyl, piperidinyl, piperazinyl or pyridinyl;

wherein $R_a$ may be further optionally substituted by one or two $R_b$;

$R_b$ is C3–6 cycloalkyl, phenyl, benzyl, C1–5 alkoxy, halogen, hydroxy, oxo, carboxy, cyano, nitro or carboxamide;

or $R_b$ is a C1–6 saturated or unsaturated alkyl group, or is a C1–4alkoxycarbonyl group;

or a pharmaceutically acceptable salt, tautomer, prodrug ester or prodrug amide thereof.

9. A compound according to claim 8, wherein:

$R_1$ is hydrogen, C1–6alkyl or C1–6alkanoyl, each optionally substituted by cyclohexyl, phenyl, or naphthyl, or $R_1$ is benzyloxylC1–3alkyl or benzyloxyC1–3alkanoyl;

or a pharmaceutically acceptable salt, tautomer, prodrug ester or prodrug amide thereof.

10. A compound according to claim 1, wherein:

$R_2$, $R_3$, $R_5$, and $R_6$ independently are hydrogen or a C1–5 alkyl group;

$R_2$ and $R_3$ together with the carbon to which they are attached, and/or $R_5$ and $R_6$ together with the carbon to which they are attached, each may independently optionally form a cyclopropyl, cyclobutyl, cyclopentyl or cyclohexyl group;

or a pharmaceutically acceptable salt, solvate, tautomer, prodrug ester or prodrug amide thereof.

11. A compound according to claim 10 wherein:

$R_2$, $R_3$, $R_5$, and $R_6$ independently are hydrogen or C1–3 alkyl;

$R_2$ and $R_3$ together with the carbon to which they are attached, and/or $R_5$ and $R_6$ together with the carbon to which they are attached, each may independently optionally form a cyclopropyl, cyclopentyl or cyclohexyl group;

or a pharmaceutically acceptable salt, solvate, tautomer, or prodrug thereof.

12. A compound according to claim 1 wherein.

$R_4$ is hydrogen, cyclopropyl, cyclopentyl, cyclohexyl, phenylC1–3alkyl, naphthylC1–3alkyl, phenyl, naphthyl, pyridinyl or a C1–6 alkyl group where a C atom is optionally replaced by $S(O)_2$; wherein $R_4$ is optionally substituted by one or more $R_e$;

$R_e$ is C1–3 alkyl, cyclopropyl, cyclobutyl, cyclopentyl, cyclohexyl, phenyl, naphthyl, indanyl or indolyl, or $R_e$ is hydroxy, halogen, oxo, carboxy or cyano;

or a pharmaceutically acceptable salt, tautomer, prodrug ester or prodrug amide thereof.

13. A compound according to claim 12 wherein:

$R_4$ is hydrogen, a C1–6 alkyl group, phenylC1–6alkyl, cyclopropylC1–6alkyl, cyclohexylC1–6alkyl or pyridinyl;

or a pharmaceutically acceptable salt, tautomer, prodrug ester or prodrug amide thereof.

14. A compound according to claim 1 wherein:

Q is $R_g$, $C(O)R_g$ or $S(O)_2$ $R_g$;

wherein $R_g$ is C1–5alkyl wherein one or more C atoms are optionally replaced by O or NH, phenyl, naphthyl, pyrrolidinyl, piperidinyl, morpholinyl, thiomorpholinyl, piperazinyl, furanyl, thienyl, thiazolyl, benzofuranyl, benzothienyl, quinolyl, isoquinolyl, isoindolinyl, tetrahydroisoquinolyl, pyrazinyl or quinoxalinyl, or amino; wherein $R_g$ is optionally substituted by one or more $R_h$;

$R_h$ is C1–5 alkyl, C1–5alkoxy, halogen, phenyl, naphthyl, indenyl, indanyl, morpholinyl, thiomorpholinyl, pyridinyl, isoquinolinyl, isoindolinyl, tetrahydroisoquinolyl, benzodioxolyl, piperidinylamino or piperazinylcarbonylamino;

$R_h$ may be further optionally substituted by one or more $R_i$;

$R_i$ is C1–3 alkyl, C3–6 cycloalkyl, phenyl, naphthyl, benzyl, morpholinyl, C1–5 alkoxy, C1–5 alkoxycarbonyl, halogen, hydroxy, oxo, carboxy, cyano or nitro;

or a pharmaceutically acceptable salt, tautomer, prodrug ester or prodrug amide thereof.

15. A compound according to claim 14, wherein:

Q is $C(O)R_g$;

wherein $R_g$ is piperidinyl, morpholinyl, thiomorpholinyl, piperazinyl, isoindolinyl, benzofuranyl, tetrahydroisoquinolyl, phenylC1–5alkylamino or naphthylC1–5alkylamino, each optionally substituted by C1–5alkyl, morpholinyl or morpholinylC1–5alkoxy;

or a pharmaceutically acceptable salt, tautomer, prodrug ester or prodrug amide thereof.

16. A compound according to claim 1 having the following formula (Ia):

(Ia)

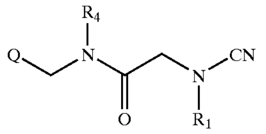

wherein Q is independently selected from groups A1 to A34; $R_4$ is independently selected from groups B1 to B26; and $R_1$ is independently selected from groups C1 to C41; wherein groups A1 to A34, B1 to B26 and C1 to C41 are as defined in the following Table:

| A | Q | B | $R_4$ | C | $R_1$ |
|---|---|---|---|---|---|
| A1 | 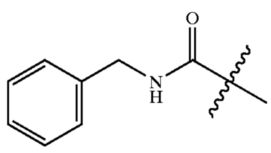 | B1 | —H | C1 | —H |
| A2 | 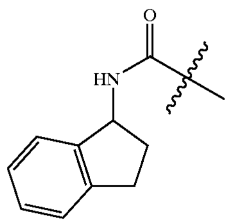 | B2 | $—CH_3$ | C2 | 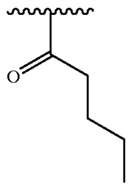 |

-continued
| A | Q | B | $R_4$ | C | $R_1$ |
| --- | --- | --- | --- | --- | --- |
| A3 | 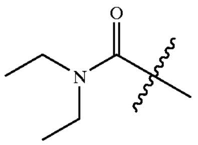 | B3 | 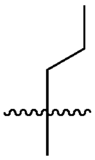 | C3 | 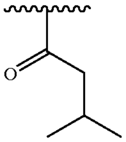 |
| A4 | 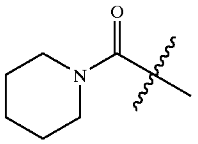 | B4 | 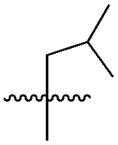 | C4 | 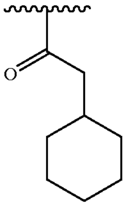 |
| A5 | 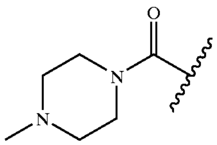 | B5 | 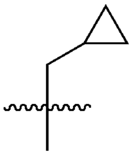 | C5 | 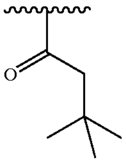 |
| A6 | 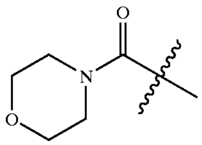 | B6 | 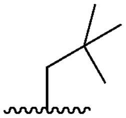 | C6 | 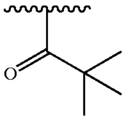 |
| A7 | 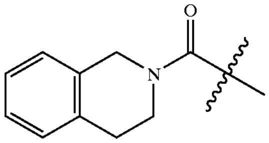 | B7 | 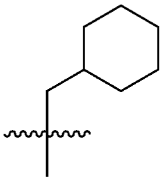 | C7 | 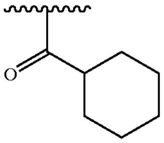 |
| A8 | 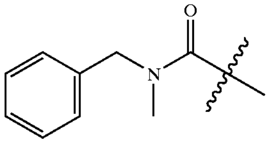 | B8 | 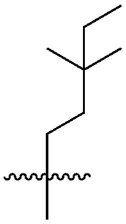 | C8 | 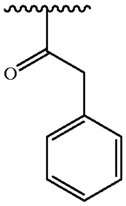 |
| A9 | 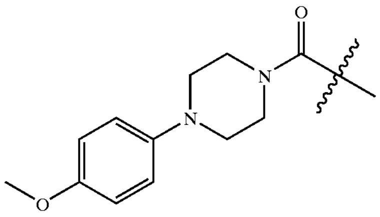 | B9 | 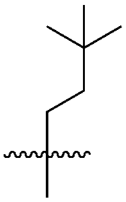 | C9 | 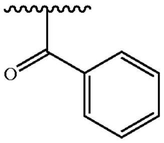 |
| A10 | 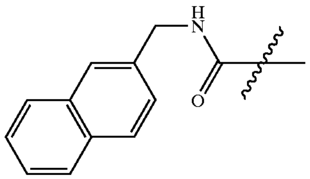 | B10 | 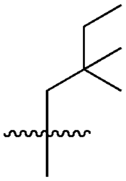 | C10 | 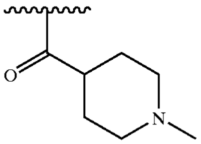 |

-continued
| A | Q | B | $R_4$ | C | $R_1$ |
|---|---|---|---|---|---|
| A11 | 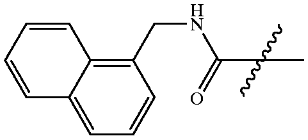 | B11 | 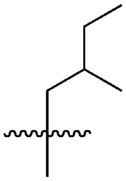 | C11 | 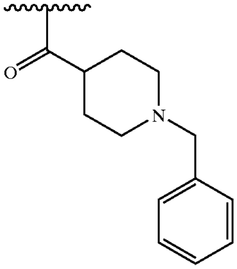 |
| A12 | 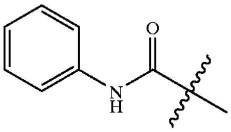 | B12 | 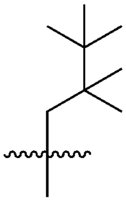 | C12 | 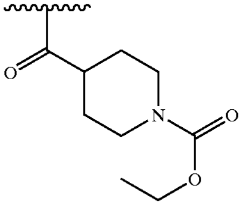 |
| A13 | 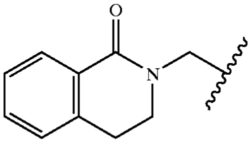 | B13 | 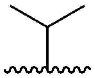 | C13 | 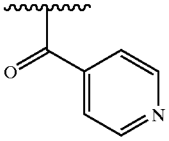 |
| A14 | 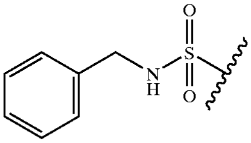 | B14 | 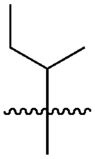 | C14 | 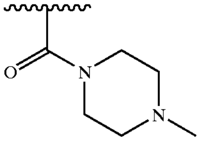 |
| A15 | 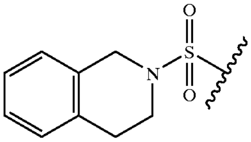 | B15 | 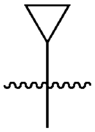 | C15 | 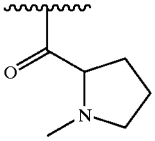 |
| A16 | 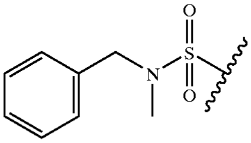 | B16 | 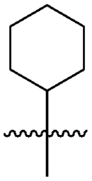 | C16 | 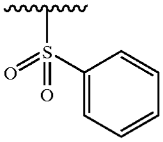 |
| A17 | 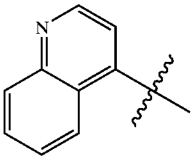 | B17 | 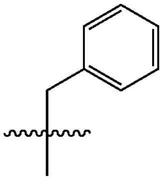 | C17 | 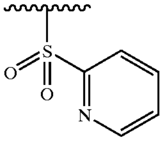 |

-continued
| A | Q | B | $R_4$ | C | $R_1$ |
|---|---|---|---|---|---|
| A18 | 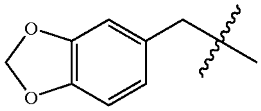 | B18 | 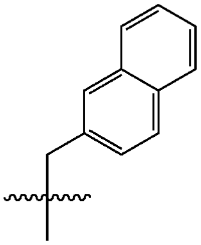 | C18 | $-CH_3$ |
| A19 | 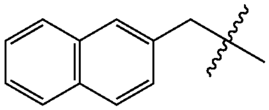 | B19 | 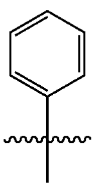 | C19 | 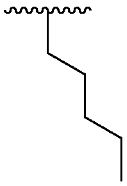 |
| A20 | 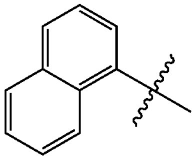 | B20 | 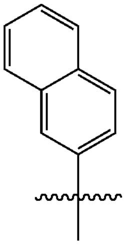 | C20 | 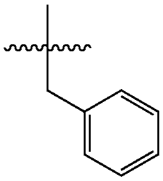 |
| A21 | 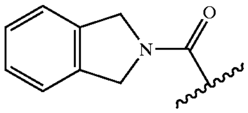 | B21 | 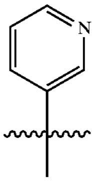 | C21 | 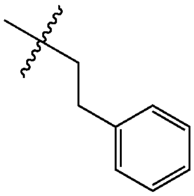 |
| A22 | 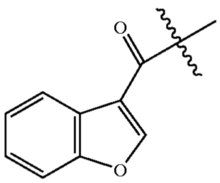 | B22 | 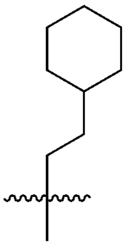 | C22 | 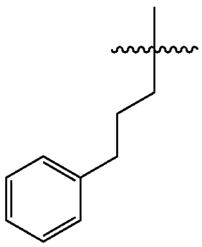 |
| A23 | 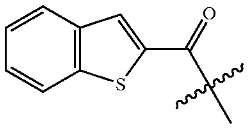 | B23 | 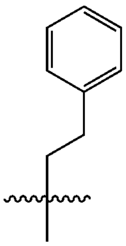 | C23 | 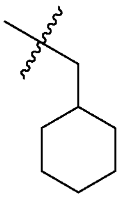 |

-continued
| A | Q | B | $R_4$ | C | $R_1$ |
|---|---|---|---|---|---|
| A24 | 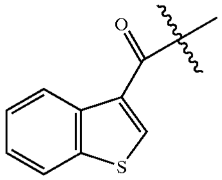 | B24 | 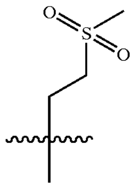 | C24 | 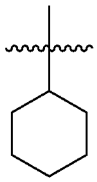 |
| A25 | 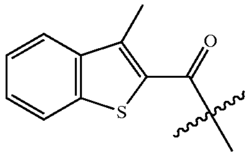 | B25 | 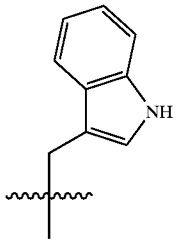 | C25 | 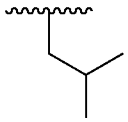 |
| A26 | 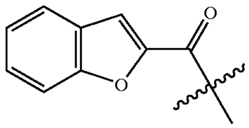 | B26 | 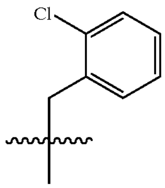 | C26 | 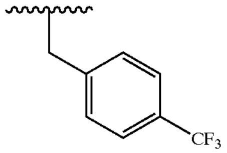 |
| A27 | 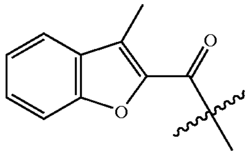 | | | C27 | 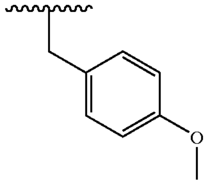 |
| A28 | 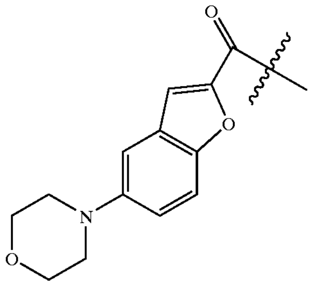 | | | C28 | 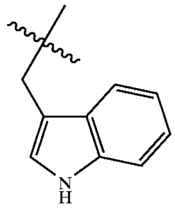 |
| A29 | 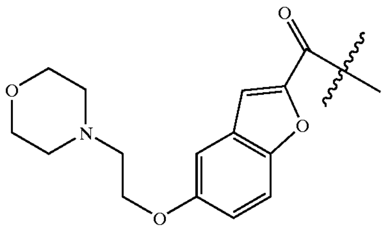 | | | C29 | 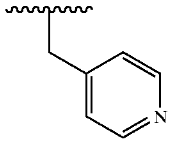 |
| A30 | 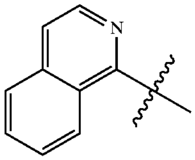 | | | C30 | 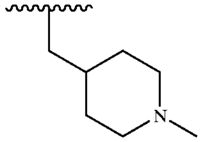 |

-continued
| A | Q | B | $R_4$ | C | $R_1$ |
|---|---|---|---|---|---|
| A31 | 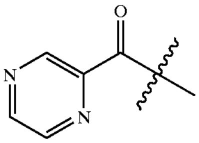 | | | C31 | 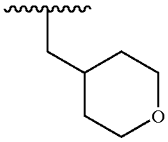 |
| A32 | 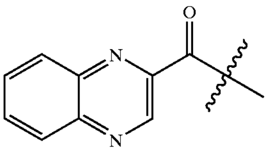 | | | C32 | 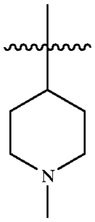 |
| A33 | 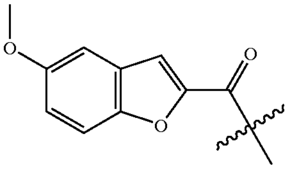 | | | C33 | 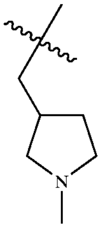 |
| A34 | 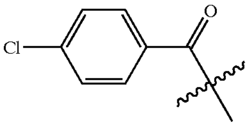 | | | C34 | 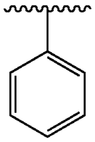 |
| | | | | C35 | 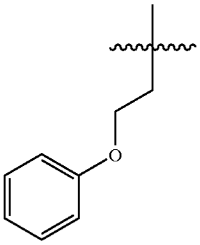 |
| | | | | C36 | 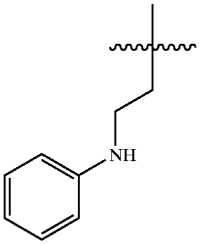 |
| | | | | C37 | 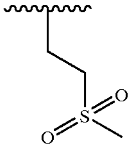 |

-continued
| A | Q | B | $R_4$ | C | $R_1$ |
|---|---|---|---|---|---|
| | | | | C38 | 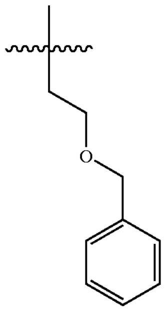 |
| | | | | C39 | 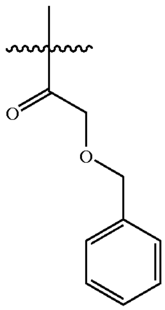 |
| | | | | C40 | 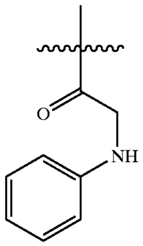 |
| | | | | C41 | 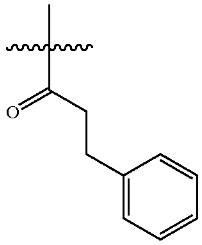 |

or a pharmaceutically acceptable salt, tautomer prodrug ester or prodrug amide thereof.

17. A compound according to claim 16, wherein:

$R_1$ is selected from the following groups:

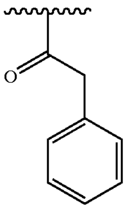
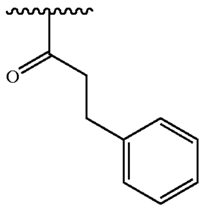
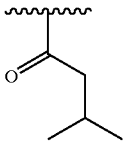
and
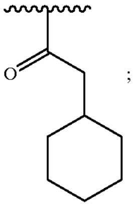
;

$R_4$ is selected from the following groups:

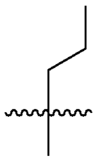
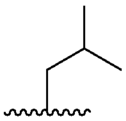
and
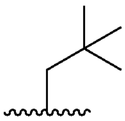
;

and Q is selected from the following groups:

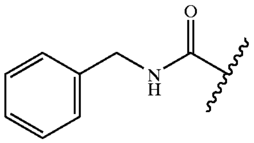
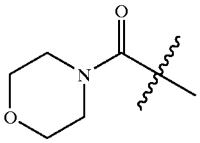
and
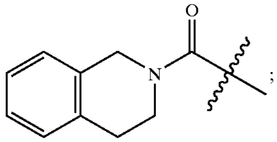
;

or a pharmaceutically acceptable salt, tautomer, prodrug ester or prodrug amide thereof.

18. A compound according to claim 1 selected from the following compounds:

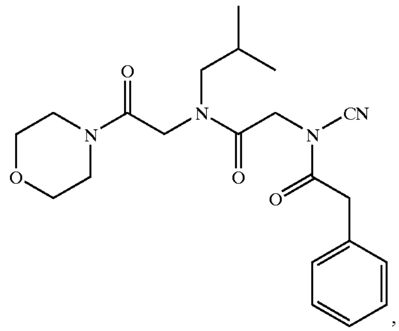
,

-continued

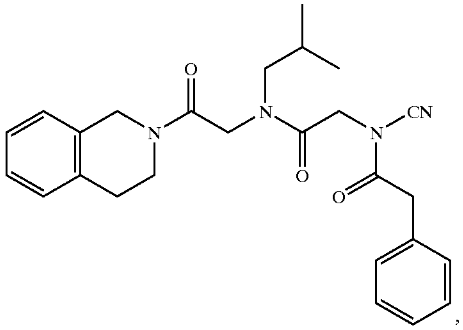
,

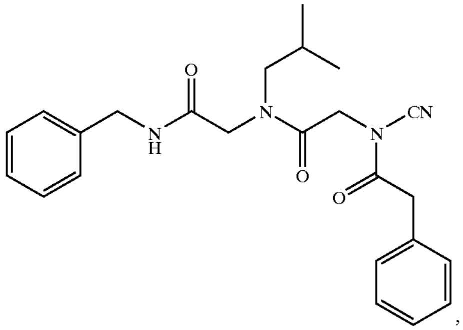
,

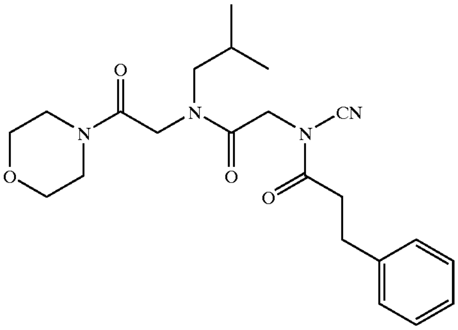
,

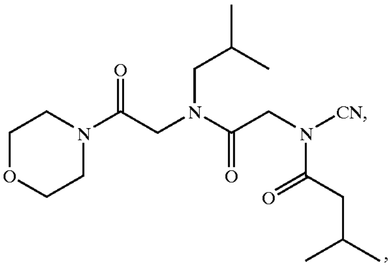
,

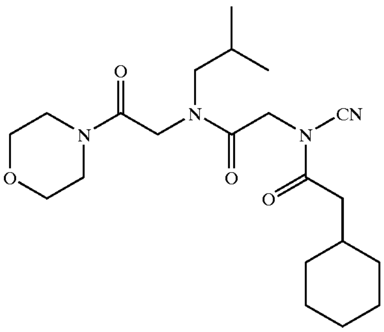
,

-continued

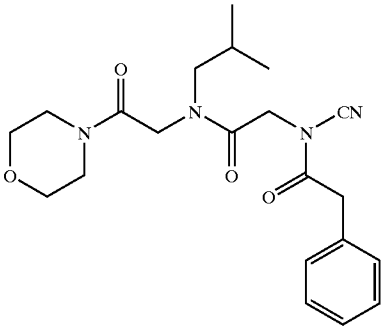

and

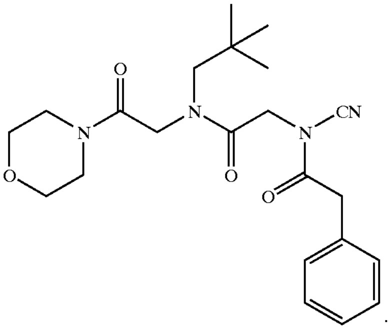

.

19. A process for preparing a compound of formula (I) according to claim 1, said process comprising reacting a compound of formula V with a cyanamide of formula VIII in the presence of a suitable base to obtain a compound of formula (I):

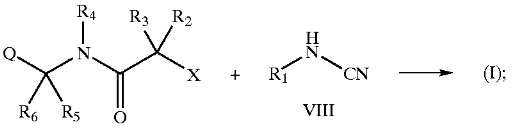

V VIII wherein $R_1$, $R_2$, $R_3$, $R_4$, $R_5$, $R_6$ and Q are as defined in claim 1, and X is a leaving group.

20. A process according to claim 19, wherein the compound of formula (V) is prepared by a process comprising:

reacting the compound of formula (III) with a compound of formula (IV) where X is a leaving group to obtain a compound of formula (V):

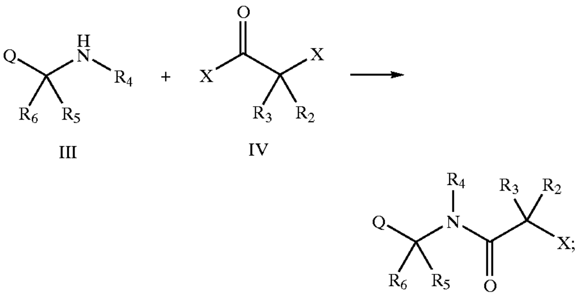

III IV V wherein $R_2$, $R_3$, $R_4$, $R_5$, $R_6$ and Q are as defined in claim 19.

21. A process according to claim 20, wherein the compound of formula III is prepared by a process comprising:

(a) reacting a compound of formula II where X is a leaving group with a compound of the formula $H_2N—R_4$ to obtain a compound of formula III:

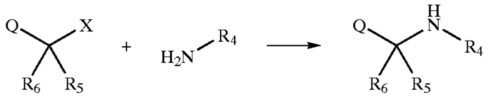

II III wherein $R_4$, $R_5$, $R_6$ and Q are as defined in claim 20; or (b) reacting a compound of the formula IX with an aldehyde of the formula R'CHO under reductive amination conditions to provide a compound of the formula III:

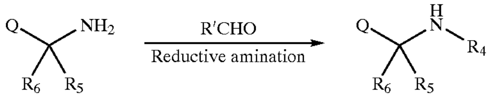

IX $III\ R_4 = R'CH_2$ wherein $R_5$, $R_6$ and Q are as defined in claim 20, and $R_4$ is selected from an $R_4$ group as defined in claim 20 having a $—CH_2—$ group bonded to the nitrogen atom in the backbone of formula (III), and R' is that terminal portion of said $R_4$ group which is bonded to said $—CH_2—$ group.

22. A process for preparing a compound of formula (I) according to claim 1, said process comprising reacting a compound of formula (XIII) with a compound $R_1X$ where X is a leaving group in the presence of a suitable base to obtain a compound of formula (I):

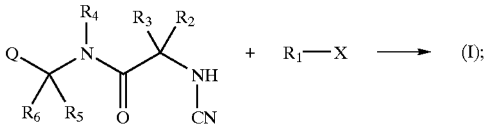

XIII wherein $R_1$, $R_2$, $R_3$, $R_4$, $R_5$, $R_6$ and Q are as defined in claim 1.

23. A process according to claim 22, wherein the compound of formula (XIII) is prepared by a process comprising:

(a) reacting a compound of formula (III) with a compound of formula (X) wherein PG is a protecting group and X is a leaving group to obtain a compound of formula (XI):

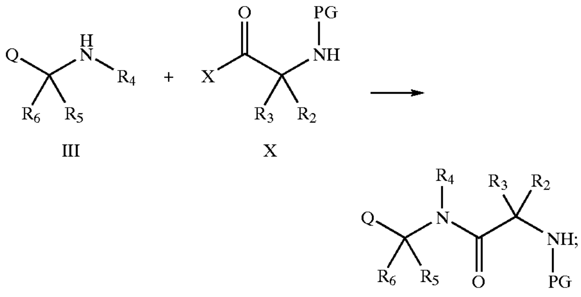

III X XI (b) deprotecting a compound of formula (XI) to obtain a compound of formula (XII):

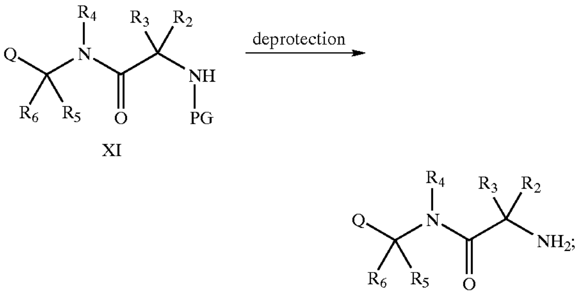

XI

XII (c) reacting a compound formula (XII) with cyanogen bromide to obtain a compound of formula (XIII):

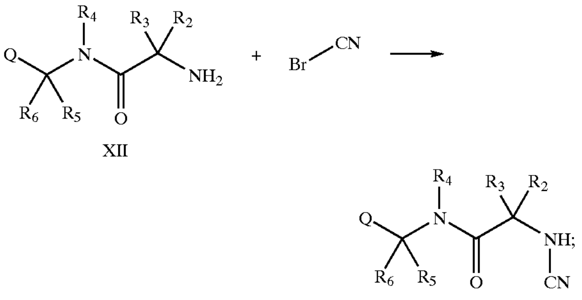

XII

XIII wherein $R_2$, $R_3$, $R_4$, $R_5$, $R_6$ and Q are as defined in claim 22.

24. A process according to claim 23, wherein the compound of formula III is prepared by a process comprising:

(a) reacting a compound of formula II where X is a leaving group with a compound of the formula $H_2N—R_4$ to obtain a compound of formula III:

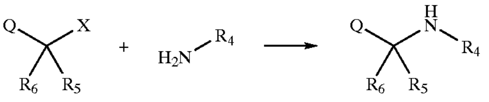

II III wherein $R_4$, $R_5$, $R_6$ and Q are as defined in claim 23; or (b) reacting a compound of the formula IX with an aldehyde of the formula R'CHO under reductive amination conditions to provide a compound of the formula III:

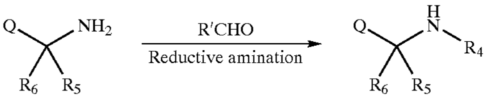

IX $III\ R_4 = R'CH_2$ wherein $R_5$ , $R_6$ and Q are as defined in claim 23, and $R_4$ is selected from an $R_4$ group as defined in claim 23 having a $—CH_2—$ group bonded to the nitrogen atom in the backbone of formula (III), and R' is that terminal portion of said $R_4$ group which is bonded to said $CH_2—$ group.

25. A pharmaceutical composition comprising a therapeutically effective amount of a compound according to claim 1 or a pharmaceutically acceptable salt, solvate, tautomer or prodrug thereof.

* * * * *